US005646029A

United States Patent [19]
Chen et al.

[11] Patent Number: 5,646,029
[45] Date of Patent: Jul. 8, 1997

[54] PLANT ARABINOGALACTAN PROTEIN (AGP) GENES

[75] Inventors: Chao-Guang Chen, Brunswick; Shaio-Lim Mau, Waverley; He Du, North Melbourne; Alison M. Gane, North Carlton; Antony Bacic, Eltham; Adrienne E. Clarke, Parkville, all of Australia

[73] Assignee: Cooperative Research Centre for Industrial Plant Biopolymers, Parkville, Australia

[21] Appl. No.: 276,452

[22] Filed: Jul. 18, 1994

Related U.S. Application Data

[63] Continuation-in-part of Ser. No. 161,944, Dec. 3, 1993, abandoned.
[51] Int. Cl.[6] .................. C12N 1/21; C12N 5/00; C12N 5/14; C12N 5/06
[52] U.S. Cl. .............. 435/325; 435/252.3; 435/320.1; 435/365; 435/419; 536/23.6; 800/205
[58] Field of Search ................ 536/23.6; 435/320.1, 435/240.4, 240.2, 252.3, 240.1; 800/205

[56] References Cited

FOREIGN PATENT DOCUMENTS

| WO90/02804 | 3/1990 | WIPO | ............................ C12N 15/53 |
| WO92/01792 | 2/1992 | WIPO | ............................ C12N 15/56 |
| WO93/20237 | 10/1993 | WIPO | ............................ C12Q 1/68 |

OTHER PUBLICATIONS

Schmidt et al. (1988) J. Bacteriol. vol. 170: pp. 3404–3414.
Monaghan et al. (1991) Development vol. 112: pp. 1053–1061.
Pogson et al. (1995) Plant Molecular Biology vol. 28(2): pp. 347–352.
Kiebler et al (1993) Cell vol. 74(3): pp. 483–492.
Hiles et al. (1987) J. Mol. Biol. vol. 195: pp. 125–142.
Fincher et al. (1983) "Arabinogalactan–Proteins: Structure, Biosynthesis, and Function," *Ann. Rev. Plant Physiol.* 34:47–70.
Anderson et al. (1977) "A Carbohydrate–binding Arabinogalactan–Protein from Liquid Suspension Cultures of Endosperm from *Lolium multiflorum*," *Aust. J. Plant Physiol.* 4:143–158.
Clarke et al. (1979) "Form and Function of Arabinogalactans and Arabinogalactan–Proteins," *Photochem.* 18:521–540.
Jermyn et al. (1985) "A Final Assault on the Structure of Carrot AGPs," *AGP News* 5:30–36.
Gleeson et al. (1989) "Characterization of the Hydroxyproline–rich Protein Core of an Arabinogalactan–Protein Secreted from Suspension–cultured *Lolium multiflorum* (Italian ryegrass) Endosperm Cells," *Biochem. J.* 264:857–862.

Komalavilas et al. (1991) "Arabinogalactan–Proteins from the Suspension Culture Medium and Plasma Membrane of Rose Cells," *J. Biol. Chem.* vol. 266: pp. 15956–15965.
Gleeson, et al. (1985) "Cloning the cDNA for the Arabinogalactan–Protein from *Lolium multiflorum* (RyeGrass)," *AGP News* 5:30–36.
Sheng et al., (1993) Abstract No. 639 "PCR–based cDNA Cloning for Potato Tuber Lectin, Arabinogalactan–Proteins and Extensins"; *Supplement to Plant Physiol.* 102, No. 1, May 1993 (reported at a conference in Minnesota, USA, Jul. 31–Aug. 4, 1993).
Fincher et al. (1974) "A Water–soluble Arabinogalactan––Peptide from Wheat Endosperm," *Aust. J. Biol. Sci.* 27:117–132.
Jermyn, et al. (1975) "A Class of Lectins present in the Tissues of Seed Plants," *Aust. J. Plant Physiol.* 2:501–531.
Gleeson, et al. (1979) "Structural Studies on the Major Component of *Gladiolus* Style Mucilage, an Arabinogalactan–Protein," *Biochem. J.*181:607–621.
Bacic, et al. (1988) "Arabinogalactan Proteins from Stigmas of *Nicotiana alata*," *Phytochem.* 27:679–684.
Osman, M.E., Menzies, A.R., Williams, P.A., Phillips, G.O. and Baldwin, T.C. (1993) "The molecular characterisation of the polysaccharide gum from *Acacia senegal*," *Carbohydrate Research* 246:303–318.
Sanford, P.A. and Baird, J. (1983) "Industrial utilization of polysaccharides." In *The Polysaccharides* vol. 2, Academic Press Inc.
Randall, R.C., Phillips, G.O., and Williams, P.A. (1989) "Fractionation and characterization of gum from *Acacia senegal*," *Food Hydrocolloids* 3:65–75.

*Primary Examiner*—Che S. Chereskin
*Attorney, Agent, or Firm*—Greenlee, Winner and Sullivan, P.C.

[57] ABSTRACT

This invention provides plant arabinogalactan proteins (AGPs) and their genes. AGPs were isolated from *Nicotiana alata*, *Nicotiana plumbaginafolia*, and *Pyrus communis*. Amino acid sequences of isolated AGP peptide fragments are presented. Isolated AGP fragments were used to synthesize oligonucleotide probes to prepare oligonucleotide primers for PCR or prepare RNA probes to screen cDNA libraries of *N. alata*, *N. plumbaginafolia*, and *P. communis*. cDNA clones encoding amino acid sequences of isolated AGP fragments were isolated. The invention presents for the first time an intact AGP amino acid sequence derived from a corresponding AGP gene. The instant invention further provides methods useful in obtaining AGP genes encoding an AGP peptide comprising a specific isolated hydroxyproline-rich (OAST-rich) sequence or a specific isolated hydroxyproline-poor sequence.

56 Claims, 55 Drawing Sheets

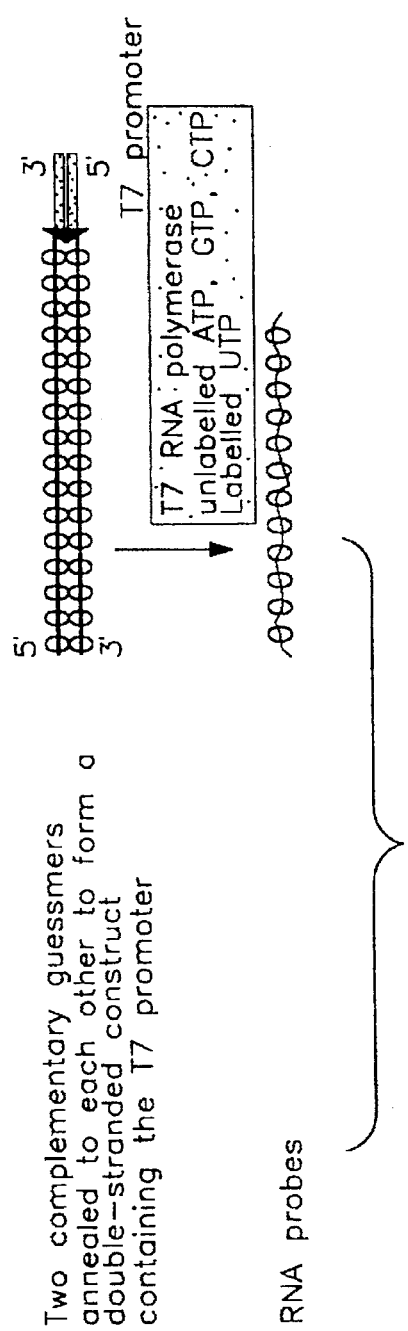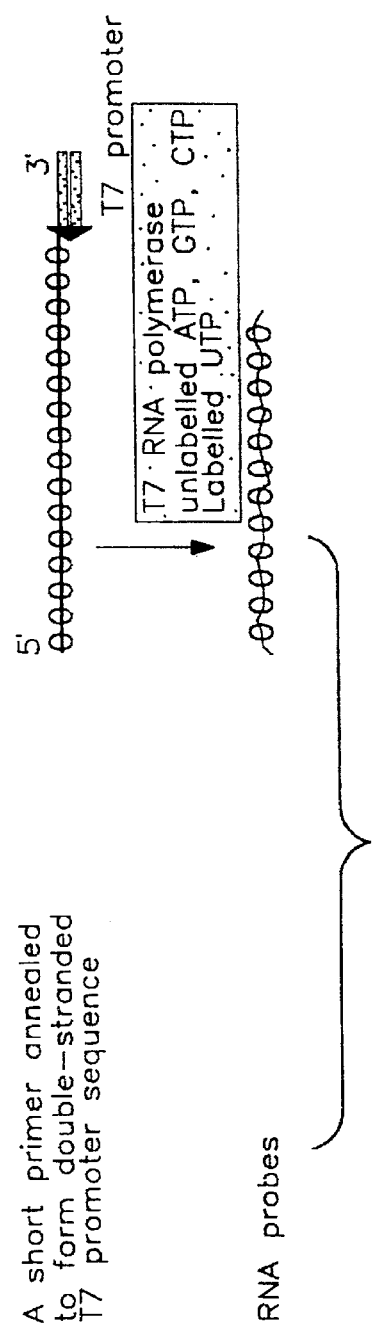

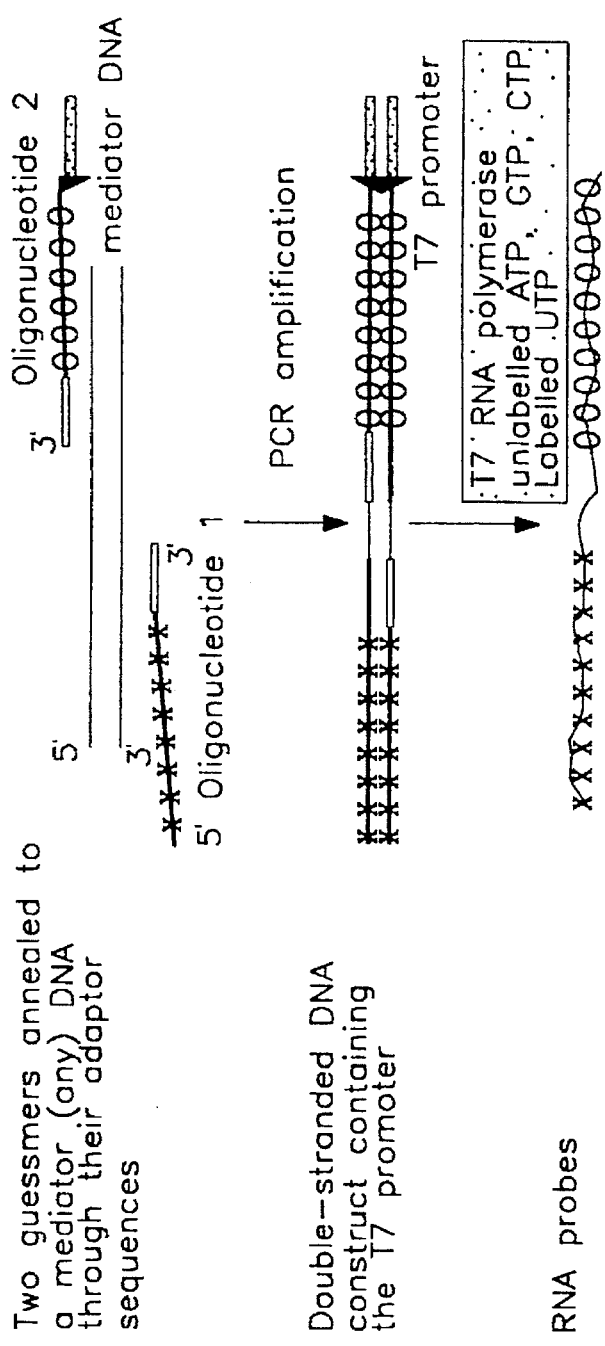

```
AGAGAACCAAGAGAACCAACACATCAAATATTCTCTTCCCTTTTGTTCTATTTTCATT
 R  T  K  K  P  T  H  Q  I  F  F  F  P  F  C  S  I  F  I           59

NaF1 primer >>              NaF2 primer >>
ATGGGTCATTTCACTAAGCAAATGACATTCTTCTTGTTCTTGGTGATCTCAACTCCATTG
 M  G  H  F  T  K  Q  M  T  F  F  L  F  L  V  I  S  T  P  L      119

GTGCAAATTGAAGGTAGAAAAAGCAAGTTTATGATCATACC
 V  Q  I  E  G  R  K  S  K  F  M  I  I  P                         160
        A     *  *  *  *  *  *  *  *  *  *
```

FIG.1E

AGAGAACCAAGAAACCAACACATCAAATATTCTTCTTTCCCTTTTGTTCTATTTTCATTATGGGTCATTTCACT 74
                                                                  M  G  H  F  T   5

AAGCAAATGACATTCTTCTTGTTCTTGGTGATCTCAACTCCATTGGTGCAAATTGAAGGTAGAAAAGCAAG 146
K  Q  M  T  F  F  L  F  L  V  I  S  T  P  L  V  Q  I  E  G  R  K  S  K  29
          A  *  *  *  *  *  *  *  *  *  *  *  *              A  *  *  *

TTTATGATCATACCTGCATCTCCTACACCAGCTCCAACACCAATCAATGAAATTAGTTTTCCTCCATTTCA 218
F  M  I  P  A  S  P  T  P  A  P  T  P  I  N  E  I  S  F  P  P  F  S  53
*  *  *  *  *  *  (H) *  *  *  *

TCCCTTACTCCAACTCCATCACCAACAGCACCAGCACCGTTTTTTAATGATTTTGCG 290
S  L  T  P  T  P  S  P  T  P  A  P  A  T  A  P  P  F  F  N  D  F  A  77

TTTCCTCCATTGTCATCTTTAAGTCCAACACCAGTACCAGTAGGTAATGTTCAAGATCCTGATGTG 362
F  P  P  L  S  S  L  S  P  T  P  A  P  V  P  V  G  N  V  Q  D  P  D  V  101

AATGGGTACCTACGGCCTGCAGGAGGGAGTGGTGAAGATCCAGAGGAAGGTGGCATTGAAGCG 434
N  G  V  P  T  P  A  L  A  P  G  G  S  G  E  D  P  E  E  G  G  I  E  A  125

CCAGCACCACTTTTGACTGATACTCCCTATGGTCTTTATGGTCTAGGTCCTCATTCTCAGGAAATTCTTCTACTGTC 506
P  A  P  L  L  T  D  T  P  Y  G  L  Y  G  P  H  S  Q  E  I  S  S  T  V  149

ACAAATCTTGATGAGGTTGAAACTCAAACTCCTGCCAAGGAATTCCAAGGTGCTAGAGATTAATACAGATGAG 578
T  N  L  D  E  V  E  T  Q  T  P  A  K  E  F  Q  G  A  R  F  N  T  D  E  173

TCCTACAATAACGATGATGGCTTCTCCGAGAATTACAATAACAACAACGGATGCTACTCGGAGAATGCTAATAACAAC 650
S  Y  N  N  D  D  G  F  S  E  N  Y  N  N  N  N  G  Y  D  S  N  N  N  N  197

AACAATAACGATGATGGCTTCTCCGAGAATTACAATAACAACAACGGATACTCGGAGAATGCTAATAACAAGAAC 722
N  N  D  D  G  F  S  E  N  Y  N  N  N  N  G  Y  S  E  N  A  N  N  K  N  221

AACAATGGCTACTCAGAGAATTACAACAACAACAACAATAACAACAACAATTACAACAACAATGGCTAC 794
N  N  G  Y  S  E  N  Y  N  N  N  N  N  N  N  N  N  Y  A  K  N  Y  N  N  G  Y 245

FIG.1F-1

```
TCTCAGAGTTACAACAACAATAATTTTTACTCGGAGAATTACAACAACAACAACAATGTTTTCTCG  866
 S  Q  S  Y  N  N  N  N  F  Y  S  E  N  Y  N  N  N  N  N  V  F  S  269
GAGAATTCCAACAACAATGGCTTCTCCGAGTTACAACAACAATCAACAAAAGATCAACAATGGCTACTCCCAGAATTACATGAACAAC  938
 E  N  S  N  N  G  F  S  E  S  Y  N  N  N  N  G  Y  S  K  K  I  N  N  G  Y  S  Q  N  Y  M  N  N  293
AACAATGGCTTCTCCGAGTTACAACAACAATAACAACAATGTTTTCTCCGAGAATTACAACAACAACAACAACGTTTTCTCTGAGAAT 1010
 N  N  G  F  S  E  S  Y  N  N  N  N  N  N  N  V  F  S  E  N  Y  N  N  N  N  N  N  V  F  S  E  N  317
TACAACAACAACAACAATAACAATGTTTTTCTCCGAGAATTACAACAACAATAACAACTACAATCAGGCTAGCAGCTACAATAACAATGCTTTCTAC 1082
 Y  N  N  N  N  N  N  N  V  F  S  E  N  Y  N  N  N  N  N  N  Y  N  Q  A  S  S  Y  N  N  N  A  F  Y  341
GAGAATTACAACAACAACAACAATGGCTACTCAGAGAACTACAATCAGGCTACAGCTACAATAACAATGCTTTCTACGAGAATTATTATGATATCAAG 1154
 E  N  Y  N  N  N  N  N  N  G  Y  S  E  N  Y  N  Q  A  S  S  Y  N  N  N  A  F  Y  E  N  Y  Y  D  I  K  365
AATACGGTGGAAAGGCAAGGATTAAGTGATACAAGATTCTTGGAAAATGGCAAGTATTATTATGATATCAAG 1226
 N  T  V  E  R  Q  G  L  S  D  T  R  F  L  E  N  G  K  Y  Y  Y  D  I  K  389
AATGAGAATACCAACAACAATGGCTACTCTGAGAATTACAACCATGTTAGCAGCTACAATGTTATAGCAACTACTTTTATAGCAACAATAACAAT 1298
 N  E  N  T  N  N  N  G  Y  S  E  N  Y  N  H  V  S  S  Y  N  N  N  N  N  N  413
ATGGTGGAAAGGCAAGGATTGAGTGACACAAGATTCTTAGATAATGGTAACTACTTTTATAGCAACACTGAAGATCAGTAGATACGAACTTCCT 1370
 M  V  E  R  Q  G  L  S  D  T  R  F  L  D  N  G  N  Y  F  Y  S  N  N  G  437
GAGAAAATGTCAGTGGAAGAGTCTGAAAGACAGCAGGAATATCCAGACACTGAAGAGATCAGTAGATCAGTACGAACTTCCT 1442
 E  K  M  S  V  E  E  S  E  R  Q  Q  E  Y  P  D  T  E  D  Q  Y  E  L  P  461
TGAAGATAAATATTATTAGTTGGTCCAGAGAAGAGGGACAAACGCAGAGGACGTGAAAATAGATTTAATGAT 1514
 -
TGAATTTTAAGTTATTTTGAGTGTTGTTCATTAGTTCCACTTGAGTCTGCAAACACCTTTTTTTCTTTTT 1586
TTATAGTTCTGCAAATCAGACCGAGGGAACTTTGAGTTGTTTAACACTTTTTAAAAACTTTTT         1658
ATAATGATCTTGAAGCTTCACGCCTAAAAAAA                                        1700
```

FIG.1F-2

```
GTTCTTGGTGATCTCAACTCCACTAGTACAAATTGAAGCAAGTTTATGATCATTCCTGCATC--72
 F  L  V  I  S  T  P  L  V  Q  I  E  A  R  K  S  K  M  I  P  A  S  24
                                      *  *  *  *  *  *  *  *  *  *

TCCTGCACCAGTCCAACTCCAATCAATGAAAATTAGTTTTCCTCCATTTCATCCTTTACTCCAACTCCATC--144
 P  A  P  V  S  Q  S  Q  S  N  E  N  *  F  P  P  F  H  P  L  L  Q  L  H  48

ACCAACACCACCAACATCAGCACCACCAGTAGTGATCAAGATCCTGATGTGAACGGTGTACCGGCGCCTGC--216
 P  A  P  P  T  P  N  E  I  S  F  P  P  F  N  D  F  A  F  P  P  L  S  72
 *  *  *  *  O  T  O  *  O  *  O  *

AACAACACCAACATCAGCACCACCAGTAGTGATCAAGATCCTGATGTGAACGGTGTACCGGCGCCTGC--216
 P  T  P  T  P  T  S  A  P  T  P  F  F  N  D  F  A  F  P  P  L  S  72

ATCTTTAAGTCCAACTCCAGCACCAGTAGTGATCAAGATCCTGATGTGAACGGTGTACCGGCGCCTGC--288
 S  L  S  P  T  P  A  P  V  G  S  D  Q  D  P  D  V  N  G  V  P  A  P  A  96

AGTGGCACCAATAGGGAGTGGTCAAGATCCAGAAGAAGGTGGCATTGAAGCACCAGCACCACTTTTAACTGA--360
 V  A  P  I  G  S  G  Q  D  P  E  E  G  G  I  E  A  P  A  P  L  L  T  D  120

TACTCCTTATGGACTTTATGGTCCTCATTCTCAGGAATTCCTTCAACTGTCACAAATCTTGATGAGGTTGA--432
 T  P  Y  G  L  Y  G  P  H  S  Q  E  I  P  S  T  V  T  N  L  D  E  V  E  144

AACTCAAACTCCTGCCGAGGAATTCCAAGGTGCTAGATTTAATACAGATGAGTCCTACAATAACAATGGTTA--504
 T  Q  T  P  A  E  E  F  Q  G  A  R  F  N  T  D  E  S  Y  N  N  N  G  Y  168

TGATTCCAACAACAATGGCTACTCCGAGAATAACAACAAGAACAACAATGGCTACTCCGGAGAATTACAA--576
 D  S  N  N  N  G  Y  S  E  N  N  N  K  N  N  N  G  Y  S  E  N  Y  N  192

CAACAACAACAACAATGGCTACTCCGAGAATTACAACAACAACAACAATGGCTACTCCAAGAATTACAACAA--648
 N  N  N  N  N  G  Y  S  E  N  Y  N  N  N  N  N  G  Y  S  K  N  Y  N  N  216

CAATGGCTACTCCAAAAAAATCAACAATAATGGTTACTCCCAGAATTACATGAACAACAACAACGGCTTCTC--720
 N  G  Y  S  K  K  I  N  N  N  G  Y  S  Q  N  Y  M  N  N  N  N  G  F  S  240
```

FIG.1H-1

```
CGAGAGTTACAACAGCAACAACAACAACAATATTTCTCCGAGAATTACAACAACAATAACAATAA--792
  E  S  Y  N  S  N  N  N  N  N  I  F  S  E  N  Y  N  N  N  N  N  N    264

TGTTTCTCCGAGAATTACAACAACAATAATGTTTTCTCCGAGAATTACAACAACAATAACAA--864
  V  F  S  E  N  Y  N  N  N  N  N  V  F  S  E  N  Y  N  N  N  N  N    288

CAATGCTTTCTCCGAGAACTACAACAACAATAATGTTTTCTCCGAGAATTACAACAAAACAATAACAACAA--936
  N  A  F  S  E  N  Y  N  N  N  N  V  F  S  E  N  Y  N  K  N  N  N  N    302

TGCTTTCTCTGAGAATTACAACAACAAAAACAACAATAATCAAGCTACAATCAAGCTAGCAGCTA--1008
  A  F  S  E  N  Y  N  K  N  N  N  A  Y  S  E  N  Y  N  Q  A  S  S  Y    326

CAATAACAATGGCAATACGGTTGGAGAGGCAAGGATTAAGTGATACAAGATTCTTGGAGAATGGCAAGTACTA--1080
  N  N  G  N  T  V  E  R  Q  G  L  S  D  T  R  F  L  E  N  G  K  Y  Y    350

TTATGATATCAAGAATGAGAATCCCAACCACAACCACAATACAATCATGTTAGCAGCTA--1152
  Y  D  I  K  N  E  N  P  N  H  N  N  G  Y  S  E  N  Y  N  H  V  S  S  Y    374

CAATAACAATAACAATGGTGAAGGCAAGGATTGAGTGACACAAGATTCTTAGATAATGGCAACTACTT--1224
  N  N  N  N  M  V  E  R  Q  G  L  S  D  T  R  F  L  D  N  G  N  Y  F    398

TTATAGTAACAATAACAATGTCAATGGAGAAAATGTCAATGGAAGAATCTGAAAGACAGCAGGAATATCCAAATACTGAAGA---1296
  Y  S  N  N  G  E  K  M  S  M  E  E  S  E  R  Q  Q  E  Y  P  N  T  E  D    432

TCAGTATGAACTTCCTTGAAGACTAACATTATCAGTTGGCTTAAAGAAGAGGGACAAATGCAGGGAACATG---1367
  Q  Y  E  L  P  ---                                                       437

AGAATAGATTTAATTTACAGAGTTTGATTGAATTTTAAGTAAAAAAAAAAAAAAAAAAAAA           ---1430
```

FIG.1H-2

```
NaAGP1  -- MGHFTKQMTFFLFLVISTPLVQIEGRKSKFMIIPASPTPAPTPINEISFP           -50
NpAGP1  --                FLVISTPLVQIEARKSKFMIIPASPAPTPINEISFP           -38

NaAGP1  -- PFSSLTPTPSPTPAPA--TAPTPFFNDFAFPPLSSLSPTPAPVPVGNVQD              -98
NpAGP1  -- PFSSFTPTPSPTPTPTPTSAPTPFFNDFAFPPLSSLSPTPAPVG--SDQD              -86

NaAGP1  -- PDVNGVPTPALAPGGSGEDPEEGGIEAPAPLLTDTPYGLYGPHSQEISST             -148
NpAGP1  -- PDVNGVPAPAVAPIGSGQDPEEGGIEAPAPLLTDTPYGLYGPHSQEIPST             -136

NaAGP1  -- VTNLDEVETQTPAKEFQGARFNTDESYNNNGYDSNNNDNNNGYDSNNNNN             -198
NpAGP1  -- VTNLDEVETQTPAEEFQGARFNTDESYNNNGYDSNNNG                         -174

NaAGP1  -- NNDDGFSENYNNNGYSENANNKNNNGYAKNYNNGYSQS                         -248
NpAGP1  --                 YSENNNNKNNNGYSENYNNNNNGYS                     -200
```

FIG. 1I-1

```
NaAGP1  -- YNNNNNFYSENYNYNNNNNVFSENSNNNGYSKKINNNGYSQNYMNNNNGFS   -298
NpAGP1  -- ---------ENYNNNNNGY-SKNYNNNGYSKKINNNGYSQNYMNNNNGFS   -240
NaAGP1  -- ESYNYNNNNNNNVFSENYNNNNNNNNNAFYENYNNNN               -348
NpAGP1  -- ESYN----SNNNNNNIFSENYNNNNNNNNNNVFSENYNNNN            -287
NaAGP1  -- N---------------------------GYSENYNQASSYN           -362
NpAGP1  -- NNAFSENYNNNNVFSENYNNKNNNNAYSENYNQASSYN               -337
NaAGP1  -- NNDNTVERQGLSDTRFLENGKYYYDIKNENTN-NNGYSENYNHVSSYNNN   -411
NpAGP1  -- NNGNTVERQGLSDTRFLENGKYYYDIKNENPNHNNGYSENYNHVSSYNNN   -387
NaAGP1  -- NNMVERQGLSDTRFLDNGNYFYSNNGEKMSVEESERQQEYPDTEDQYELP   -461
NpAGP1  -- NNMVERQGLSDTRFLDNGNYFYSNNGEKMSMEESERQQEYPNTEDQYELP   -437
```

FIG. 1I-2

```
NaAGP1  -  AGAACCAAGAAACCAACACATCAAATATTCTTCTTCCCTTTGTTCTATTTCA  -55
NaAGP1  -  TTATGGGTCATTTCACTAAGCAAATGACATTCTTCTTGTTCTTGGTGATCTCAAC  -110
NpAGP1  -                                GTTCTTGGTGATCTCAAC  -18

NaAGP1  -  TCCATTGGTGCAAATTGAAGGTAGAAAAGCAAGTTTATGATCATACCTGCATCT  -165
NpAGP1  -  TCCACTAGTACAAATTGAAGCAAGAAAAGCAAGTTTATGATCATTCCTGCATCT  -73

NaAGP1  -  CCTACACCAGCTCCAACACCAATCAATGAAATTAGTTTTCCTCCATTTTCATCCC  -220
NpAGP1  -  CCTGCACCAGCTCCAACTCCAATCAATGAAATTAGTTTTCCTCCATTTTCATCCT  -128

NaAGP1  -  TTACTCCAACTCCATCACCAACACCAGCAACA-----GCACCAACACC  -269
NpAGP1  -  TTACTCCAACTCCATCACCAACACCAACAACATCAGCACCAACACC  -183

NaAGP1  -  GTTTTTAATGATTTTGCGTTTCCTCCATTGTCATCTTTAAGTCCAACACACCAGCA  -324
NpAGP1  -  GTTTTTTAATGATTTTCGCGTTTCCTCCATTGTCATCTTTAAGTCCAACACCAGCA  -238

NaAGP1  -  CCAGTACCAGTAGGTAATGTTCAAGATCCTGATGTGAATGGCGTACCTACGCCTG  -379
NpAGP1  -  CCAGTA------GGTAGTGATCAAGATCCTGATGTGAACGGTGTACCGGCGCCTG  -287

NaAGP1  -  CATTGGCACCAGGAGGAGTGGTGTGAAGATCCAGAGGAAGGTGGCATTGAAGCGCC  -434
NpAGP1  -  CAGTGGCACCAATAGGGAGTGGTGTCAAGATCCAAGAAGAAGGTGGCATTGAAGCACC  -342

NaAGP1  -  AGCACCACTTTTGACTGATACTCCCTATGGACTTTATGGTCCTCATTCTCAGGAA  -489
NpAGP1  -  AGCACCACTTTTAACTGATACTCCTTATGGACTTTATGGTCCTCATTCTCAGGAA  -397
```

FIG.1J-1

```
NaAGP1   ATTTCTTCTACTGTCACAAATCTTGATGAGGTTGAAACTCCTGCCAAGG   -544
              ||| || ||||||||||||||||||||||||||||||||| ||||||
NpAGP1   ATTCCTTCAACTGTCACAAATCTTGATGAGGTTGAAACTCAAACTCCTGCCGAGG   -452

NaAGP1   AATTTCAAGGTGCTAGATTTAATACAGATGAGTCCTACAATAACAATGGTTATGA   -599
         ||||| ||||||||||||| ||||||||||||||||||||||||||||||||||
NpAGP1   AATTCCAAGGTGCTAGATTTAATACAGATGAGTCCTACAATAACAATGGTTATGA   -507

NaAGP1   TTCCAACAACGACAACAACAATGGTTATGATTCCAACAATAACAACAACAAT   -654
              ||||||                |||  |||        ||||||||
NpAGP1   TTCCAACAAC------------------AATGGCTACTCGGAG----AATAACAACAACAAG   -547

NaAGP1   AACGATGATGGCTTCTCCGAGAATTACAACAAC----------AATGGCTACTCGG   -700
                    |||||||||||||||||||||||          |||||||||||||
NpAGP1   AACAACAATGGCTACTCTCAGAGAATTACAACAACAACAACAACAATGGCTACTCCG   -602

NaAGP1   AGAATGCTAATAACAAAATAACAATGGCTACTCAGAGAATTACAACAATAA   -755
         |||||    |  ||||   |||| |||||||||||||||||||||||||
NpAGP1   AGAAT---TACAACAACAACAATGGCTACTCCAAGAATTACAACAAT--   -652

NaAGP1   CAACAATGGCTACGCCAAGAATTACAACAAT---GGCTACTCTCAGAGTTACAAC   -807
         |||||||||||||  ||||||||| |||||   ||||||| || |||||||||
NpAGP1   ------GGCTACTCCAAAAAATCAACAATAATGTTACTCCCAGAATTACACATG   -700

NaAGP1   AACAACAATAATTTTTACTCGGAGAATTAC-------AACAACAACAACAATG   -856
         |||||||| ||  |  |||||||||||||       ||||||||||||||||
NpAGP1   AACAACAACGGCTTCTCCGAGAGTTACAACAGCAACAACAACAACAACAATA   -755

NaAGP1   TTTTCTCGGAGAATTCCAACAACAATGGCTACTCCAAAAAGATCAACAATGG   -911
         ||| | ||||||||| ||||| |||                |||||||||
NpAGP1   TTTTCTCCGAGAATTACAACAAC-----------------AATAATAACAATAATGT   -795
```

FIG.1J-2

```
NaAGP1  CTACTCCCAGAATTAC----ATGAACAACAACAATGGCTTCTCTCCGAGAGTTAC  -960
              ||||||||||||||||    |    ||||||||||||||||||||||||||||||
NpAGP1  TTTCTCCGAGAATTACAACAACAACAACAACAACAACAATAACAATGTTTTCTCCGAGAATTAC  -850

NaAGP1  TACAACAACAACAACAACAACAACAACAACGTTTTCTCTGAGAATTACAACA  -1015
              ||||||||||||| |||||||    |||||||||||||||||||||
NpAGP1  AACAACAATAACAACAATG-------CTTTCTCCGAGAACTAC-----  -886

NaAGP1  ACAACAATAACAATGTTTTCTCCGAGAATTACAACAACAACAATAACAACAA  -1070
                  |||||||||||||||||||||||||||||||||||||||||||||
NpAGP1  ----AACAACAATAACAATGTTTTCTCCGAGAATTACAACAAAACAATAACAACAA  -936

NaAGP1  TGCTTTCTACGAGAATTACAACAAC---AACAACAATGGCTACTCAGAGAACTAC  -1122
              ||||||||| ||||||||||||||    |||||||||||||||| |||||||||
NpAGP1  TGCTTTCTCTGAGAATTACAACAACAACAACAAAACAACAATGCCTACTCTGAGAACTAC  -991

NaAGP1  GCAGCTACAACAATAACGACAATCGGTGGAAAGGAATCAGGCTACAAGGATTAA  -1177
              |||||||| |||||||||||||||||||||||||||||| |||||||||||||
NpAGP1  GCAGCTACAACAATAACAACAATGGCAATCAAGCTACAAGGATTAA  -1046

NaAGP1  GTGATACAAGATTCTTGGAAAATGGCAAGTATTATTATGATATCAAGAATGAGAA  -1242
              |||||||||||||| ||||||||||||||||||||||||||||||||||||||||
NpAGP1  GTGATACAAGATTCTTGGAGAATGGCAAGTACTATTATGATATCAAGAATGAGAA  -1101

NaAGP1  TACCAAC---AACAATGGCTACTCTGAGAATTACAACCATGTTAGCAGCTACAAT  -1294
              |||||||    ||||||||||||||||||||||||||||||| |||||||||||||
NpAGP1  TCCCAACCACAACAATGGCTACTCCGAGAACTACAATCATGTTAGCAGCTACAAT  -1156
```

FIG.1J-3

```
NaAGP1  -  AACAATAACAATATGGTGGAAAGGCAAGGATTGAGTGACACAAGATTCTTAGATA  -1349
              ||||||||||||||||||||||||||||||||||||||||||||||||||||||
NpAGP1  -  AACAATAACAATATGGTGGAAAGGCAAGGATTGAGTGACACAAGATTCTTAGATA  -1211

NaAGP1  -  ATGGTAACTACTTTTATAGCAACAATGGTGAGAAAATGTCAGTGGAAGAGTCTGA  -1404
              |||| ||||||||||||| |||||||||||||||||||||||||||||||||
NpAGP1  -  ATGGCAACTACTTTTATAGTAACAATGGTGAGAAAATGTCAATGGAAGAATCTGA  -1266

NaAGP1  -  AAGACAGCAGGAATATCCAGACACTGAAGATCAGTACGAACTTCCTTGAAGATAA  -1459
              |||||||||||||||||||| ||||||||| ||||||||||||||||||| ||
NpAGP1  -  AAGACAGCAGGAATATCCAAATACTGAAGATCAGTATGAACTTCCTTGAAGACTA  -1321

NaAGP1  -  ATATTATTAGTTGGTCCAGAGAAGAGGGACAAACGCCAGAGACGTGAAAATAGAT  -1514
              ||||| ||| ||| |  |||||||| ||   ||||||||||||||||||||
NpAGP1  -  ACATTATCAGTTGGCTTAAAGAAGAGGGAACAAATGCAGGGAACATGGAAATAGAT  -1376

NaAGP1  -  TTAAT------GATTGAATTT-TAAGTTATTTTGAGTGTTTGTTTCATT  -1557
              |||||      |||||||||| |||||
NpAGP1  -  TTAATTTTACAGAGTTTGATTGAATTTTTAAGTTAAAAAAAAAAAAAAAA  -1430

NaAGP1  -  AGTTCCACTTGAGTCTGCAAACACCTTTTTTTCTTTTTTATAGTTCTGCAAATC  -1612
NaAGP1  -  AGACCGAGGGAACTTTGAGTTGTTTAACACTTTTGGATTATTTTAAAAACTTTTT  -1667
NaAGP1  -  ATAATGATCTTGAAGCTTCACGCCTAAAAAAAAA  -1700
```

FIG. 1J-4

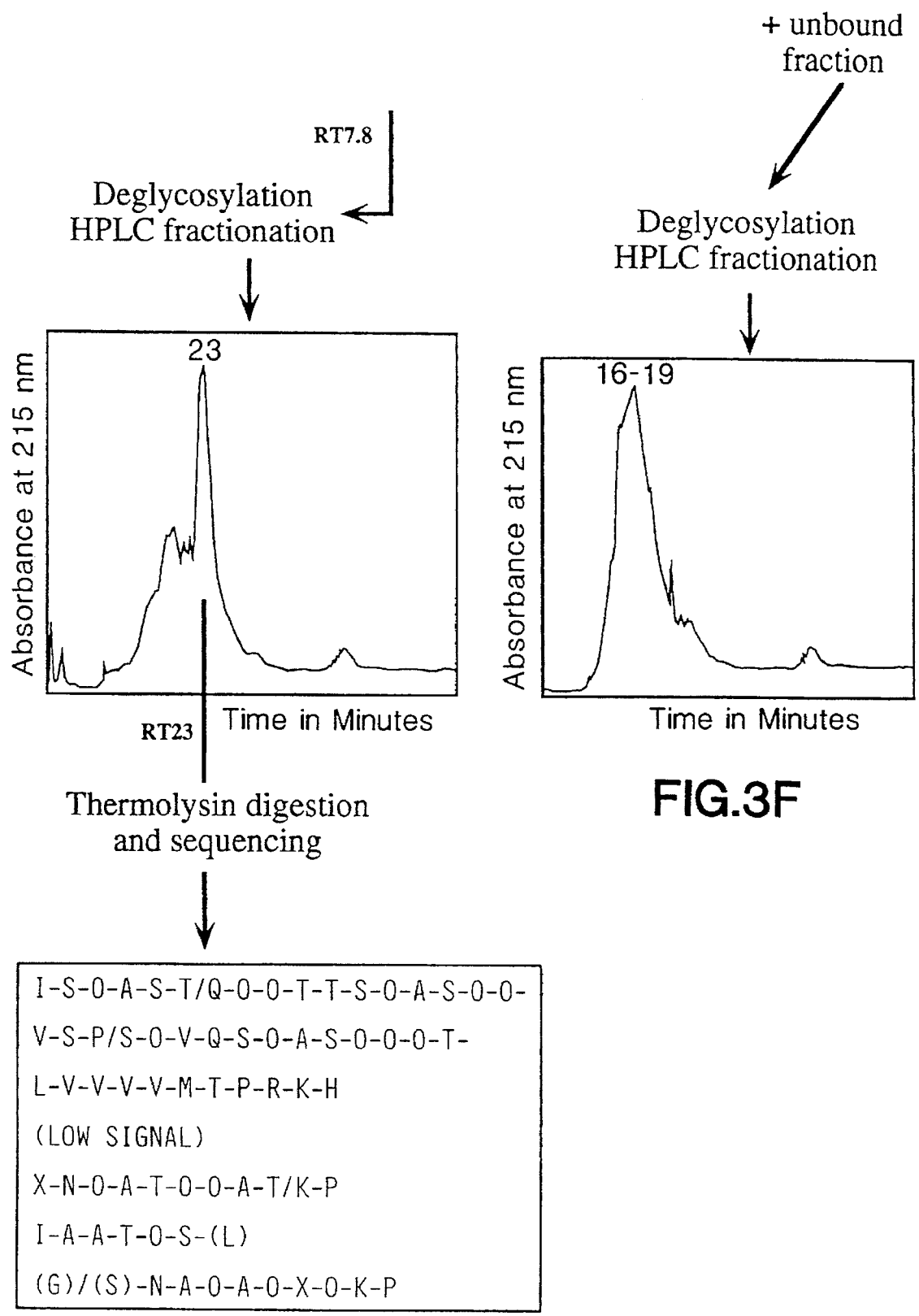

```
         10              20              30              40              50              60
GTAGTGATGACGCCGAGGAAGCACCTCGGTATTTCTCCCGCTCCTTCTCCGGCAGGGAA
 V  V  M  T  P  R  K  H  L  G  I  S  P  A  P  S  P  A  G  E 70              80              90             100             110             120
GTCGACGGGTCCTGCTATTGCTCCCGACAAGCGGCGCTACAAGCTTGAAGGGTGGTGTTCTG
 V  D  G  P  A  I  A  P  T  S  G  A  T  S  L  K  G  G  V  L 130             140             150             160             170             180
ACTGTGGTGGCATTGGGAGGTTTTGTCTGTGGTTTAGCGAGGGGAGATTTTTTGAAC
 T  V  V  A  L  G  G  F  C  L  W  F  * * *

190             200             210             220             230             240
CGTGGTTGTTATCTTTCTGGGTTTTGTTTTGAGAGTGGGGGATAATTATTTGTTTAATT 250             260             270             280             290             300
CTTTATTTTTTTATACATATGAGACGAGATATTATGTAATTCTATTTCGAATGTCATAA 310             320             330             340             350
TATCAATATATTCATTCCTAAATATAAAAAAAAAAAAAAAAAAAAAAAAAA
```

FIG.3G

```
  10                 20                 30                 40                 50                 60
CGCTCTCTAAAATTTCAAATGGCTGGCTTTTCATCCTCAAAAGCTCTGTCATACTCCTC
                  M  A  G  F  S  S  S  K  A  L  S  Y  S  S
                                                                                      ↑
  70                 80                 90                100                110                120
TCTTCTCGTCGTCTTCCTCCTTCGGCTTCTGAGGCCAGAGAGATCACCGTCGGTGG
 L  L  V  F  L  L  E  G  F  S  E  A  R  E  I  T  V  G  G 130                140                150                160                170                180
CAAGAATGGGCTCATGGGCCAGTCCCCTCCTCCGAATCGCAATCCCTCAACAAATGGGCCGA
 K  N  G  S  W  A  V  P  S  S  E  S  S  Q  S  L  N  K  W  A  E 190                200                210                220                230                240
AAGCACCCGCTTCGCGTCGGCGACACTCTTGTGTGGAAGTACGACAGCGCCAAAGACTC
 S  T  R  F  R  V  G  D  T  L  V  W  K  Y  D  S  A  K  D  S 250                260                270                280                290                300
AGTCTTGCGAGTGACGAAAGAAGACTACTCAAACTGCAATGCGTCAAACCCAATTGAGCA
 V  L  R  V  T  K  E  D  Y  S  N  C  N  A  S  N  P  I  E  Q 310                320                330                340                350                360
GCTCAAGGACGGCGAAACAAAGCTCCACCTTGACCAGCCAGGGCCTTACTACTTCATCAG
 L  K  D  G  E  T  K  L  H  L  D  Q  P  G  P  Y  Y  F  I  S
```

FIG.3H-1

```
       370          380          390          400          410          420
CGGAACCAAGGGGCACTGCGAGAAGGGCAGAAACTGGTGGTGGTTATGACTCCAAG
  G  T  K  G  H  C  E  K  G  Q  K  L  V  V  M  T  P  R 430          440          450          460          470          480
GAAGCACCTCGGTATTCTCCCGCTCCTTCTCCGGCAGGGAAGTCGACGGTCCTGCTAT
  K  H  L  G  I  S  P  A  P  S  P  A  G  E  V  D  G  P  A  I
                           O          O                      O 490          500          510          520          530          540
TGCTCCGACAAGCGGCGCTACAAGCTTGAAGGGGTGTTCTGACTGTGGTGGCATTGGG
  A  P  T  S  G  A  T  S  L  K  G  G  V  L  T  V  V  A  L  G 550          560          570          580          590          600
AGGGTTTTGTCTGTGGTTTTAGCGAGGGGAGATTTTTGAACCGTGGTTGTTATCTTTC
  G  F  C  L  W  F  ***

610          620          630          640          650          660
TGGGTTTTGTTTGAGAGTGGGGATAATTATTGTTAATTCTTTATTTTTTTATAC
       670          680          690          700          710          720
ATATGAGACGAGATATTATGTAATTCTATTTCGAATGTCATAATATCAATATATTCATTT
       730          740          750          760
CCTAAATATAAAAAAAAAAAAAAAAAAAAAAAAAAAA
```

FIG.3H-2

```
GCGATCAACACGGAGTTCGGCCCTGAGGAATGTAACCAGTATGAATTTGCCATGATCAAA  60
 A  I  N  T  E  E  F  G  P  E  E  C  N  Q  Y  E  F  A  M  I  K  20
AATCAGTGTGCAAATCAAGCTGCTCCTCCTACAGATTACTAAGTTATTAAGGGGATG     120
 N  Q  C  A  N  Q  A  A  P  P  P  T  D  Y  -                   34
TATGTGTACGTGCCGTGTTTATATAGCCCGACCTTGTTTGGACTTAGGCGTAGTTTG     180
CATTATTGTTATTTTATATATGTGTTATTAGTATGTGTGTATTCATATAGTCGACCCCAACTTGTTTGGGA  240
TTGAGACGTAATTGGTGTTATTAGTATGTGTGTATTTTGATGAGAATAAATTA         300
ATGAAGTGATTTGCTTATTGGGTTATCACAAAAAAAAAAAAAAAAA                350
```

FIG. 4E

```
TCTTTTTCATGTTATAAGCCATGTCTAGAGTAAGAAACTTATTTTCTTTTCCTTATTTTCT  60
                     M   S   R   V   R   N   L   F   S   F   L   I   F   13

TTCTCATTATTGCCTTAAATTTCACTAATGGATTAGCCATTGATCATAAATCTGATGCTA  120
 F   L   I   I   A   L   N   F   T   N   G   L   A   I   D   H   K   S   D   A   33

ATATTGCATTAATCCCACAAAAGAAAGGATTAAAATGGTTGCATTGGCCATTGCACATG  180
 N   I   A   L   I   P   Q   K   K   G   L   K   W   L   H   W   P   F   A   H   53

CACCACCACCACCTTTCATCTCTTTTTCCTAAGTTTTCCATTTCCAAAATATTTCCCTGGC  240
 A   P   P   P   S   F   F   P   K   F   F   P   K   I   F   P   W   73

CGGGATTTTTTGCCACCTAAGCCTTTTTCGCCCTAGTGAAAAACGCGTCAGTGACATAAACA  300
 P   R   F   L   P   P   K   P   F   S   P   S   E   K   R   V   S   D   I   N   93

TAGACAACAGTCAGAACGTGTTGGACAAGAAATATTATTGTGCTTTAATTATTGAGGCGT  360
 I   D   N   S   Q   N   V   L   D   K   K   Y   C   A   L   I   I   E   A   113
```

FIG.4F-1

```
GTATGCTTGAGAGGGATATGCTTTGCCTTCGCAATAGATGTACCTTCTCTTATGATTGTT  420
 V  M  L  E  R  D  M  L  C  V  R  N  R  C  T  F  S  Y  D  C   133
GTACTGCCATTAATACTGAATTTGGTCCTGAGGAATGTAACCAGTATGAATTTGCCATGA  480
 C  T  A  I  N  T  E  F  G  P  E  E  C  N  Q  Y  E  F  A  M   153
TCAAAAATCAGTGTGCAAATCAAGCTGCTCCTCCTACAGATTACTAAGTTATTAAGG    540
 I  K  N  Q  C  A  N  Q  A  A  P  P  P  T  D  Y  -            169
GGATGTATGTGTACGTGCCGTGTTATATAGCCGACCTTGTTTGGGACTTAGGCGT       600
AGTTTGCATTATTGTTATTTTATATATGTGTATGTGTATTCATATAGTCGACCCCAACTTGT  660
TTGGGATTGAGACGTAATTGGTGTTTATTAGTATGTGTGTATTTGATGAGAAT         720
AAATTAATGAAGTGATTTGCTTATTGGGTTATCAAAAAAAA                     762
```

FIG.4F-2

```
TGAAGAAACTTACACTTTCTCTCTGAAACTGCTCAAACACTTCAAATCAGAGTTTTCG         60
AAAAGCTTCTAGAGAGAGAAAGAAATGGCTTACTCAAGGATGATGTTCGCTTTCATTTTC        120
                 M  A  Y  S  R  M  M  F  A  F  I  F               12
GCTTTGGTGGCCGGGATCTGCTTTGCTCAGGCTCAGGCTⓅGGAGCTTCTCCCGCAGCTTCACCG    180
 A  L  V  A  G  S  A  F  A  Q  A ⓅG  A  S  P  A  A  S  P          32
                 ―――――――――――――――――――
AAGGCATCACCGGTTGCACCAGTAGCACTCACCTCCAACTGCTGTTACACGGTATCC           240
 K  A  S  P  V  A  P  V  A  S  P  P  T  A  V  V  T  P  V  S        52
GCTCCATCACAATCTCCTACTGCTGCTGCAAGTCCTTCTGAATCTCCATTGGCATCCA          300
 A Ⓟ S  Q  S  Q  S  T  A  A  A  S  P  S  E  S  P  L  A  S Ⓟ        72
   ―――――――――――――――         T2-1
CCAGCTCCACCAGCTCCAGCATTGCTCCCGGGCGGCGTTGCTCTTCCT                    360
 P  A Ⓟ P  T  A  D  T Ⓟ A  F  A Ⓟ S  G  G  V  A  L  P              92
   ――――――――――――――       T3                 A2
```

FIG. 4K-1

```
CCATCCATCGGCTCTGCTCCCGCGGTTCTCCAACCTGCTCTCCTAACGCTGCTTCCTTG     420
 P  S  I  G  S  A ⓟ A  G  S ⓟ T  S  S  P  N  A  A  S  L         112
 T5              T2-1         T2-2

AACAGAGTCGCCGTCGCTGGATCTGCAGTTGTAGGCGATCTTCGCTGCATCTTTGATGTTT   480
 N  R  V  A  V  A  G  S  A  V  V  A  I  F  A  A  S  L  M  F    132

TAGATCTGAGGAGAGTTTGCATTTTGGATTTTCACGAGATGTTTATTATTTTAGGATTTA    540

TTTAGTTCATCTTACTCGTTGATGTTTATTCGTTTTGTTTTACTTTTTACCCGTGGGCGGT   600

GGTGACTGCGTACATGCTATTGATTTTACTCTGGTTATTGTTTATTGTTTACTAC         660

CACTATTATTATTATGGATTCTTTGTTTATTTATGAAGCACTATGATTTACA            712
```

FIG.4K-2

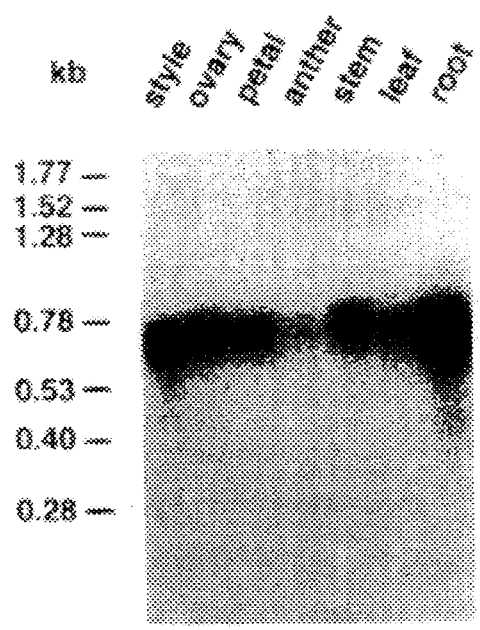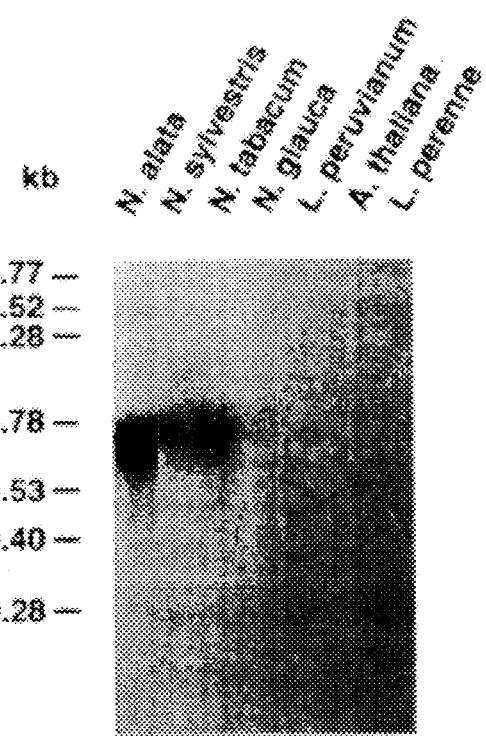
FIG.4M-1  FIG.4M-2

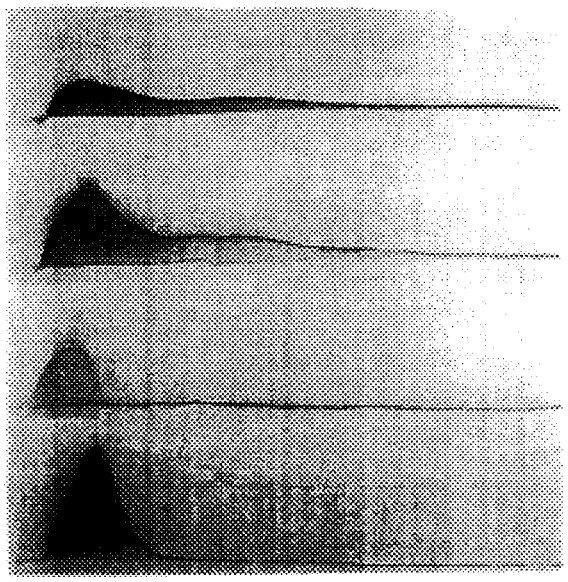
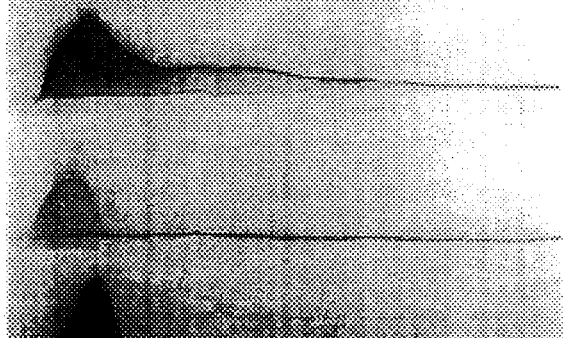
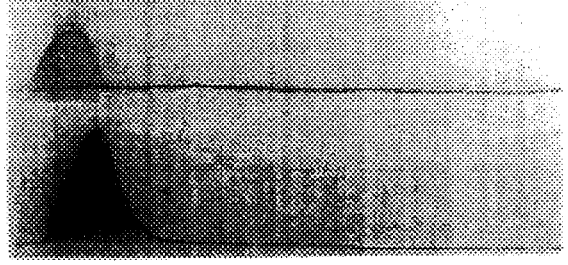
FIG.40-1
FIG.40-2
FIG.40-3
FIG.40-4

```
         10         20         30         40         50         60
CTCTCTCGCTCACTCATCAAATTCTCTCTCTCTCTCTCTCTCTCTCTTCTCTCTCTCTCTC
         70         80         90        100        110        120
TCTCTAAAAATGAAGATGGGTTTTGCAGGGTTCCAAGTTTTGATGGTTTTGGGTCTGTTG
                M  K  M  G  F  A  G  F  Q  V  L  M  V  L  G  L  L
        130        140        150        160        170        180
GCCACACATCATGCATAGCCCCAGGAGCAGCAAGCCCCCAGCTTCACCCCCAACCGCA
 A  T  S  C  I  A  Q  A  P  G  A  A  P  T  A  S  P  P  T  A
                  ↑
        190        200        210        220        230        240
AAGTCGGCCAACCGGCCACCCCACCGCCACCAACCGGCCATCAGCCGTACCAGTTCCATCA
 K  S  P  T  A  T  P  P  T  A  T  P  P  S  A  V  P  V  P  S
           o           o           o
        250        260        270        280        290        300
AAGTCGGCCAAAACACCAACCGGCGTCACCAGTCAACTCCATCACCAGTGACACAGCCCAAGT
 K  S  P  T  A  S  P  T  P  S  P  V  T  A  P  T  P  S
           o           o           o                      o
        310        320        330        340        350        360
CCCCAGCAAACCACCAACCGGCCACCCCACCGCCACCCCACCAACCCCCAAGT
GCCTCCCCACCATCTTCCACACGCTTCCACTCCAGCAGCTAAGTCT
 A  S  P  P  S  T  P  A  S  T  P  A  A  K  S
           o                    x
```

FIG.5A-1

```
           370       380       390       400       410       420
CCATCGTCGTCAGCTGCTCCCTCAGGCTCAAGCCCGAACTCCCCACCGGCTGACGCTATT
 P  S  S  S  A  A  P  S  G  S  S  P  N  S  P  P  A  D  A  I
           430       440       450       460       470       480
CCTCCAAGTGGCACCTCCGCGCCATCAGCCGCGTTGCTATTGCTGGAACTGCTCTTGCTGGA
 P  P  S  G  T  S  A  I  S  R  V  A  I  A  G  T  A  L  A  G
           490       500       510       520       530       540
GTTTTCTTCGCGATTGTGTTGGCTTAGATTCATGGGATTTGCTCTTTCGGGTTTTCCTAT
 V  F  F  A  I  V  L  A  ***
           550       560       570       580       590       600
TGGTCCACGTGGAGACTCACATCTGCTCTCTTAGATCTGGGTTTTGATGGACGGTCGAGATC
           610       620       630       640       650       660
TATTAATTTCTTTTTATTTGTTGCTTATTTCGTTAATGTTTTTTGTATTTTGTTTAA
           670       680       690       700       710       720
CTCTGTTTTCATGCCATATGGTGATTATTGGTTTGGCAGTCTATGGTGGATTTGGACGGT
           730       740       750       760       770       780
CGTGATGTGATTAATTATGGTGATTGTTTTAGAGTTGACAAGTGCACCCATTTGTA
           790       800       810       820       830       840
GATGAGTCGTTGGATGTACATCTGTCCGATCATAGTTTAATAAACAGTTTGTCATTCTT
           850       860       870       880       890       900
TTTCTTATGGATCTTCAAAAAAAAAAAAAAAAAAAAAAAAAAAAAAAAAAAAAAAA
```

FIG.5A-2

```
AGCAATGGCTTCCTTTGCAAAACCACTTCCATTTTTCTTCCTTCTGGTGCTAGTTTGCTC   60
 .. M  A..S..F..A..K..P..L..P..F..F..L..L..V..L..V...C...S...   19
TTCCTTTATACACATCATTCATGCTAGACAGAGGTGTCCTTCAGCAAGGTCACCCACAA   120
 ..S.. F  I  H  H  A  R  Q  S  V  S  F  S  K  V  T  H  N       39
     ←
CGACAACAACAACAACGATAATTATGTTATGGAGGCCGAAGCACCAAC               180
 D  N  N  N  N  D  N  Y  V  M  E  A  E  A  P  T                59
                                            Q
GCCAGCACTACAAGTAGTAGCAGAGGCACCCGAACTAGTACCGGTACCGGTACCGGTACC   240
 P  A  L  Q  V  V  A  E  P  E  L  V  P  T  P  V  P  T  P       79
 Q                                                  O  O  O
AAGTTACACCGAAAGAGACCATGGCAGCAACAGCCCTGTATGGTCTTGGCTCGACCAA   300
 S  Y  T  E  R  D  H  G  S  N  S  A  L  Y  G  L  G  S  T  N    99
TTCCCCTTCCACGAAGGAGACTCCAACCACAATTACTGATGTTGAAGATCAAATTTTGAG  360
 S  P  S  T  K  E  T  P  T  T  I  T  D  V  E  D  Q  I  L  S   119
TGAAGAACTTAGCGGTGAAAGTTTTGATCATCCGAAAGGTAATTACGAAAGCACCAACTT  420
 E  E  L  S  G  E  S  F  D  H  P  K  G  N  Y  E  S  T  N  L   139
GTTCAACAAGGACAACATTAATCAAAACACTGGCTACACCGGCTACAACAGTACTATGTCAA  480
 F  N  K  D  N  I  N  Q  N  T  G  Y  T  G  N  S  Y  Y  V  K   159
```

FIG.5E-1

```
AAACTACGATGGCAGAGAGGCTACAACCGCAATCCCCGGGCGGAGGCAATGGGATTAG     540
 N  Y  D  G  R  G  G  Y  N  R  N  P  P  G  G  G  N  G  I  S    179
TGAACAGCAAGGGATTAGTAATCAGGACATTGGCTACACCGGCAACAGTTACTACGTCAA   600
 E  Q  Q  G  I  S  N  Q  D  I  G  Y  T  G  N  S  Y  Y  V  K    199
AAACTACGATGGCAGAGAGGCTACAACCGCAATCCCCGGGTGGAGGCAATGAGATTAG     660
 N  Y  D  G  R  G  G  Y  N  R  N  P  P  G  G  G  N  E  I  S    219
TGAACAGCAAGGGATGAGTGATACAAGGTTTCTGGAAAATGGTAAATACTATCATGATGT   720
 E  Q  Q  G  M  S  D  T  R  F  L  E  N  G  K  Y  Y  H  D  V    239
GAAGAATGAGATTAAAAAAATAATAATTTCAATGGTAACTCCGAATCAGATGGGAGAGGAAG 780
 K  N  E  I  K  N  N  N  F  N  G  N  S  E  S  D  G  R  G  S    259
TAACAGAAATGATGTTGAGCGCTACTATGCCAACAGTCCACATGAGTTCAACAC         840
 N  R  N  D  V  E  R  Y  Y  A  N  S  H  S  N  E  F  N  T       279
CATGGAGGAGTATGATAAGTACCAGAAGACCCAAGGATATGTGCCCTAAATGATATTCCA   900
 M  E  E  Y  D  K  Y  Q  K  T  Q  G  Y  V  P  *                294
TGTTTTTAGGTGTGCGTTGAAAACTTAATCAATATATAAGAGATTTATGGTTTGTTTTG    960
GAATTCCATTGTCTTTGAATATGTTTTCGCTATAAAAATTAAACCCTTTCCACTCCAA    1020
AAAAAAAAAAAAAAAAAAAAA                                         1040
```

FIG.5E-2

SEQUENCE LISTING ( 1 ) GENERAL INFORMATION:

( i i i ) NUMBER OF SEQUENCES: 91

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 2
        ( D ) OTHER INFORMATION: /note="X=D/N"

( i x ) FEATURE:
        ( A ) NAME/KEY: Peptide
        ( B ) LOCATION: 4..8
        ( D ) OTHER INFORMATION: /note="At positions 4, 6, 8 X=O=Hydroxyproline"

( i x ) FEATURE:
        ( A ) NAME/KEY: Peptide
        ( B ) LOCATION: 9
        ( D ) OTHER INFORMATION: /note="X=A/T"

( i x ) FEATURE:
        ( A ) NAME/KEY: Peptide
        ( B ) LOCATION: 10
        ( D ) OTHER INFORMATION: /note="X=O/S, where O=Hydroxyproline"

( i x ) FEATURE:
        ( A ) NAME/KEY: Peptide
        ( B ) LOCATION: 11
        ( D ) OTHER INFORMATION: /note="X=(O)=0 without absolute certainty, where O =Hydroxyproline"

( x i ) SEQUENCE DESCRIPTION: SEQ ID NO:1:

Ala  Xaa  Ala  Xaa  Ala  Xaa  Ser  Xaa  Xaa  Xaa  Xaa
    1                 5                        10

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 4..10
        ( D ) OTHER INFORMATION: /note="At positions 4, 6, 8, 10
            X=O=Hydroxyproline"

( x i ) SEQUENCE DESCRIPTION: SEQ ID NO:2:

```
Asp  Glu  Ala  Xaa  Ala  Xaa  Ala  Xaa  Ser  Xaa  Met
  1              5                           10
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note="X=G/E"

( i x ) FEATURE:
        ( A ) NAME/KEY: Peptide
        ( B ) LOCATION: 2..8
        ( D ) OTHER INFORMATION: /note="At positions 2, 4, 6, 8
            X=O=Hydroxyproline"

( i x ) FEATURE:
        ( A ) NAME/KEY: Peptide
        ( B ) LOCATION: 9
        ( D ) OTHER INFORMATION: /note="X=(Q)=Q without absolute
            certainty"

( i x ) FEATURE:
        ( A ) NAME/KEY: Peptide
        ( B ) LOCATION: 10
        ( D ) OTHER INFORMATION: /note="X=(V)=V without absolute
            certainty"

( x i ) SEQUENCE DESCRIPTION: SEQ ID NO:3:

```
Xaa  Xaa  Ala  Xaa  Ala  Xaa  Ala  Xaa  Xaa  Xaa
  1              5                           10
```

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 4..8
        ( D ) OTHER INFORMATION: /note="At positions 4, 6, 8
            X=O=Hydroxyproline"

( x i ) SEQUENCE DESCRIPTION: SEQ ID NO:4:

```
Ala  Glu  Ala  Xaa  Ala  Xaa  Ala  Xaa  Ala  Ser
  1              5                           10
```

( 2 ) INFORMATION FOR SEQ ID NO:5:

( i ) SEQUENCE CHARACTERISTICS:
  ( A ) LENGTH: 12 amino acids
  ( B ) TYPE: amino acid
  ( D ) TOPOLOGY: linear ( i i ) MOLECULE TYPE: peptide ( i x ) FEATURE:
  ( A ) NAME/KEY: Peptide
  ( B ) LOCATION: 6..11
  ( D ) OTHER INFORMATION: /note="At positions 6, 7, 9, 11
   X=O=Hydroxyproline"

( x i ) SEQUENCE DESCRIPTION: SEQ ID NO:5:

```
Lys  Ala  Ala  Ala  Ser  Xaa  Xaa  Ala  Xaa  Ala  Xaa  Lys
 1                    5                        10
```

( 2 ) INFORMATION FOR SEQ ID NO:6:

( i ) SEQUENCE CHARACTERISTICS:
  ( A ) LENGTH: 10 amino acids
  ( B ) TYPE: amino acid
  ( D ) TOPOLOGY: linear ( i i ) MOLECULE TYPE: peptide ( i x ) FEATURE:
  ( A ) NAME/KEY: Peptide
  ( B ) LOCATION: 2..8
  ( D ) OTHER INFORMATION: /note="At positions 2, 4, 6, 8
   X=O=Hydroxyproline"

( i x ) FEATURE:
  ( A ) NAME/KEY: Peptide
  ( B ) LOCATION: 7
  ( D ) OTHER INFORMATION: /note="X=V/H"

( x i ) SEQUENCE DESCRIPTION: SEQ ID NO:6:

```
Ala  Xaa  Ala  Xaa  Ala  Xaa  Xaa  Xaa  Glu  Ala
 1                    5                        10
```

( 2 ) INFORMATION FOR SEQ ID NO:7:

( i ) SEQUENCE CHARACTERISTICS:
  ( A ) LENGTH: 12 amino acids
  ( B ) TYPE: amino acid
  ( D ) TOPOLOGY: linear ( i i ) MOLECULE TYPE: peptide ( i x ) FEATURE:
  ( A ) NAME/KEY: Peptide
  ( B ) LOCATION: 1
  ( D ) OTHER INFORMATION: /note="X=S/L"

( i x ) FEATURE:
  ( A ) NAME/KEY: Peptide
  ( B ) LOCATION: 4..12
  ( D ) OTHER INFORMATION: /note="At positions 4, 8, 11
   X=O=Hydroxyproline"

( i x ) FEATURE:
  ( A ) NAME/KEY: Peptide
  ( B ) LOCATION: 11
  ( D ) OTHER INFORMATION: /note="X=(X)=without absolute
   certainty"

( x i ) SEQUENCE DESCRIPTION: SEQ ID NO:7:

```
Xaa  Thr  Ala  Xaa  Val  Ala  Ala  Xaa  Thr  Thr  Xaa  Xaa
 1                    5                        10
```

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 2..5
        ( D ) OTHER INFORMATION: /note="At positions 2 and 5
            X=O=Hydroxyproline"

( x i ) SEQUENCE DESCRIPTION: SEQ ID NO:8:

Ser  Xaa  Pro  Ala  Xaa  Ala
  1                     5

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 4
        ( D ) OTHER INFORMATION: /note="X=(S)=S without absolute
            certainty"

( i x ) FEATURE:
        ( A ) NAME/KEY: Peptide
        ( B ) LOCATION: 6
        ( D ) OTHER INFORMATION: /note="X=(K)=K without absolute
            certainty"

( x i ) SEQUENCE DESCRIPTION: SEQ ID NO:9:

Ala  Ala  Ala  Xaa  Leu  Xaa
  1                     5

( 2 ) INFORMATION FOR SEQ ID NO:10:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note="X=(A)=A without absolute
            certainty"

( i x ) FEATURE:
        ( A ) NAME/KEY: Peptide
        ( B ) LOCATION: 4..8
        ( D ) OTHER INFORMATION: /note="At positions 4, 6, 8
            X=O=Hydroxyproline"

( x i ) SEQUENCE DESCRIPTION: SEQ ID NO:10:

Xaa  Asp  Ala  Xaa  Ala  Xaa  Ser  Xaa  Val
  1                     5

( 2 ) INFORMATION FOR SEQ ID NO:11:

( i ) SEQUENCE CHARACTERISTICS:
        ( A ) LENGTH: 15 amino acids ( B ) TYPE: amino acid
            ( D ) TOPOLOGY: linear ( i i ) MOLECULE TYPE: peptide ( x i ) SEQUENCE DESCRIPTION: SEQ ID NO:11:

Ala  Lys  Ser  Lys  Phe  Met  Ile  Ile  Pro  Ala  Ser  Xaa  Thr  Xaa  Ala
    1              5                        10                       15

( 2 ) INFORMATION FOR SEQ ID NO:12:

( i ) SEQUENCE CHARACTERISTICS:
            ( A ) LENGTH: 39 base pairs
            ( B ) TYPE: nucleic acid
            ( C ) STRANDEDNESS: single
            ( D ) TOPOLOGY: linear ( i i ) MOLECULE TYPE: cDNA ( i x ) FEATURE:
            ( A ) NAME/KEY: misc_feature
            ( B ) LOCATION: 7..9
            ( D ) OTHER INFORMATION: /note="Positions 7-9 can also be
                AGY"

( i x ) FEATURE:
            ( A ) NAME/KEY: misc_feature
            ( B ) LOCATION: 31..33
            ( D ) OTHER INFORMATION: /note="Positions 31-33 can also be
                AGY"

( x i ) SEQUENCE DESCRIPTION: SEQ ID NO:12:

GCNAARTCNA  ARTTYATGAT  HATHCCNGCN  TCNACNGCN                              39

( 2 ) INFORMATION FOR SEQ ID NO:13:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:13:

GGDATDATCA  TRAACTT                                                        17

( 2 ) INFORMATION FOR SEQ ID NO:14:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:14:

GGDATDATCA  TRAATTT                                                        17

( 2 ) INFORMATION FOR SEQ ID NO:15:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:15:

GGDAATGATC ATAAACTT                                                                              18

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GGDAATAATC ATAAACTT                                                                              18

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GGDAATTATC ATAAACTT                                                                              18

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

GGDAATGATC ATGAACTT                                                                              18

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GGDAATAATC ATGAACTT                                                                              18

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

GGDAATTATC ATGAACTT                                                                              18

(2) INFORMATION FOR SEQ ID NO:21:

( i ) SEQUENCE CHARACTERISTICS:
  ( A ) LENGTH: 161 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: CDS
  ( B ) LOCATION: 3..161

( i x ) FEATURE:
  ( A ) NAME/KEY: misc_feature
  ( B ) LOCATION: 56..78
  ( D ) OTHER INFORMATION: /note="NaF1 primer"

( i x ) FEATURE:
  ( A ) NAME/KEY: misc_feature
  ( B ) LOCATION: 102..123
  ( D ) OTHER INFORMATION: /note="NaF2 primer"

( i x ) FEATURE:
  ( A ) NAME/KEY: misc_feature
  ( B ) LOCATION: 138..161
  ( D ) OTHER INFORMATION: /note="Amino acids of the peptide
    obtained by direct microsequencing which are
    identical with the derived sequence"

( i x ) FEATURE:
  ( A ) NAME/KEY: misc_feature
  ( B ) LOCATION: 148..160
  ( D ) OTHER INFORMATION: /note="Nucleotide sequence
    corresponding to the NaR1 primers"

( i x ) FEATURE:
  ( A ) NAME/KEY: misc_feature
  ( B ) LOCATION: 161
  ( D ) OTHER INFORMATION: /note="Nucleotide 161 was not
    included in the 160 base pair primer extension
    fragment"

( x i ) SEQUENCE DESCRIPTION: SEQ ID NO:21:

```
AG AGA ACC AAG AAA CCA ACA CAT CAA ATA TTC TTC TTT CCC TTT TGT      47
   Arg Thr Lys Lys Pro Thr His Gln Ile Phe Phe Phe Pro Phe Cys
   1               5                   10                  15

TCT ATT TTC ATT ATG GGT CAT TTC ACT AAG CAA ATG ACA TTC TTC TTG     95
Ser Ile Phe Ile Met Gly His Phe Thr Lys Gln Met Thr Phe Phe Leu
                20              25                      30

TTC TTG GTG ATC TCA ACT CCA TTG GTG CAA ATT GAA GGT AGA AAA AGC    143
Phe Leu Val Ile Ser Thr Pro Leu Val Gln Ile Glu Gly Arg Lys Ser
                35              40              45

AAG TTT ATG ATC ATA CCC                                            161
Lys Phe Met Ile Ile Pro
        50
```

( 2 ) INFORMATION FOR SEQ ID NO:22:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:22:

CATTATGGGT CATTTCACTA AGC                                          23

( 2 ) INFORMATION FOR SEQ ID NO:23:

( i ) SEQUENCE CHARACTERISTICS:
    ( A ) LENGTH: 23 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:23:

```
GGTGATCTCA ACTCCATTGG TGC                                              23
```

(2) INFORMATION FOR SEQ ID NO:24:

(i) SEQUENCE CHARACTERISTICS:
(A) LENGTH: 1690 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 60..1442

(ix) FEATURE:
(A) NAME/KEY: misc_feature
(B) LOCATION: 1..38
(D) OTHER INFORMATION: /note="Nucleotide sequence obtained by PCR which does not overlap with the cDNA clone"

(ix) FEATURE:
(A) NAME/KEY: misc_feature
(B) LOCATION: 60..128
(D) OTHER INFORMATION: /note="Predicted transmembrane segment"

(ix) FEATURE:
(A) NAME/KEY: misc_feature
(B) LOCATION: 135..179
(D) OTHER INFORMATION: /note="Derived amino acid sequence corresponding to the peptide sequence by protein microsequencing"

(ix) FEATURE:
(A) NAME/KEY: misc_feature
(B) LOCATION: 135..179
(D) OTHER INFORMATION: /note="Amino acids 27 to 36, 38, and 40 are identical to that in the peptide obtained by direct microsequencing"

(ix) FEATURE:
(A) NAME/KEY: misc_feature
(B) LOCATION: 135..179
(D) OTHER INFORMATION: /note="Amino acid 26 may also be Ala; 37 and 39 can also be undetermined residues"

(xi) SEQUENCE DESCRIPTION: SEQ ID NO:24:

```
AGAGAACCAA GAAACCAACA CATCAAATAT TCTTCTTTCC CTTTTGTTCT ATTTTCATT      59

ATG GGT CAT TTC ACT AAG CAA ATG ACA TTC TTC TTG TTC TTG GTG ATC      107
Met Gly His Phe Thr Lys Gln Met Thr Phe Phe Leu Phe Leu Val Ile
 1               5                  10                  15

TCA ACT CCA TTG GTG CAA ATT GAA GGT AGA AAA AGC AAG TTT ATG ATC      155
Ser Thr Pro Leu Val Gln Ile Glu Gly Arg Lys Ser Lys Phe Met Ile
             20                  25                  30

ATA CCT GCA TCT CCT ACA CCA GCT CCA ACA CCA ATC AAT GAA ATT AGT      203
Ile Pro Ala Ser Pro Thr Pro Ala Pro Thr Pro Ile Asn Glu Ile Ser
                 35                  40                  45

TTT CCT CCA TTT TCA TCC CTT ACT CCA ACT CCA TCA CCA ACA CCA GCA      251
Phe Pro Pro Phe Ser Ser Leu Thr Pro Thr Pro Ser Pro Thr Pro Ala
             50                  55                  60

CCA GCA ACA GCA CCA ACA CCG TTT TTT AAT GAT TTT GCG TTT CCT CCA      299
Pro Ala Thr Ala Pro Thr Pro Phe Phe Asn Asp Phe Ala Phe Pro Pro
```

-continued

| | 65 | | | | | 70 | | | | | 75 | | | | | 80 | | |
|---|---|---|---|---|---|---|---|---|---|---|---|---|---|---|---|---|---|---|

| TTG | TCA | TCT | TTA | AGT | CCA | ACA | CCA | GCA | CCA | GTA | CCA | GTA | GGT | AAT | GTT | | 347 |
|---|---|---|---|---|---|---|---|---|---|---|---|---|---|---|---|---|---|
| Leu | Ser | Ser | Leu | Ser | Pro | Thr | Pro | Ala | Pro | Val | Pro | Val | Gly | Asn | Val | | |
| | | | | 85 | | | | | 90 | | | | | 95 | | | |

| CAA | GAT | CCT | GAT | GTG | AAT | GGC | GTA | CCT | ACG | CCT | GCA | TTG | GCA | CCA | GGA | | 395 |
|---|---|---|---|---|---|---|---|---|---|---|---|---|---|---|---|---|---|
| Gln | Asp | Pro | Asp | Val | Asn | Gly | Val | Pro | Thr | Pro | Ala | Leu | Ala | Pro | Gly | | |
| | | | 100 | | | | | 105 | | | | | 110 | | | | |

| GGG | AGT | GGT | GAA | GAT | CCA | GAG | GAA | GGT | GGC | ATT | GAA | GCG | CCA | GCA | CCA | | 443 |
|---|---|---|---|---|---|---|---|---|---|---|---|---|---|---|---|---|---|
| Gly | Ser | Gly | Glu | Asp | Pro | Glu | Glu | Gly | Gly | Ile | Glu | Ala | Pro | Ala | Pro | | |
| | | 115 | | | | | 120 | | | | | 125 | | | | | |

| CTT | TTG | ACT | GAT | ACT | CCC | TAT | GGA | CTT | TAT | GGT | CCT | CAT | TCT | CAG | GAA | | 491 |
|---|---|---|---|---|---|---|---|---|---|---|---|---|---|---|---|---|---|
| Leu | Leu | Thr | Asp | Thr | Pro | Tyr | Gly | Leu | Tyr | Gly | Pro | His | Ser | Gln | Glu | | |
| | 130 | | | | | 135 | | | | | 140 | | | | | | |

| ATT | TCT | TCT | ACT | GTC | ACA | AAT | CTT | GAT | GAG | GTT | GAA | ACT | CAA | ACT | CCT | | 539 |
|---|---|---|---|---|---|---|---|---|---|---|---|---|---|---|---|---|---|
| Ile | Ser | Ser | Thr | Val | Thr | Asn | Leu | Asp | Glu | Val | Glu | Thr | Gln | Thr | Pro | | |
| 145 | | | | | 150 | | | | | 155 | | | | | 160 | | |

| GCC | AAG | GAA | TTT | CAA | GGT | GCT | AGA | TTT | AAT | ACA | GAT | GAG | TCC | TAC | AAT | | 587 |
|---|---|---|---|---|---|---|---|---|---|---|---|---|---|---|---|---|---|
| Ala | Lys | Glu | Phe | Gln | Gly | Ala | Arg | Phe | Asn | Thr | Asp | Glu | Ser | Tyr | Asn | | |
| | | | | 165 | | | | | 170 | | | | | 175 | | | |

| AAC | AAT | GGT | TAT | GAT | TCC | AAC | AAC | AAC | GAC | AAC | AAC | AAT | GGT | TAT | GAT | | 635 |
|---|---|---|---|---|---|---|---|---|---|---|---|---|---|---|---|---|---|
| Asn | Asn | Gly | Tyr | Asp | Ser | Asn | Asn | Asn | Asp | Asn | Asn | Asn | Gly | Tyr | Asp | | |
| | | | 180 | | | | | 185 | | | | | 190 | | | | |

| TCC | AAC | AAT | AAC | AAC | AAC | AAT | AAC | GAT | GAT | GGC | TTC | TCC | GAG | AAT | TAC | | 683 |
|---|---|---|---|---|---|---|---|---|---|---|---|---|---|---|---|---|---|
| Ser | Asn | Asn | Asn | Asn | Asn | Asn | Asn | Asp | Asp | Gly | Phe | Ser | Glu | Asn | Tyr | | |
| | | 195 | | | | | 200 | | | | | 205 | | | | | |

| AAC | AAC | AAT | GGC | TAC | TCG | GAG | AAT | GCT | AAT | AAC | AAA | AAT | AAC | AAT | GGC | | 731 |
|---|---|---|---|---|---|---|---|---|---|---|---|---|---|---|---|---|---|
| Asn | Asn | Asn | Gly | Tyr | Ser | Glu | Asn | Ala | Asn | Asn | Lys | Asn | Asn | Asn | Gly | | |
| | | 210 | | | | | 215 | | | | | 220 | | | | | |

| TAC | TCA | GAG | AAT | TAC | AAC | AAC | AAT | AAC | AAC | AAT | GGC | TAC | GCC | AAG | AAT | | 779 |
|---|---|---|---|---|---|---|---|---|---|---|---|---|---|---|---|---|---|
| Tyr | Ser | Glu | Asn | Tyr | Asn | Asn | Asn | Asn | Asn | Asn | Gly | Tyr | Ala | Lys | Asn | | |
| 225 | | | | | 230 | | | | | 235 | | | | | 240 | | |

| TAC | AAC | AAT | GGC | TAC | TCT | CAG | AGT | TAC | AAC | AAC | AAT | AAT | TTT | TAC | | | 827 |
|---|---|---|---|---|---|---|---|---|---|---|---|---|---|---|---|---|---|
| Tyr | Asn | Asn | Gly | Tyr | Ser | Gln | Ser | Tyr | Asn | Asn | Asn | Asn | Phe | Tyr | | | |
| | | | | 245 | | | | | 250 | | | | | 255 | | | |

| TCG | GAG | AAT | TAC | AAC | AAC | AAC | AAC | AAC | AAT | GTT | TTC | TCG | GAG | AAT | TCC | | 875 |
|---|---|---|---|---|---|---|---|---|---|---|---|---|---|---|---|---|---|
| Ser | Glu | Asn | Tyr | Asn | Asn | Asn | Asn | Asn | Asn | Val | Phe | Ser | Glu | Asn | Ser | | |
| | | | 260 | | | | | 265 | | | | | 270 | | | | |

| AAC | AAC | AAT | GGC | TAC | TCC | AAA | AAG | ATC | AAC | AAT | AAT | GGC | TAC | TCC | CAG | | 923 |
|---|---|---|---|---|---|---|---|---|---|---|---|---|---|---|---|---|---|
| Asn | Asn | Asn | Gly | Tyr | Ser | Lys | Lys | Ile | Asn | Asn | Asn | Gly | Tyr | Ser | Gln | | |
| | | 275 | | | | | 280 | | | | | 285 | | | | | |

| AAT | TAC | ATG | AAC | AAC | AAC | AAT | GGC | TTC | TCC | GAG | AGT | TAC | AAC | AAC | AAC | | 971 |
|---|---|---|---|---|---|---|---|---|---|---|---|---|---|---|---|---|---|
| Asn | Tyr | Met | Asn | Asn | Asn | Asn | Gly | Phe | Ser | Glu | Ser | Tyr | Asn | Asn | Asn | | |
| | 290 | | | | | 295 | | | | | 300 | | | | | | |

| AAC | AAC | AAC | AAC | AAC | AAC | AAC | AAC | GTT | TTC | TCT | GAG | AAT | TAC | AAC | AAC | | 1019 |
|---|---|---|---|---|---|---|---|---|---|---|---|---|---|---|---|---|---|
| Asn | Asn | Asn | Asn | Asn | Asn | Asn | Asn | Val | Phe | Ser | Glu | Asn | Tyr | Asn | Asn | | |
| 305 | | | | | 310 | | | | | 315 | | | | | 320 | | |

| AAC | AAT | AAC | AAT | AAT | GTT | TTC | TCC | GAG | AAT | TAC | AAC | AAC | AAC | AAT | AAC | | 1067 |
|---|---|---|---|---|---|---|---|---|---|---|---|---|---|---|---|---|---|
| Asn | Asn | Asn | Asn | Asn | Val | Phe | Ser | Glu | Asn | Tyr | Asn | Asn | Asn | Asn | Asn | | |
| | | | | 325 | | | | | 330 | | | | | 335 | | | |

| AAC | AAT | GCT | TTC | TAC | GAG | AAT | TAC | AAC | AAC | AAC | AAC | AAT | GGC | TAC | TCA | | 1115 |
|---|---|---|---|---|---|---|---|---|---|---|---|---|---|---|---|---|---|
| Asn | Asn | Ala | Phe | Tyr | Glu | Asn | Tyr | Asn | Asn | Asn | Asn | Asn | Gly | Tyr | Ser | | |
| | | | 340 | | | | | 345 | | | | | 350 | | | | |

| GAG | AAC | TAC | AAT | CAG | GCT | AGC | AGC | TAC | AAT | AAC | AAT | GAC | AAT | ACG | GTG | | 1163 |
|---|---|---|---|---|---|---|---|---|---|---|---|---|---|---|---|---|---|
| Glu | Asn | Tyr | Asn | Gln | Ala | Ser | Ser | Tyr | Asn | Asn | Asn | Asp | Asn | Thr | Val | | |
| | | 355 | | | | | 360 | | | | | 365 | | | | | |

| GAA | AGG | CAA | GGA | TTA | AGT | GAT | ACA | AGA | TTC | TTG | GAA | AAT | GGC | AAG | TAT | | 1211 |
|---|---|---|---|---|---|---|---|---|---|---|---|---|---|---|---|---|---|
| Glu | Arg | Gln | Gly | Leu | Ser | Asp | Thr | Arg | Phe | Leu | Glu | Asn | Gly | Lys | Tyr | | |
| | 370 | | | | | 375 | | | | | 380 | | | | | | |

| TAT | TAT | GAT | ATC | AAG | AAT | GAG | AAT | ACC | AAC | AAC | AAT | GGC | TAC | TCT | GAG | | 1259 |
|---|---|---|---|---|---|---|---|---|---|---|---|---|---|---|---|---|---|
| Tyr | Tyr | Asp | Ile | Lys | Asn | Glu | Asn | Thr | Asn | Asn | Asn | Gly | Tyr | Ser | Glu | | |

| | | | | | | | | | | | | | | | | |
|---|---|---|---|---|---|---|---|---|---|---|---|---|---|---|---|---|
| | 385 | | | | | 390 | | | | | 395 | | | | 400 | |
| AAT | TAC | AAC | CAT | GTT | AGC | AGC | TAC | AAT | AAC | AAT | AAC | AAT | ATG | GTG | GAA | 1307 |
| Asn | Tyr | Asn | His | Val | Ser | Ser | Tyr | Asn | Asn | Asn | Asn | Asn | Met | Val | Glu | |
| | | | | 405 | | | | | 410 | | | | | 415 | | |
| AGG | CAA | GGA | TTG | AGT | GAC | ACA | AGA | TTC | TTA | GAT | AAT | GGT | AAC | TAC | TTT | 1355 |
| Arg | Gln | Gly | Leu | Ser | Asp | Thr | Arg | Phe | Leu | Asp | Asn | Gly | Asn | Tyr | Phe | |
| | | | 420 | | | | | 425 | | | | | 430 | | | |
| TAT | AGC | AAC | AAT | GGT | GAG | AAA | ATG | TCA | GTG | GAA | GAG | TCT | GAA | AGA | CAG | 1403 |
| Tyr | Ser | Asn | Asn | Gly | Glu | Lys | Met | Ser | Val | Glu | Glu | Ser | Glu | Arg | Gln | |
| | | 435 | | | | | 440 | | | | | 445 | | | | |
| CAG | GAA | TAT | CCA | GAC | ACT | GAA | GAT | CAG | TAC | GAA | CTT | CCT | TGAAGATAAA | | | 1452 |
| Gln | Glu | Tyr | Pro | Asp | Thr | Glu | Asp | Gln | Tyr | Glu | Leu | Pro | | | | |
| | 450 | | | | 455 | | | | | 460 | | | | | | |

| | | | | | |
|---|---|---|---|---|---|
| TATTATTAGT | TGGTCCAGAG | AAGAGGGACA | AACGCAGAGG | ACGTGAAAAT | AGATTAATG | 1512 |
| ATTGAATTTT | AAGTTATTTT | GAGTGTTTGT | TTCATTAGTT | CCACTTGAGT | CTGCAAACAC | 1572 |
| CTTTTTTTCT | TTTTTATAG | TTCTGCAAAT | CAGACCGAGG | GAACTTTGAG | TTGTTTAACA | 1632 |
| CTTTGGATT | ATTTTAAAAA | CTTTTATAA | TGATCTTGAA | GCTTCACGCC | TAAAAAAA | 1690 |

( 2 ) INFORMATION FOR SEQ ID NO:25:

( i ) SEQUENCE CHARACTERISTICS:
        ( A ) LENGTH: 1430 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 2..1312

( i x ) FEATURE:
        ( A ) NAME/KEY: misc_feature
        ( B ) LOCATION: 41..112
        ( D ) OTHER INFORMATION: /note="Derived amino acid sequence
            corresponding to the peptide sequence by protein
            microsequencing"

( i x ) FEATURE:
        ( A ) NAME/KEY: misc_feature
        ( B ) LOCATION: 41..112
        ( D ) OTHER INFORMATION: /note="Derived amino acids 14-24,
            28, 30, 32- 37 are identical to sequences obtained
            by protein microsequencing"

( i x ) FEATURE:
        ( A ) NAME/KEY: misc_feature
        ( B ) LOCATION: 25..31
        ( D ) OTHER INFORMATION: /note="Amino acids 25, 27, 29, and
            31 are hydroxylated proline residues; amino acid
            26 can be T instead of A"

( x i ) SEQUENCE DESCRIPTION: SEQ ID NO:25:

| | | | | | | | | | | | | | | | | |
|---|---|---|---|---|---|---|---|---|---|---|---|---|---|---|---|---|
| G | TTC | TTG | GTG | ATC | TCA | ACT | CCA | CTA | GTA | CAA | ATT | GAA | GCA | AGA | AAA | 46 |
| | Phe | Leu | Val | Ile | Ser | Thr | Pro | Leu | Val | Gln | Ile | Glu | Ala | Arg | Lys | |
| | 1 | | | | 5 | | | | | 10 | | | | | 15 | |
| AGC | AAG | TTT | ATG | ATC | ATT | CCT | GCA | TCT | CCT | GCA | CCA | GCT | CCA | ACT | CCA | 94 |
| Ser | Lys | Phe | Met | Ile | Ile | Pro | Ala | Ser | Pro | Ala | Pro | Ala | Pro | Thr | Pro | |
| | | | | 20 | | | | | 25 | | | | | 30 | | |
| ATC | AAT | GAA | ATT | AGT | TTT | CCT | CCA | TTT | TCA | TCC | TTT | ACT | CCA | ACT | CCA | 142 |
| Ile | Asn | Glu | Ile | Ser | Phe | Pro | Pro | Phe | Ser | Ser | Phe | Thr | Pro | Thr | Pro | |
| | | | | 35 | | | | | 40 | | | | | 45 | | |
| TCA | CCA | ACA | CCA | ACA | CCA | ACA | CCA | ACA | TCA | GCA | CCA | ACA | CCG | TTT | TTT | 190 |
| Ser | Pro | Thr | Pro | Thr | Pro | Thr | Pro | Thr | Ser | Ala | Pro | Thr | Pro | Phe | Phe | |
| | | 50 | | | | | 55 | | | | | 60 | | | | |

```
AAT GAT TTC GCG TTT CCT CCA TTG TCA TCT TTA AGT CCA ACA CCA GCA      238
Asn Asp Phe Ala Phe Pro Pro Leu Ser Ser Leu Ser Pro Thr Pro Ala
    65              70                  75

CCA GTA GGT AGT GAT CAA GAT CCT GAT GTG AAC GGT GTA CCG GCG CCT      286
Pro Val Gly Ser Asp Gln Asp Pro Asp Val Asn Gly Val Pro Ala Pro
80              85                  90                      95

GCA GTG GCA CCA ATA GGG AGT GGT CAA GAT CCA GAA GAA GGT GGC ATT      334
Ala Val Ala Pro Ile Gly Ser Gly Gln Asp Pro Glu Glu Gly Gly Ile
                100                 105                 110

GAA GCA CCA GCA CCA CTT TTA ACT GAT ACT CCT TAT GGA CTT TAT GGT      382
Glu Ala Pro Ala Pro Leu Leu Thr Asp Thr Pro Tyr Gly Leu Tyr Gly
            115                 120                 125

CCT CAT TCT CAG GAA ATT CCT TCA ACT GTC ACA AAT CTT GAT GAG GTT      430
Pro His Ser Gln Glu Ile Pro Ser Thr Val Thr Asn Leu Asp Glu Val
        130                 135                 140

GAA ACT CAA ACT CCT GCC GAG GAA TTC CAA GGT GCT AGA TTT AAT ACA      478
Glu Thr Gln Thr Pro Ala Glu Glu Phe Gln Gly Ala Arg Phe Asn Thr
    145                 150                 155

GAT GAG TCC TAC AAT AAC AAT GGT TAT GAT TCC AAC AAC AAT GGC TAC      526
Asp Glu Ser Tyr Asn Asn Asn Gly Tyr Asp Ser Asn Asn Asn Gly Tyr
160             165                 170                     175

TCG GAG AAT AAC AAC AAC AAG AAC AAC AAT GGC TAC TCG GAG AAT TAC      574
Ser Glu Asn Asn Asn Asn Lys Asn Asn Asn Gly Tyr Ser Glu Asn Tyr
                180                 185                 190

AAC AAC AAC AAC AAC AAT GGC TAC TCC GAG AAT TAC AAC AAC AAC AAC      622
Asn Asn Asn Asn Asn Asn Gly Tyr Ser Glu Asn Tyr Asn Asn Asn Asn
            195                 200                 205

AAT GGC TAC TCC AAG AAT TAC AAC AAC AAT GGC TAC TCC AAA AAA ATC      670
Asn Gly Tyr Ser Lys Asn Tyr Asn Asn Asn Gly Tyr Ser Lys Lys Ile
        210                 215                 220

AAC AAT AAT GGT TAC TCC CAG AAT TAC ATG AAC AAC AAC AAC GGC TTC      718
Asn Asn Asn Gly Tyr Ser Gln Asn Tyr Met Asn Asn Asn Asn Gly Phe
    225                 230                 235

TCC GAG AGT TAC AAC AGC AAC AAC AAC AAC AAT ATT TTC TCC GAG          766
Ser Glu Ser Tyr Asn Ser Asn Asn Asn Asn Asn Ile Phe Ser Glu
240                 245                 250                 255

AAT TAC AAC AAC AAT AAT AAC AAT AAT GTT TTC TCC GAG AAT TAC AAC      814
Asn Tyr Asn Asn Asn Asn Asn Asn Asn Val Phe Ser Glu Asn Tyr Asn
            260                 265                 270

AAC AAT AAT AAC AAT AAT GTT TTC TCC GAG AAT TAC AAC AAC AAT AAC      862
Asn Asn Asn Asn Asn Asn Val Phe Ser Glu Asn Tyr Asn Asn Asn Asn
        275                 280                 285

AAC AAT GCT TTC TCC GAG AAC TAC AAC AAC AAT AAT GTT TTC TCC GAG      910
Asn Asn Ala Phe Ser Glu Asn Tyr Asn Asn Asn Asn Val Phe Ser Glu
    290                 295                 300

AAT TAC AAC AAA AAC AAT AAC AAT GCT TTC TCT GAG AAT TAC AAC          958
Asn Tyr Asn Lys Asn Asn Asn Asn Ala Phe Ser Glu Asn Tyr Asn
305                 310                 315

AAC AAA AAC AAC AAT GCC TAC TCT GAG AAC TAC AAT CAA GCT AGC AGC     1006
Asn Lys Asn Asn Asn Ala Tyr Ser Glu Asn Tyr Asn Gln Ala Ser Ser
320                 325                 330                 335

TAC AAT AAC AAT GGC AAT ACG GTG GAG AGG CAA GGA TTA AGT GAT ACA     1054
Tyr Asn Asn Asn Gly Asn Thr Val Glu Arg Gln Gly Leu Ser Asp Thr
            340                 345                 350

AGA TTC TTG GAG AAT GGC AAG TAC TAT TAT GAT ATC AAG AAT GAG AAT     1102
Arg Phe Leu Glu Asn Gly Lys Tyr Tyr Tyr Asp Ile Lys Asn Glu Asn
        355                 360                 365

CCC AAC CAC AAC AAT GGC TAC TCC GAG AAC TAC AAT CAT GTT AGC AGC     1150
Pro Asn His Asn Asn Gly Tyr Ser Glu Asn Tyr Asn His Val Ser Ser
    370                 375                 380
```

| TAC | AAT | AAC | AAT | AAC | AAT | ATG | GTG | GAA | AGG | CAA | GGA | TTG | AGT | GAC | ACA | 1198 |
|---|---|---|---|---|---|---|---|---|---|---|---|---|---|---|---|---|
| Tyr | Asn 385 | Asn | Asn | Asn | Asn | Met 390 | Val | Glu | Arg | Gln | Gly 395 | Leu | Ser | Asp | Thr | |

| AGA | TTC | TTA | GAT | AAT | GGC | AAC | TAC | TTT | TAT | AGT | AAC | AAT | GGT | GAG | AAA | 1246 |
|---|---|---|---|---|---|---|---|---|---|---|---|---|---|---|---|---|
| Arg 400 | Phe | Leu | Asp | Asn 405 | Gly | Asn | Tyr | Phe | Tyr | Ser 410 | Asn | Asn | Gly | Glu | Lys 415 | |

| ATG | TCA | ATG | GAA | GAA | TCT | GAA | AGA | CAG | CAG | GAA | TAT | CCA | AAT | ACT | GAA | 1294 |
|---|---|---|---|---|---|---|---|---|---|---|---|---|---|---|---|---|
| Met | Ser | Met | Glu | Glu 420 | Ser | Glu | Arg | Gln | Gln 425 | Glu | Tyr | Pro | Asn | Thr 430 | Glu | |

| GAT | CAG | TAT | GAA | CTT | CCT | TGAAGACTAA | CATTATCAGT | TGGCTTAAAG | 1342 |
|---|---|---|---|---|---|---|---|---|---|
| Asp | Gln | Tyr | Glu 435 | Leu | Pro | | | | |

AAGAGGGACA AATGCAGGGA ACATGAGAAT AGATTTAATT TACAGAGTTT GATTGAATTT    1402

TTAAGTTAAA AAAAAAAAA AAAAAAA    1430

( 2 ) INFORMATION FOR SEQ ID NO:26:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 4..8
        ( D ) OTHER INFORMATION: /note="At positions 4, 5, 7, 8
            X=O=Hydroxyproline"

( x i ) SEQUENCE DESCRIPTION: SEQ ID NO:26:

Leu  Ala  Ser  Xaa  Xaa  Ala  Xaa  Xaa  Thr  Ala
    1                   5                    10

( 2 ) INFORMATION FOR SEQ ID NO:27:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 4..13
        ( D ) OTHER INFORMATION: /note="At positions 4, 5, 7, 8, 13
            X=O=Hydroxyproline"

( x i ) SEQUENCE DESCRIPTION: SEQ ID NO:27:

Leu  Ala  Ser  Xaa  Xaa  Ala  Xaa  Xaa  Thr  Ala  Asp  Thr  Xaa  Ala
    1                   5                    10

( 2 ) INFORMATION FOR SEQ ID NO:28:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 3..11
        ( D ) OTHER INFORMATION: /note="At positions 3 and 11
            X=O=Hydroxyproline"

( i x ) FEATURE:
        ( A ) NAME/KEY: Peptide (B) LOCATION: 4
(D) OTHER INFORMATION: /note="X=S/N"

(xi) SEQUENCE DESCRIPTION: SEQ ID NO:28:

Phe Ala Xaa Xaa Gly Gly Val Ala Leu Pro Xaa Ser
1               5                   10

(2) INFORMATION FOR SEQ ID NO:29:

(i) SEQUENCE CHARACTERISTICS:
    (A) LENGTH: 14 amino acids
    (B) TYPE: amino acid
    (D) TOPOLOGY: linear (ii) MOLECULE TYPE: peptide (ix) FEATURE:
    (A) NAME/KEY: Peptide
    (B) LOCATION: 5..9
    (D) OTHER INFORMATION: /note="At positions 5 and 9
         X=O=Hydroxyproline"

(xi) SEQUENCE DESCRIPTION: SEQ ID NO:29:

Ile Gly Ala Ala Xaa Ala Gly Ser Xaa Thr Ser Ser Pro Asn
1               5                   10

(2) INFORMATION FOR SEQ ID NO:30:

(i) SEQUENCE CHARACTERISTICS:
    (A) LENGTH: 24 amino acids
    (B) TYPE: amino acid
    (D) TOPOLOGY: linear (ii) MOLECULE TYPE: peptide (ix) FEATURE:
    (A) NAME/KEY: Peptide
    (B) LOCATION: 12..18
    (D) OTHER INFORMATION: /note="At positions 12, 14, 16, 18
         X=O=Hydroxyproline"

(xi) SEQUENCE DESCRIPTION: SEQ ID NO:30:

Arg Lys Ser Lys Phe Met Ile Ile Pro Ala Ser Xaa Thr Xaa Ala Xaa
1               5                   10                  15
Thr Xaa Ile Asn Glu Ile Ser Phe
        20

(2) INFORMATION FOR SEQ ID NO:31:

(i) SEQUENCE CHARACTERISTICS:
    (A) LENGTH: 19 amino acids
    (B) TYPE: amino acid
    (D) TOPOLOGY: linear (ii) MOLECULE TYPE: peptide (ix) FEATURE:
    (A) NAME/KEY: Peptide
    (B) LOCATION: 3..17
    (D) OTHER INFORMATION: /note="At positions 3, 7, 10, 12,
         16, 17 X=O=Hydroxyproline"

(ix) FEATURE:
    (A) NAME/KEY: Peptide
    (B) LOCATION: 14
    (D) OTHER INFORMATION: /note="X=(S)=S without absolute
         certainty"

(ix) FEATURE:
    (A) NAME/KEY: Peptide
    (B) LOCATION: 19
    (D) OTHER INFORMATION: /note="X=(T)=T without absolute
         certainty"

(xi) SEQUENCE DESCRIPTION: SEQ ID NO:31:

```
Leu Ser Xaa Lys Lys Ser Xaa Thr Ala Xaa Ser Xaa Ser Xaa Thr Xaa
1               5                   10                  15

Xaa Thr Xaa
```

(2) INFORMATION FOR SEQ ID NO:32:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note="X=V/A"

(ix) FEATURE:
        (A) NAME/KEY: Peptide
        (B) LOCATION: 2
        (D) OTHER INFORMATION: /note="X=A/T"

(ix) FEATURE:
        (A) NAME/KEY: Peptide
        (B) LOCATION: 4
        (D) OTHER INFORMATION: /note="X=O=Hydroxyproline"

(ix) FEATURE:
        (A) NAME/KEY: Peptide
        (B) LOCATION: 5
        (D) OTHER INFORMATION: /note="X=S/O, where
            O=Hydroxyproline"

(ix) FEATURE:
        (A) NAME/KEY: Peptide
        (B) LOCATION: 6
        (D) OTHER INFORMATION: /note="X=O/Y, where
            O=Hydroxyproline"

(ix) FEATURE:
        (A) NAME/KEY: Peptide
        (B) LOCATION: 9
        (D) OTHER INFORMATION: /note="X=T/A"

(ix) FEATURE:
        (A) NAME/KEY: Peptide
        (B) LOCATION: 11
        (D) OTHER INFORMATION: /note="X=O=Hydroxyproline"

(xi) SEQUENCE DESCRIPTION: SEQ ID NO:32:

```
Xaa Xaa Ala Xaa Xaa Xaa Ser Ser Xaa Xaa Xaa Ser Ala Thr Xaa Thr
1               5                   10                  15

Xaa Xaa Val Ala
                20
```

(2) INFORMATION FOR SEQ ID NO:33:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note="X=V/A"

(ix) FEATURE:
        (A) NAME/KEY: Peptide (B) LOCATION: 3
(D) OTHER INFORMATION: /note="X=D/A/O, where
O=Hydroxyproline"

(ix) FEATURE:
(A) NAME/KEY: Peptide
(B) LOCATION: 4
(D) OTHER INFORMATION: /note="X=S/O, where
O=Hydroxyproline"

(ix) FEATURE:
(A) NAME/KEY: Peptide
(B) LOCATION: 5
(D) OTHER INFORMATION: /note="X=T/O/K, where
O=Hydroxyproline"

(ix) FEATURE:
(A) NAME/KEY: Peptide
(B) LOCATION: 6
(D) OTHER INFORMATION: /note="X=O=Hydroxyproline"

(ix) FEATURE:
(A) NAME/KEY: Peptide
(B) LOCATION: 7
(D) OTHER INFORMATION: /note="X=S/O"

(xi) SEQUENCE DESCRIPTION: SEQ ID NO:33:

```
Xaa  Ala  Xaa  Xaa  Xaa  Xaa  Xaa  Pro  Gln  Ser
1                  5                        10
```

(2) INFORMATION FOR SEQ ID NO:34:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: Peptide
(B) LOCATION: 5..9
(D) OTHER INFORMATION: /note="At positions 5, 7, 9
X=O=Hydroxyproline"

(ix) FEATURE:
(A) NAME/KEY: Peptide
(B) LOCATION: 15
(D) OTHER INFORMATION: /note="X=(G)=G without absolute
certainty"

(xi) SEQUENCE DESCRIPTION: SEQ ID NO:34:

```
Leu  Gly  Ile  Ser  Xaa  Ala  Xaa  Ser  Xaa  Ala  Gly  Glu  Val  Asp  Xaa
1                  5                        10                       15
```

(2) INFORMATION FOR SEQ ID NO:35:

(i) SEQUENCE CHARACTERISTICS:
(A) LENGTH: 11 amino acids
(B) TYPE: amino acid
(D) TOPOLOGY: linear (ii) MOLECULE TYPE: peptide (ix) FEATURE:
(A) NAME/KEY: Peptide
(B) LOCATION: 3..7
(D) OTHER INFORMATION: /note="At positions 3, 4, 7
X=O=Hydroxyproline"

(ix) FEATURE:
(A) NAME/KEY: Peptide
(B) LOCATION: 11
(D) OTHER INFORMATION: /note="X=O/S, where
O=Hydroxyproline"

( x i ) SEQUENCE DESCRIPTION: SEQ ID NO:35:

Xaa Xaa Xaa Xaa Ala Ala Xaa Val Xaa Ala Xaa
1               5                   10

( 2 ) INFORMATION FOR SEQ ID NO:36:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 4..11
        ( D ) OTHER INFORMATION: /note="At positions 4, 6, 10, 11
            X=O=Hydroxyproline"

( i x ) FEATURE:
        ( A ) NAME/KEY: Peptide
        ( B ) LOCATION: 15..19
        ( D ) OTHER INFORMATION: /note="At positions 15 and 19
            X=(T)=T without absolute certainty"

( x i ) SEQUENCE DESCRIPTION: SEQ ID NO:36:

Val Thr Ala Xaa Thr Xaa Ser Ala Ser Xaa Xaa Ser Ser Thr Xaa Ala
1               5                   10                  15

Ala Thr Xaa Ala
            20

( 2 ) INFORMATION FOR SEQ ID NO:37:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 4..14
        ( D ) OTHER INFORMATION: /note="At positions 4, 8, 9, 13
            and 14 X=O=Hydroxyproline"

( x i ) SEQUENCE DESCRIPTION: SEQ ID NO:37:

Ala Lys Ser Xaa Thr Ala Thr Xaa Xaa Thr Ala Thr Xaa Xaa Ser Ala
1               5                   10                  15

Val ( 2 ) INFORMATION FOR SEQ ID NO:38:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 4..15
        ( D ) OTHER INFORMATION: /note="At positions 4, 6, 10, 11,
            15 X=O=Hydroxyproline"

( i x ) FEATURE:
        ( A ) NAME/KEY: Peptide
        ( B ) LOCATION: 17
        ( D ) OTHER INFORMATION: /note="X=(S)=S without absolute
            certainty"

( x i ) SEQUENCE DESCRIPTION: SEQ ID NO:38:

Val Thr Ala Xaa Thr Xaa Ser Ala Ser Xaa Xaa Ser Ser Thr Xaa Ala
1               5                          10                         15

Xaa Thr Xaa Ala
        20

( 2 ) INFORMATION FOR SEQ ID NO:39:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 3..16
        ( D ) OTHER INFORMATION: /note="At positions 3, 7, 8, 12,
              15 X=O=Hydroxyproline"

( i x ) FEATURE:
        ( A ) NAME/KEY: Peptide
        ( B ) LOCATION: 6
        ( D ) OTHER INFORMATION: /note="X=T/Q"

( x i ) SEQUENCE DESCRIPTION: SEQ ID NO:39:

Ile Ser Xaa Ala Ser Xaa Xaa Xaa Thr Thr Ser Xaa Ala Ser Xaa Xaa
1               5                          10                         15

Thr ( 2 ) INFORMATION FOR SEQ ID NO:40:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 3
        ( D ) OTHER INFORMATION: /note="X=P/S"

( i x ) FEATURE:
        ( A ) NAME/KEY: Peptide
        ( B ) LOCATION: 4..13
        ( D ) OTHER INFORMATION: /note="At positions 4, 8, 11, 12,
              13 X=O=Hydroxyproline"

( i x ) FEATURE:
        ( A ) NAME/KEY: Peptide
        ( B ) LOCATION: 15
        ( D ) OTHER INFORMATION: /note="X=(T)=T without absolute
              certainty"

( x i ) SEQUENCE DESCRIPTION: SEQ ID NO:40:

Val Ser Xaa Xaa Val Gln Ser Xaa Ala Ser Xaa Xaa Xaa Thr Xaa
1               5                          10                         15

( 2 ) INFORMATION FOR SEQ ID NO:41:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:41:

```
Leu Val Val Val Val Met Thr Pro Arg Lys His
1               5                   10
```

(2) INFORMATION FOR SEQ ID NO:42:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 3..7
        (D) OTHER INFORMATION: /note="At positions 3, 6, 7
            X=O=Hydroxyproline"

(ix) FEATURE:
        (A) NAME/KEY: Peptide
        (B) LOCATION: 9
        (D) OTHER INFORMATION: /note="X=T/K"

(xi) SEQUENCE DESCRIPTION: SEQ ID NO:42:

```
Xaa Asn Xaa Ala Thr Xaa Xaa Ala Xaa Pro
1               5                   10
```

(2) INFORMATION FOR SEQ ID NO:43:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 5
        (D) OTHER INFORMATION: /note="X=O=Hydroxyproline"

(ix) FEATURE:
        (A) NAME/KEY: Peptide
        (B) LOCATION: 7
        (D) OTHER INFORMATION: /note="X=(L)=L without absolute
            certainty"

(xi) SEQUENCE DESCRIPTION: SEQ ID NO:43:

```
Ile Ala Ala Thr Xaa Ser Xaa
1               5
```

(2) INFORMATION FOR SEQ ID NO:44:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note="X=(G)/(S)=G/S without
            absolute certainty"

(ix) FEATURE:
        (A) NAME/KEY: Peptide
        (B) LOCATION: 4..8
        (D) OTHER INFORMATION: /note="At positions 4, 6, 8
            X=O=Hydroxyproline"

(xi) SEQUENCE DESCRIPTION: SEQ ID NO:44:

```
Xaa Asn Ala Xaa Ala Xaa Xaa Xaa Lys Pro
```

( 2 ) INFORMATION FOR SEQ ID NO:45:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:45:

```
GTNGTNGTNG  TNATGAC                                               17
```

( 2 ) INFORMATION FOR SEQ ID NO:46:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:46:

```
GTAGTNATGA  CNCCNRGAAA                                            20
```

( 2 ) INFORMATION FOR SEQ ID NO:47:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:47:

```
GTAGTNATGA  CNCCNCGNAA                                            20
```

( 2 ) INFORMATION FOR SEQ ID NO:48:

( i ) SEQUENCE CHARACTERISTICS:
        ( A ) LENGTH: 350 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..156

( i x ) FEATURE:
        ( A ) NAME/KEY: misc_feature
        ( B ) LOCATION: 1..24
        ( D ) OTHER INFORMATION: /note="Derived amino acid sequence
            matching the peptide sequence by protein
            sequencing"

( i x ) FEATURE:
        ( A ) NAME/KEY: misc_feature
        ( B ) LOCATION: 1..20
        ( D ) OTHER INFORMATION: /note="Nucleotide sequence
            corresponding to the PcA23F2a primers"

( x i ) SEQUENCE DESCRIPTION: SEQ ID NO:48:

```
GTA  GTG  ATG  ACG  CCG  AGG  AAG  CAC  CTC  GGT  ATT  TCT  CCC  GCT  CCT  TCT      48
Val  Val  Met  Thr  Pro  Arg  Lys  His  Leu  Gly  Ile  Ser  Pro  Ala  Pro  Ser
 1              5                        10                       15
```

```
CCG GCA GGG GAA GTC GAC GGT CCT GCT ATT GCT CCG ACA AGC GGC GCT                 96
Pro Ala Gly Glu Val Asp Gly Pro Ala Ile Ala Pro Thr Ser Gly Ala
            20              25                  30

ACA AGC TTG AAG GGT GGT GTT CTG ACT GTG GTG GCA TTG GGA GGG TTT                144
Thr Ser Leu Lys Gly Gly Val Leu Thr Val Val Ala Leu Gly Gly Phe
        35              40                  45

TGT CTG TGG TTT TAGCGAGGGG GAGATTTTTT GAACCGTGGT TGTTATCTTT                    196
Cys Leu Trp Phe
    50

CTGGGTTTTT GTTTGAGAG TGGGGGATAA TTATTTGTTT AATTCTTTAT TTTTTTATA                256

CATATGAGAC GAGATATTAT GTAATTCTAT TTCGAATGTC ATAATATCAA TATATTCATT              316

TCCTAAATAT AAAAAAAAAA AAAAAAAAA AAAA                                           350
```

( 2 ) INFORMATION FOR SEQ ID NO:49:

( i ) SEQUENCE CHARACTERISTICS:
        ( A ) LENGTH: 760 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 20..559

( i x ) FEATURE:
        ( A ) NAME/KEY: misc_feature
        ( B ) LOCATION: 20..100
        ( D ) OTHER INFORMATION: /note="The predicted secretion
            signal"

( i x ) FEATURE:
        ( A ) NAME/KEY: misc_feature
        ( B ) LOCATION: 126..132
        ( D ) OTHER INFORMATION: /note="Potential N-glycosylation
            site"

( i x ) FEATURE:
        ( A ) NAME/KEY: misc_feature
        ( B ) LOCATION: 279..285
        ( D ) OTHER INFORMATION: /note="Potential N-glycosylation
            site"

( i x ) FEATURE:
        ( A ) NAME/KEY: misc_feature
        ( B ) LOCATION: 395..471
        ( D ) OTHER INFORMATION: /note="Sequence matches the
            peptide sequences obtained from the AGP protein
            backbone"

( i x ) FEATURE:
        ( A ) NAME/KEY: misc_feature
        ( B ) LOCATION: 441..453
        ( D ) OTHER INFORMATION: /note="Proline residues are
            hydroxylated"

( x i ) SEQUENCE DESCRIPTION: SEQ ID NO:49:

```
CGCTCTCTAA AATTTTCAA ATG GCT GGC TTT TCA TCC TCA AAA GCT CTG TCA                52
                     Met Ala Gly Phe Ser Ser Ser Lys Ala Leu Ser
                      1               5                      10

TAC TCC TCT CTT CTC GTC GTC TTC CTC CTC TTC GGC TTC TCG GAA GCC                100
Tyr Ser Ser Leu Leu Val Val Phe Leu Leu Phe Gly Phe Ser Glu Ala
            15              20                  25

AGA GAG ATC ACC GTC GGT GGC AAG AAT GGC TCA TGG GCA GTC CCC TCC                148
Arg Glu Ile Thr Val Gly Gly Lys Asn Gly Ser Trp Ala Val Pro Ser
            30              35                  40

TCC GAA TCG CAA TCC CTC AAC AAA TGG GCC GAA AGC ACC CGC TTT CGC                196
```

|  |  |  |  |  | Ser | Glu | Ser | Gln | Ser | Leu | Asn | Lys | Trp | Ala | Glu | Ser | Thr | Arg | Phe | Arg |  |
|---|---|---|---|---|---|---|---|---|---|---|---|---|---|---|---|---|---|---|---|---|---|
|  |  |  |  |  |  | 45 |  |  |  | 50 |  |  |  |  | 55 |  |  |  |  |  |  |

```
GTC GGC GAC ACT CTT GTG TGG AAG TAC GAC AGC GCC AAA GAC TCA GTC          244
Val Gly Asp Thr Leu Val Trp Lys Tyr Asp Ser Ala Lys Asp Ser Val
60              65              70              75

TTG CGA GTG ACG AAA GAA GAC TAC TCA AAC TGC AAT GCG TCA AAC CCA          292
Leu Arg Val Thr Lys Glu Asp Tyr Ser Asn Cys Asn Ala Ser Asn Pro
            80              85              90

ATT GAG CAG CTC AAG GAC GGC GAA ACA AAG CTC CAC CTT GAC CAG CCA          340
Ile Glu Gln Leu Lys Asp Gly Glu Thr Lys Leu His Leu Asp Gln Pro
        95              100             105

GGG CCT TAC TAC TTC ATC AGC GGA ACC AAG GGG CAC TGC GAG AAG GGG          388
Gly Pro Tyr Tyr Phe Ile Ser Gly Thr Lys Gly His Cys Glu Lys Gly
        110             115             120

CAG AAA CTG GTG GTG GTG GTT ATG ACT CCA AGG AAG CAC CTC GGT ATT          436
Gln Lys Leu Val Val Val Val Met Thr Pro Arg Lys His Leu Gly Ile
    125             130             135

TCT CCC GCT CCT TCT CCG GCA GGG GAA GTC GAC GGT CCT GCT ATT GCT          484
Ser Pro Ala Pro Ser Pro Ala Gly Glu Val Asp Gly Pro Ala Ile Ala
140         145             150             155

CCG ACA AGC GGC GCT ACA AGC TTG AAG GGT GGT GTT CTG ACT GTG GTG          532
Pro Thr Ser Gly Ala Thr Ser Leu Lys Gly Gly Val Leu Thr Val Val
                160             165             170

GCA TTG GGA GGG TTT TGT CTG TGG TTT TAGCGAGGGG GAGATTTTTT                579
Ala Leu Gly Gly Phe Cys Leu Trp Phe
            175             180

GAACCGTGGT TGTTATCTTT CTGGGTTTTT GTTTGAGAG TGGGGGATAA TTATTTGTTT         639

AATTCTTTAT TTTTTTATA CATATGAGAC GAGATATTAT GTAATTCTAT TTCGAATGTC         699

ATAATATCAA TATATTCATT TCCTAAATAT AAAAAAAAAA AAAAAAAAAA AAAAAAAAA         759
A                                                                        760
```

( 2 ) INFORMATION FOR SEQ ID NO:50:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: cDNA ( i x ) FEATURE:
        ( A ) NAME/KEY: Peptide
        ( B ) LOCATION: 3..11
        ( D ) OTHER INFORMATION: /note="At positions 3 and 11
            X=O=Hydroxyproline"

( x i ) SEQUENCE DESCRIPTION: SEQ ID NO:50:

```
Phe Ala Xaa Ser Gly Gly Val Ala Leu Pro Xaa Ser
1               5                   10
```

( 2 ) INFORMATION FOR SEQ ID NO:51:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 4..13
        ( D ) OTHER INFORMATION: /note="Positions 4-5, 7-8, 13
            X=O=Hydroxyproline"

(xi) SEQUENCE DESCRIPTION: SEQ ID NO:51:

Leu Ala Ser Xaa Xaa Ala Xaa Xaa Thr Ala Asp Thr Xaa Ala
1               5                   10

(2) INFORMATION FOR SEQ ID NO:52:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note="X=I/V"

(ix) FEATURE:
        (A) NAME/KEY: Peptide
        (B) LOCATION: 2
        (D) OTHER INFORMATION: /note="X=G/S"

(ix) FEATURE:
        (A) NAME/KEY: Peptide
        (B) LOCATION: 3
        (D) OTHER INFORMATION: /note="X=A/S"

(ix) FEATURE:
        (A) NAME/KEY: Peptide
        (B) LOCATION: 4
        (D) OTHER INFORMATION: /note="X=A/O, where
            O=Hydroxyproline"

(ix) FEATURE:
        (A) NAME/KEY: Peptide
        (B) LOCATION: 5
        (D) OTHER INFORMATION: /note="X=O/S, where
            O=Hydroxyproline"

(ix) FEATURE:
        (A) NAME/KEY: Peptide
        (B) LOCATION: 6
        (D) OTHER INFORMATION: /note="X=A/Q"

(ix) FEATURE:
        (A) NAME/KEY: Peptide
        (B) LOCATION: 7
        (D) OTHER INFORMATION: /note="X=G/S"

(ix) FEATURE:
        (A) NAME/KEY: Peptide
        (B) LOCATION: 8
        (D) OTHER INFORMATION: /note="X=S/O, where
            O=Hydroxyproline"

(ix) FEATURE:
        (A) NAME/KEY: Peptide
        (B) LOCATION: 9
        (D) OTHER INFORMATION: /note="X=O/S, where
            O=Hydroxyproline"

(ix) FEATURE:
        (A) NAME/KEY: Peptide
        (B) LOCATION: 10
        (D) OTHER INFORMATION: /note="X=T/A"

(ix) FEATURE:
        (A) NAME/KEY: Peptide
        (B) LOCATION: 11
        (D) OTHER INFORMATION: /note="X=S/A"

(ix) FEATURE:
        (A) NAME/KEY: Peptide
        (B) LOCATION: 12
        (D) OTHER INFORMATION: /note="X=S/A"

( i x ) FEATURE:
    ( A ) NAME/KEY: Peptide
    ( B ) LOCATION: 14
    ( D ) OTHER INFORMATION: /note="X=O=Hydroxyproline"

( x i ) SEQUENCE DESCRIPTION: SEQ ID NO:52:

Xaa Xaa Xaa Xaa Xaa Xaa Xaa Xaa Xaa Xaa Xaa Xaa Pro Xaa
1               5                           10

( 2 ) INFORMATION FOR SEQ ID NO:53:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 5..9
        ( D ) OTHER INFORMATION: /note="At positions 5 and 9
                X=O=Hydroxyproline"

( x i ) SEQUENCE DESCRIPTION: SEQ ID NO:53:

Ile Gly Ser Ala Xaa Ala Gly Ser Xaa Thr Ser Ser Pro Asn
1               5                   10

( 2 ) INFORMATION FOR SEQ ID NO:54:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 7
        ( D ) OTHER INFORMATION: /note="X=O=Hydroxyproline"

( i x ) FEATURE:
        ( A ) NAME/KEY: Peptide
        ( B ) LOCATION: 10
        ( D ) OTHER INFORMATION: /note="X=(D)=D without absolute
                certainty"

( x i ) SEQUENCE DESCRIPTION: SEQ ID NO:54:

Xaa Xaa Xaa Gln Ser Ala Xaa Ala Ala Xaa Xaa Asn
1               5                   10

( 2 ) INFORMATION FOR SEQ ID NO:55:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 4
        ( D ) OTHER INFORMATION: /note="X=S/A"

( i x ) FEATURE:
        ( A ) NAME/KEY: Peptide
        ( B ) LOCATION: 5
        ( D ) OTHER INFORMATION: /note="X=Y/L"

( i x ) FEATURE:
        ( A ) NAME/KEY: Peptide
        ( B ) LOCATION: 6

(D) OTHER INFORMATION: /note="X=D/I"

(ix) FEATURE:
  (A) NAME/KEY: Peptide
  (B) LOCATION: 8
  (D) OTHER INFORMATION: /note="X=K/E"

(ix) FEATURE:
  (A) NAME/KEY: Peptide
  (B) LOCATION: 9
  (D) OTHER INFORMATION: /note="X=T/A"

(ix) FEATURE:
  (A) NAME/KEY: Peptide
  (B) LOCATION: 18
  (D) OTHER INFORMATION: /note="X=(E)=E without absolute certainty"

(xi) SEQUENCE DESCRIPTION: SEQ ID NO:55:

Xaa Thr Phe Xaa Xaa Xaa Ile Xaa Xaa Ala Ile Asn Thr Glu Phe Gly
1               5                   10                  15
Pro Xaa (2) INFORMATION FOR SEQ ID NO:56:

(i) SEQUENCE CHARACTERISTICS:
    (A) LENGTH: 22 amino acids
    (B) TYPE: amino acid
    (D) TOPOLOGY: linear (ii) MOLECULE TYPE: peptide (ix) FEATURE:
    (A) NAME/KEY: Peptide
    (B) LOCATION: 4
    (D) OTHER INFORMATION: /note="X=S/A"

(ix) FEATURE:
    (A) NAME/KEY: Peptide
    (B) LOCATION: 5
    (D) OTHER INFORMATION: /note="X=Y/L/V"

(ix) FEATURE:
    (A) NAME/KEY: Peptide
    (B) LOCATION: 6
    (D) OTHER INFORMATION: /note="X=D/I/A"

(xi) SEQUENCE DESCRIPTION: SEQ ID NO:56:

Xaa Thr Phe Xaa Xaa Xaa Ile Glu Thr Ala Ile Asn Thr Glu Phe Gly
1               5                   10                  15
Pro Xaa Glu Xaa Xaa Gln
        20

(2) INFORMATION FOR SEQ ID NO:57:

(i) SEQUENCE CHARACTERISTICS:
    (A) LENGTH: 18 amino acids
    (B) TYPE: amino acid
    (D) TOPOLOGY: linear (ii) MOLECULE TYPE: peptide (ix) FEATURE:
    (A) NAME/KEY: Peptide
    (B) LOCATION: 6
    (D) OTHER INFORMATION: /note="X=D/I"

(ix) FEATURE:
    (A) NAME/KEY: Peptide
    (B) LOCATION: 7
    (D) OTHER INFORMATION: /note="X=K/E"

(ix) FEATURE:
    (A) NAME/KEY: Peptide (B) LOCATION: 15
(D) OTHER INFORMATION: /note="X=G/M"

(x i) SEQUENCE DESCRIPTION: SEQ ID NO:57:

Xaa Thr Phe Ser Tyr Xaa Xaa Thr Ala Ile Asn Thr Glu Phe Xaa Pro
1               5                   10                  15

Ala Glu (2) INFORMATION FOR SEQ ID NO:58:

(i) SEQUENCE CHARACTERISTICS:
    (A) LENGTH: 9 amino acids
    (B) TYPE: amino acid
    (D) TOPOLOGY: linear (i i) MOLECULE TYPE: peptide (x i) SEQUENCE DESCRIPTION: SEQ ID NO:58:

Thr Ala Ile Asn Thr Glu Phe Gly Pro
1               5

(2) INFORMATION FOR SEQ ID NO:59:

(i) SEQUENCE CHARACTERISTICS:
    (A) LENGTH: 16 amino acids
    (B) TYPE: amino acid
    (D) TOPOLOGY: linear (i i) MOLECULE TYPE: peptide (x i) SEQUENCE DESCRIPTION: SEQ ID NO:59:

Ala Val Phe Lys Asn Lys Xaa Xaa Leu Thr Xaa Xaa Pro Xaa Ile Ile
1               5                   10                  15

(2) INFORMATION FOR SEQ ID NO:60:

(i) SEQUENCE CHARACTERISTICS:
    (A) LENGTH: 7 amino acids
    (B) TYPE: amino acid
    (D) TOPOLOGY: linear (i i) MOLECULE TYPE: peptide (x i) SEQUENCE DESCRIPTION: SEQ ID NO:60:

Ala Ile Asn Thr Glu Phe Gly
1               5

(2) INFORMATION FOR SEQ ID NO:61:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE: cDNA (i x) FEATURE:
    (A) NAME/KEY: misc_feature
    (B) LOCATION: 3
    (D) OTHER INFORMATION: /note="N=I"

(x i) SEQUENCE DESCRIPTION: SEQ ID NO:61:

GCNATHAA YA CNCARTT YGG                                          20

(2) INFORMATION FOR SEQ ID NO:62:

(i) SEQUENCE CHARACTERISTICS:
    (A) LENGTH: 350 base pairs (B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..102

(ix) FEATURE:
(A) NAME/KEY: misc_feature
(B) LOCATION: 1..19
(D) OTHER INFORMATION: /note="RT35-specific primer sequence"

(ix) FEATURE:
(A) NAME/KEY: misc_feature
(B) LOCATION: 1..24
(D) OTHER INFORMATION: /note="Derived amino acid sequence corresponding to the peptide sequence by protein microsequencing"

(xi) SEQUENCE DESCRIPTION: SEQ ID NO:62:

```
GCG ATC AAC ACG GAG TTC GGT CCT GAG GAA TGT AAC CAG TAT GAA TTT     48
Ala Ile Asn Thr Glu Phe Gly Pro Glu Glu Cys Asn Gln Tyr Glu Phe
 1               5                  10                  15

GCC ATG ATC AAA AAT CAG TGT GCA AAT CAA GCT GCT CCT CCT CCT ACA     96
Ala Met Ile Lys Asn Gln Cys Ala Asn Gln Ala Ala Pro Pro Pro Thr
             20                  25                  30

GAT TAC TAAGTTATTA AGGGGATGTA TGTGTACGTG CGTGTTTATA TAGCCGACCC     152
Asp Tyr

CAACTTGTTT GGACTTAGGC GTAGTTTGCA TTATTGTTAT TTTATATATG TGTATGTATT    212

CATATAGTCG ACCCCAACTT GTTTGGGATT GAGACGTAAT TGGTGTTTAT TAGTATGTAT    272

GTGTGTGTAT TTTGATGAGA ATAAATTAAT GAAGTGATTT GCTTATTGGG TTATCACAAA    332

AAAAAAAAAA AAAAAAA                                                   350
```

(2) INFORMATION FOR SEQ ID NO:63:

(i) SEQUENCE CHARACTERISTICS:
(A) LENGTH: 762 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 21..527

(ix) FEATURE:
(A) NAME/KEY: misc_feature
(B) LOCATION: 342..449
(D) OTHER INFORMATION: /note="Amino acids 108-113, 128-132, and 135-143 correspond to the peptide sequences by protein microsequencing"

(xi) SEQUENCE DESCRIPTION: SEQ ID NO:63:

```
TCTTTTTCAT GTTATAAGCC ATG TCT AGA GTA AGA AAC TTA TTT TCT TTC      50
                     Met Ser Arg Val Arg Asn Leu Phe Ser Phe
                      1               5                  10

CTT ATT TTC TTT CTC ATT ATT GCC TTA AAT TTC ACT AAT GGA TTA GCC     98
Leu Ile Phe Phe Leu Ile Ile Ala Leu Asn Phe Thr Asn Gly Leu Ala
             15                  20                  25

ATT GAT CAT AAA TCT GAT GCT AAT ATT GCA TTA ATC CCA CAA AAG AAA    146
Ile Asp His Lys Ser Asp Ala Asn Ile Ala Leu Ile Pro Gln Lys Lys
             30                  35                  40
```

| | | | | | | | | | | | | | | | | |
|---|---|---|---|---|---|---|---|---|---|---|---|---|---|---|---|---|
| GGA | TTA | AAA | TGG | TTG | CAT | TGG | CCA | TTT | GCA | CAT | GCA | CCA | CCA | CCA | CCT | 194 |
| Gly | Leu | Lys<br>45 | Trp | Leu | His | Trp | Pro<br>50 | Phe | Ala | His | Ala<br>55 | Pro | Pro | Pro | Pro | |
| TCA | TCT | TTT | TTT | CCT | AAG | TTT | CCA | TTT | CCA | AAA | ATA | TTT | CCC | TGG | CCG | 242 |
| Ser | Ser<br>60 | Phe | Phe | Pro | Lys<br>65 | Phe | Pro | Phe | Pro | Lys | Ile<br>70 | Phe | Pro | Trp | Pro | |
| CGA | TTT | TTG | CCA | CCT | AAG | CCT | TTT | TCG | CCT | AGT | GAA | AAA | CGC | GTC | AGT | 290 |
| Arg<br>75 | Phe | Leu | Pro | Pro<br>80 | Lys | Pro | Phe | Ser | Pro<br>85 | Ser | Glu | Lys | Arg | Val | Ser<br>90 | |
| GAC | ATA | AAC | ATA | GAC | AAC | AGT | CAG | AAC | GTG | TTG | GAC | AAG | AAA | TAT | TAT | 338 |
| Asp | Ile | Asn | Ile | Asp<br>95 | Asn | Ser | Gln | Asn | Val<br>100 | Leu | Asp | Lys | Lys | Tyr<br>105 | Tyr | |
| TGT | GCT | TTA | ATT | ATT | GAG | GCG | TGT | ATG | CTT | GAG | AGG | GAT | ATG | CTT | TGC | 386 |
| Cys | Ala | Leu | Ile<br>110 | Ile | Glu | Ala | Cys | Met<br>115 | Leu | Glu | Arg | Asp | Met<br>120 | Leu | Cys | |
| GTT | CGC | AAT | AGA | TGT | ACC | TTC | TCT | TAT | GAT | TGT | TGT | ACT | GCC | ATT | AAT | 434 |
| Val | Arg | Asn<br>125 | Arg | Cys | Thr | Phe | Ser<br>130 | Tyr | Asp | Cys | Cys | Thr<br>135 | Ala | Ile | Asn | |
| ACT | GAA | TTT | GGT | CCT | GAG | GAA | TGT | AAC | CAG | TAT | GAA | TTT | GCC | ATG | ATC | 482 |
| Thr | Glu<br>140 | Phe | Gly | Pro | Glu | Glu<br>145 | Cys | Asn | Gln | Tyr | Glu<br>150 | Phe | Ala | Met | Ile | |
| AAA | AAT | CAG | TGT | GCA | AAT | CAA | GCT | GCT | CCT | CCT | CCT | ACA | GAT | TAC | | 527 |
| Lys<br>155 | Asn | Gln | Cys | Ala | Asn<br>160 | Gln | Ala | Ala | Pro | Pro<br>165 | Pro | Thr | Asp | Tyr | | |

```
TAAGTTATTA AGGGGATGTA TGTGTACGTG CGTGTTTATA TAGCCGACCC CAACTTGTTT      587

GGGACTTAGG CGTAGTTTGC ATTATTGTTA TTTTATATAT GTGTATGTAT TCATATAGTC      647

GACCCCAACT TGTTTGGGAT TGAGACGTAA TTGGTGTTTA TTAGTATGTA TGTGTGTGTA      707

TTTTGATGAG AATAAATTAA TGAAGTGATT TGCTTATTGG GTTATCAAAA AAAAA          762
```

( 2 ) INFORMATION FOR SEQ ID NO:64:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..20
        ( D ) OTHER INFORMATION: /note="T3 promoter sequence"

( i x ) FEATURE:
        ( A ) NAME/KEY: misc_feature
        ( B ) LOCATION: 63..80
        ( D ) OTHER INFORMATION: /note="Adaptor sequence is equal
            to nucleotides 150-167 of the NaAGP1 cDNA"

( x i ) SEQUENCE DESCRIPTION: SEQ ID NO:64:

```
TGTTATTAAC CCTCACTAAA GCATCACCAC CAGCACCACC AACAGCAGAC ACACCAGCAG      60

CTATGATCAT ACCTGCATCT                                                  80
```

( 2 ) INFORMATION FOR SEQ ID NO:65:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:

-continued (A) NAME/KEY: misc_feature
(B) LOCATION: 1..19
(D) OTHER INFORMATION: /note="T7 promoter sequence"

(ix) FEATURE:
(A) NAME/KEY: misc_feature
(B) LOCATION: 68..85
(D) OTHER INFORMATION: /note="Adaptor sequence is equal
to nucleotides 444-461 of the NaAGP1 cDNA"

(xi) SEQUENCE DESCRIPTION: SEQ ID NO:65:

| | | | | | |
|---|---|---|---|---|---|
| NCTAATACGA | CTCACTATAG | GCTGATGGTG | GTGTTGCTGT | TGGTGGTGTT | GCTGTTGGTG | 60 |
| ATTTTGCGGG | AGTATCAGTC | AAAAG | | | | 85 |

(2) INFORMATION FOR SEQ ID NO:66:

(i) SEQUENCE CHARACTERISTICS:
(A) LENGTH: 893 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 70..504

(ix) FEATURE:
(A) NAME/KEY: misc_feature
(B) LOCATION: 70..138
(D) OTHER INFORMATION: /note="Putative secretion signal
peptide"

(ix) FEATURE:
(A) NAME/KEY: misc_feature
(B) LOCATION: 70..339
(D) OTHER INFORMATION: /note="Amino acids 70-138, 38-53,
and 71-90 are sequences which match the peptide
sequences obtained by protein sequencing"

(ix) FEATURE:
(A) NAME/KEY: misc_feature
(B) LOCATION: 87..324
(D) OTHER INFORMATION: /note="Amino acids 40, 44, 45, 49,
50, 74, 76, 80, 81, and 85 are hydroxylated
prolines"

(xi) SEQUENCE DESCRIPTION: SEQ ID NO:66:

```
CTCTCTCGCT CACTCATCAA ATTCTCTCTC TCTCTCTCTC TCTCTCTTTC TCTCTCTCTC         60

TCTCTAAAA ATG AAG ATG GGT TTT GCA GGG TTC CAA GTT TTG ATG GTT            108
           Met Lys Met Gly Phe Ala Gly Phe Gln Val Leu Met Val
             1               5                  10

TTG GGT CTG TTG GCC ACA TCA TGC ATA GCC CAA GCC CCA GGA GCA GCA          156
Leu Gly Leu Leu Ala Thr Ser Cys Ile Ala Gln Ala Pro Gly Ala Ala
         15                  20                  25

CCC ACA GCT TCA CCC CCA ACC GCA AAG TCG CCA ACC GCC ACC CCA CCA          204
Pro Thr Ala Ser Pro Pro Thr Ala Lys Ser Pro Thr Ala Thr Pro Pro
 30                  35                  40                  45

ACC GCC ACA CCG CCA TCA GCC GTA CCA GTT CCA TCA CCC AGC AAA ACA          252
Thr Ala Thr Pro Pro Ser Ala Val Pro Val Pro Ser Pro Ser Lys Thr
                 50                  55                  60

CCA ACC GCG TCA CCA ACT CCA TCA CCA GTG ACA GCA CCA ACC CCA AGT          300
Pro Thr Ala Ser Pro Thr Pro Ser Pro Val Thr Ala Pro Thr Pro Ser
                     65                  70                  75

GCC TCC CCA CCA TCT TCC ACA CCA GCT TCC ACC CCA GCT TCC ACT CCA          348
Ala Ser Pro Pro Ser Ser Thr Pro Ala Ser Thr Pro Ala Ser Thr Pro
             80                  85                  90

GCA GCT AAG TCT CCA TCG TCG TCA GCT GCT CCC TCA GGC TCA AGC CCG          396
```

5,646,029

115

116

-continued

| | | | | Ala | Ala | Lys | Ser | Pro | Ser | Ser | Ser | Ala | Ala | Pro | Ser | Gly | Ser | Ser | Pro | |
|---|---|---|---|---|---|---|---|---|---|---|---|---|---|---|---|---|---|---|---|---|
| | | | | | 95 | | | | 100 | | | | | 105 | | | | | | |
| AAC | TCC | CCA | CCG | GCT | GAC | GCT | ATT | CCT | CCA | AGT | GGC | ACC | TCC | GCC | ATC | | | | | 444 |
| Asn | Ser | Pro | Pro | Ala | Asp | Ala | Ile | Pro | Pro | Ser | Gly | Thr | Ser | Ala | Ile | | | | | |
| 110 | | | | | 115 | | | | | 120 | | | | | 125 | | | | | |
| AGC | CGC | GTT | GCT | ATT | GCT | GGA | ACT | GCT | CTT | GCT | GGA | GTT | TTC | TTC | GCG | | | | | 492 |
| Ser | Arg | Val | Ala | Ile | Ala | Gly | Thr | Ala | Leu | Ala | Gly | Val | Phe | Phe | Ala | | | | | |
| | | | | 130 | | | | | 135 | | | | | 140 | | | | | | |
| ATT | GTG | TTG | GCT | TAGATTCATG | | GGATTTGCTC | | TTTCGGGTTT | | TCCTATTGGT | | | | | | | | | | 544 |
| Ile | Val | Leu | Ala | | | | | | | | | | | | | | | | | |
| | | | 145 | | | | | | | | | | | | | | | | | |

| CCACGTGGAG | ACTCACATCT | GCTCTTAGAT | CTGGGTTTTG | ATGGACGGTC | GAGATCTATT | 604 |
|---|---|---|---|---|---|---|
| AATTTCTTTT | TATTTGTTG | CTTATTTCG | TTAATGTTTT | TTGTATTTTT | GTTAACTCT | 664 |
| GTTTTCATGC | CATATGGTGA | TTATTGGTTT | GGCAGTCTAT | GGTGGATTTG | GACGGTCGTG | 724 |
| ATGTGATTAA | TTATGGTGAT | TCATTGTTTT | AGAGTTGACA | AGTGCACCCA | TTTGTAGATG | 784 |
| AGTCGTTGGA | TGTACATCTG | TCCGATCATA | GTTAATAAA | ACAGTTTGTC | ATTCTTTTC | 844 |
| TTATGGATCT | TCAAAAAAAA | AAAAAAAAAA | AAAAAAAAA | AAAAAAAA | | 893 |

( 2 ) INFORMATION FOR SEQ ID NO:67:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 4..8
        ( D ) OTHER INFORMATION: /note="At positions 4 and 8
            X=O=Hydroxyproline."

( x i ) SEQUENCE DESCRIPTION: SEQ ID NO:67:

Val  Ser  Ala  Xaa  Ser  Gln  Ser  Xaa  Ser  Thr  Ala  Ala
    1                  5                      10

( 2 ) INFORMATION FOR SEQ ID NO:68:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 3..7
        ( D ) OTHER INFORMATION: /note="At positions 3 and 7
            X=O=Hydroxyproline"

( x i ) SEQUENCE DESCRIPTION: SEQ ID NO:68:

Asp  Thr  Xaa  Ala  Phe  Ala  Xaa  Ser  Gly  Gly  Val  Ala  Leu
    1                  5                      10

( 2 ) INFORMATION FOR SEQ ID NO:69:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( i x ) FEATURE:

(A) NAME/KEY: Peptide
(B) LOCATION: 4..25
(D) OTHER INFORMATION: /note="At positions 4, 5, 7, 8, 13, 17, and 25 X=O=Hydroxyproline"

(xi) SEQUENCE DESCRIPTION: SEQ ID NO:69:

```
Leu Ala Ser Xaa Xaa Ala Xaa Xaa Thr Ala Asp Thr Xaa Ala Phe Ala
1               5                   10                  15
Xaa Ser Gly Gly Val Ala Leu Pro Xaa Ser
                20                  25
```

(2) INFORMATION FOR SEQ ID NO:70:

(i) SEQUENCE CHARACTERISTICS:
(A) LENGTH: 7 amino acids
(B) TYPE: amino acid
(D) TOPOLOGY: linear (ii) MOLECULE TYPE: peptide (ix) FEATURE:
(A) NAME/KEY: Peptide
(B) LOCATION: 5
(D) OTHER INFORMATION: /note="X=O=Hydroxyproline"

(xi) SEQUENCE DESCRIPTION: SEQ ID NO:70:

```
Thr Ala Asp Thr Xaa Ala Phe
1               5
```

(2) INFORMATION FOR SEQ ID NO:71:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: misc_feature
(B) LOCATION: 3..6
(D) OTHER INFORMATION: /note="At positions 3 and 6 N=I."

(xi) SEQUENCE DESCRIPTION: SEQ ID NO:71:

ACNGCNGAYA CNCCNGCNTT                    20

(2) INFORMATION FOR SEQ ID NO:72:

(i) SEQUENCE CHARACTERISTICS:
(A) LENGTH: 712 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 85..480

(ix) FEATURE:
(A) NAME/KEY: misc_feature
(B) LOCATION: 85..147
(D) OTHER INFORMATION: /note="Putative secretion signal."

(ix) FEATURE:
(A) NAME/KEY: misc_feature
(B) LOCATION: 154..393
(D) OTHER INFORMATION: /note=
" 154-156,244-246,256-258,298-300,301-303,307-309 =
hydroxyproline."

-continued (ix) FEATURE:
    (A) NAME/KEY: misc_feature
    (B) LOCATION: 235..408
    (D) OTHER INFORMATION: /note="235-268, 289-330, 331-365,
        and 366-408 are internal peptide sequences from
        amino acid sequencing."

(ix) FEATURE:
    (A) NAME/KEY: misc_feature
    (B) LOCATION: 205..408
    (D) OTHER INFORMATION: /note="235-268 =SEQ ID NO:67;
        289-330 =SEQ ID NO:51; 319-357 =SEQ ID NO:68;
        331-365 =SEQ ID NO:50; 366-408 =SEQ ID NO:53"

(ix) FEATURE:
    (A) NAME/KEY: misc_feature
    (B) LOCATION: 154..393
    (D) OTHER INFORMATION: /note=
        " 310-312,325-327,337-339,361-363,378-380,391-393 =
        Hydroxyproline."

(xi) SEQUENCE DESCRIPTION: SEQ ID NO:72:

```
TGAAGAAACT TACACTTTCT CTCTCTGAAA ACTGCTCAAC ACTTCAAATC AGAGTTTTCG      60

AAAAGCTTCT AGAGAGAGAA AGAA ATG GCT TAC TCA AGG ATG ATG TTC GCT       111
                          Met Ala Tyr Ser Arg Met Met Phe Ala
                           1               5

TTC ATT TTC GCT TTG GTC GCC GGA TCT GCT TTT GCT CAG GCT CCG GGA      159
Phe Ile Phe Ala Leu Val Ala Gly Ser Ala Phe Ala Gln Ala Pro Gly
 10              15                  20                  25

GCT TCT CCC GCA GCT TCA CCG AAG GCA TCA CCG GTT GCA CCA GTA GCA      207
Ala Ser Pro Ala Ala Ser Pro Lys Ala Ser Pro Val Ala Pro Val Ala
                 30              35                  40

TCA CCT CCA ACT GCT GTT GTT ACA CCG GTA TCC GCT CCA TCA CAA TCT      255
Ser Pro Pro Thr Ala Val Val Thr Pro Val Ser Ala Pro Ser Gln Ser
             45              50                  55

CCT TCT ACT GCT GCA TCT CCT TCT GAA TCT CCA TTG GCA TCT CCA CCA      303
Pro Ser Thr Ala Ala Ser Pro Ser Glu Ser Pro Leu Ala Ser Pro Pro
         60              65                  70

GCT CCA CCA ACT GCT GAC ACT CCA GCA TTT GCT CCC TCC GGC GGC GTT      351
Ala Pro Pro Thr Ala Asp Thr Pro Ala Phe Ala Pro Ser Gly Gly Val
     75              80                  85

GCT CTT CCT CCA TCC ATC GGC TCT GCT CCC GCC GGT TCT CCA ACC TCG      399
Ala Leu Pro Pro Ser Ile Gly Ser Ala Pro Ala Gly Ser Pro Thr Ser
 90              95                  100                 105

TCT CCT AAC GCT GCT TCC TTG AAC AGA GTC GCC GTC GCT GGA TCT GCA      447
Ser Pro Asn Ala Ala Ser Leu Asn Arg Val Ala Val Ala Gly Ser Ala
             110                 115                 120

GTT GTA GCG ATC TTC GCT GCA TCT TTG ATG TTT TAGATCTGAG GAGAGTTTGC    500
Val Val Ala Ile Phe Ala Ala Ser Leu Met Phe
             125                 130

ATTTTGGATT TTCACGAGAT GTTTATTATT TTAGGATTTA TTTAGTTCAT CTTACTCGTT    560

GATGTTTATT CGTTTGTTT TACTTTTACC CGTGGGCGGT GGTGACTGCG TACATGCTAT     620

TGATTTGATT TTTACTCTGG TTATTGTTTA TTGTTACTAC CACTATTATT ATTATGGATT    680

CTTTGTTTAT TTATGAAGCA CTATGATTTA CA                                   712
```

(2) INFORMATION FOR SEQ ID NO:73:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide ( x i ) SEQUENCE DESCRIPTION: SEQ ID NO:73:

Gln Ala Pro Gly Ala Ala
1               5

( 2 ) INFORMATION FOR SEQ ID NO:74:

( i ) SEQUENCE CHARACTERISTICS:
      ( A ) LENGTH: 19 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:74:

Ala Glu Ala Glu Ala Xaa Thr Xaa Ala Leu Gln Val Val Ala Glu Ala
1               5                   10                  15

Xaa Glu Leu ( 2 ) INFORMATION FOR SEQ ID NO:75:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 2..4
      ( D ) OTHER INFORMATION: /note="In positions 2 and 4
         X=O=Hydroxyproline."

( x i ) SEQUENCE DESCRIPTION: SEQ ID NO:75:

Thr Xaa Ala Xaa Ala
1               5

( 2 ) INFORMATION FOR SEQ ID NO:76:

( i ) SEQUENCE CHARACTERISTICS:
      ( A ) LENGTH: 19 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 6..17
      ( D ) OTHER INFORMATION: /note="At positions 6, 8, and 17
         X=O=Hydroxyproline."

( x i ) SEQUENCE DESCRIPTION: SEQ ID NO:76:

Ala Glu Ala Glu Ala Xaa Thr Xaa Ala Leu Gln Val Val Ala Glu Ala
1               5                   10                  15

Xaa Glu Leu ( 2 ) INFORMATION FOR SEQ ID NO:77:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
    ( A ) NAME/KEY: Peptide
    ( B ) LOCATION: 4..11
    ( D ) OTHER INFORMATION: /note="At positions 4, 8, 11
        X=O=Hydroxyproline."

( x i ) SEQUENCE DESCRIPTION: SEQ ID NO:77:

```
Val Ser Xaa Xaa Val Gln Ser Xaa Ala Xaa Xaa
1               5                   10
```

( 2 ) INFORMATION FOR SEQ ID NO:78:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 4..13
        ( D ) OTHER INFORMATION: /note="At positions 4,8,11-13
        X=O=Hydroxyproline."

( x i ) SEQUENCE DESCRIPTION: SEQ ID NO:78:

```
Val Xaa Xaa Xaa Val Gln Ser Xaa Ala Ser Xaa Xaa Xaa Thr Thr
1               5                   10                  15
```

( 2 ) INFORMATION FOR SEQ ID NO:79:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 3..8
        ( D ) OTHER INFORMATION: /note="At positions 3,7,8
        X=O=Hydroxyproline."

( x i ) SEQUENCE DESCRIPTION: SEQ ID NO:79:

```
Ile Ser Xaa Ala Ser Thr Xaa Xaa Thr
1               5
```

( 2 ) INFORMATION FOR SEQ ID NO:80:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 3..14
        ( D ) OTHER INFORMATION: /note="X=O=Hydroxyproline."

( x i ) SEQUENCE DESCRIPTION: SEQ ID NO:80:

```
Ile Ser Xaa Ala Ser Thr Xaa Xaa Thr Xaa Ala Ser Xaa Xaa Thr
1               5                   10                  15
```

( 2 ) INFORMATION FOR SEQ ID NO:81:

( i ) SEQUENCE CHARACTERISTICS:

( A ) LENGTH: 8 amino acids
( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 3..7
( D ) OTHER INFORMATION: /note="At positions 3 and 7 X=O=Hydroxyproline."

( x i ) SEQUENCE DESCRIPTION: SEQ ID NO:81:

Phe Ser Xaa Thr Ile Ser Xaa Ala
1               5

( 2 ) INFORMATION FOR SEQ ID NO:82:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 3
( D ) OTHER INFORMATION: /note="At position 3 X=(A)=A without absolute certainty."

( i x ) FEATURE:
( A ) NAME/KEY: Peptide
( B ) LOCATION: 5..12
( D ) OTHER INFORMATION: /note="At positions 5 and 12 X=O=Hydroxyproline."

( x i ) SEQUENCE DESCRIPTION: SEQ ID NO:82:

Xaa Ala Xaa Thr Xaa Ser Leu Asp Val Gly Ile Xaa Ser Ser Asn Ala
1               5                   10                  15
Thr ( 2 ) INFORMATION FOR SEQ ID NO:83:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1
( D ) OTHER INFORMATION: /note="X=T/P"

( i x ) FEATURE:
( A ) NAME/KEY: Peptide
( B ) LOCATION: 3..7
( D ) OTHER INFORMATION: /note="At positions 3,6,7 X=O=Hydroxyproline."

( x i ) SEQUENCE DESCRIPTION: SEQ ID NO:83:

Xaa Ser Xaa Ala Thr Xaa Xaa Ala Thr
1               5

( 2 ) INFORMATION FOR SEQ ID NO:84:

( i ) SEQUENCE CHARACTERISTICS:
( A ) LENGTH: 13 amino acids
( B ) TYPE: amino acid ( C ) STRANDEDNESS: single
( D ) TOPOLOGY: linear ( i i ) MOLECULE TYPE: peptide ( i x ) FEATURE:
    ( A ) NAME/KEY: Peptide
    ( B ) LOCATION: 4..6
    ( D ) OTHER INFORMATION: /note="At positions 4 and 6
        X=O=Hydroxyproline."

( i x ) FEATURE:
    ( A ) NAME/KEY: Peptide
    ( B ) LOCATION: 8
    ( D ) OTHER INFORMATION: /note="X=(O)=O without absolute
        certainty, where O=Hydroxyproline."

( i x ) FEATURE:
    ( A ) NAME/KEY: Peptide
    ( B ) LOCATION: 12
    ( D ) OTHER INFORMATION: /note="X=(N)=N without absolute
        certainty."

( x i ) SEQUENCE DESCRIPTION: SEQ ID NO:84:

```
Xaa  Ala  Ala  Xaa  Ala  Xaa  Ser  Xaa  Xaa  Pro  Thr  Xaa  Thr
1                  5                             10
```

( 2 ) INFORMATION FOR SEQ ID NO:85:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 6..16
        ( D ) OTHER INFORMATION: /note="At positions 6,10,12,14,16
            X=O=Hydroxyproline."

( x i ) SEQUENCE DESCRIPTION: SEQ ID NO:85:

```
Val  Val  Ala  Glu  Ala  Xaa  Glu  Leu  Val  Xaa  Thr  Xaa  Val  Xaa  Thr  Xaa
1                  5                             10                            15
Ser
```

( 2 ) INFORMATION FOR SEQ ID NO:86:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 3..9
        ( D ) OTHER INFORMATION: /note="At positions 3,5,7,9
            X=O=Hydroxyproline."

( x i ) SEQUENCE DESCRIPTION: SEQ ID NO:86:

```
Leu  Val  Xaa  Thr  Xaa  Val  Xaa  Thr  Xaa  Ser  Tyr
1                  5                             10
```

( 2 ) INFORMATION FOR SEQ ID NO:87:

( i ) SEQUENCE CHARACTERISTICS:
        ( A ) LENGTH: 4 amino acids
        ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:87:

Tyr Thr Glu Arg
1

(2) INFORMATION FOR SEQ ID NO:88:

(i) SEQUENCE CHARACTERISTICS:
(A) LENGTH: 29 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 6..27
(D) OTHER INFORMATION: /note="X=O=Hydroxyproline."

(xi) SEQUENCE DESCRIPTION: SEQ ID NO:88:

Ala Glu Ala Glu Ala Xaa Thr Xaa Ala Leu Gln Val Val Ala Glu Ala
1               5                   10                  15

Xaa Glu Leu Val Xaa Thr Xaa Val Xaa Thr Xaa Ser Tyr
            20              25

(2) INFORMATION FOR SEQ ID NO:89:

(i) SEQUENCE CHARACTERISTICS:
(A) LENGTH: 59 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:89:

TTCCTGCAGA AGCAGAAGCA CCAACACCAG CACTACAAGT AGTAGCAGAA GCACCACAA        59

(2) INFORMATION FOR SEQ ID NO:90:

(i) SEQUENCE CHARACTERISTICS:
(A) LENGTH: 60 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:90:

CTGGAGCTCA TATGATGGTG TTGGTACTGG TGTTGGTACT AGTTCTGGTG CTTCTCCTAC        60

(2) INFORMATION FOR SEQ ID NO:91:

(i) SEQUENCE CHARACTERISTICS:
(A) LENGTH: 1040 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 5..886

(ix) FEATURE:

(A) NAME/KEY: misc_feature
(B) LOCATION: 5..63
(D) OTHER INFORMATION: /note="Predicted secretion signal."

(ix) FEATURE:
(A) NAME/KEY: misc_feature
(B) LOCATION: 452..552
(D) OTHER INFORMATION: /note="A long direct repeat."

(ix) FEATURE:
(A) NAME/KEY: misc_feature
(B) LOCATION: 572..672
(D) OTHER INFORMATION: /note="A long direct repeat."

(ix) FEATURE:
(A) NAME/KEY: misc_feature
(B) LOCATION: 161..255
(D) OTHER INFORMATION: /note="A sequence matching the peptide sequences obtained from the AGP protein backbone."

(ix) FEATURE:
(A) NAME/KEY: misc_feature
(B) LOCATION: 176..178
(D) OTHER INFORMATION: /note="Codes for Hydroxyproline."

(ix) FEATURE:
(A) NAME/KEY: misc_feature
(B) LOCATION: 182..184
(D) OTHER INFORMATION: /note="Codes for Hydroxyproline."

(ix) FEATURE:
(A) NAME/KEY: misc_feature
(B) LOCATION: 209..211
(D) OTHER INFORMATION: /note="Codes for Hydroxyproline."

(ix) FEATURE:
(A) NAME/KEY: misc_feature
(B) LOCATION: 221..223
(D) OTHER INFORMATION: /note="Codes for Hydroxyproline."

(ix) FEATURE:
(A) NAME/KEY: misc_feature
(B) LOCATION: 227..229
(D) OTHER INFORMATION: /note="Codes for Hydroxyproline."

(ix) FEATURE:
(A) NAME/KEY: misc_feature
(B) LOCATION: 233..235
(D) OTHER INFORMATION: /note="Codes for Hydroxyproline."

(ix) FEATURE:
(A) NAME/KEY: misc_feature
(B) LOCATION: 239..241
(D) OTHER INFORMATION: /note="Codes for Hydroxyproline."

(xi) SEQUENCE DESCRIPTION: SEQ ID NO:91:

```
AGCA ATG GCT TCC TTT GCA AAA CCA CTT CCA TTT TTC TTC CTT CTG GTG          49
     Met Ala Ser Phe Ala Lys Pro Leu Pro Phe Phe Phe Leu Leu Val
     1               5                   10                  15

CTA GTT TGC TCT TCC TTT ATA CAC ATC ATT CAT GCT AGA CAG AGC GTG           97
Leu Val Cys Ser Ser Phe Ile His Ile Ile His Ala Arg Gln Ser Val
                    20                  25                  30

TCC TTC AGC AAG GTC ACC CAC AAC GAC AAC AAC AAC AAC AAC GAT              145
Ser Phe Ser Lys Val Thr His Asn Asp Asn Asn Asn Asn Asn Asp
                35                  40                  45

AAT TAT GTT ATG GAG GCG GAG GCC GAA GCA CCA ACG CCA GCA CTA CAA          193
Asn Tyr Val Met Glu Ala Glu Ala Glu Ala Pro Thr Pro Ala Leu Gln
            50                  55                  60

GTA GTA GCA GAG GCA CCG GAA CTA GTA CCA ACA CCG GTA CCG ACA CCA          241
Val Val Ala Glu Ala Pro Glu Leu Val Pro Thr Pro Val Pro Thr Pro
        65                  70                  75

AGT TAC ACC GAA AGA GAC CAT GGC AGC AAC AGC GCC CTG TAT GGT CTT          289
```

```
           Ser  Tyr  Thr  Glu  Arg  Asp  His  Gly  Ser  Asn  Ser  Ala  Leu  Tyr  Gly  Leu
           80                       85                       90                       95

GGC  TCG  ACC  AAT  TCC  CCT  TCC  ACG  AAG  GAG  ACT  CCA  ACC  ACA  ATT  ACT       337
           Gly  Ser  Thr  Asn  Ser  Pro  Ser  Thr  Lys  Glu  Thr  Pro  Thr  Thr  Ile  Thr
                              100                      105                      110

GAT  GTT  GAA  GAT  CAA  ATT  TTG  AGT  GAA  GAA  CTT  AGC  GGT  GAA  AGT  TTT       385
           Asp  Val  Glu  Asp  Gln  Ile  Leu  Ser  Glu  Glu  Leu  Ser  Gly  Glu  Ser  Phe
                              115                      120                      125

GAT  CAT  CCG  AAA  GGT  AAT  TAC  GAA  AGC  ACC  AAC  TTG  TTC  AAC  AAG  GAC       433
           Asp  His  Pro  Lys  Gly  Asn  Tyr  Glu  Ser  Thr  Asn  Leu  Phe  Asn  Lys  Asp
                         130                      135                      140

AAC  ATT  AAT  CAA  AAC  ACT  GGC  TAC  ACC  GGC  AAC  AGC  TAC  TAT  GTC  AAA       481
           Asn  Ile  Asn  Gln  Asn  Thr  Gly  Tyr  Thr  Gly  Asn  Ser  Tyr  Tyr  Val  Lys
                145                      150                      155

AAC  TAC  GAT  GGC  AGA  GGA  GGC  TAC  AAC  CGC  AAT  CCC  CCG  GGC  GGA  GGC       529
           Asn  Tyr  Asp  Gly  Arg  Gly  Gly  Tyr  Asn  Arg  Asn  Pro  Pro  Gly  Gly  Gly
           160                      165                      170                      175

AAT  GGG  ATT  AGT  GAA  CAG  CAA  GGG  ATT  AGT  AAT  CAG  GAC  ATT  GGC  TAC       577
           Asn  Gly  Ile  Ser  Glu  Gln  Gln  Gly  Ile  Ser  Asn  Gln  Asp  Ile  Gly  Tyr
                              180                      185                      190

ACC  GGC  AAC  AGT  TAC  TAC  GTC  AAA  AAC  TAC  GAT  GGC  AGA  GGA  GGC  TAC       625
           Thr  Gly  Asn  Ser  Tyr  Tyr  Val  Lys  Asn  Tyr  Asp  Gly  Arg  Gly  Gly  Tyr
                              195                      200                      205

AAC  CGC  AAT  CCC  CCG  GGT  GGA  GGC  AAT  GAG  ATT  AGT  GAA  CAG  CAA  GGG       673
           Asn  Arg  Asn  Pro  Pro  Gly  Gly  Gly  Asn  Glu  Ile  Ser  Glu  Gln  Gln  Gly
                         210                      215                      220

ATG  AGT  GAT  ACA  AGG  TTT  CTG  GAA  AAT  GGT  AAA  TAC  TAT  CAT  GAT  GTG       721
           Met  Ser  Asp  Thr  Arg  Phe  Leu  Glu  Asn  Gly  Lys  Tyr  Tyr  His  Asp  Val
                225                      230                      235

AAG  AAT  GAG  ATT  AAA  AAT  AAT  AAT  TTC  AAT  GGT  AAC  TCC  GAA  TCA  GAT       769
           Lys  Asn  Glu  Ile  Lys  Asn  Asn  Asn  Phe  Asn  Gly  Asn  Ser  Glu  Ser  Asp
           240                      245                      250                      255

GGG  AGA  GGA  AGT  AAC  AGA  AAT  GAT  GTT  GAG  CGC  TAC  TAT  GCC  AAC  AGT       817
           Gly  Arg  Gly  Ser  Asn  Arg  Asn  Asp  Val  Glu  Arg  Tyr  Tyr  Ala  Asn  Ser
                              260                      265                      270

CAC  AGC  TCC  AAT  GAG  TTC  AAC  ACC  ATG  GAG  GAG  TAT  GAT  AAG  TAC  CAG       865
           His  Ser  Ser  Asn  Glu  Phe  Asn  Thr  Met  Glu  Glu  Tyr  Asp  Lys  Tyr  Gln
                         275                      280                      285

AAG  ACC  CAA  GGA  TAT  GTG  CCC  TAAATGATAT  TCCATGTTTT  TAGGTGTGCG              916
           Lys  Thr  Gln  Gly  Tyr  Val  Pro
                         290

TTGAAAACTT  AATCAATATA  TAAGAGATTT  TATGGTTTGT  TTTGGAATTC  CATTTGTCTT              976

TTGAATATGT  TTTCGCTATA  AAAATTAAAC  CCTTTCCACT  CCAAAAAAAA  AAAAAAAAA              1036

AAAA                                                                                1040
```

PLANT ARABINOGALACTAN PROTEIN (AGP) GENES

RELATEDNESS OF THE INVENTION

The subject application is a continuation-in-part of U.S. application Ser. No. 08/161,944, filed on Dec. 3, 1993, now abandoned, which is incorporated herein in the entirety by reference.

FIELD OF THE INVENTION

The subject matter of the invention relates to the isolation of arabinogalactan proteins (AGPs) from plants, e.g., *Nicotiana alata*, *Nicotiana plumbaginafolia* and *Pyrus communis*, and the utilization of amino acid sequences of various AGP fragments for the isolation of corresponding plant genes encoding the protein backbone of AGPs.

BACKGROUND OF THE INVENTION

Arabinogalactan proteins (AGPs) are found in flowering plants from every taxonomic group tested. These proteoglycans are widely distributed in most higher plants, occurring in almost all tissues including leaves, stems, roots, floral parts, seeds, and in many of their secretions. These macromolecules are found predominantly in soluble form in the intercellular wall space [Clarke et al. (1975) *J. Cell Sci.* 19:157–167; Clarke et al. (1978) *Aust. J. Plant Physiol,* 5:707–722], and are also localized in cytoplasmic organelles [Anderson et al. (1977) *Aust. J. Plant Physiol.* 4:143–158], at the protoplast surface [Clarke et al. (1975), supra and (1978), supra; Komalavilas et al. (1991) *J. Biol. Chem.* 266:15956–15965; Pennell et al. (1991) *Plant Cell* 3:1317–1326; Kieliszewski et al. (1992) *Plant Physiol.* 99:538–547] and in the cell wall [Bacic et al. (1988), *The Biochemistry of Plants*, Preiss, J. ed., Vol. 14, pp. 297–371 Academic Press, San Diego; Knox (1990) *J. Cell Science* 96:557–561; Roberts (1990) *Current Opinion in Cell Biology* 2:920–928; Knox (1992) *Protoplasma* 167: 1–9; Pennell (1992) *Soc. Expt. Biol. Seminar Series* 48: Perspectives in Plant Cell Recognition (ed. J. A. Callow and J. R. Green) Cambridge University Press pp. 105–121; Showalter (1993) *Plant Cell* 5:9–23; Wycoff et al. (Ref.)].

In cell cultures, AGPs are secreted into the medium [Fincher et al. (1983), *Ann. Rev. Plant Physiol.* 34:47–70]. Several AGPs from culture media have been investigated, including those from ryegrass cells [Anderson et al. (1977), supra; Glesson et al. (1989) *Biochem. J.* 264:857–262]; tobacco cells [Akiyama et al. (1981) *Phytochemistry* 20:2507–2510]; blackberry cells [Cartier et al. (1987) *Carbohydrate Res.* 168:275–283]; sycamore cells [Aspinall et al. (1969) *Can. J. Biochem.* 47:1063–1070]; carrot cells [Jermyn et al. (1985) *AGP News* 5:4–25; Kreuger et al. (1993) *Planta* 189:243–248]; Rosa cell suspension culture [Komalavilas et al. (1991) *J. Biol. Chem.* 266:15956–15965]; gladiolus cells [Glesson et al. (1979) *Biochem. J.* 181:607–621]; and maize cells [Kieliszewski et al. (1992) *Plant Physiol.* 99:538–547].

The multi-site localization of AGPs appears to be analogous to the multi-site localization of some animal proteoglycans. As regards chemical structure, however, little similarity seems to exist between plant AGPs and animal proteoglycans.

The AGPs are a family of structurally related glycosylated molecules containing high proportions of carbohydrate and usually less than 10 percent by weight of protein [Clarke et al. (1979), supra; Fincher et al. (1983), supra], although AGPs having a protein content of about 59% are known [Fincher et al. (1983), supra; Anderson et al. (1979) *Phytochem.* 18:609–610]. The carbohydrate consists of polysaccharide chains having a 1,3-β-D-galactopyranosyl backbone and side chains of (1,3-β- or 1,6-β-)D-galactopyranosyl (Gal) residues and often terminating in β-D-Galp and α-L-arabinofuranosyl Araf residues [Kreuger et al. (1993) *Planta* 189:243–248]. Other neutral sugars and uronic acids have also been detected, although at low levels. Monosaccharides which can be present are L-rhamnopyranose, D-mannopyranose, D-xylopyranose, D-glucopyranose, D-glucuronic acid and its 4-0-methyl derivative and D-galacturonic acid and its 4-0-methyl derivative [Fincher et al. (1983), supra]. In most cases, however, Gal and Ara predominate.

The protein content is usually between two and ten percent [Fincher et al. (1983), supra]. In contrast with the polysaccharide component, relatively little is known about the structure and organization of the protein core of AGPs, except that the protein appears to have domains rich in alanine, hydroxyproline, serine, and threonine [Fincher et al. (1983), supra]. This is reflected in the amino acid sequences that were obtained for AGP peptide fragments from carrot [Jermyn et al. (1985) supra]; Italian ryegrass [Glesson et al. (1989), supra]; and Rose (Komalavilas et al. (1991), supra]. A common feature of many of these isolated peptide fragments is the dipeptide Ala-Hyp, which is directly repeated in various AGP peptide fragments. To date, the entire amino acid sequence of an intact isolated AGP is not available publicly. The high carbohydrate content of AGPs appears to cause difficulties in sequencing; attempts to chemically remove the carbohydrate moiety usually results in incomplete deglycosylation and products with variable levels of carbohydrate content. The carbohydrate-protein linkage has been identified as a β-galactosyl-hydroxyproline linkage in AGPs isolated from wheat and ryegrass [Glesson et al. (1985) *AGP News* 5:30–36 and McNamara and Stone (1981) *Lebensm.-Wiss. u-Technol.* 14:182–187].

AGPs are components of Gum arabic, a gummy exudation originating from the Acacia tree and known to be produced by stress conditions such as heat, drought, and wounding [Clarke et al. (1979) *Biochemistry* 18:520–540]. The gum finds wide use as a flavor encapsulator in dry mix products such as puddings, desserts, cake mixes and soup mixes, and is also used to emulsify essential oils in soft drinks and to prevent sugar crystallization in confectionery products [Randall et al. (1989) *Food Hydrocolloids* 3:65–75]. More recently, the significance of the protein component to the overall structural and functional characteristics of gums has been realized [Vandevelde et al. (1985) *Carbohydr. Polymers* 5:251–273; Connolly et al. (1987) *Food Hydrocolloids* 1:477–480 and Connolly et al. (1988) *Carbohydr. Polymers* 8:23–32]. The importance of the protein-rich fraction to the emulsification properties of the gum has been demonstrated [Randall et al. (1988) *Food Hydrocolloids,* 2:131–140].

AGPs function in several biological processes including plant development, cell-cell adhesion, pollen-stigma recognition, water retention, and disease resistance. AGPs may serve as glues or provide nutrients for growing pollen tubes. It has been suggested [Fincher et al. (1983) supra] that AGP proteins may interact with lectins or other proteins in the extracellular spaces and may be involved in the cellular response to extracellular oligosaccharide signal molecules [Norman et al. (1990) *Planta* 181:365–373]. Since AGPs interact with Yariv antigens and flavonol glycosides [Jermyn (1978) *J. Plant Physiol.* 5:563–571], they have been thought to have lectin-like properties. The molecular structure of AGPs has been proposed [Randall et al. (1989) *Food Hydrocolloids* 3:65–75] to resemble a type of block copolymer wherein carbohydrate blocks are covalently linked to a central polypeptide chain, thus explaining its ability to sterically stabilize emulsions and dispersions.

Plant AGP genes are not known in the prior art and the nucleotide sequence of a plant AGP gene has not been published to date. Very recently, it was reported [Sheng et al. (1993) Abstract no. 639 in *Supplement to Plant Physiol.* 102, Number 1, May 1993] that a PCR strategy is being used to clone potato tuber lectin, extensins and AGP sequences from a potato tuber cDNA library. It was reported that PCR products which hybridized to a carrot extensin probe gave several putative clones which are currently under investigation. No clones corresponding to AGP genes were disclosed.

The process of obtaining an AGP clone has been found to be complex and problematic. Two of the problems associated with AGPs and their genes are (1) the very high redundancy associated with the characteristic amino acid sequence of an AGP peptide, i.e., (a) a high hydroxyproline content and (b) regions containing a high content of hydroxyproline, alanine, serine, and threonine (OAST); and (2) the GC-richness of corresponding oligonucleotides leading to problems with the specificity of hybridization. Indistinct and imprecise alignment during nucleic acid hybridization, for example, in the PCR technique, has resulted in lack of success in the ability to obtain an AGP clone. This results in the amplification of incorrect sequences when compared to the original template. Plants are also known to contain a variety of glycine-rich proteins which are also encoded by GC-rich DNA. Applicants' disclosure circumvents this problem and enables the isolation of AGP genes.

Two approaches to the isolation of the AGPs from plant extracts have been used in previous studies. One approach consists of classical fractionation of plant extracts [Fincher et al. (1974) *Aust. J. Biol. Sci.* 27:117–132; Aspinall (1969) *Adv. Carbohydrate Chem.* 24:333–379]. A convenient initial fractionation of extracts is treatment to saturation with $(NH_4)_2SO_4$, which does not usually precipitate AGPs. Subsequent ion-exchange and affinity chromatography can be used to isolate the AGPs.

Another approach to the isolation of AGPs from plant extracts is precipitation with a class of dyes prepared by coupling diazotized 4-aminophenyl glycosides to phloroglucinol [Jermyn et al. (1975), supra]. These dyes were first prepared by Yariv et al. (1962) *Biochem. J.* 85:383–388) as precipitating antigens for antibodies to glycoside determinants, and the β-glycosyl artificial carbohydrate antigen was shown to precipitate an arabinose-and-galactose-containing polymer from soya bean, jack bean and maize [Yariv et al. (1967) *Biochem. J.* 105:1c–2c]. Since then, this precipitation reaction has been widely used to isolate AGPs from extracts of seeds of every taxonomic group of flowering plants, as well as leaf extracts and callus-culture filtrates [Jermyn & Yeow (1975) *Aust. J. Plant Physiol.* 2:501–531; Anderson et al. (1977), supra; and review by Clarke et al. (1979), *Phytochemistry* 18:521–540].

These dyes have also been used as cytochemical reagents for the localization of AGPs in plant tissues [Clarke et al. (1975), *J. Cell Sci.* 19:157–167; Clarke et al. (1978), *Q. Rev. Biol.* 53:3–28]. The nature of the binding of AGP to the Yariv reagent is not understood, but it is likely to involve both carbohydrate and protein residues. The binding of Yariv's reagent to AGP is not affected by removal of the arabinose residues [Glesson et al. (1979), supra; Akiyama et al. (1981), supra], but is abolished by progressive acid hydrolysis of the AGP [Fincher et al. (1983), supra].

In higher plants AGPs are also classified as belonging to a group of proteins characterized by hydroxyproline-rich domains. These hydroxyproline-rich glycoproteins (HRGPs) are also characterized by carbohydrate side chains that contain arabinose and galactose. The group has been traditionally divided into three main classes: the cell wall associated extensins; the soluble arabinogalactan-proteins (AGPs), and the solanaceous lectins. The differences between these groups are summarized in Table 1.0. The most important factors in the classification of the HRGPs are: the amount, composition, and sequence of their carbohydrate component, the sequence and composition of the polypeptide backbone, the linkage between carbohydrate and protein and its localization.

A new group of proteins, the proline-rich proteins, has been described recently. The proline-rich proteins (PRPs) have also been referred to as the hydroxyproline/proline-rich proteins or the repetitive proline-rich proteins. Amino acid compositions of some PRPs [Averyhart-Fullhard et al. (1988) *Proc. Natl. Acad.* 85:1082–1085; Datta et al. (1989) *Plant Cell* 1:945–952; Kleis-San Francisco et al. (1990) *Plant Physiol.* 94:1897–1902] indicated equimolar amounts of proline and hydroxyproline. However, the PRPs do not appear to be glycosylated and, in this way, are distinguished from the HRGPs (hydroxyproline-rich glycoproteins).

As indicated in Table 1.0, AGPs are readily distinguished from extensin and lectin HRGPs. Extensins are highly positively charged HRGPs, are rich in hydroxyproline, lysine, tyrosine, serine, and proline, possess carbohydrate side chains that are rich in arabinose, and are tightly associated with cell walls. The high lysine content of the extensins contributes to their positive charge, and the tyrosine in extensin may form intermolecular [Stafstrom and Staehelin (1986), *Plant Physiol.* 81:234–241] and intermolecular isodityrosine linkages that have been implicated in cross-linking extensin in vitro [Everdeen et al. (1988) *Plant Physiol.* 87:616–621] and in vivo [Cooper and Varner (1983) *Biochem. Biophys. Res. Comm.* 112:161–167; Biggs and Fry (1990) *Plant Physiol.* 92:197–204].

Hydroxyproline accounts for 30–50% of the amino acids in extensin and is found in short peptides that are repeated a number of times in the molecule. The core peptide that is most commonly encoded by extensin genes is $Ser(Pro)_4$ (Table 1.0), which may be post-translationally modified to $Ser(Hyp)_4$. Recently, amino acid sequences have been obtained from extensin-like molecules that do not contain the $Ser(Hyp)_4$ peptides [Kieliszewski et al. (1990) *Plant Physiol.* 92:316–326; Li et al. (1990) *Plant Physiol.* 92: 327–333].

The carbohydrate side chains of extensins consist of short arabinosides linked to hydroxyproline, and single galactose residues linked to serine. The function of the carbohydrate side chains of extensins is not clear, but there is some evidence that they stabilize the polyproline II helix, which gives extensin its characteristic rod-like shape; Stafstrom and Staehelin (1986) *Plant Physiol.* 81:242–246.

The solanaceous lectins are positively charged glycoproteins that are identical to the extensins in the composition and structure of their carbohydrate side chains. Two important features discriminate the solanaceous lectins from extensins; their localization in the vacuole and cytoplasm [Millar et al. (1992) *Biochem. J.* 283:813–821], and their relatively high cysteine content (10–12 Mol %; Showalter (1993) *Plant Cell* 5:9–23]. The cysteine in the potato lectin is concentrated in a single domain of the molecule that contains the carbohydrate binding site, and is distinct from the domain that is rich in hydroxyproline and glycosylated [Ashford et al. (1982) *Biochem. J.* 201:641–645]. The different lectins are immunologically cross-reactive [Kilpatrick et al. (1980), *Biochem. J.* 185:269–272], and contain both carbohydrate and protein epitopes [Ashford et al. (1982) supra].

The features that distinguish the AGPs from the extensins and solanaceous lectins are listed in Table 1.0. The AGPs usually have a negative to neutral overall charge, and are soluble in aqueous buffers. A characteristic feature of the AGPs is their ability to bind β-glucosyl Yariv reagent, whereas extensins and lectins do not bind the Yariv reagent.

Carbohydrate forms a major portion of the mass of AGPs [Clarke et al. (1979), supra; Fincher et al. (1983), supra]. The majority of the AGPs that have been chemically characterized contain less than 10% (w/w) protein [Clarke et al. (1979), supra; Fincher et al. (1983), supra], but the AGPs from *Cannabis sativa* leaves (25% [w/w] protein), rice bran (27% [w/w] protein), and sycamore suspension cultures (19–38% [w/w] protein), are notable exceptions [Clarke et al. (1979), *Phytochem.* 18:521–540]. The protein backbones of AGPs often contain domains that are rich in hydroxyproline, alanine, serine, and threonine.

SUMMARY OF THE INVENTION

The present invention provides for the first time DNA fragments encoding protein backbones of plant arabinogalactan proteins (nonglycosylated AGPs). Specific embodiments of the invention present cDNA clones encoding nonglycosylated AGPs from cell suspension cultures of *Nicotiana alata* (NaAGP1), *Nicotiana plumbaginafolia* (NpAGP1), and *Pyrus communis* (PcAGP23 and PcAGP9) and from *Nicotiana alata* styles (Na35_1). Full length and partial nucleotide sequences of the cDNAs encoding said nonglycosylated AGPs are disclosed. DNA recombinant vectors containing these cDNAs are also provided. In further embodiments of the invention, genomic DNAs encoding plant nonglycosylated AGPs and recombinant vectors containing said genomic DNAs are provided. This invention further contemplates the use of oligonucleotide probes based on the amino acid sequence of plant AGPs for the detection of hybridizing sequences and the isolation of monocot and dicot AGP genes.

TABLE 1.0

Biochemical and structural features of hydroxyproline-rich glycoproteins (HRGPs)

| | HRGPs | | |
|---|---|---|---|
| Property | Extensins | Arabinogalactan-proteins (AGPs) | Solanaceous Lectins |
| % Protein (w/w) | 40–50 | 2–10 | 50–60 |
| Galactose/Arabinose | <1 | >1 | <1 |
| Galactose Linkage Types | terminal | 1,3-linked 1,3,6-linked 1,6-linked terminal | terminal |
| Arabinose Linkage Types | 1,2-linked 1,3-linked terminal | terminal | 1,2-linked 1,3-linked terminal |
| Glycopeptide linkages | O-linked: Ara—Hyp & Gal—Ser | O-linked: Gal—Hyp | O-linked: Ara—Hyp & Gal—Ser |
| Abundant Amino Acids | Hyp, Lys, Tyr, Ser & Pro | Hyp, Ala & Ser | Hyp, Cys, Gly & Ser |
| mol % Hyp (of protein domains) | >30 | >15 | >13 |
| Amino Acid Repeats | Ser(Hyp)$_4$ | ? | ? |
| Isoelectric Point | 9.5–11 | 2–5 | 9.5 |
| Localization | Cell wall | Extracellular matrix; plasma membrane | Cytoplasm & vacuole |
| β-glucosyl Yariv reagent binding | No | Yes | No |

The invention also provides isolated plant AGP peptides and amino acid sequences of AGP peptide fragments. AGP peptides were isolated from *Nicotiana alata*, *Nicotiana plumbaginafolia*, and *Pyrus communis*. The amino acid sequences obtained from isolated AGP peptide fragments were either enriched in hydroxyproline or not enriched in hydroxyproline. In particular, hydroxyproline-enriched sequences were characterized by having (i) a high content of hydroxyproline and/or (ii) a high content of hydroxyproline, alanine, serine, and threonine (OAST-enriched). The sequences that were immediately useful in obtaining an AGP gene were those sequences that were not enriched in hydroxyproline, and not enriched in hydroxyproline, alanine, serine, and threonine content (not OAST-enriched). To date the amino acid sequence of an intact plant AGP is not publicly available. cDNAs thought to encode AGPs have been described, but evidence of a match between these sequences and amino acid sequence data from isolated AGPs is missing in these cases.

The invention further provides a substantially pure AGP having an amino acid sequence which is essentially that derived from a nucleotide sequence of an AGP gene. Specific embodiments of the invention provide an AGP comprising an amino acid sequence consisting essentially of that derived from the nucleotide sequence of an AGP gene from *Nicotiana alata, Nicotiana plumbaginafolia,* or *Pyrus communis.*

It is also an object of the invention to provide a method for obtaining a plant AGP gene. This method comprises the step of obtaining from an AGP peptide a fragment having an amino acid sequence that is hydroxyproline-poor, e.g., not enriched in OAST content. This hydroxyproline-poor sequence is then used to design a nucleotide primer which can be used to obtain, for example, a PCR fragment useful in screening a plant gene library for a hybridizing clone. Applicants' approach is novel and contrary to that generally used. Usually, a sequence which particularly characterizes an AGP (i.e., a sequence that is hydroxyproline-rich or enriched in OAST content) is utilized to design an oligonucleotide primer for use in obtaining a hybridizing clone. In Applicants' approach, a hydroxyproline-rich peptide sequence which particularly characterizes an AGP protein is not utilized, and is avoided; instead, a sequence which does not comprise a characterizing sequence of an AGP (i.e., a hydroxyproline-poor sequence) is utilized for the isolation of an AGP gene. In specific embodiments of the invention, peptide sequences which were not enriched in hydroxyproline or OAST content were isolated from *N. alata, N. plumbaginafolia,* and *P. communis.* These peptide sequences enabled the isolation of corresponding cDNA clones.

The present invention also provides a method for obtaining an AGP gene by utilizing a hydroxyproline-rich AGP sequence. Prior to the instant disclosure, public knowledge of hydroxyproline-rich AGP fragments has not enabled the isolation of corresponding AGP genes, due to difficulties imposed by resultant GC-rich domains. A method is provided herein that enables the use of a specific hydroxyproline-rich AGP peptide sequence for the isolation of a corresponding gene. The approach for using a hydroxyproline-rich sequence comprises the use of long guessmers combined with single-stranded antisense RNA probes for the screening of a library. The use of a long guessmer together with an RNA probe overcomes the problems presented upon using short oligonucleotide probes. A long guessmer can more easily accommodate mismatches and the use of an antisense RNA probe allows "U" to be used at the third position of the anticodon for AST amino acids, thus increasing the likelihood of the guessmer hybridizing to the target sequence. The resultant RNA molecule can be heavily labeled, permitting greater levels of detection, and also can bind more strongly to its target sequences than a DNA probe.

The invention also provides specific AGP cDNA sequences and specific oligonucleotide probe sequences for screening cDNA libraries to isolate specific plant AGP genes. For example, in specific embodiments, the following cDNA clones are provided:

| Source | cDNA clone |
| --- | --- |
| *N. alata* cell suspension culture | NaAGP1 (SEQ ID NO:24) |
| *N. plumbaginafolia* cell suspension culture | NpAGP1 (SEQ ID NO:25) |
| *P. communis* cell suspension culture | PcAGP23 (SEQ ID NO:49) |
| *P. communis* cell suspension culture | PcAGP9 (SEQ ID NO:66) |

-continued

| Source | cDNA clone |
| --- | --- |
| *P. communis* cell suspension | PcAGP2 (SEQ ID NO:91) |
| *N. alata* style | Na35_1 (SEQ ID NO:63) |
| *N. alata* style | AGPNal 1 (SEQ ID NO:72) |

The invention further provides antisense RNA probes designed such that they comprise one or more nucleotide sequences encoding amino acid sequences that are OAST-rich, representing the same or different AGPs. Also provided are RNA probes comprising a nucleotide sequence encoding an OAST-rich consensus sequence for plant AGPs. A guessmer-antisense RNA probe approach may also be used with an OAST-poor AGP sequence to isolate a corresponding AGP gene.

It is also an object of the present invention to provide an antibody to a substantially pure plant AGP, or fragment thereof, comprising an amino acid sequence consisting essentially of a whole or partial amino acid sequence derived from a plant AGP gene. Also provided is an antibody to an isolated AGP peptide fragment that is not enriched in hydroxyproline. Also provided by the invention is an antibody to a synthetic AGP peptide, or fragment thereof.

This invention further contemplates the use of antibodies to substantially pure AGP peptides, AGP peptide fragments not enriched in hydroxyproline or OAST content, or synthetic AGP peptides for (a) the detection, isolation, or diagnosis of AGPs in AGP-containing mixtures or tissues, and (b) in reducing or inhibiting natural biological and chemical AGP activities. It is recognized that polyclonal and monoclonal antibodies to AGPs or AGP peptides are most effective in AGP-containing specimens that are deglycosylated or otherwise preconditioned to expose the protein backbone of the AGP.

This invention also provides a genetically-engineered DNA molecule comprising a plant AGP gene under control of a heterologous promoter such that a nonglycosylated AGP is expressed. In a specific embodiment of the invention, an AGP gene obtained from *N. alata., N. plumbaginafolia,* or *P. communis* is inserted behind a heterologous promoter (e.g. a bacterial, viral, plant, etc., promoter) in a host cell such that a nonglycosylated AGP is expressed.

It is also an object of the invention to provide a recombinant DNA molecule comprising a plant AGP gene under control of a heterologous promoter such that a glycosylated AGP is expressed. For example, this invention contemplates the utilization of the expressed nonglycosylated AGP as a substrate for glycosylating and carbohydrate-protein linking enzymes (e.g., prolyl hydroxylase, glycosyl transferase, etc., to produce a glycosylated AGP). It is also an object of the invention to provide a host cell (for example, monocots, dicots, etc.) transformed with genetically-engineered DNA comprising a plant AGP gene under control of a heterologous promoter such that a glycosylated AGP is expressed. It is a further object of the invention to provide a plant AGP gene-transformed host cell capable of over-producing or under-producing nonglycosylated AGP. It is an additional object of the invention to provide an AGP gene-transformed host cell capable of further metabolic processing of an expressed nonglycosylated AGP.

This invention further provides a DNA fragment comprising a plant AGP promoter. In specific embodiments of the invention, AGP promoters are isolated from *N. alata, N. plumbaginafolia,* and *P. communis.* Subsequently, a recombinant DNA molecule is genetically engineered to comprise a plant AGP promoter situated adjacent to a heterologous structural gene such that the structural gene is expressed under the control of the plant AGP promoter. Also, the coding region of the gene could be used behind tissue-specific promoters to express the AGP at particular sites in a whole plant. This could change the phenotypes with respect to such functions as pest resistance, for example.

The instant invention provides a source of AGP that is not dependent upon its isolation from plant exudates, e.g., gum arabic, guar gum, etc. The availability of natural sources of AGP-containing gums, e.g., from trees, roots, seeds, seaweed, microbes, etc., present problems associated with harvesting, climate, man-power, fermentation, isolation, purity, and high costs. The production of AGPs using recombinant gene technology ensures (a) a method of supplying AGP that is independent of harvesting or fermentation requirements and problems, (b) that enables high levels of quality control, (c) that provides a supply of substantially pure AGP product, (d) that permits an overproduction of AGP in a host cell, and (e) that can be adapted to produce a specifically engineered AGP having desired properties. Thus, this invention provides a means for supplying the functions and utilities of plant gums, e.g., gum arabic, etc., without the need for finding renewable but shrinking natural sources of plant gums. These functions find wide applications as thickening, gelling, emulsifying, dispersing, suspending, stabilizing, encapsulating, flocculating, film-forming, sizing, adhesive, binding and/or coating agents, and/or as lubricants, water-retention agents, and coagulants.

BRIEF DESCRIPTION OF DRAWINGS

FIG. 1A-1 presents two complementary guessmers annealed to each other to form a double-stranded construct containing the T7 promoter. FIG. 1A-2 presents a short primer annealed to form double-stranded T7 promoter sequence. B. Double oligonucleotide probes: FIG. 1B-1 presents two guessmers annealed to each other through the complementary adaptor sequences at their 3'-ends. FIG. 1B-2 presents two guessmers annealed to a mediator DNA through their adaptor sequences ▭: adaptor sequence. Other promoters, for example, T3 or Sp6 RNA polymerases, may also be used.

FIGS. 1D-1 and 1D-2 present a PCR strategy for cloning of the NaAGP1 gene corresponding to an amino acid sequence of a deglycosylated AGP backbone from N. alata cell suspension culture. The sequences of the NaR1, NaF1, and NaF2 primers used to isolate the clone for NaAGP1 are given in Table 1.1 and FIG. 1E.

FIG. 1E presents a nucleotide and the derived amino acid sequences (SEQ ID NO:21) of the 160-bp primer extension fragment. The derived amino acid sequence corresponding to the peptide sequence by protein microsequencing is underlined. The asterisks (*) indicate the amino acids of the peptide obtained by direct microsequencing which are identical with the derived sequence. The sequences of the two oligonucleotides (NaF1, NaF2) designed for the amplification of the 3'-fragment of the AGP gene are double-underlined. The nucleotide sequence corresponding to the primers (NaR1) is underlined.

FIGS. 1F-1 and 1F-2 present the nucleotide and predicted amino acid sequences (SEQ ID NO:24) the NaAGP1 cDNA from N. alata cell suspension culture (NaAGP1). The nucleotide sequence obtained by PCR, which does not overlap with the cDNA clone, is in italics. The derived amino acid sequence corresponding to the peptide sequence by protein microsequencing is underlined. The asterisks (*) indicate the amino acids of the peptide obtained by direct microsequencing which are identical with the derived sequence. A predicted signal sequence is dot-underlined. X=undetermined residue.

FIGS. 1H-1 and 1H-2 present the nucleotide and predicted amino acid (SEQ ID NO:25) sequences of an N. plumbaginafolia AGP derived from cell suspension culture (NpAGP1). The derived amino acid sequences corresponding to the peptide sequence by protein microsequencing is underlined. The asterisks (*) indicate the amino acids of the peptide obtained by direct microsequencing which are identical with the derived sequence. O: hydroxyproline.

FIGS. 1I-1 and 1I-2 present the alignment of the derived amino acid sequences of the NaAGP1 (SEQ ID NO:24) and NpAGP1 (SEQ ID NO:25) cDNAs. The derived amino acid sequence of NaAGP1 cDNA is shown in the upper line and that of the NpAGP1 shown in the lower line. Identical aligned residues are indicated with 'l'. Gaps were introduced when required to maximize the alignment.

FIGS. 1J-1, 1J-2, 1J-3 and 1J-4 present the alignment of the NaAGP1 (SEQ ID NO:24) and the NpAGP1 (SEQ ID NO:25) cDNA sequences. The nucleotide sequence of the NaAGP1 cDNA is shown in the upper line and that of the NpAGP1 shown in the lower line. Identical aligned residues are indicated with 'l'. Gaps were introduced when required to maximize the alignment.

FIGS. 1K-1 and 1K-2 present northern blot analyses of the NaAGP1 and NpAGP1 genes.

FIG. 1K-1: Total RNA was isolated from N. alata (1) leaves, (2) pollen, (3) styles, (4) stems, (5) petals, (6) roots and (7) suspension-cultured cells. Equal amounts (10 µg/lane) of RNA were fractionated on formaldehyde agarose gels, transferred to Hybond-N membranes, and hybridized with $^{32}$P-labeled 5'-probe (1–540 bp) and 3'-probe (541–1700 bp) of the NaAGP1 cDNA respectively.

FIG. 1K-2: Total RNA (10 µg/lane) isolated from suspension-cultured cells of N. alata and N. plumbaginafolia was blotted and hybridized with the NaAGP1 cDNA.

The size of RNA transcripts is indicated at the right.

Figure 2A:
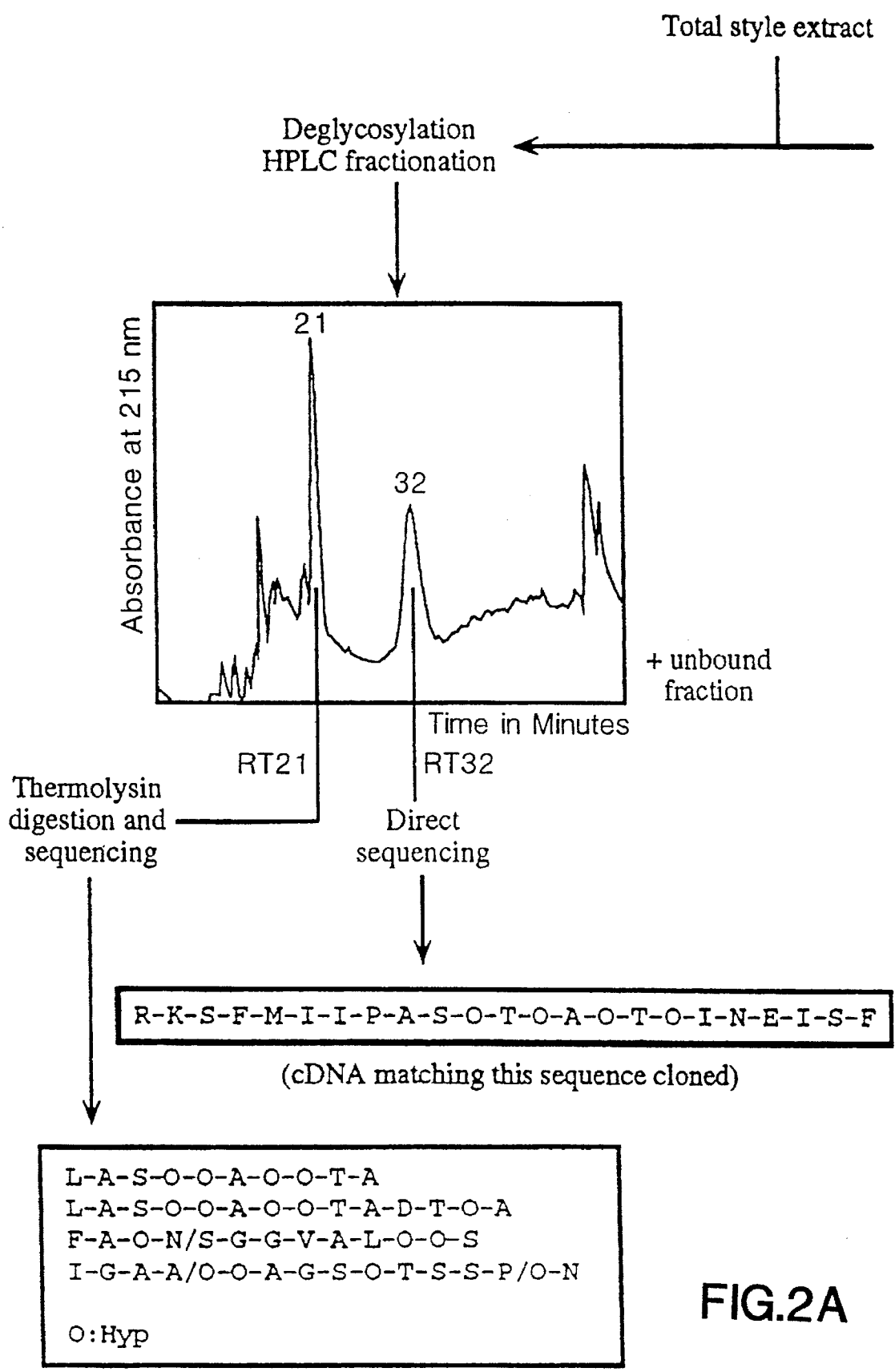

FIGS. 2A–2D present a flow chart describing the isolation and sequencing of AGP peptides from cell suspension culture filtrates of Nicotiana plumbaginafolia. FIG. 2A indicates that four sequences (SEQ ID NOS:26, 27, 28 and 29, respectively) were obtained from Peak RT21 and a sequence (SEQ ID NO:30) was obtained from peak RT32.

Figure 3A:
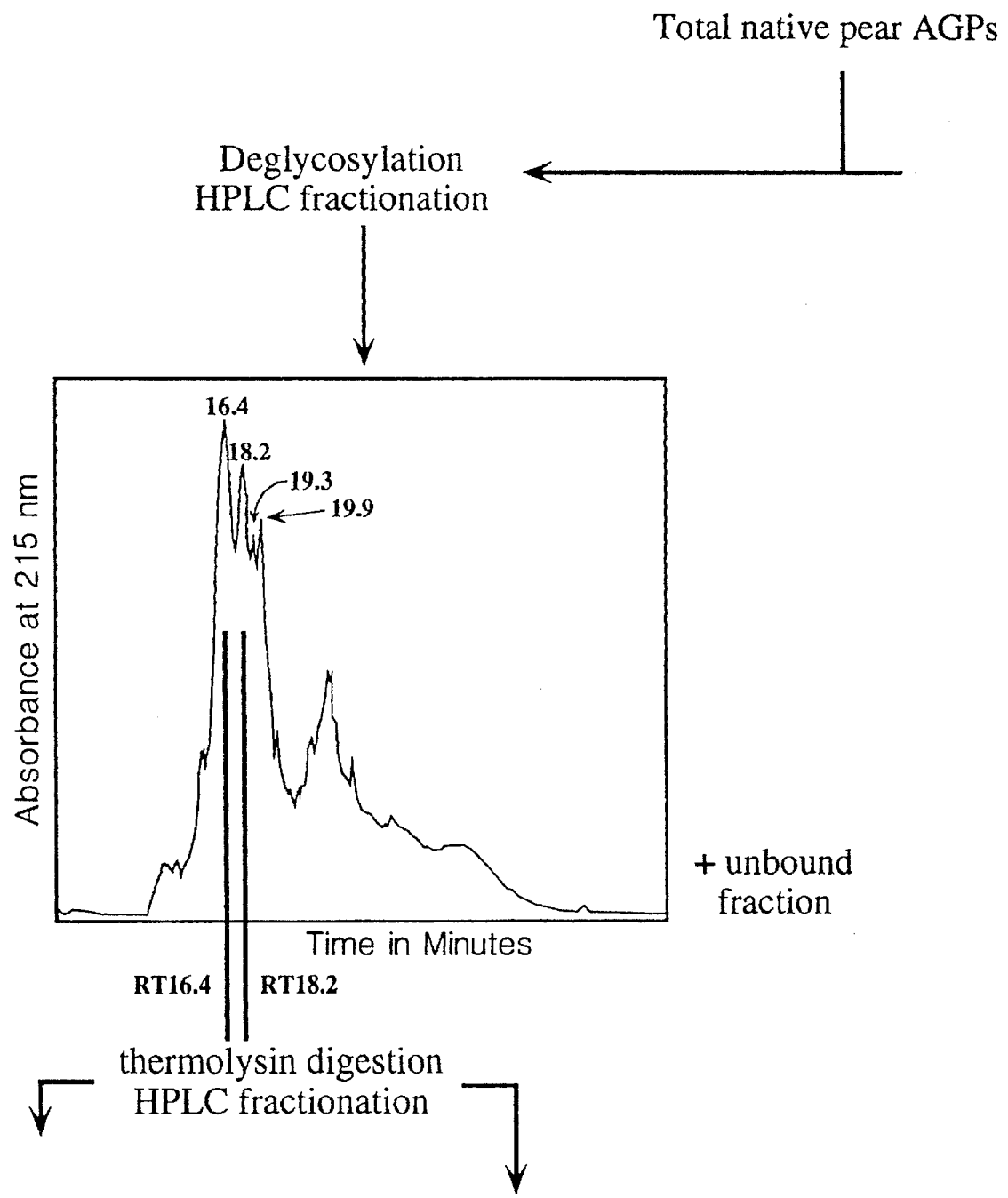
Figure 3B:
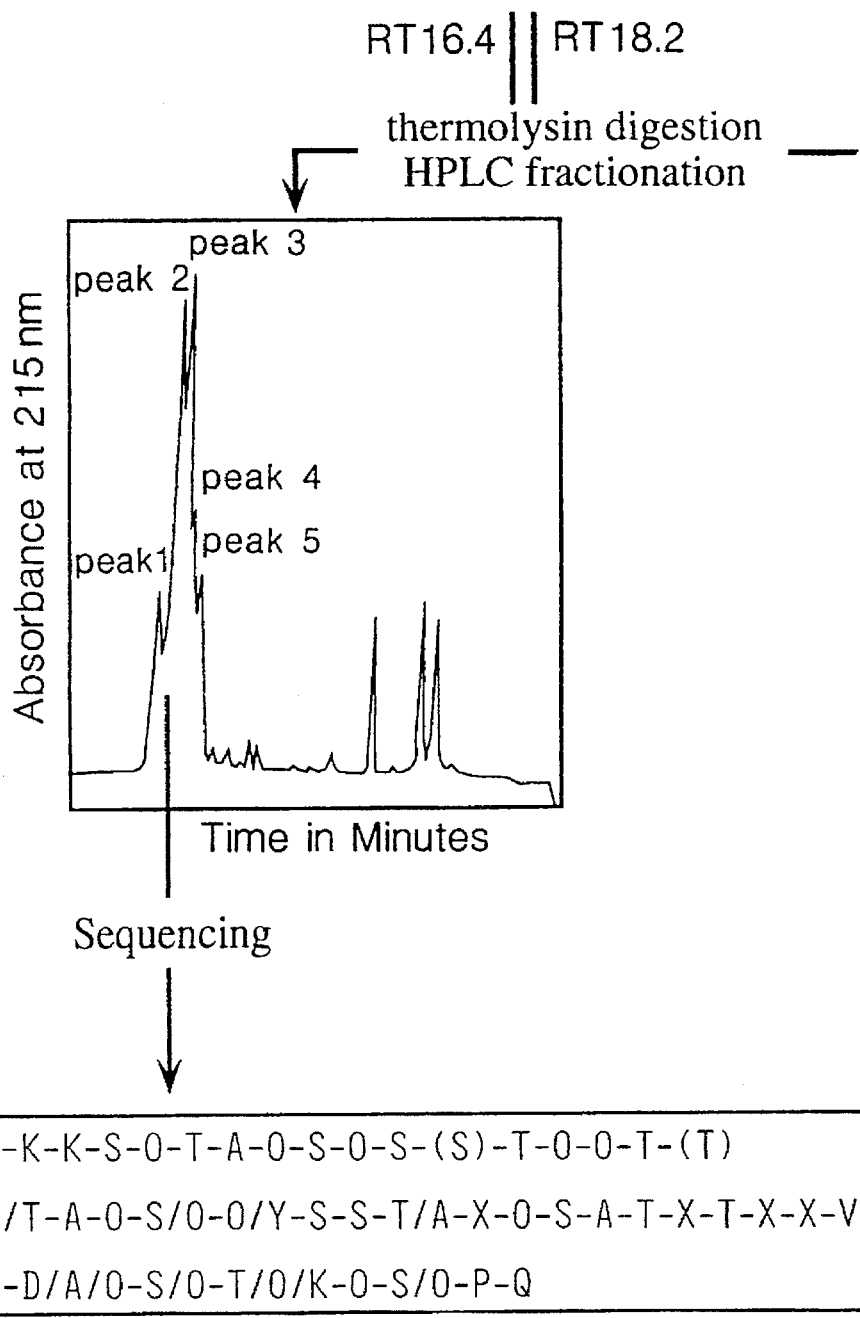
Figure 3C:
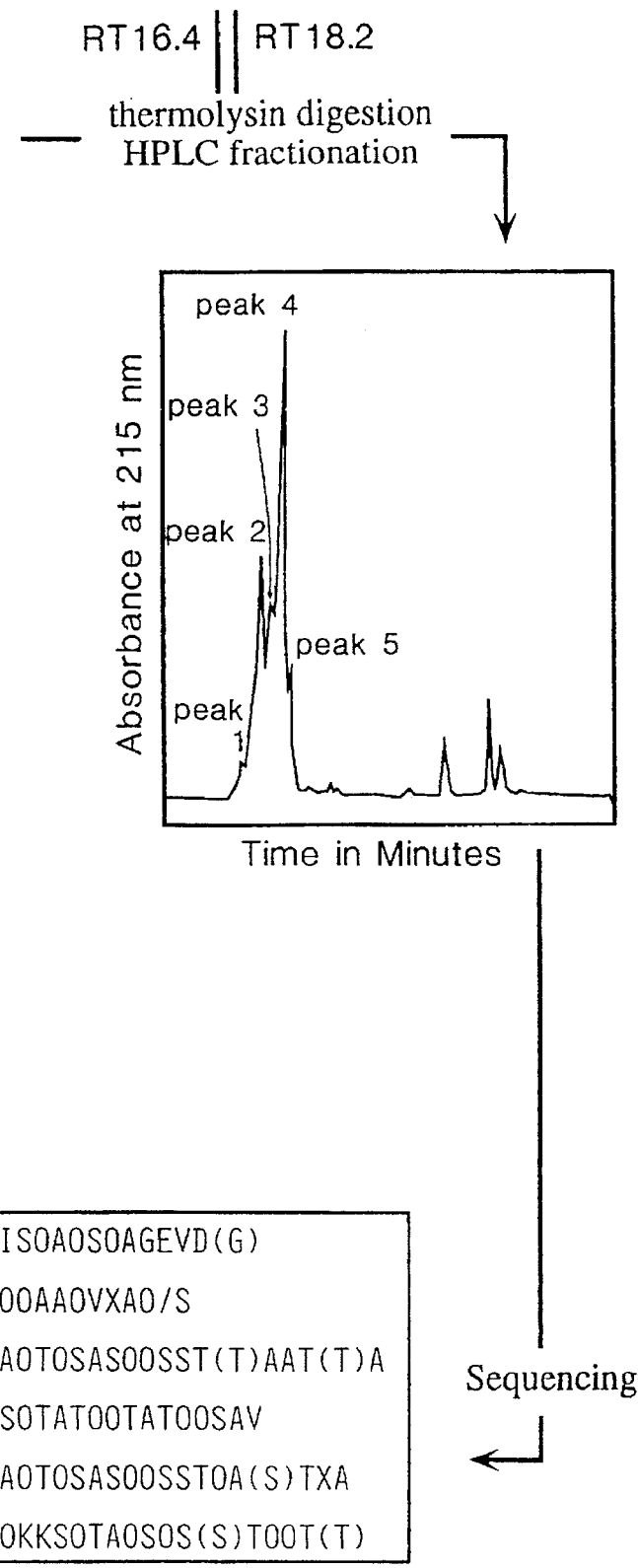

FIGS. 3A–3F present a flow chart describing the isolation and sequencing of AGP peptides from cell suspension culture filtrates of *Pyrus communis*. FIG. 3B indicates the resolution of Peak RT16.4 into three sequences (SEQ ID NOS:31, 32 and 33, respectively). FIG. 3C present the resolution of Peak RT18.2 into six sequences, namely, SEQ ID NOS:34, 35, 36, 37, 38 and 31, respectively. FIGS. 3E and 3F presents the resolution of the deglycosylated Peak RT7.8 into six peptides having sequences SEQ ID NOS:39–44, respectively.

FIG. 3G presents the nucleotide and derived amino acid sequences (SEQ ID NO:48) of the 350-bp PCR fragment. The derived amino acid sequence matching the peptide sequence by protein sequencing is underlined. The nucleotide sequence corresponding to the PcA23F2a primers is double-underlined.

Figures 1, 1B:
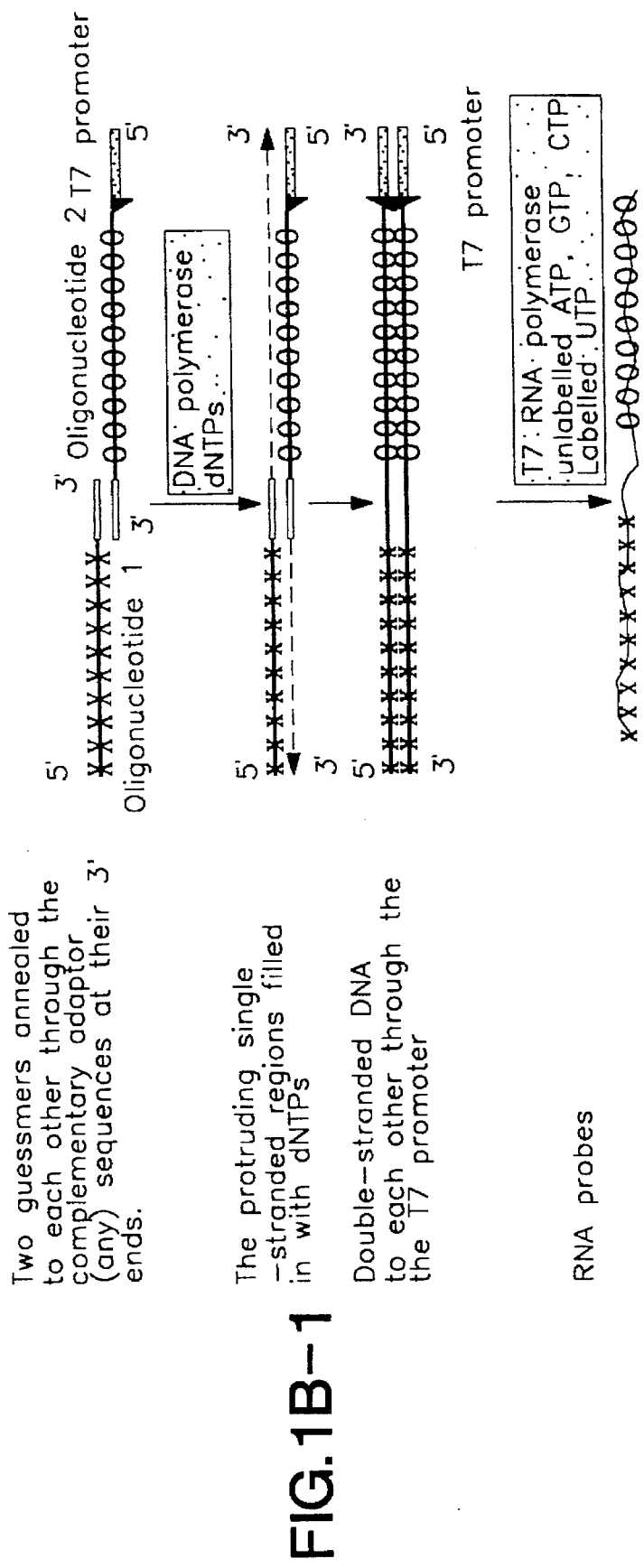
Figure 1C:
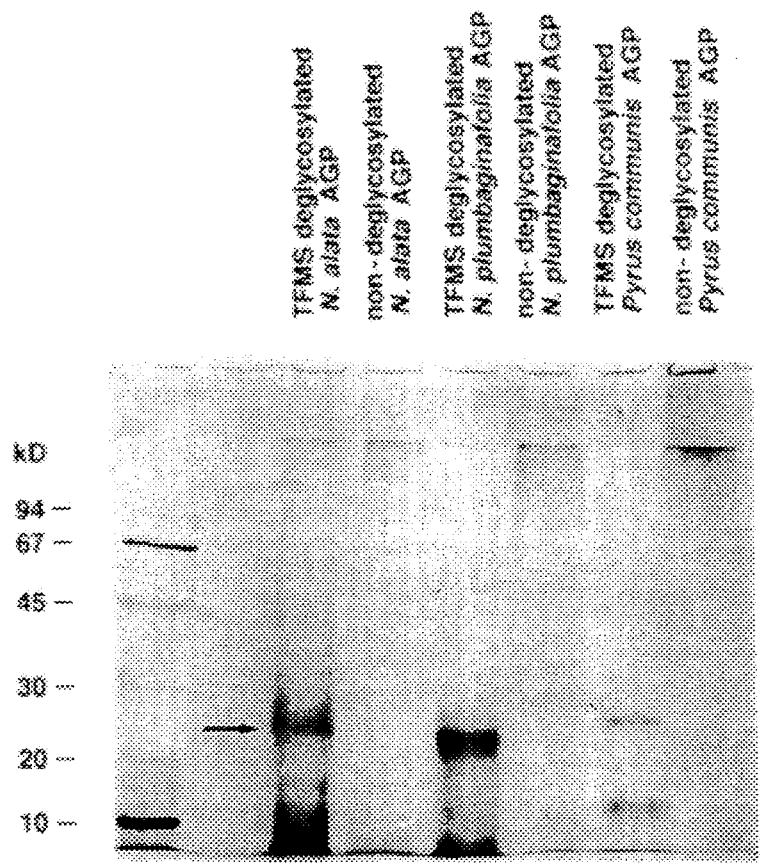
FIG. 1C presents a Coomassie blue stained SDS-PAGE gel blot of deglycosylated and non-deglycosylated AGPs from various sources. AGPs were isolated from suspension culture filtrates of N. alata; N. plumbaginafolia and pear (Pyrus communis) by Yariv precipitation and deglycosylated with trifluoromethanesulfonic acid (TFMS). The deglycosylated and non-deglycosylated AGPs were separated on a 17.5% SDS-PAGE gel and blotted onto a PVDF membrane. After staining with Coomassie blue, the major band (MW 20–30 kD, indicated by an arrow) from deglycosylated N. alata AGPs was excised and sequenced.
Figures 1, 1D:
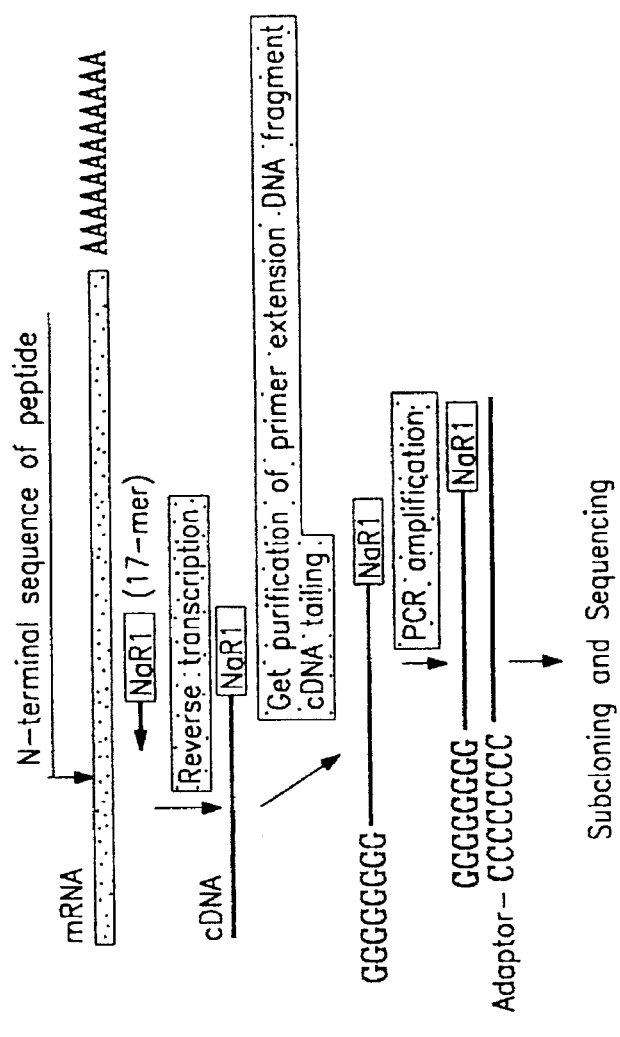
Figures 1, 1D, 2:
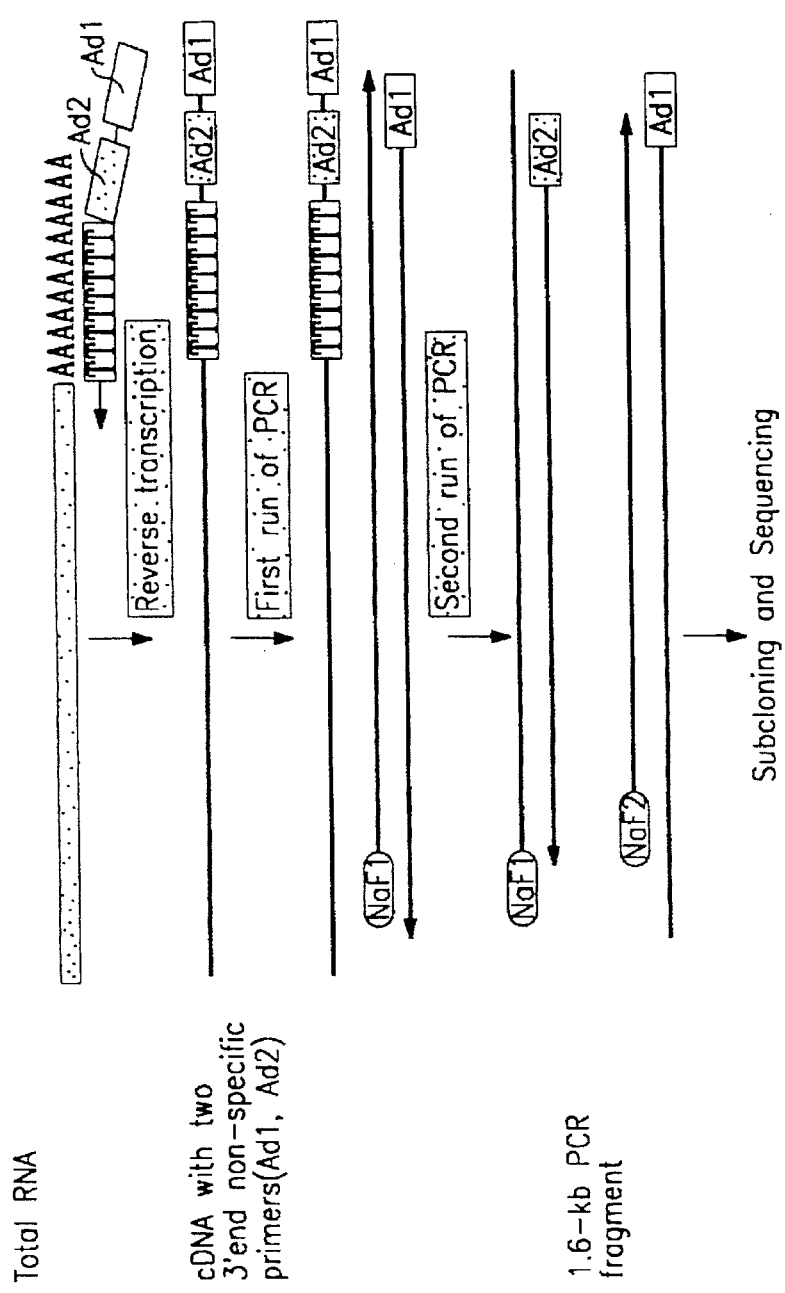

FIGS. 3H-1 and 3H-2 present the nucleotide and predicted amino acid sequences (SEQ ID NO:49) of PcAGP23 cDNA clone encoding an AGP backbone from pear cell suspension culture. The translational initiation and stop sites are in bold-face. The predicted secretion signal is underlined with dots. The two potential N-glycosylation sites are double-underlined. The sequence matching the peptide sequences obtained from the AGP protein backbone are underlined. The proline residues which are hydroxylated, as identified by protein sequencing, are indicated by an "O" underneath.

Figure 4A:
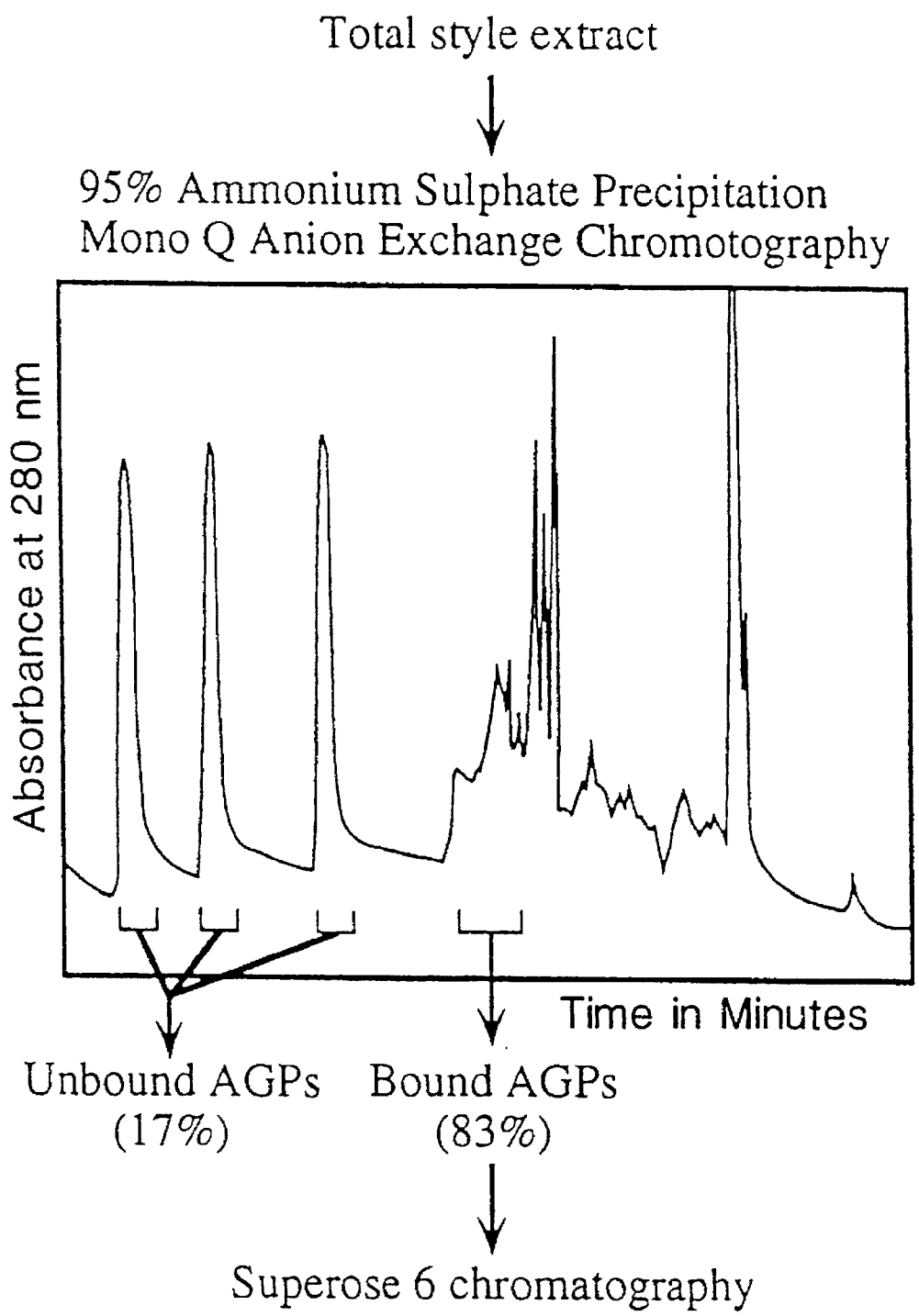
Figure 4B:
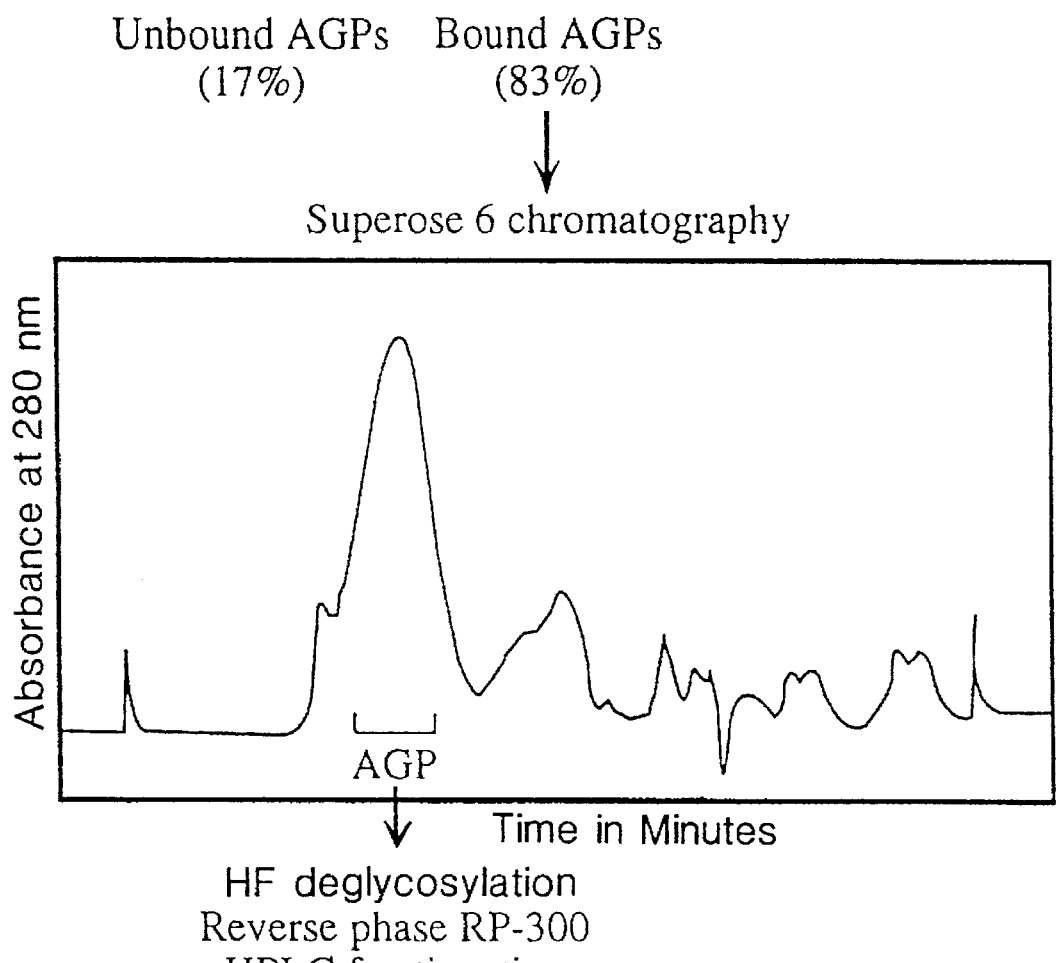
Figure 4C:
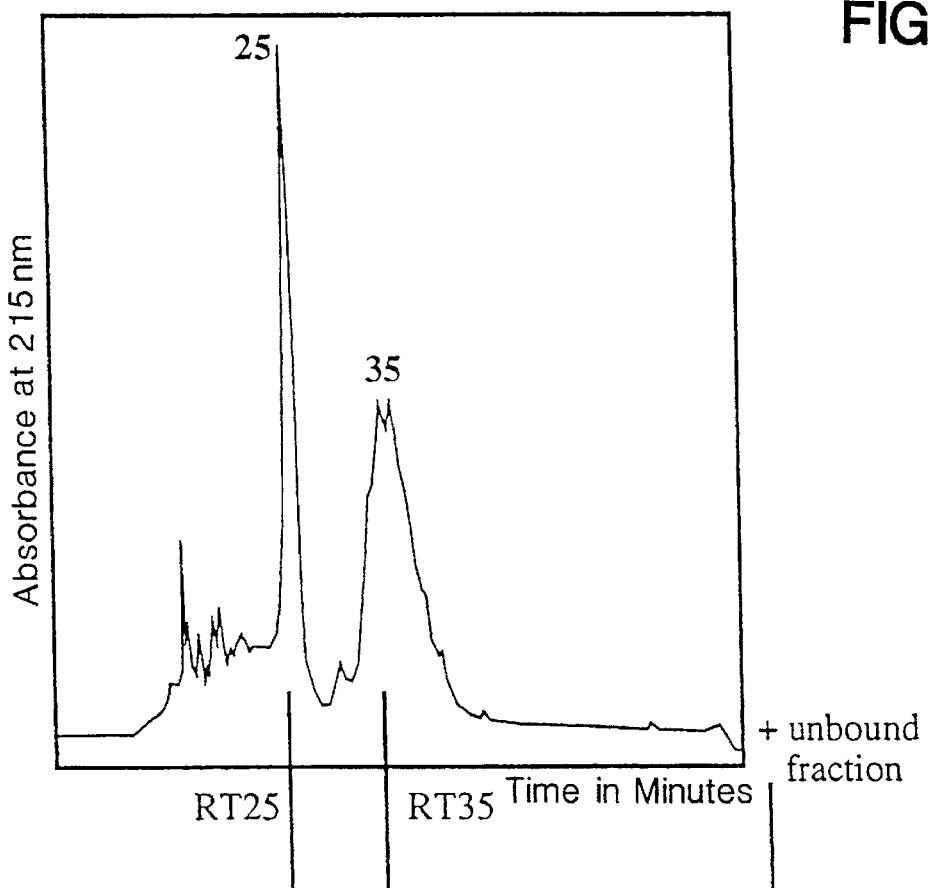

FIGS. 4A–4C present a flow chart describing the isolation and sequencing of AGP peptides from style extract of *Nicotiana alata*. Peak RT25 comprised four sequences (SEQ ID NOS:50, 51, 52 and 53) and Peak RT35 also comprised four sequences (SEQ ID NOS:54, 55, 56 and 57).

Figure 4D:
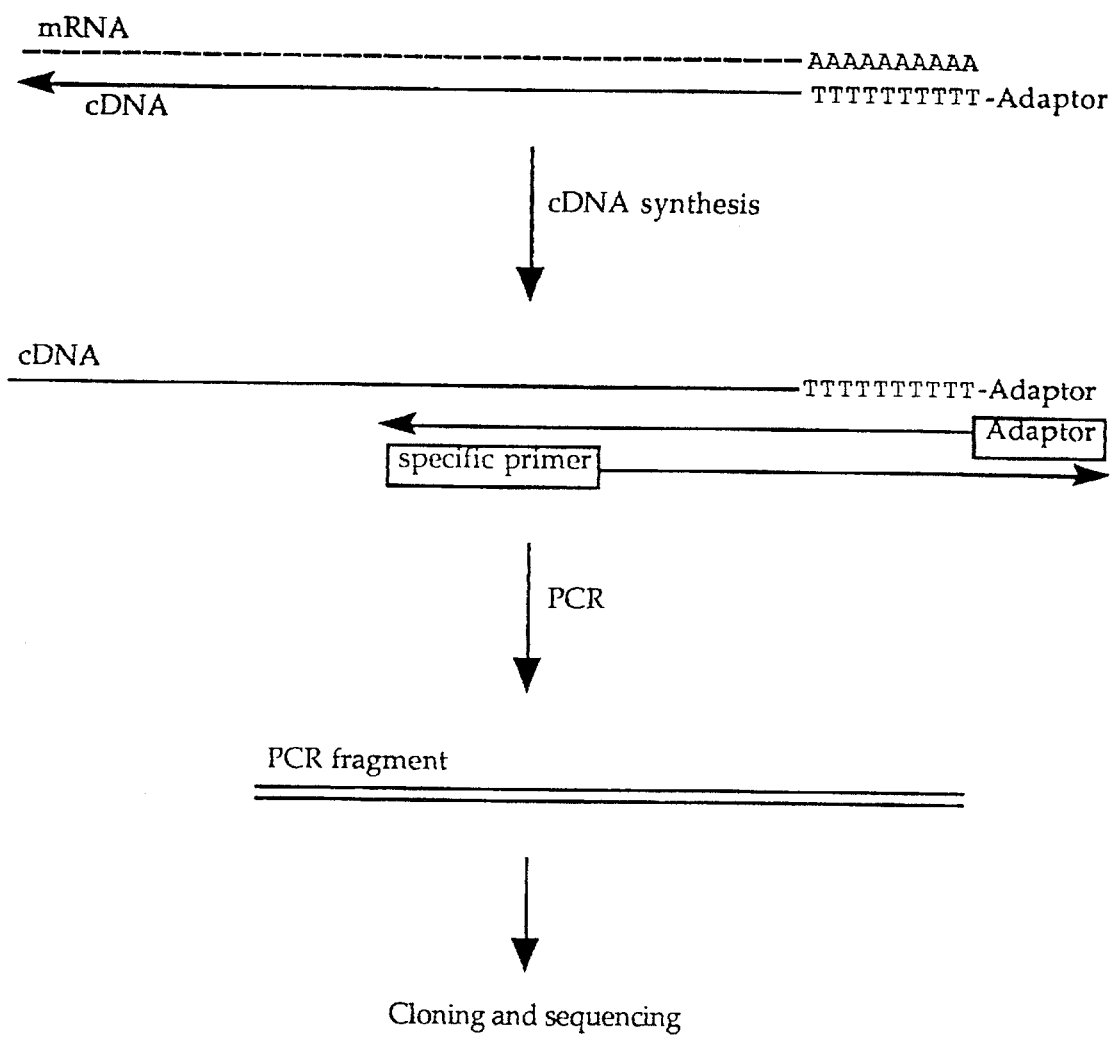

FIG. 4D presents the cloning strategy of the Na35_1 gene.

FIG. 4E presents the nucleotide sequence (SEQ ID NO:62) of the PCR fragment by using RT35-specific primer and the predicted amino acid sequences. The derived amino acid sequence corresponding to the peptide sequence by protein microsequencing is underlined. The RT35 specific primer sequence is double underlined.

FIGS. 4F-1 and 4F-2 present the nucleotide sequence of NA35_1 cDNA clone and the predicted amino acid sequences (SEQ ID NO:63). The derived amino acid sequence corresponding to the peptide sequence by protein microsequencing is underlined.

Figure 4G:
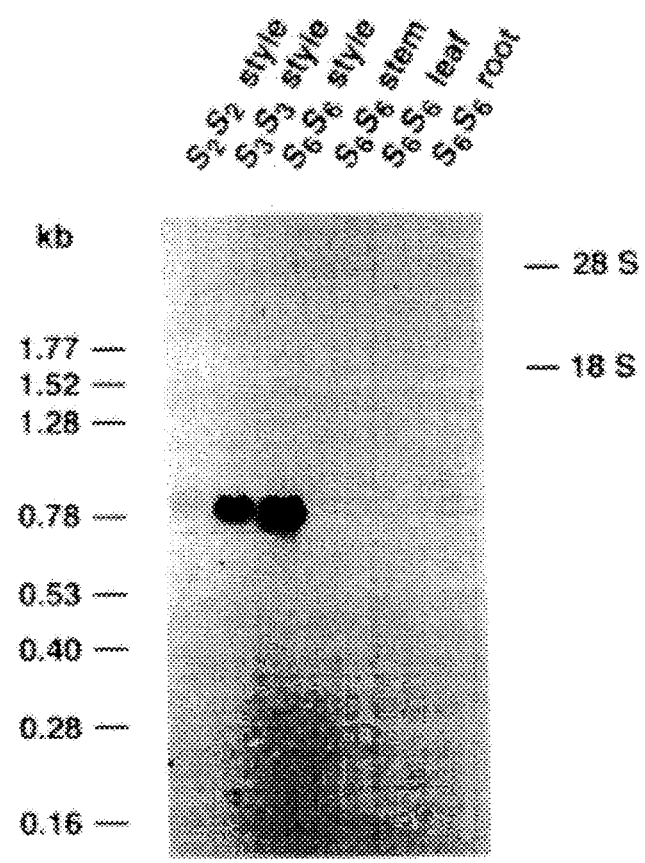

FIG. 4G presents northern blot analyses of the NA35_1 gene expression in various parts of *N. alata*. Total RNAs from *N. alata* styles ($S_2S_2$, $S_3S_3$, $S_6S_6$; 10 µg each), leaves ($S_6S_6$, 10 µg), stems ($S_6S_6$, 10 µg) and roots ($S_6S_6$, 6.3 µg) were fractionated on a formaldehyde agarose gel, transferred to a nylon membrane, and hybridized with $^{32}$p labeled NA35_1 probe. The size of the RNA transcripts is indicated in kilo nucleotides.

Figure 4H:
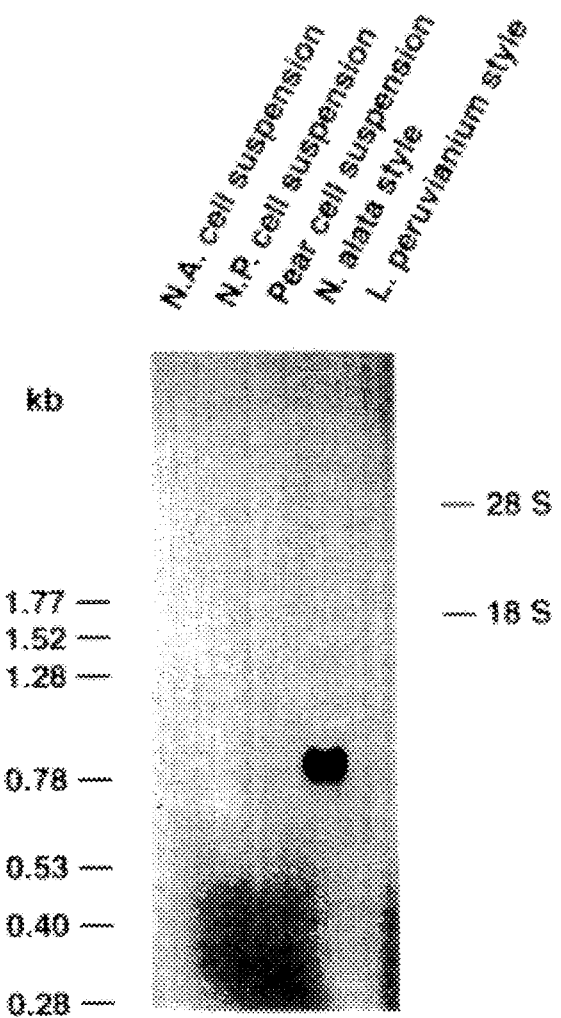

FIG. 4H presents northern blot analyses of the NA35_1 gene expression in various suspension-cultured cells and plants. Total RNAs (10 µg/lane) isolated from suspension cultured cells of *N. alata* and *N. plumbaginafolia*, Pyrus, and styles of *N. alata* ($S_6S_6$) and *L. peruvianum* were blotted and hybridized with the NA35_1 probe. The size of the RNA transcripts is indicated in kilo nucleotides.

Figure 4I:
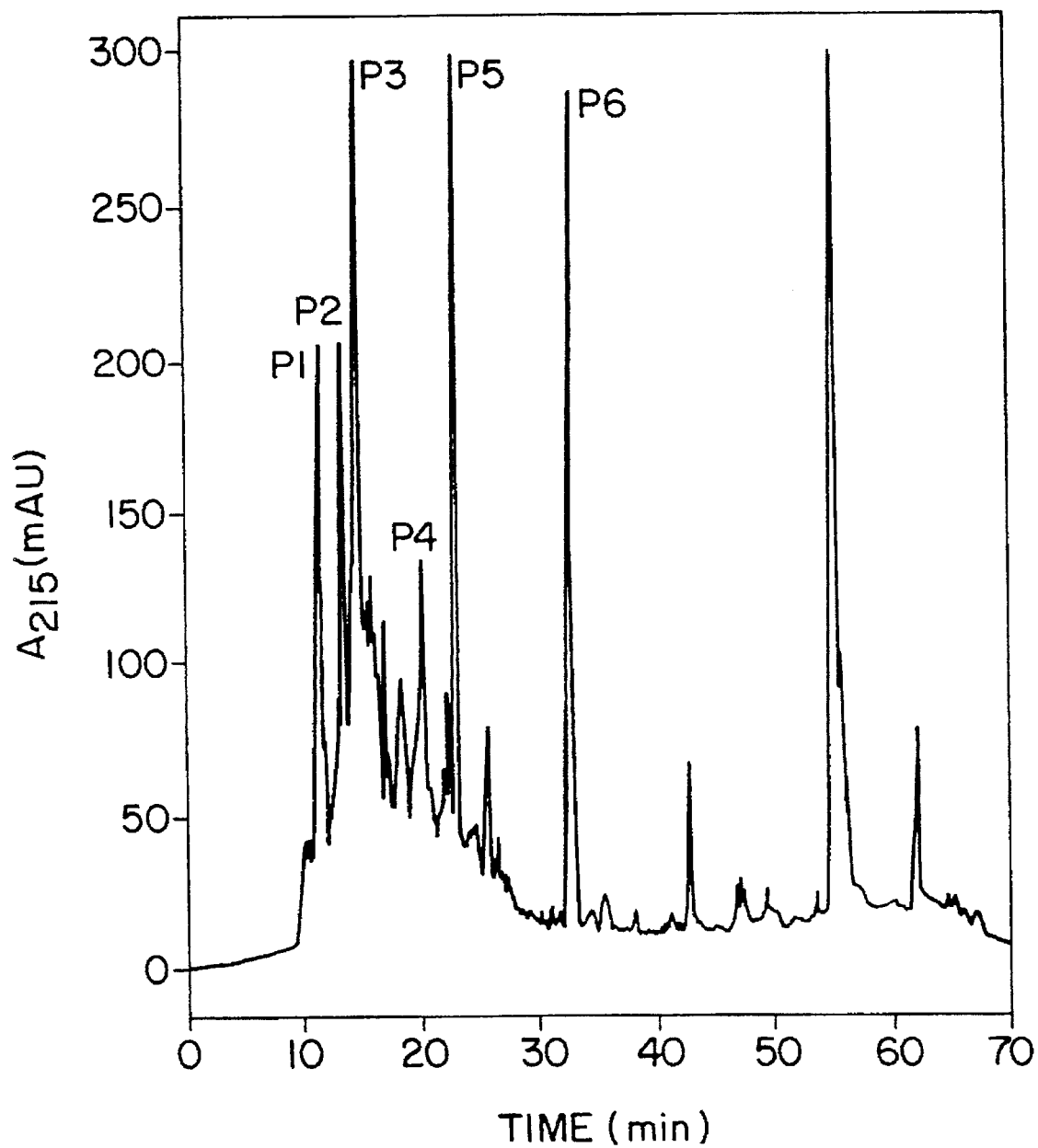

FIG. 4I presents reversed phase HPLC (RP-HPLC) separation of thermolysin cleavage products of the RT25 protein backbone. RT25 protein backbone (5–10 µg) was digested with thermolysin and loaded onto an RP-300 column (2.1× 100 mm, C8, ABT) equilibrated in 0.1% TFA at 1 ml/min. Unbound material was collected and bound material eluted with a linear gradient (0–60% acetonitrile in 0.1% TFA; 60 min; 100 µl/min). Peptides (P1–6) eluted from the column were monitored at $A_{215nm}$. Thermolysin was eluted after retention time 40 min. Individual peptides were subjected to amino acid sequencing.

Figure 4J:
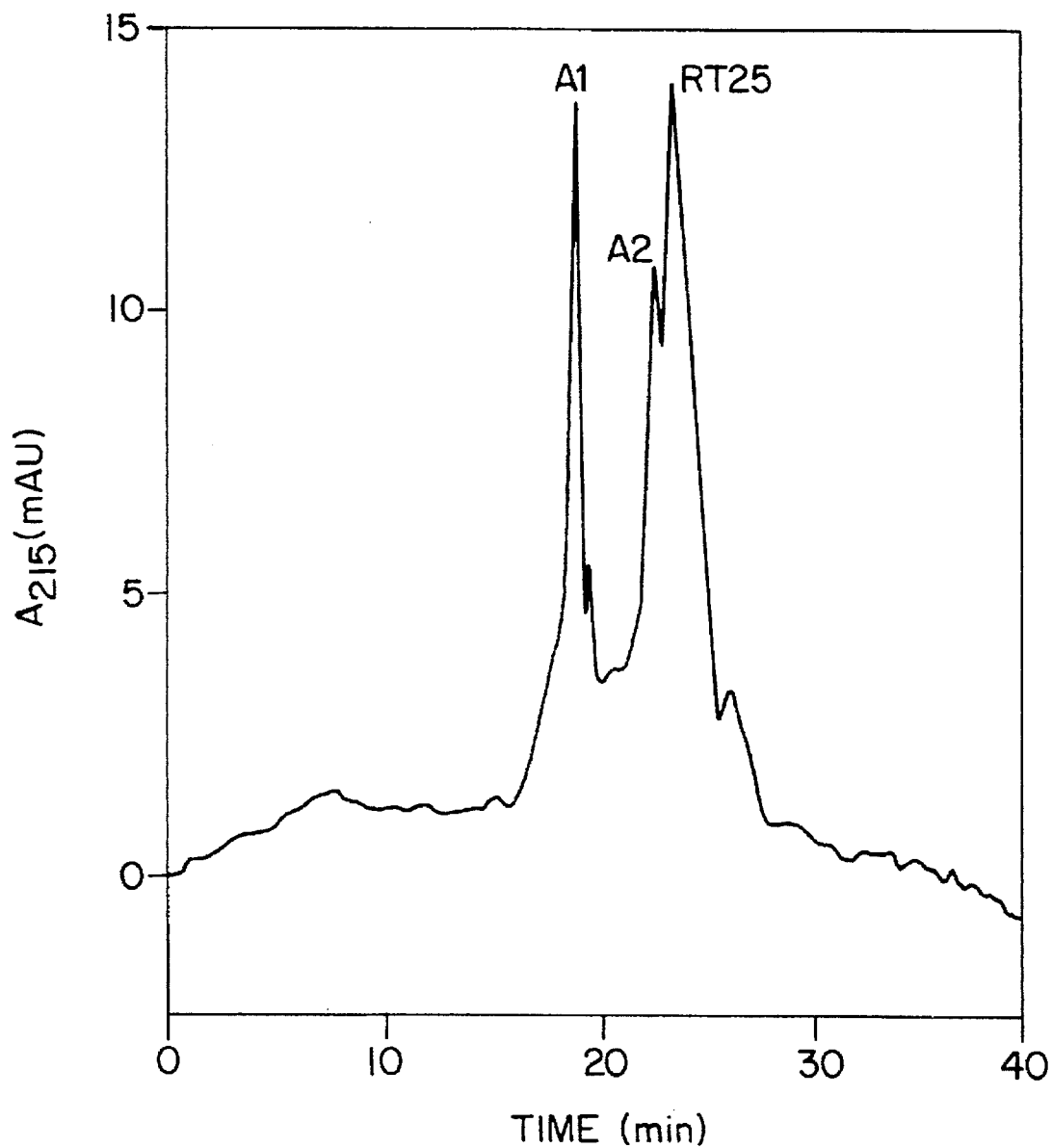

FIG. 4J presents reversed phase HPLC separation of endoproteinase Asp-N cleavage products of the RT25 protein backbone. RT25 protein backbone was digested with endoproteinase Asp-N. The resulting peptides were loaded onto an RP-300 column (2.1×100 mm, C8, ABI) equilibrated in 0.1% TFA at 1 ml/min. Unbound material was collected and bound material eluted with a linear gradient (0–60% acetonitrile in 0.1% TFA; 60 min; 100 µl/min). Peptides eluted from the column were monitored at $A_{215nm}$. Peptides, A1 and A2 were subject to amino acid sequencing. Undigested starting material (RT25) was also detected.

FIGS. 4K-1 and 4K-2 present nucleotide and deduced amino acid sequences (SEQ ID NO:72) of the AGPNa1 1 cDNA clone. The putative secretion signal (dot underlined) was predicted by using the PSIGNAL program (PC/Gene software, IntelliGenetics) based on the method described by Von Heijne (1986) *Nucl. Acids Res.* 14:4683–4690. Internal peptide sequences from amino acid sequencing are indicated by solid underlines and Hyp is shown encircled. Dash (-) indicates the stop codon.

Figure 4L:
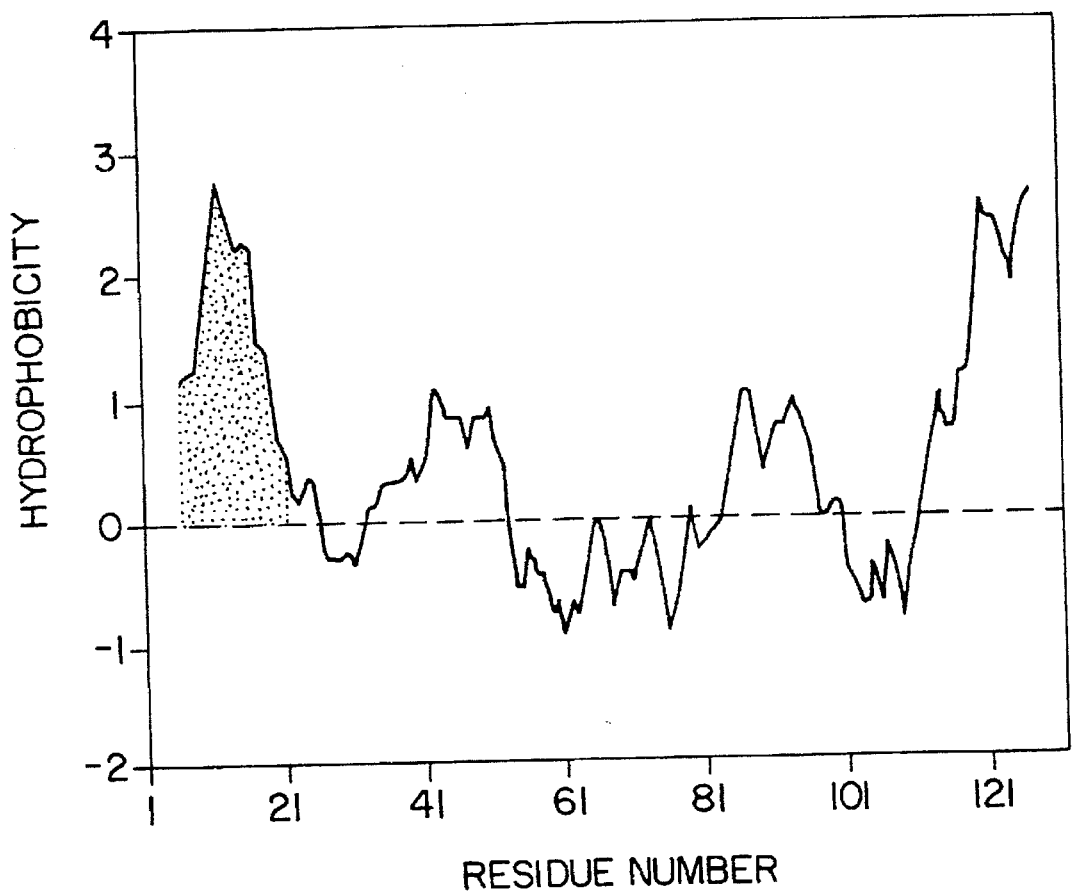

FIG. 4L presents a hydropathy plot of the deduced amino acid sequence from the AGPNa1 1 cDNA clone. The hydrophobicity of the deduced amino acid sequence was calculated by the SOAP program (PC/Gene software, IntelliGenetics) based on the method developed by Kyte and Doolittle (1982) *J. Mol. Biol.* 157:105–132. The putative secretion signal (shadowed) was predicted by using the PSIGNAL program (PC/Gene software, IntelliGenetics) based on the method described by Von Heijne (1986) supra.

FIGS. 4M-1 and 4M-2 present an RNA blot analysis of expression of the AGPNa1 1 gene in *N. alata* and other plants. Total RNA (10 µg/lane) isolated from (FIG. 4M-1) tissues of *N. alata* (genotype $S_6S_6$): style, ovary, petal, anther, stem, leaf and root; and (FIG. 4M-2) styles of *N. alata*, *N. sylvestris*, *N. tabacum*, *N. glauca*, *L. peruvianum* and leaves of Arabidopsis and rye grass were run in a 2% agarose gel (15% formaldehyde; 40 mM MOPS buffer, pH 7.0) and blotted onto a Hybond-N nylon membrane (Amersham). AGPNa1 1 cDNA fragment was labeled to $10^8$ cpm/µg with $^{32}$P-dCTP. Hybridization was performed at 60° C. overnight in 0.22M NaCl, 15 mM NaH$_2$PO$_4$, 1.5 mM EDTA, 1% SDS, 1% BLOTTO and 4 mg/ml herring sperm DNA. The membrane was washed for 2×10 min., at room temperature, in 2×SSC, 1% SDS; 2×10 min., 60° C., in 0.2×SSC, 1% SDS.

Figures 1, 4N:
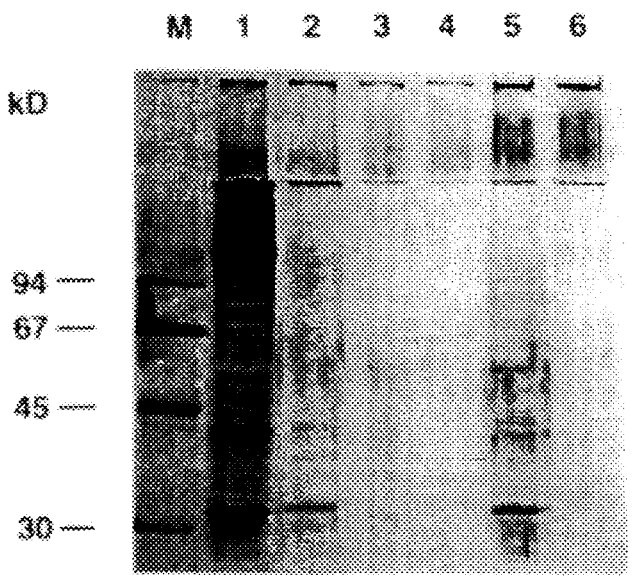
FIG. 1 presents different strategies for the preparation of single-stranded antisense RNA probes from oligonucleotides. A. Single oligonucleotide probes.
Figures 2, 4N:
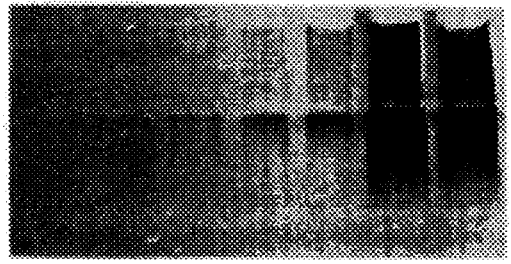

FIGS. 4N-1 and 4N-2 present an SDS-PAGE analysis of *N. alata* style AGPs at various stages of purification. SDS-PAGE (10% gel) followed by (N-1) silver staining and (N-2) staining with β-glucosyl Yariv reagent. Lane 1, total style extract (1 µg AGP). Lane 2, 95% (NH$_4$)$_2$SO$_4$-supernatant (4 µg AGP). Lane 3, Mono Q-bound AGP-containing fraction (4 µg AGP). Lane 4, Superose 6 AGP-containing fraction (4 µg AGP). Lane 5, as Lane 3, but containing 20 µg AGP. Lane 6, as Lane 4, but containing 20 µg AGP. Protein molecular weight markers (M) are shown on the left.

FIGS. 4O-1 through 4O-4 present crossed-electrophoresis of AGPs from styles of *N. alata* during fractionation. AGPs from (FIG. 4O-1) crude style extract, (FIG. 4O-2) 95% (NH$_4$)$_2$SO$_4$-supernatant, (FIG. 4O-3) Mono Q-unbound AGP-containing fraction, and (FIG. 4O-4) Mono Q-bound fraction were first electrophoresed in a 1% agarose gel horizonatally then vertically into a gel containing the β-glucosyl Yariv reagent.

FIGS. 5A-1 and 5A-2 present the nucleotide and predicted amino acid sequences of PcAGP9 (SEQ ID NO:66) encoding the protein backbone of an AGP from *Pyrus communis* cell suspension culture. The putative secretion signal peptide is underlined with dots. The sequences which match the peptide sequences obtained by protein sequencing are underlined. The proline residues which are modified post-translationally to hydroxyprolines are indicated by "O" underneath. X: undetermined residue.

FIGS. 5B-1 and 5B-2 present northern blot analyses of the PcAGP9 gene. FIG. 5B-1: Total RNA was isolated from pedicels (1) and cultured cells (2) of *Pyrus communis*; cultured cells of *Nicotiana plumbaginafolia* (3), shoots of *Brassica napus* (4), *Arabidopsis thaliana* (5) and *Lycopersicon esculentum* (6) and leaves of *Lolium temulentum* (7). Equal amounts (10 μg/lane) of RNA were fractionated on formaldehyde agarose gels, transferred to Hybond-N membranes, and hybridized with $^{32}$P-labeled PcAGP9 cDNA at 55° C. The final wash was carried out at 55° C. for 30 min with 1×SSC+0.1% SDS. FIG. 5B-2: The same RNA blot was hybridized and washed at higher stringency (65° C.). The size of the PcAGP9 RNA transcript in *Pyrus communis* cultured cells is indicated at the left.

Figure 5C:
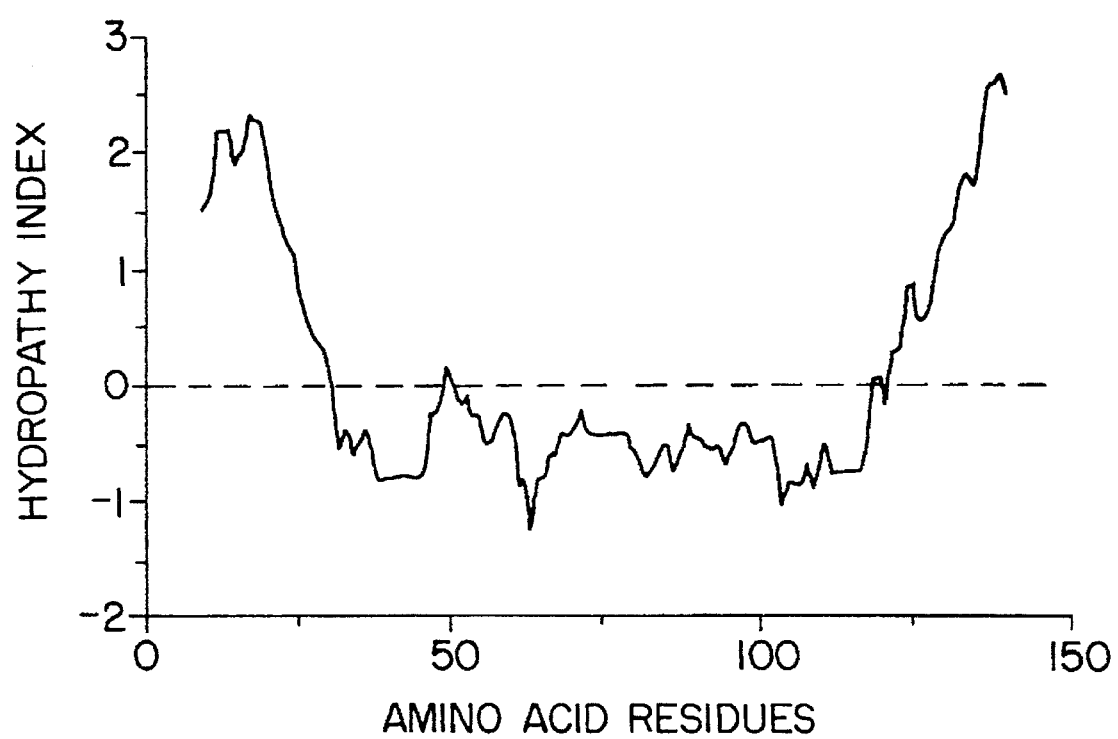

FIG. 5C presents a hydropathy plot of the deduced amino acid sequence of PcAGP9 (SEQ ID NO:66). The hydropathy values of each amino acid have been determined by using an interval of five amino acids according to Kyte and Doolittle (1982) supra. Values above the dotted line indicate hydrophobic regions and values below the dotted line represent hydrophilic regions.

Figures 1, 5D:
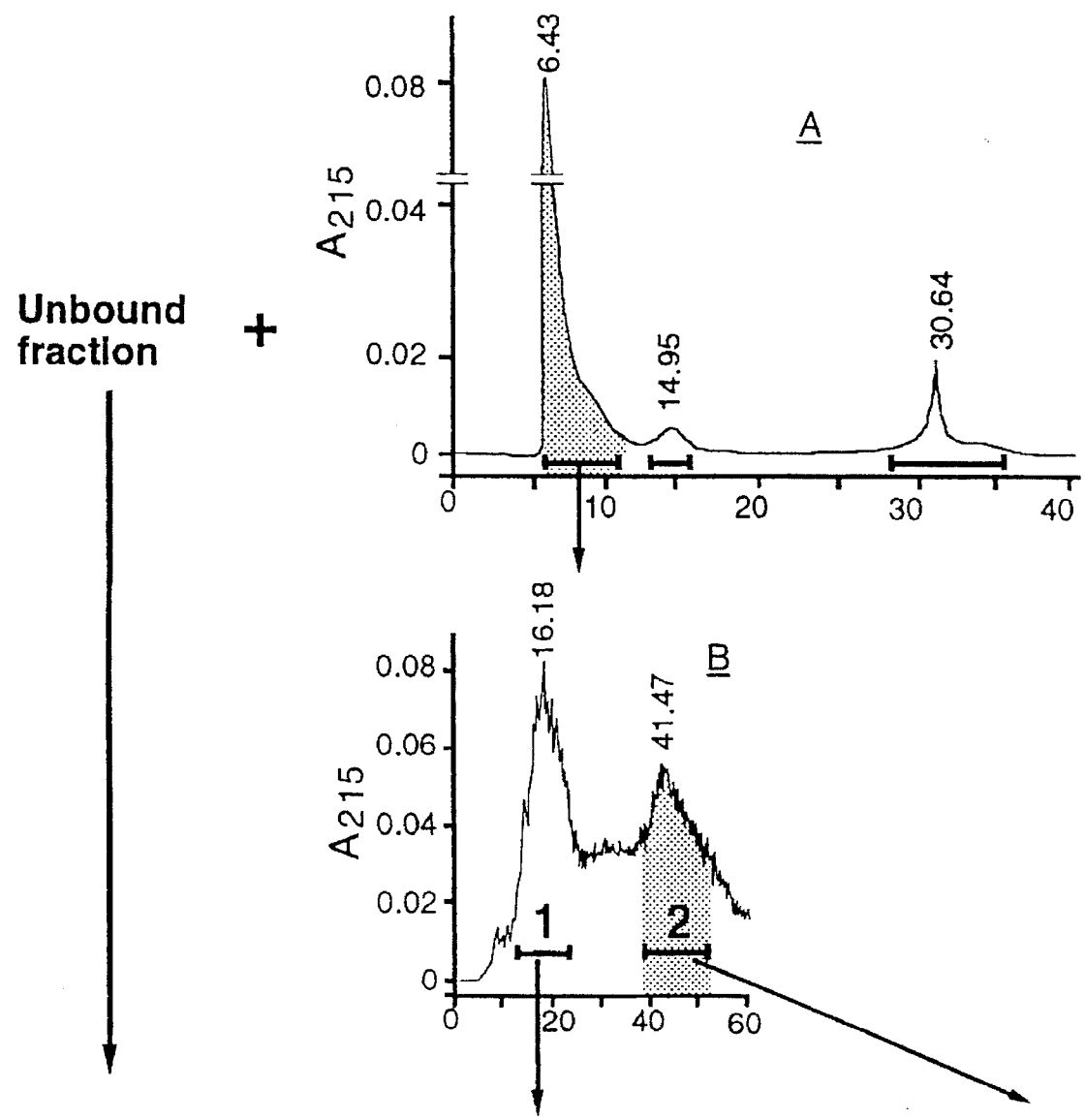
Figures 2, 5D:
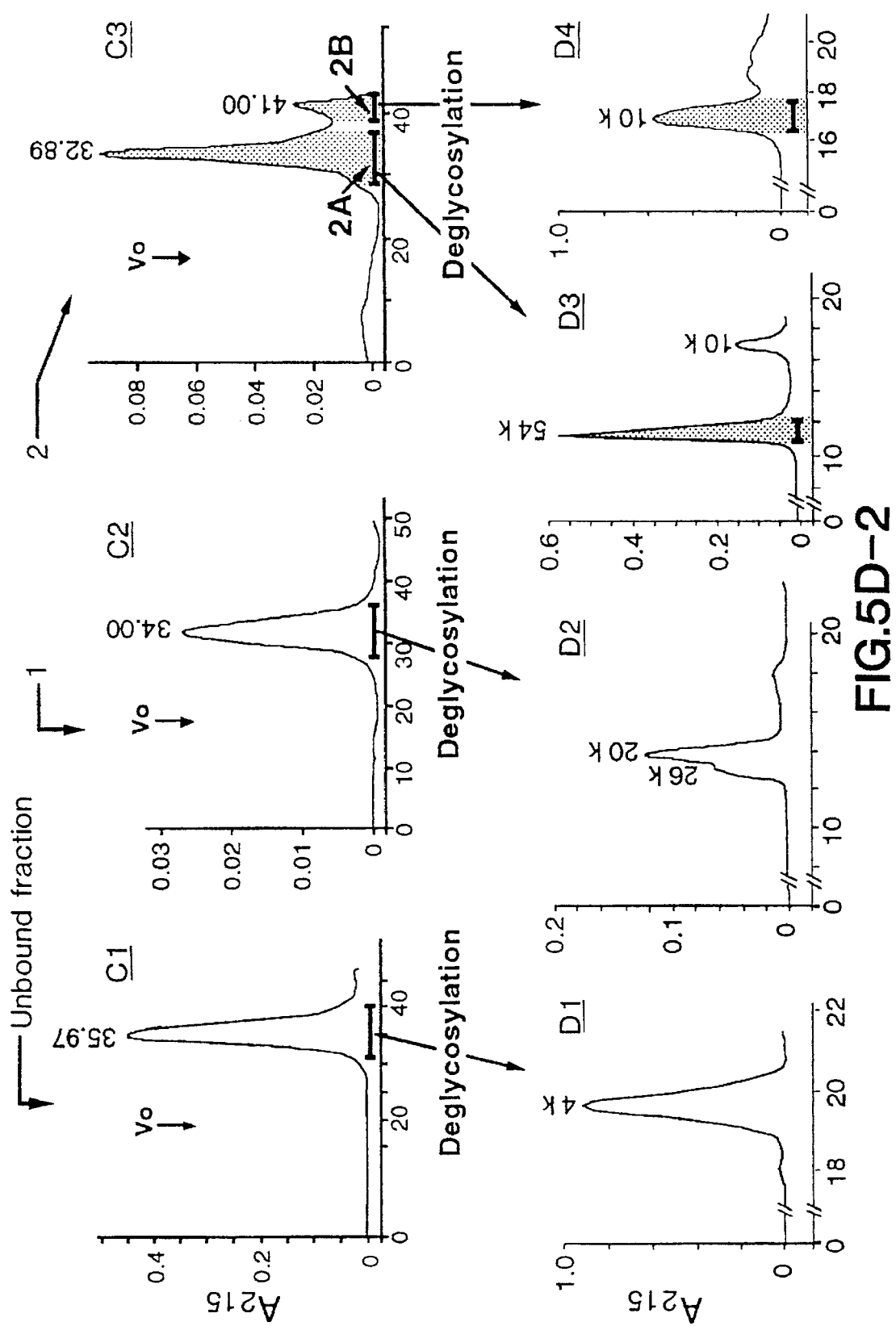

FIGS. 5D-1 and 5D-2 present a flow chart of the separation of AGPs from *Pyrus communis* (pear) cell suspension culture and the isolation of their protein backbones.

A. RP-HPLC (RP-300 column, 4.6×100 mm) profile of AGPs prepared by precipitation with the β-glucosyl Yariv reagent. AGPs were loaded and the column washed with solvent A (0.1% TFA in H$_2$O). The unbound fraction was collected (not shown). The bound material was eluted with a linear gradient (0–100% solvent B; flow rate 1 ml/min; 60 min) (solvent B: 60% acetonitrile in solvent A). Individual fractions from five separate runs were pooled for subsequent purification.

B. RP-HPLC (RP-300 column, 4.6×100 mm) profile of AGPs from the major bound peak shown in A (retention time 5.0–10.57 min). Bound material was eluted with a shallow gradient (0–15% solvent B; flow rate 1 ml/min; 60 min). Two fractions (1 and 2) were separately collected and subjected to size-exclusion FPLC.

C. Superose-6 FPLC profiles of AGPs in the unbound fraction from A and two eluted fractions from B. Samples were eluted in 25% acetonitrile, 0.2M KCl, 5 mM KH$_2$PO$_4$ (flow rate 0.4 ml/min). The unbound fraction and Fraction 1 gave single peaks; Fraction 2 resolved into two peaks (Peak 2A and 2B).

D. Superdex-75 FPLC profiles of protein backbones derived from AGPs in C by HF deglycosylation. Samples were eluted in the same buffer used in C (flow rate of 0.8 ml/min). The size of the protein was estimated from standard protein markers (Pharmacia).

The x axis is retention time (min). The pathway for purification of the AGP fractions, from which peptide sequences were obtained, is stippled.

FIGS. 5E-1 and 5E-2 present the nucleotide and predicted amino acid sequence of PcAGP2 cDNA (SEQ ID NO:91) encoding a putative AGP backbone from suspension cultured cells of *P. communis*. The translational initiation and stop sites are in bold-face. The predicted secretion signal is underlined with dots. The two long direct repeats are double-underlined. The sequence matching the peptide sequences obtained from the AGP protein backbone are underlined. The proline residues modified to HYP are indicated by an "O."

DETAILED DESCRIPTION OF THE INVENTION

The following definitions are provided in order to provide clarity as to the intent or scope of their usage in the specification and claims.

The term arabinogalactan protein or AGP as used herein refers to a Yariv reagent-precipitable, glycosylated molecule in which the protein constituent typically accounts for approximately 2 to 10% of the molecular weight of the molecule [although AGPs having protein values outside this range are known (Anderson et al. (1979) supra)] and in which carbohydrate usually accounts for most of the weight of the molecule. Galactose and arabinose form the major carbohydrate constituents with other monosaccharides and uronic acids as minor components; the galactosyl residues are organized to form a backbone of 3-linked galactose with branches through c(0)6; the arabinosyl residues are predominantly in terminal positions. AGPs specifically bind to and are precipitated by β-glycosyl-Yariv reagents as a red colored complex. AGPs usually comprise a domain(s) enriched in hydroxyproline, alanine, serine, and threonine.

The term Yariv reagent-precipitable as used herein refers to an AGP that is capable of being precipitated by β-glucosyl-Yariv reagents.

The term native AGP as used herein refers to an AGP in its native state, i.e., glycosylated.

The term glycosylated AGP as used herein refers to an AGP molecule comprising a carbohydrate component.

The term deglycosylated AGP as used herein refers to a native AGP or a glycosylated AGP which has been subjected to treatment for removal of carbohydrate and as a result of which contains a decreased but variable carbohydrate content.

The term nonglycosylated AGP or AGP backbone as used herein refers to a protein skeleton or backbone of an AGP molecule which is not glycosylated.

The term synthetic AGP as used herein refers to an AGP molecule which is chemically synthesized.

The term synthetic nonglycosylated AGP as used herein refers to a peptide backbone of an AGP which is chemically synthesized.

The term enriched in hydroxyproline or hydroxyproline-enriched or hydroxyproline-rich as used herein refers to a region or domain or segment of an amino acid sequence that has a hydroxyproline content of greater than 15%, and usually about 50% or greater.

The term OAST-enriched or high content of hydroxyproline, alanine, serine, and threonine or enriched in OAST content as used herein refers to a region of an amino acid sequence wherein the sum of the hydroxyprolyl, alanyl, seryl, and threonyl residues constitutes at least about 35%, and preferably at least about 60%, of the total amino acyl residues.

The term hydroxyproline-poor or not enriched in hydroxyproline as used herein refers to a region or domain of a peptide sequence that has a hydroxyproline content that is preferably less than 15%, more preferably less than 10% and most preferably less than 5%. A hydroxyproline-poor region may also have an OAST content that is preferably less than 50%, more preferably less than 35% and most preferably less than 20%.

The term a characterizing sequence or a sequence characterizing an AGP as used herein refers to a sequence that is hydroxyproline-rich and/or sequences that are enriched in OAST content.

The term a guessmer as used herein refers to an oligonucleotide that contains only a subset of the possible codons at each position. Guessmer is a term used routinely in the art and is thoroughly elucidated in Molecular Cloning, A Laboratory Manual, J. Sambrook, E. F. Fritsh and T. Maniatis, 2nd edition. Cold Spring Harbor Laboratory Press, 1989, pp. 11.11–11.16. In many cases, a guessmer is a chemically-synthesized, single oligonucleotide, 30–70 nucleotides in length, that contains the combination of codons most likely to match the authentic gene.

The term antisense RNA probe as used herein refers to a RNA strand produced from a DNA template encoding a desired amino acid sequence. The nucleotide sequence of the RNA is complementary to the coding strand of the DNA template sequence.

The term substantially pure as used herein refers to a protein that is substantially free of other proteins with which it is associated in nature.

The isolation of AGP genes from *N. alata, N. plumbaginafolia,* and *P. communis* suspension cultures and *N. alata* styles, as illustrated herein, exemplifies Applicants' invention which embraces the utilization of an amino acid sequence of a region of an AGP peptide from a plant cell to isolate a corresponding plant AGP gene. Not all regions or domains of AGP peptide sequences can be used equivalently to produce viable oligonucleotide primers for the isolation of AGP genes. Applicants succeeded in isolating AGP genes by using two different strategies:

(A) the use of a non-hydroxyproline-rich sequence as a primer template to obtain a corresponding AGP gene, and (B) the use of a guessmer-antisense RNA probe approach wherein the guessmer can comprise a nucleotide sequence encoding a hydroxyproline-rich segment to obtain an AGP gene encoding the sequence of the hydroxyproline-rich segment.

In strategy A, the preferred sequences are those that have a low content, or are deficient in, hydroxyproline. Hydroxyproline-poor sequences are found in terminal regions as well as in internal domains of AGP peptides. It is also preferable that sequences of AGP peptides or fragments thereof, selected for synthesis of synthetic oligonucleotide primers, have a low hydroxyproline, alanine, serine, and threonine (OAST) content. It is particularly preferable that the content of the sum of these four amino acid residues be less than 50%, and more preferably less than 35%, and most preferably less than 20%, of the total amino acid residues. AGP sequences that are useful in isolating an AGP gene using PCR technology, i.e., sequences that are hydroxyproline-poor, or OAST-poor, are not available in the prior art.

The amino acid sequence selected as a template for the synthesis of an oligonucleotide primer should not be one that gives PCR degenerate primers having concentrated "GC-rich" regions. Primers having concentrated "GC-rich" sequences frustrate and make futile the attempts to obtain cDNA by the PCR technique. For example, AGP peptide fragments published in the art are the following:

from carrot (Jermyn, 1985, supra)*

(1) A—D/N—A—O—A—O—S—O—A/T—O/S—(O)  (SEQ ID NO:1)

(2) D—E—A—O—A—O—A—O—S—O—M—  (SEQ ID NO:2)

(3) G/E—O—A—O—A—O—A—O—(Q)—(V)—  (SEQ ID NO:3)

from ryegrass, Lolium multiflorum (Gleeson et al., 1989, supra)*

(1) A—E—A—O—A—O—A—O—A—S— (SEQ ID NO:4) (N-terminal)
(2) K—A—A—A—S—O—O—A—O—A—O—K— (SEQ ID NO:5)
(3) A—O—A—O—A—O—V/H—O—E—A (SEQ ID NO:6)
(4) S/L—T—A—O—V—A—A—O—T—T—(X)—O— (SEQ ID NO:7)
(5) S—O—P—A—O—A— (SEQ ID NO:8)
(6) A—A—A—(S)—L—(K)— (SEQ ID NO:9)

and from rose (Komalavilas et al., 1990, supra)*

(A)—D—A—O—A—O—S—O—V  (SEQ ID NO:10)

* Residues in brackets indicate uncertain residues. X=undetermined residue.
Although these amino acid sequences of AGP peptide fragments from carrot, ryegrass, and rose are known in the art, AGP genes corresponding to these peptide fragments are still not known in the art. All of these art-known plant AGP peptide fragments have amino acid sequences that are characterized by a high content of hydroxyproline, alanine, serine, and threonine. These amino acid partial sequences are such that they give GC-rich oligonucleotide primers. For this reason, no one to date has been successful in obtaining AGP cDNAs directly from these sequences.

Initially, Applicants attempted to obtain plant AGP genes using hydroxyproline-rich sequences obtained from isolated AGP fragments. The following sequences were utilized unsuccessfully:

(i) *N.plumbaginafolia*, RT21, FAOS/NGGVALPOS  (SEQ ID NO:28)

(ii) *N.plumbaginafolia*, LASOOAOOTADTOA  (SEQ ID NO:27)

(iii) *N. plumbaginafolia*, IGAAOAGSOTSSPN  (SEQ ID NO:29)

(iv) *P.communis*, RT16.4, LSOKKSOTAOSOS(S)TOOT(T)
(SEQ ID NO:31)

Each of the sequences (i), (ii) and (iii), which are found in both *N. alata* and *N. plumbaginafolia* AGPs, were used in both *N. alata* and *N. plumbaginafolia* to isolate an AGP gene. Sequence (iv) was used to obtain an AGP gene from *P. communis*. None of these sequences led to the isolation of a corresponding gene. All of these sequences produced oligonucleotide primers that were highly redundant and very GC-rich (in some cases greater than 80%). Consequently, a problem appeared that at high stringency, hybridization bands were obtained which, on sequencing, had no relationship to the amino acid sequence. On examination of the above sequences, it may be seen that all four of these sequences are OAST-enriched, i.e., (i) 50%, (ii) 85.7%, (iii) 64.3%, and (iv) 84.2%, respectively.

The instant disclosure overcomes this problem. Whereas isolated plant AGPs in the art have been characterized exclusively by peptide fragments having high hydroxyproline or OAST contents (AGP sequences having a low content of hydroxyproline, or a low OAST content are not available in the prior art), the AGPs isolated and described in Applicants' disclosure are characterized not only by peptide fragments that are hydroxyproline-rich but also by peptide fragments that are hydroxyproline-poor, if not hydroxyproline-deficient. The fact that an AGP peptide fragment that was not enriched in hydroxyproline had been isolated and sequenced and the fact that this sequence, which is also low in hydroxyproline, alanine, serine, and threonine content, had been utilized to synthesize degenerate primers, enabled circumvention of the problems associated with GC-rich primers and led to the isolation of a corresponding AGP cDNA.

The N-terminal region of an isolated plant AGP can be used to obtain a corresponding plant AGP gene. In a particular embodiment of the invention, the N-terminal region of an AGP peptide obtained from *N. alata* suspension culture comprised a hydroxyproline-poor region. The N-terminal peptide sequence, A-K-S-K-F-M-I-I-P-A-S-X-T-X-A (SEQ ID NO:11) was used as a template for the synthesis of an oligonucleotide primer which was further utilized for the isolation of a hybridizing AGP gene from both *N. alata* and *N. plumbaginafolia*.

In other specific embodiments of the invention, hydroxyproline-poor sequences from internal regions of AGPs from *P. communis* suspension culture and from *N. alata* style were used to obtain corresponding AGP genes. For example, in the case of *P. communis*, the AGP backbone encoded by the PcAGP23 gene (SEQ ID NO:49) is hydroxyproline-poor not only at the terminal regions but also internally, and an internal sequence (SEQ ID NO:41) was used to obtain a pear AGP gene. Similarly, for the *N. alata* style AGP backbone encoded by the Na35_1 cDNA clone (FIGS. 4F-1 and 4F-2) the N-terminal region and internal regions have low hydroxyproline contents, and, internal sequence (SEQ ID NO:58) was used to obtain an *N. alata* style AGP gene.

This basic approach (strategy A) for obtaining a plant AGP gene enabled the successful isolation of AGP genes from *N. alata*, *N. plumbaginafolia*, and *P. communis* cell suspension cultures, as well as from *N. alata* styles. In each case, the cDNA clone comprised a derived amino acid sequence which contained a hydroxyproline-poor domain and a hydroxyproline-enriched domain (a region enriched in OAST content).

In strategy B, a method is provided that enables the use of a specific OAST-rich AGP peptide sequence for the isolation of a corresponding gene. This method involves the screening of libraries with RNA probes prepared from a single long guessmer (oligonucleotides containing only a subset of the possible codons at each position) encoding a desired specific OAST-rich AGP peptide sequence. In order to produce an RNA probe from a DNA oligonucleotide, a bacteriophage promoter (e.g., T7 or T3 RNA polymerase promoter) is linked at the 5'-end of the oligonucleotide. In addition, the oligonucleotide, which is single-stranded, must be converted into a partial or complete, double-stranded DNA fragment, because the T7 (or T3) RNA polymerase will not recognize single-stranded promoter sequences. Relevant procedures for obtaining either DNA or RNA probes from a DNA template are known in the art [Berger and Kimmel (1987) Methods in Enzymology 152].

FIG. 1 presents schematically several ways of producing an RNA probe involving the use of a single (FIG. 1A) or double (FIG. 1B) oligonucleotide probe. For example, in FIG. 1A-1 a second oligonucleotide, which is complementary to the guessmer encoding a desired AGP peptide, is synthesized and the two oligonucleotides are annealed to form double-stranded DNA. Alternatively, as shown in FIG. 1A-2, a short complementary primer is annealed to the promoter sequence of the guessmer to form a double-stranded RNA polymerase promoter sequence. Using a double oligonucleotide probe approach (FIG. 1B-1), an adaptor sequence (15–18 bp long) is added to the 3'-end of the guessmer (oligonucleotide 1) and a second guessmer (oligonucleotide 2), which encodes a different OAST-rich AGP peptide sequence, with an adaptor sequence complementary to the adaptor of the first oligonucleotide, is synthesized. The two guessmers are thus annealed through their complementary adaptor sequences and the protruding single-stranded regions filled in by primer extension to produce a double-stranded DNA fragment. FIG. 1B-2 further demonstrates a method whereby the adaptor sequences are designed in such a way that they bind to opposite strands of a mediator DNA, enabling the two guessmers to be joined together by a PCR reaction to form a double-stranded DNA fragment. The double oligonucleotide probe can be used to screen a library for two AGP genes simultaneously.

Single-stranded RNA probes are superior to DNA probes for the screening of libraries. RNA probes can be labeled to much higher specific activity and bind more tightly to a target DNA, thus yielding stronger signals in hybridization reactions. The greater stability of hybrids involving RNA enables the use of higher hybridization stringency, thus increasing hybridization specificity. Unhybridized RNA probes can be removed by RNase digestion further reducing the background.

A single long guessmer (40–70 bp) rather than short degenerate oligonucleotides is used to avoid the extremely high degeneracy associated with OAST-rich AGP peptide sequences. It is preferred that the guessmer be longer than 40 bp in order that the increased stability of hybrids formed by the long oligonucleotide out-weigh the detrimental effects of mismatches. Anti-codons GGU, CGU, UGU, and AGU should be used for Pro (Hyp), Ala, Thr, and Ser, respectively. This is based on the consideration that the nucleotide base "A" is the preferred base in the third position of codons for Pro, Ala, and Thr. The other consideration is that the nucleotide base "U" can pair not only with "A" but also with "G" to some extent, hence GGU can pair with CCA or CCG for proline residues, for example. Therefore, it is further contemplated that antisense RNA rather than the sense RNA probes be used for the screening of libraries.

AGP peptides were isolated from plant cell suspensions by precipitation with Yariv reagent (a red dye, β-glucosyl reagent described by Yariv in 1967). This dye was prepared by coupling diazotized 4-aminophenyl glucopyranoside to phloroglucinol and the reagent was used to precipitate AGPs. The AGPs from suspension-cultured cells were prepared by precipitation of AGPs from either the culture medium or from the Biopolymer products (the high molecular weight materials precipitated with four volumes of ethanol from a cell suspension culture filtrate). An isolation procedure independent of the Yariv reagent was also used to obtain AGPs from plant cells. (The Yariv reagent was used later in the isolation procedure to identify fractions containing AGPs.) The AGPs from *N. alata* style extracts were prepared by $(NH_4)_2SO_4$ precipitation and further fractionation of the AGP-containing supernatant by Mono Q (Pharmacia) anion-exchange chromatography. In a different procedure, AGPs were initially fractionated by immunoaffinity chromatography using the J539 myeloma antibody (specific for Gal 1–6 β Gal sequences).

As is known in the art, AGPs can be isolated by several methods, including affinity chromatography using, for example, galactose binding proteins, classical chromatography, for example, gel filtration, ion-exchange, etc., and also precipitation by selective reagents, for example, Yariv reagents, lectins, for example, lectins that binds galactosyl residues, including but not limited to, tridacnin, peanut agglutinin, the *Ricinus communis* (RCA$_{120}$) lectins and myeloma protein J539 [Clarke et al. (1979) *Phytochemistry* 18:521–540; Fincher et al. (1983) *Ann. Rev. Plant Physiol.* 34:58], or antibodies to specific carbohydrate epitopes [Pennell et al. (1989) *J. Cell Biol.* 108:1967–1977 and Norman et al. (1990) *Planta* 181:365–373].

AGP fractions were deglycosylated by treatment with trifluoromethane sulfonic acid (TFMS) or by treatment with anhydrous hydrogen fluoride (HF). Additionally, other methods for separating the protein and the carbohydrate components from each other that are known in the art are contemplated by the invention [see Jermyn et al. (1975) *Aust. J. Plant Physiol.* 2:501].

AGPs and AGP fragments, glycosylated or deglycosylated, were separated by known separation techniques, for example, SDS-PAGE, HPLC reverse phase chromatography, etc. In some cases, the peptides were further fragmented by thermolysin digestion before separation. Separated peptides obtained off HPLC reverse phase and ion-exchange columns were sequenced directly, although in some cases the separated peptides were transferred to PVDF membranes for amino acid sequencing [Ward et al. (1990) in *Electrophoresis* 11:883–891]. The use of other known proteases, instead of or in addition to thermolysin, is contemplated by this invention. Similarly, this invention contemplates the use of other techniques known in the art for the preparation of pure peptide samples for amino acid sequencing.

From every source examined, multiple AGP peptides were observed. Multiple peptides were reproducibly obtained whether the AGPs were separated first and then individually deglycosylated or whether the whole AGP preparation was deglycosylated first and then the individual peptides separated.

In a specific embodiment of the invention, total native AGPs were isolated by Yariv reagent precipitation from the suspension culture filtrate of *N. alata* and deglycosylated using TFMS. The resulting peptides were separated on a 17.5% SDS-PAGE gel and blotted to a PVDF membrane. The major band (MW: 20–30 kD; FIG. 1C) was excised and sequenced. An N-terminal peptide sequence, A-K-S-K-F-M-I-I-P-A-S-X-T-X-A (SEQ ID NO:11), was obtained.

In a particular embodiment of the invention, the *N. alata* AGP N-terminal peptide sequence (SEQ ID NO:11) was used to isolate AGP genes from *N. alata* and *N. plumbaginafolia* libraries (FIGS. 1D-1 and 1D-2). Degenerate reverse primers corresponding to part of the AGP N-terminal amino acid sequence, i.e., K-F-M-I-I-P were synthesized (Table 1.1) and used to obtain a 160-bp primer extension product (FIG. 1E) which was then amplified by PCR. The 160-bp extension fragment was subcloned and sequenced. The nucleotide sequence (SEQ ID NO:21) included a derived peptide which matched with the peptide sequence SEQ ID NO:11 isolated from *N. alata* suspension culture.

TABLE 1.1

A: Oligo primers used in the primer extension experiments

| Ala | Lys | Ser | Lys | Phe | Met | Ile | Ile | Pro | Ala | Ser | X | Thr | X | Ala | (SEQ ID NO:11) |
|---|---|---|---|---|---|---|---|---|---|---|---|---|---|---|---|
| GCA | AAA | TCA | AAA | TTT | ATG | ATA | ATA | CCA | GCA | TCA | | ACA | | GCA | (SEQ ID NO:12) |
| G | G | G | G | C | | C | C | G | G | G | | G | | G | |
| C | | C | | | | T | T | T | T | C | | C | | T | |
| T | | T | | | | | | C | C | T | | T | | C | |
| | | AGC | | | | | | | | AGC | | | | | |
| | | T | | | | | | | | T | | | | | |

B: Oligonucleotide primers designed

```
Group 1    5' GG TAT TAT CAT AAA CTT  (SEQ ID NO:13)
              G   G       G
              A   A
```

```
Group 2    5' GG TAT TAT CAT AAA TTT  (SEQ ID NO:14)
              G   G       G
              A   A
```

C: Subgroups of the group 1 primers

| NaR1 | 5' GG T/G/AAT GAT CAT AAA CTT 3' | (SEQ ID NO:15) |
| NaR2 | 5' GG T/G/AAT AAT CAT AAA CTT 3' | (SEQ ID NO:16) |
| NaR3 | 5' GG T/G/AAT TAT CAT AAA CTT 3' | (SEQ ID NO:17) |
| NaR4 | 5' GG T/G/AAT GAT CAT GAA CTT 3' | (SEQ ID NO:18) |
| NaR5 | 5' GG T/G/AAT AAT CAT GAA CTT 3' | (SEQ ID NO:19) |
| NaR6 | 5' GG T/G/AAT TAT CAT GAA GTT 3' | (SEQ ID NO:20) |

A: Amino acid sequence obtained from deglycosylated AGPs isolated from *N. alata* cell suspension culture and the corresponding codons.
B: The two groups of degenerate reverse primers designed for the primer extension experiment.
C: Subgroups of the group 1 primers.

Additional primers, corresponding in sequence to parts of the 160-bp fragment (e.g., NaF1 and NaF2; FIG. 1E), were synthesized and used to amplify the 3'-part of the AGP gene by nested PCR. A 1.6 kb fragment was amplified and sequenced. The alignment of the sequences obtained from the two PCR reactions gave rise to a DNA sequence of 1679 bp (FIGS. 1F-1 and 1F-2). The PCR fragment encoded a protein which contained the isolated peptide sequence (SEQ ID NO:11) with two mismatches: Arg for Ala at position 1 and Pro for His at position 12 (FIGS. 1F-1 and 1F-2).

The 1.6 kb PCR fragment was used to screen a cDNA library made from RNA isolated from N. alata cells in suspension culture and three positive clones were isolated and sequenced. The alignment of the PCR sequences with the cDNA sequence gave rise to a 1700-bp sequence (SEQ ID NO:24) including a poly(A) tail of 7 bp (FIGS. 1F-1 and 1F-2). This sequence was designated NaAGP1. Further primer extension experiments suggested that the 1.7 kb NaAGP1 cDNA (SEQ ID NO:24) represented the full-length sequence of the AGP transcript.

Figure 1G:
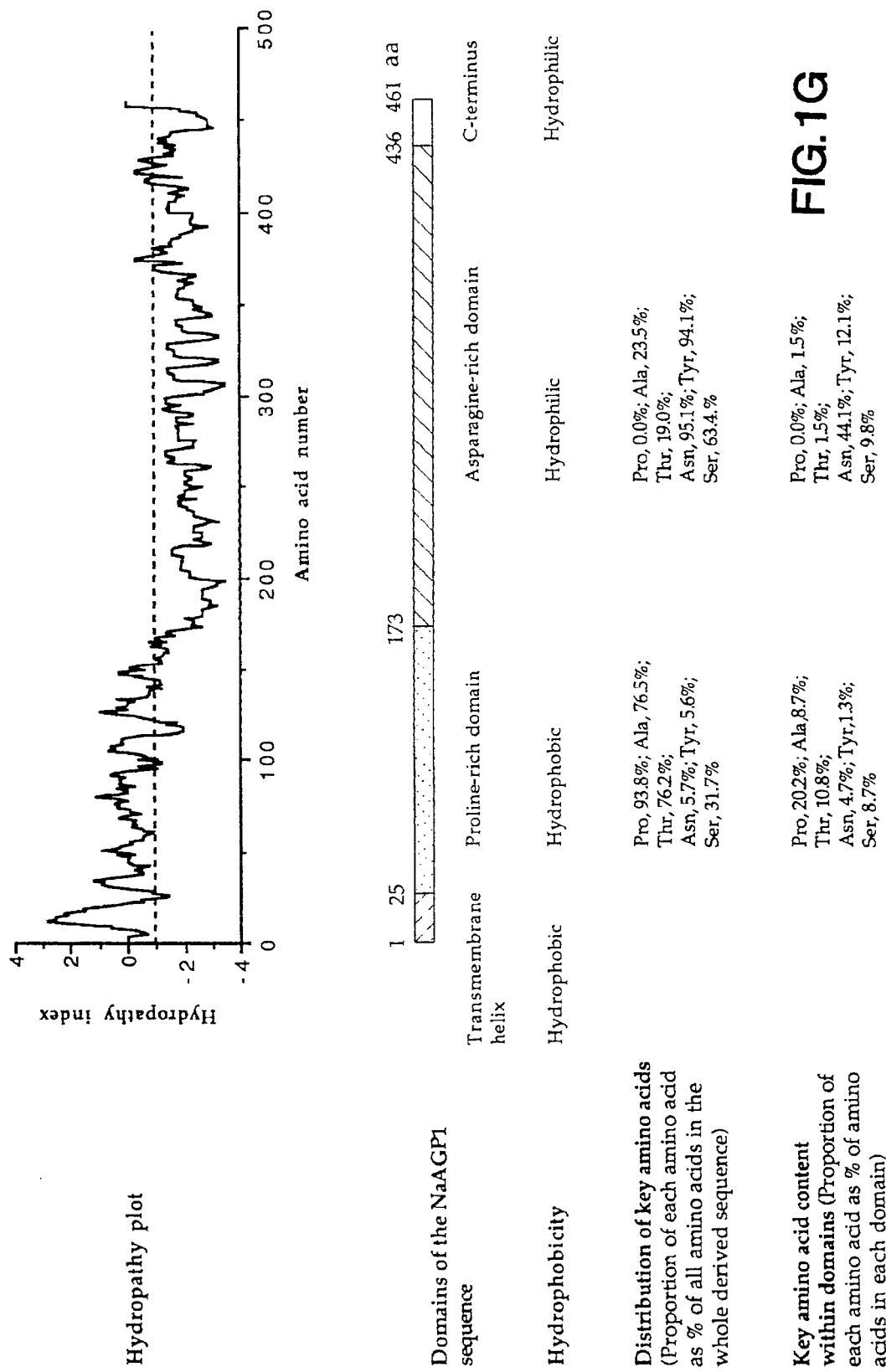
FIG. 1G presents a summary of key structural features of the derived amino acid sequence of the NaAGP1 cDNA. The hydropathy values of each amino acid have been determined using an interval of nine amino acids according to the weight system of Kyte and Doolittle (1982). Values above the dotted line indicate hydrophobic regions, and the values below the dotted line represent hydrophilic regions.

The NaAGP1 cDNA comprised an open reading frame spanning 1383 nucleotides. The open reading frame encoded a polypeptide containing 461 amino acid residues with a calculated molecular weight of 51.8 kD and a predicted pI of 3.84. The protein was highly rich in asparagine (25%), and relatively rich in serine (8.9%), tyrosine (7.5%), proline (7.2%) and glutamine (7.0%) (Table 1.2), and could be divided into four domains (FIG. 1G). At the N-terminus (residues 1–25), there was a putative transmembrane helix which was very hydrophobic.

by Gal/Ara containing chains, linked through hydroxyproline residues. The proline residues (residues 37, 39, 41, and 43 in FIGS. 1F-1 and 1F-2) are known to be hydroxylated, as they appear as hydroxyproline (residues 25, 27, 29, and 31 in FIGS. 1H-1 and 1H-2) in the peptide sequence obtained from deglycosylated AGPs of N. plumbaginafolia. Such hydroxylation and glycosylation would make the molecule considerably more hydrophilic.

The portion of the protein corresponding to amino acid positions 174–436 was hydrophilic and contained most of the asparagine (95.1%) and tyrosine (94.1%) residues which accounted for 44.1% and 12.1%, respectively, of all amino acids in this domain (FIGS. 1F-1 and 1F-2 and FIG. 1G). The asparagine residues were distributed in clusters (residues 2–10) along the polypeptide chain. This domain contained no proline residues. The final 25 residues at C-terminus were hydrophilic (FIG. 1G).

An N. plumbaginafolia cell suspension cDNA library was also screened with the PCR fragment, and four cDNA clones were isolated and sequenced. The four clones were identical and contained an insert of 1430 bp (SEQ ID NO:25; FIGS. 1H-1 and 1H-2). This AGP gene was designated NpAGP1. These cDNAs were incomplete and predicted to be about 100 bp shorter at the 5'-end than the full-length sequence of the transcript. The NpAGP1 was not identical, but very similar to the NaAGP1 at both the nucleotide and derived amino acid sequence level (86% and 84.7% identify, respectively) (FIGS. 1I-1 and 1I-2, FIGS. 1J-1 through 1J-4, and Table 1.2). The transmembrane helix was missing in the NpAGP1 cDNA due to the incomplete sequence. The dif-

TABLE 1.2

Comparison of derived amino acid composition of NaAGP1 and NpAGP1.

| Amino acid | Full sequence NaAGP1 | (Mol %)[1] NaAGP1 | Pro-rich domain NaAGP1 | (Mol %)[2] NaAGP1 | Asn-rich domain NaAGP1 | (Mol %)[3] NaAGP1 |
|---|---|---|---|---|---|---|
| Asn | 25.0 | 26.2 | 4.7 | 3.3 | 44.1 | 43.4 |
| Ser | 8.9 | 9.8 | 8.7 | 9.4 | 9.8 | 10.3 |
| Tyr | 7.5 | 7.7 | 1.3 | 1.3 | 12.1 | 11.9 |
| Pro | 7.2 | 7.9 | 20.2 | 20.8 | 0.0 | 0.3 |
| Glu | 7.0 | 7.7 | 6.7 | 6.7 | 5.7 | 6.3 |
| Gly | 6.0 | 5.4 | 6.7 | 6.0 | 6.0 | 5.5 |
| Phe | 5.8 | 4.7 | 6.0 | 6.7 | 3.8 | 3.9 |
| Thr | 5.4 | 4.5 | 10.8 | 10.7 | 1.5 | 1.1 |
| Asp | 3.9 | 3.1 | 4.7 | 5.4 | 3.8 | 1.9 |
| Ala | 3.5 | 4.1 | 8.7 | 8.7 | 1.5 | 1.5 |
| Leu | 3.3 | 2.9 | 5.4 | 4.0 | 1.5 | 1.5 |
| Val | 3.3 | 3.1 | 4.7 | 4.0 | 2.2 | 2.3 |
| Gln | 3.1 | 2.9 | 2.7 | 3.3 | 1.9 | 1.5 |
| Ile | 2.7 | 2.9 | 4.0 | 4.7 | 0.7 | 1.1 |
| Lys | 2.5 | 2.5 | 2.0 | 1.3 | 2.2 | 3.1 |
| Arg | 1.6 | 1.5 | 1.3 | 1.3 | 1.5 | 1.5 |
| Met | 1.2 | 1.1 | 0.6 | 0.6 | 0.7 | 0.7 |
| His | 0.8 | 0.6 | 0.6 | 0.6 | 0.3 | 0.7 |
| Cys | 0.4 | 0.0 | 0.0 | 0.0 | 0.0 | 0.0 |
| Trp | 0.0 | 0.0 | 0.0 | 0.0 | 0.0 | 0.0 |

[1]The NaAGP1 derived amino acid sequence is incomplete as the clone is approximately 100 bp short.
[2]The proline-rich domain is defined by amino acid residues 26-173 in NaAGP1 and 14-161 in NpAGP1.
[3]The Asn-rich domain is defined by amino acid residues 174-436 in NaAGP1 and 162-412 in NpAGP1.

The next one-third of the protein (residues 26–173) was also hydrophobic and contained most of the proline (93.8%), alanine (76.5%) and threonine (76.2%) residues. These three amino acids accounted for 39.7% of all the amino acids in this domain (Pro, 20.2%; Thr, 10.8% and Ala, 8.7%) (FIG. 1G). This domain is predicted to be the site of glycosylation ference between the two AGP genes was mainly in the middle one-third of the sequence while the N-terminal and C-terminal parts were highly conserved (FIGS. 1I-1 and 1I-2 and FIGS. 1J-1 through 1J-4).

Figures 1, 1K:
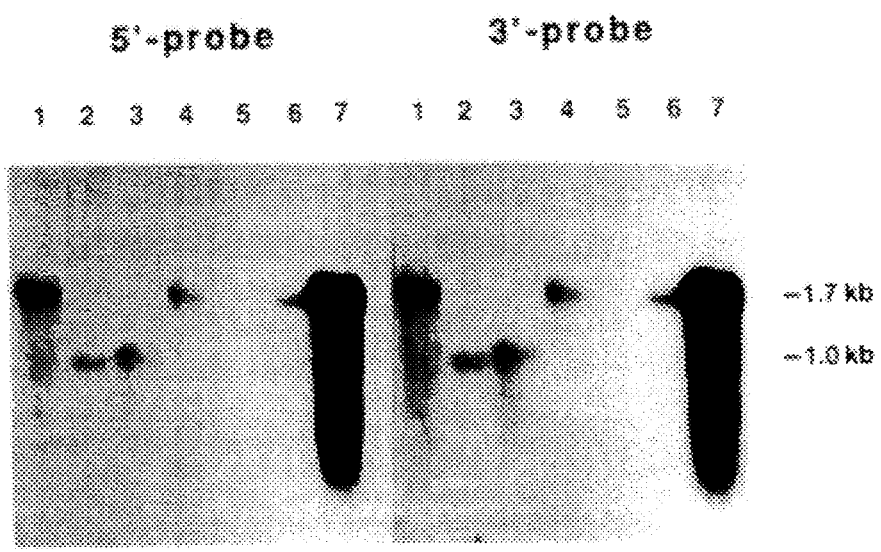
Figures 1, 1K, 2:

The NaAGP1 cDNA was cut into a 5'-half (residues 1–540) corresponding to the 5'-nontranslated part, the transmembrane helix and the proline-rich domain and a 3'-half (residues 541–1700) including the asparagine-rich domain, C-terminus, and the 3'-nontranslated part. These two parts of the cDNA were used separately to probe northern blots of RNA [Sambrook et al. (1989) supra] isolated from suspension cultured cells of N. alata and N. plumbaginafolia and various tissues of N. alata plants. The two probes gave an identical hybridization pattern, confirming that these two distinct domains are parts of the same transcript (FIGS. 1K-1 and 1K-2). The NaAGP1 cDNA probes hybridized to the RNA samples from all the tissues of N. alata tested, although the degree of hybridization and size of transcripts are different in different tissues. The highest signal was detected in RNA from N. alata suspension cultured cells whereas the signal in petals is barely detected. Pollen and style tissues have a smaller transcript of approximately 1.0 kb compared with 1.6 kb in N. plumbaginafolia cultured cells and 1.7 kb in all other tissues (FIGS. 1K-1 and 1K-2). Genomic southern blot analysis indicated that the AGP gene is a single copy or low copy gene in the genome of N. alata.

In a preferred embodiment of the invention, the cDNA library was screened with the labeled synthetic oligonucleotide probe derived from the hydroxyproline-poor or the N-terminal AGP protein sequence. In an alternative embodiment of the invention, individual recombinants within the cDNA library can be screened for expression of an antigen (antibody recognition). Procedures for selecting cloned sequences from a recombinant cDNA library are described in Kimmel (1987) Meth. Enzymol. 152:393–399.

This invention also contemplates the use of oligonucleotide probes, e.g., AGP cDNA, etc., for the detection of hybridizing sequences and the isolation of monocot and dicot AGP genes. Pear AGP (PcAGP9) transcripts were detected in RNA prepared from dicots as well as from a monocot.

cDNA clones which show a strong hybridization signal are sequenced to confirm complimentarity to the AGP amino acid sequence. In addition, the protein encoded by the cDNA is shown to possess AGP characteristics. This is done, for example, by transcribing the clone sequence with an appropriate RNA polymerase, then translating the mRNA in, for example, a commercially available wheat germ extract in vitro translation system. Thus, the identity of a clone is confirmed by transformation into a suspension-cultured cell and identifying the product using a suitable tag.

In another embodiment of the invention, the presence of AGP protein is detected immunologically. For example, antibodies raised to an AGP peptide, or fragment thereof, purified and isolated from an SDS-PAGE gel are shown to cross-react with the purified AGP peptide. AGP-specific antibodies are also utilized to bind and precipitate AGP from plant extracts as well as the product of the cloned AGP gene. Polyclonal and monoclonal antibodies specific to AGP peptide are prepared according to standard methods in the art. This type of immunological testing is further utilized, for example, for optimization of expression of the cloned AGP gene in a recipient organism.

This invention further contemplates the isolation of a genomic clone of AGP. Genomic DNA is isolated according to the methods described by Herrmann and Frischauf (1987) Methods Enzymol. 152:180–189. A PCR-based method is used to clone a gene from genomic DNA using partial protein sequence (e.g., Aarts et al. (1991) Plant Mol. Biol. 16:647) or cDNA fragment probes (e.g., King et al. (1988) Plant Mol. Biol. 10:401–412). The genomic AGP gene may be utilized instead of the cDNA to express AGP, in particular, in host systems where it appears that the native promoter or post-translational system is required for full expression, e.g., plant monocot or dicot cells, mammalian cells, e.g., COS cells, etc.

As is well known in the art [see, for example, Glover (1984) Gene Cloning, Brammar and Edidin (eds.), Chapman and Hall, NY], there are various strategies for generation of cDNA libraries and for the cloning of the cDNA into an appropriate DNA recombinant vector, e.g., the pUC family of plasmids or λgt10 or λgt11 phage vectors. In an embodiment of the invention, a DNA recombinant vector carries a constitutive or inducible promoter adjacent to the cloning site such that a transcript is made specifically to either strand of the cDNA simply by using different RNA polymerases. RNAs produced in this way can be used as hybridization probes or can be translated in cell-free protein synthesis systems.

It is understood in the art that modifications may be made to the structural arrangement and specific elements of a genetically-engineered recombinant DNA molecule described herein without destroying the activity of gene expression. For example, it is contemplated that a substitution may be made in the choices of enhancer regulatory elements and/or promoters [e.g., preferably, an inducible promoter (e.g., AdH1)] without significantly affecting the function of the recombinant DNA molecule of this invention. It will also be understood that optimization of gene expression also results from the use of preferred codons, the arrangement, orientation, and spacing of the different regulatory elements as well as the multiple copies of a particular element with respect to one another, and with respect to the position of the TATA box, as will be apparent to those skilled in the art using the teachings of this disclosure.

In another embodiment of the invention, AGPs were isolated from N. plumbaginafolia suspension cultures. The medium from the cell suspension culture of N. plumbaginafolia was separated from the cells by filtration and the high molecular weight materials precipitated with four volumes of ethanol. The total native AGPs were purified from the Biopolymer product by precipitation with the Yariv reagent after depleting the starting material of pectins by CTAB (hexadecyl trimethyl ammonium bromide) precipitation prior to Yariv precipitation. The total native AGPs were treated by two paths:

Path 1: Deglycosylation followed by reverse phase HPLC fractionation before direct sequencing, or sequencing after enzymatic (proteolytic) digestion [detailed in Example 2(c) 2–5].

Path 2: Reverse phase HPLC fractionation followed by deglycosylation and further reverse phase HPLC fractionation [detailed in Example 1(c) 6–8].

Path 1 (deglycosylation followed by separation of AGPs) produced an unbound peak and two major bound peaks, RT21 and RT32, with retention times of 21 min and 32 min, respectively, in reverse phase HPLC (see FIG. 2A). Peak RT21 was digested with thermolysin and refractionated by RP-HPLC prior to amino acid sequencing. The sequences (SEQ ID NOS:26–29) obtained from peak RT21 exhibited a high content of hydroxyproline, alanine, serine, and threonine (OAST-rich sequences).

Peak RT32 was sequenced directly and gave the sequence R-K-S-K-F-M-I-I-P-A-S-O-T-O-A-O-T-O-I-N-E-I-S-F (SEQ ID NO:30) which, at the 5'-end, very closely matched the N-terminal sequence (SEQ ID NO:11) obtained from N. alata cell cultures, and which did not show a high content of hydroxyproline nor of OAST, i.e., hydroxyproline, alanine, serine, and threonine. The 3'-end of the peak RT32 sequence (SEQ ID NO:30) comprised a domain characterized by a high OAST content.

The results of amino acid analyses of chromatographic fractions from *N. plumbaginafolia* AGPs are presented in Table 2.1.

Figure 3D:
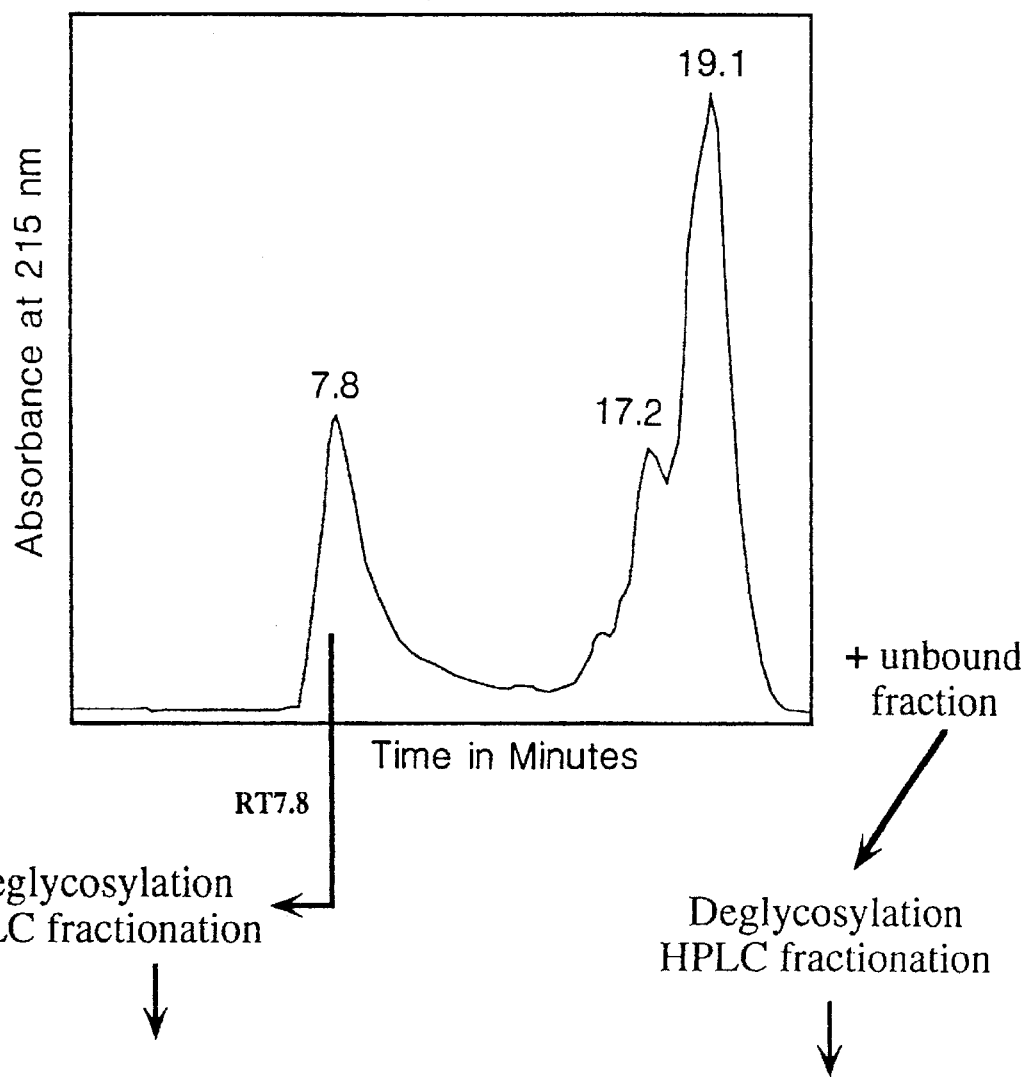

Path 2 (fractionation of the total native pear AGP fraction by reverse phase HPLC) gave the profile presented in FIG. 3D. Peak RT7.8 and the unbound fraction were analyzed for

TABLE 2.1

Amino acid analyses of fractions from *N. plumbaginafolia* AGPs

| | Fractions of *N. plumbaginafolia* AGPs after deglycosylation and RT-300 separation (FIG. 2A) | | | Native *N. plumbaginafolia* AGPs fractionated on RP-300 (FIG. 2B) | | | | | |
|---|---|---|---|---|---|---|---|---|---|
| | Unbound | RT21 | RT32 | Unbound | RT5 | RT6 | RT10 | RT21-23 | RT34 |
| Hyp | 9.6 | 20.8 | 18.2 | 16.2 | 19.6 | 16.0 | 14.6 | 2.3 | 1.0 |
| Asx | 9.6 | 3.3 | 4.9 | 8.7 | 5.7 | 1.6 | 6.4 | 8.1 | 9.2 |
| Thr | 7.6 | 8.1 | 8.9 | 4.3 | 7.3 | 11.1 | 8.5 | 8.3 | 7.0 |
| Ser | 9.2 | 16.0 | 13.0 | 12.0 | 15.0 | 18.2 | 11.6 | 10.6 | 10.3 |
| Glx | 7.8 | 5.6 | 5.5 | 9.0 | 6.9 | 5.0 | 5.9 | 6.7 | 6.4 |
| Pro | 6.2 | 2.5 | 2.2 | 4.5 | 3.4 | 4.4 | 8.3 | 5.0 | 13.3 |
| Gly | 10.1 | 6.5 | 7.9 | 6.9 | 6.0 | 5.1 | 5.5 | 7.3 | 9.6 |
| Ala | 12.7 | 18.5 | 24.6 | 20.8 | 22.7 | 22.3 | 12.3 | 18.3 | 16.1 |
| Cys | 0.0 | 0.0 | 0.0 | 0.0 | 0.0 | 0.0 | 0.0 | 0.4 | 0.1 |
| Val | 4.5 | 4.5 | 6.7 | 2.4 | 4.2 | 6.0 | 4.8 | 7.7 | 4.8 |
| Met | 0.5 | 0.0 | 0.2 | 2.2 | 1.5 | 1.5 | 1.0 | 1.5 | 0.7 |
| Ile | 4.8 | 1.2 | 1.8 | 1.2 | 1.1 | 1.5 | 4.6 | 1.8 | 2.4 |
| Leu | 6.41 | 3.6 | 3.2 | 3.2 | 2.6 | 2.4 | 5.0 | 8.8 | 7.9 |
| Tyr | 0.0 | 0.0 | 0.0 | 0.0 | 0.0 | 0.3 | 0.4 | 0.0 | 1.6 |
| Phe | 7.0 | 1.9 | 1.2 | 3.3 | 2.3 | 1.5 | 5.7 | 4.4 | 3.3 |
| His | 1.5 | 1.5 | 0.9 | 0.3 | 0.2 | 0.7 | 1.4 | 1.2 | 1.4 |
| Lys | 1.3 | 5.2 | 0.7 | 0.9 | 1.2 | 2.1 | 2.5 | 4.8 | 3.5 |
| Arg | 1.3 | 0.8 | 0.0 | 0.9 | 0.4 | 0.3 | 1.6 | 0.9 | 2.1 |
| Trp | ND | ND | ND | ND | ND | ND | ND | ND | ND |

Hyp: hydroxyproline,
ND: not determined

All AGPs that initially bound to the chromatography columns showed an enrichment in hydroxyproline, alanine, serine, and threonine residues.

In another embodiment of the invention, the total native AGPs were isolated from *Pyrus communis* (pear) Biopolymer by Yariv precipitation.

The AGPs were either deglycosylated first and then separated by reverse phase HPLC (RP-300) (Path 1), or alternatively, the total native AGPs were fractionated first by reverse phase HPLC (RP-300), and then deglycosylated, digested with thermolysin, and purified for sequencing (Path 2).

Path 1 (HPLC separation of deglycosylated AGPs) gave the profile shown in FIG. 3A. The results of amino acid analyses of major peaks (i.e., unbound, peak RT16.4 and peak RT18.2), as summarized in Table 3.1, indicated enrichment of hydroxyproline, alanine, serine, and threonine residues in the bound fractions. The RT16.4 and the RT18.2 peaks from FIG. 3A were subjected to thermolysin digestion and the digestion products were separated on a RP-300 column. The RP-300 profile for digested RT16.4 is shown in FIG. 3B and for RT18.2 is shown in FIG. 3C.

In all, only one peak (peak 1 of thermolysin-digested RT16.4, FIG. 3B) was a pure peptide and gave a clear sequence, L-S-O-K-K-S-O-T-A-O-S-O-S-(S)-T-O-O-T-(T) (SEQ ID NO:31), which showed a high content of alanine, hydroxyproline, serine, and threonine. Peaks 3 and 5 of RT16.4 (FIG. 3B) comprised sequences (SEQ ID NO:11 and SEQ ID NO:12, respectively) that also exhibited high contents of hydroxyproline, alanine, serine, and threonine.

Peaks from thermolysin-digested RT18.2 (FIG. 3C) were resolved into several peaks (SEQ ID NOS:31, 34–38). These sequences also were characterized by a high OAST content.

amino acid composition and both were found to be enriched in hydroxyproline, alanine, serine, and threonine as shown in Table 3.1. Peak RT7.8 and the unbound fraction were deglycosylated and fractionated on HPLC. The profile for the deglycosylated Peak RT7.8 (FIG. 3E) showed a major peak (Peak RT23) which, after thermolysin digestion and further purification on reverse phase HPLC (RP-300), gave six peptide sequences. Five sequences (SEQ ID NOS:39–44) were OAST-enriched, whereas one of the sequences, L-V-V-V-V-M-T-P-R-K-H (SEQ ID NO:41) was also present in sequence obtained by direct sequencing of the native AGP in RT7.8.

The unbound fraction of FIG. 3D after deglycosylation and further fractionation on HPLC (Path 2), gave the profile presented in FIG. 3F. The major peaks RT16–19 in FIG. 3F [obtained by Path 2 (separation followed by deglycosylation)] had retention times similar to those of peaks RT16–19.9 in FIG. 3A [obtained by Path 1 (deglycosylation followed by separation)].

It would appear from FIG. 3D that Peak RT7.8 represents about 27% of the total AGPs from pear. At least four N-terminal were observed in one fraction which may represent multiple chains. The unbound fraction represents about 67% of the total AGPs from pear and gives peaks which correspond to the RT16.4–19.9 of FIG. 3A which gave several OAST-enriched sequences. Thus, the invention provides amino acid sequence data from each of the two major AGPs from *Pyrus communis*.

In a particular embodiment of the invention, an AGP gene was obtained from *P. communis*.

TABLE 3.1

| | Fractions of pear AGPs after deglycosylation and RP-300 separation (FIG. 3A) | | | Fractions of native AGPs produced by HPLC (RT-300) fractionation (FIG. 3D) | | RT7.8 after deglycosylation and RP-300 separation (FIG. 3E) |
|---|---|---|---|---|---|---|
| | Unbound | RT16.4 | RT18.2 | Unbound | RT7.8 | RT23 |
| Hyp | 17.68 | 24.5 | 24.4 | 20.8 | 17.2 | 23.0 |
| Asx | 3.2 | 3.1 | 2.9 | 6.0 | 4.0 | 9.7 |
| Thr | 7.9 | 9.3 | 10.8 | 8.4 | 7.0 | 8.7 |
| Ser | 10.3 | 22.1 | 17.6 | 16.4 | 10.5 | 20.1 |
| Glx | 7.1 | 4.9 | 3.6 | 8.1 | 6.5 | 14.0 |
| Pro | 4.8 | 1.3 | 1.8 | 3.0 | 5.2 | 1.0 |
| Gly | 7.7 | 2.3 | 4.0 | 4.1 | 6.7 | 2.0 |
| Ala | 15.8 | 19.7 | 21.6 | 19.4 | 17.3 | 15.1 |
| Cys | 0.0 | 0.0 | 0.0 | 0.0 | 0.0 | 0.0 |
| Val | 8.3 | 3.2 | 4.1 | 2.8 | 7.4 | 0.5 |
| Met | 0.5 | 0.0 | 0.0 | 0.1 | 0.6 | 0.0 |
| Ile | 2.8 | 0.2 | 0.8 | 1.7 | 3.0 | 0.1 |
| Leu | 4.4 | 1.7 | 1.9 | 2.3 | 4.7 | 0.2 |
| Tyr | 0.9 | 1.0 | 0.3 | 2.3 | 1.7 | 0.0 |
| Phe | 0.9 | 0.0 | 0.1 | 0.0 | 0.7 | 0.9 |
| His | 2.0 | 0.5 | 0.8 | 0.6 | 1.9 | 3.4 |
| Lys | 4.4 | 5.1 | 4.7 | 3.5 | 4.0 | 1.6 |
| Arg | 1.6 | 1.2 | 0.6 | 0.6 | 1.6 | 0.0 |
| Trp | ND | ND | ND | ND | ND | ND |

Hyp: hydroxyproline,
ND: not determined

The sequence L-V-V-V-V-M-T-P-R-K-H (SEQ ID NO:41), which was hydroxyproline-poor and OAST-poor, was selected as template for obtaining an AGP gene from pear cell suspension culture.

A number of primers corresponding to the L-V-V-V-V-M-T-P-R-K-H sequence (SEQ ID NO:41) was designed and synthesized for PCR experiments (Table 3.2).

TABLE 3.2

Sequences of the oligonucleotide primers used in PCR

Peptide sequence L—V—V—V—V—M—T—P—R—K—H (SEQ ID NO:41)

Primer designation:

| PcA23F1 | 5' GTN GTN GTN GTN ATG AC 3' | (SEQ ID NO:45) |
|---|---|---|
| PcA23F2a | 5' GTA GTN ATG ACN CCN AGA AA 3' <br>                                                         G | (SEQ ID NO:46) |
| PcA23F2b | 5' GTA GTN ATG ACN CCN CGN AA 3' | (SEQ ID NO:47) |

N = A, T, G, or C

The same nested PCR procedure used for the cloning of the NaAGP1 gene (FIG. 1D-2) was used to clone the gene encoding the above peptide, except that the annealing temperature was 52° C. in this case. A 350-bp fragment was amplified after two successive PCR reactions using the PcA23F1 as the first primer and the PcA23F2a as the second primer. The fragment was sequenced and found to encode the correct peptide sequence (SEQ ID NO:48; FIG. 3G).

The PCR fragment was used to screen a cDNA library made from mRNA from pear cell suspension culture, as described above for N. alata cell suspension. One positive clone (PcAGP23) was isolated and sequenced. This clone contained an insert of 760 bp and matched the PCR sequence.

The PcAGP23 cDNA (SEQ ID NO:49) encodes an open reading frame, which starts with an initiation codon (ATG) at position 20 and ends with a termination codon (TAG) at position 560 (FIGS. 3H-1 and 3H-2). The open reading frame encodes a polypeptide containing 180 amino acid residues with a calculated molecular weight of 19.2 kD and a predicted pI of 8.46. The predicted amino acid sequence contains the peptide sequence, L-V-V-V-V-M-T-P-R-K-H (SEQ ID NO:41), which was used for the cloning of the PCR fragment. In addition, another peptide sequence, L-G-I-S-O-A-O-S-O-A-G-E-V-D-(G) predicted from nucleotides 428–472, matches SEQ ID NO:34 obtained from RT18.2 (FIG. 3C). However, other sequences from peak RT7.8 (SEQ ID NOS:39–44) are absent from the PcAGP23 sequence, indicating they are from different AGP backbones.

The most abundant amino acid residues in the predicted protein sequence are Ser (12.2%), Gly (10.5%), Leu (9.4%), Val (8.8%), Ala (7.2%) and Lys (7.2%) Table 3.3. The PcAGP23 contains 5.5% Pro residues, some of which are post-translationally modified to hydroxyproline, as identified by peptide sequencing. The Pro and Ala residues are, relatively speaking, concentrated in the last one-third of the sequence (at C-terminus).

In the sequence of the PcAGP23 cDNA (SEQ ID NO:49), there is a putative secretion signal at the N-terminus (1–27) with a potential cleavage site between Ala$^{27}$ and Arg$^{28}$. There are also two potential N-glycosylation sites at amino acid positions 36 and 87 (FIGS. 3H-1 and 3H-2).

In another embodiment of the invention, the AGPs in a pear cell culture filtrate were further purified as illustrated in the flow chart of FIGS. 5D-1 and 5D-2. The unbound fraction and the two minor bound fractions (FIG. 5D-1) which accounted for 72%, 0.9% and 0.1%, respectively, of total AGPs loaded on the column, were purified as described above and in Example 3(a).

TABLE 3.3

Amino acid composition of the predicted PcAGP23 protein

| Amino Acid | Mol % | |
|---|---|---|
| | +SP | −SP |
| Ser | 12.2 | 9.8 |
| Gly | 10.5 | 11.1 |
| Leu | 9.4 | 7.8 |
| Val | 8.8 | 9.1 |
| Ala | 7.2 | 6.5 |
| Lys | 7.2 | 7.8 |
| Thr | 5.5 | 6.5 |
| Pro | 5.5 | 6.5 |
| Glu | 5.0 | 5.2 |
| Phe | 4.4 | 2.6 |
| Asp | 3.8 | 4.5 |
| Asn | 2.7 | 3.2 |
| Tyr | 2.7 | 2.6 |
| Arg | 2.7 | 3.2 |
| Ile | 2.7 | 3.2 |
| Gln | 2.2 | 2.6 |
| Trp | 2.2 | 2.6 |
| Cys | 1.6 | 1.9 |
| His | 1.6 | 1.9 |
| Met | 1.1 | 0.6 |

+SP: The putative secretion signal peptide is included.
−SP: The putative secretion signal peptide is excluded.

The major peak of FIG. 5D-1, which accounted for approximately 27% of the AGPs, was collected and reapplied to the same column. Upon elution with a shallow gradient, two peaks (Fractions 1 and 2) were resolved (FIG. 5D-2). The AGPs in Fraction 1 were described above and in Example 3(a).

Size-exclusion FPLC fractionation of Fraction 2 resolved two components (peaks 2A and 2B, FIGS. 5D-2,C3). Arabinose and galactose were the major monosaccharides of each fraction (Table 3.4).

TABLE 3.4

Linkage analysis of AGP fractions

| Monosaccharide and deduced linkage (mol %) | Unbound fraction (FIG. 5D-2, C1) | Fraction 1 (FIG. 5D-2, C2) | Fraction 2 | |
|---|---|---|---|---|
| | | | Peak 2A (FIG. 5D-2, C3) | Peak 2B (FIG. 5D-2, C3) |
| Araf: terminal | 34 | 36 | 24 | 18 |
| 3− | 3 | 3 | 4 | 4 |
| 5− | 2 | 3 | 1 | 1 |
| Galp: terminal | 7 | 8 | 12 | 14 |
| 3− | 5 | 4 | 8 | 5 |
| 6− | 10 | 10 | 8 | 23 |
| 3,6− | 38 | 36 | 44 | 35 |

Araf: Arabinofuranose;
Galp: Galactopyranose

Arabinose was present mainly in the terminal position with small amounts of 3-linked and 5-linked residues. Galactose was present mainly as 3,6-linked and terminal residues in both peaks. However, the proportion of 6-linked galactosyl residues was greater in Peak 2B than 2A, and both had small proportions of 3-linked residues. Amino acid composition analysis of the AGPs in Peaks 2A and 2B are shown in Table 3.5. N-terminal amino acid sequencing of material in Peak 2B gave the sequence A-E-A-E-A-X-T-X-A-L-Q-V-V-A-E-A-X-E-L (SEQ ID NO:74).

TABLE 3.5

Amino acid composition (mol %) of AGPs in Peaks 2A and 2B, their deglycosylated backbone and the protein deduced from PcAGP2 cDNA.

| Amino acid (Mol %) | Peak 2A (FIG. 5D-2, C3) | Deglycosylated Peak 2A (FIG. 5D-2, D3) | Peak 2B (FIG. 5D-2, C3) | Deglycosylated Peak 2B (FIG. 5D-2, D4) | Deduced peptide fragment* | | Deduced protein** | |
|---|---|---|---|---|---|---|---|---|
| Hyp | 28.2 | 27.5 | 19.2 | 19.5 | | | | |
| Pro | 3.3 | 4.3 | 2.8 | 2.8 | | 19.4 | | 5.4 |
| Asx | 1.2 | 2.0 | 2.2 | 2.0 | Asn | 0.0 | Asn | 14.2 |
| | | | | | Asp | 2.7 | Asp | 5.4 |
| Glx | 6.9 | 6.6 | 14.9 | 14.3 | Glu | 13.8 | Glu | 8.0 |
| | | | | | Gln | 2.7 | Gln | 4.0 |
| Ser | 18.6 | 18.4 | 6.6 | 6.0 | | 5.5 | | 9.1 |
| Gly | 4.1 | 4.5 | 3.4 | 5.5 | | 2.7 | | 10.5 |
| His | 0.4 | 0.6 | 1.3 | 1.9 | | 2.7 | | 2.5 |
| Arg | 0.6 | 0.0 | 2.5 | 2.7 | | 2.7 | | 3.6 |
| Thr | 11.6 | 10.7 | 10.4 | 9.6 | | 11.1 | | 6.5 |
| Ala | 13.1 | 12.5 | 16.7 | 16.6 | | 16.6 | | 3.2 |
| Tyr | 0.2 | 0.1 | 2.5 | 0.1 | | 2.7 | | 7.6 |
| Val | 4.9 | 4.2 | 9.3 | 10.0 | | 11.1 | | 4.7 |
| Met | 0.4 | 1.8 | 0.3 | 0.2 | | 0.0 | | 1.0 |
| Ile | 2.8 | 2.1 | 0.8 | 0.8 | | 0.0 | | 4.0 |
| Leu | 1.3 | 1.5 | 5.9 | 6.4 | | 5.5 | | 2.9 |
| Phe | 0.0 | 0.0 | 0.4 | 0.5 | | 0.0 | | 2.5 |
| Lys | 2.9 | 2.1 | 1.0 | 1.3 | | 0.0 | | 4.0 |
| Cys | nd | nd | nd | nd | | 0.0 | | 0.0 |
| Trp | nd | nd | nd | nd | | 0.0 | | 0.0 |

*Amino acid residues 53–88 (FIGS. 2A–2D).
**Complete deduced protein sequence excluding the 20-amino acid signal sequence (FIGS. 2A–2D).
nd: Not determined AGPs in Peaks 2A and 2B were separately deglycosylated and the resulting protein backbones isolated by size-exclusion FPLC (FIG. 5D-2, D1–D4). The apparent $M_r$ of the proteins was different for each fraction. Peak 2B gave one protein backbone ($M_r$ 10k), Peak 2A resulted in two protein peaks (M, 10k and 54k). The 10k protein backbone in Peak 2A is a contamination from Peak 2B. N-terminal amino acid sequencing of the 54k protein backbone gave the sequence T-O-A-O-A (SEQ ID NO:75) while the 10k protein backbone in Peak 2B gave the sequence A-E-A-E-A-O-T-O-A-L-Q-V-V-A-E-A-O-E-L (SEQ ID NO:76). The latter sequence is identical to the N-terminal sequence obtained from the AGP in Peak 2B before deglycosylation, assuming the unassigned residues "X" are Hyp. The amino acid compositions of the 54k and 10k protein backbones are very similar to that of their parent AGPs in Peaks 2A and 2B, respectively. The 54k protein backbone contained a higher proportion of Hyp (27.5%), Ser (18.4%) than the 10k protein backbone in Peak 2B (Hyp, 19.5%; Ser, 6.0%). On the other hand, the 10k protein backbone had a higher content of Glx (14.3%) and Val (10.1%) than the 54k protein backbone in Peak 2A (Glx, 6.6%; Val, 4.2%) (Table 3.5). The 10k and 54k protein backbones were digested separately with thermolysin and the resulting peptides purified by RP-HPLC for sequencing. Sequences of eight peptides were obtained from the 54k protein Peak 2A and three from the 10k protein in Peak 2B (Table 3.6). Two of the three sequences and the N-terminal sequence overlap to give a sequence A-E-A-E-A-O-T-O-A-L-Q-V-V-A-E-A-O-E-L-V-O-T-O-V-O-T-O-S-Y (SEQ ID NO:88) for the 10k protein in Peak 2B.

TABLE 4.1

Amino acid analysis of AGPs isolated from the styles of *N. alata* (genotype $S_6S_6$)

| Amino Acid | Total native AGPs separated by MonoQ column | | MonoQ bound AGPs separated by GPC chromatography deglycosylated and further fractionated by RP300 HPLC | | |
|---|---|---|---|---|---|
| | MonoQ Unb. | MonoQ Bound | RP-Unbound | RT25 | RT35 |
| Hyp | 19.2 | 7.5 | ND | 18.1 | 0.4 |
| Asx | 6.3 | 13.0 | 8.8 | 3.6 | 14.8 |
| Thr | 3.9 | 7.7 | 4.0 | 6.9 | 5.3 |
| Ser | 10.3 | 6.0 | 11.5 | 14.8 | 6.2 |
| Glx | 8.8 | 11.2 | 13.3 | 6.2 | 14.0 |
| Pro | 9.2 | 3.0 | 3.6 | 2.7 | 2.7 |
| Gly | 6.1 | 5.5 | 20.7 | 9.3 | 7.9 |
| Ala | 16.6 | 15.9 | 6.2 | 20.1 | 10.6 |
| Val | 3.7 | 3.4 | 4.4 | 6.3 | 3.8 |
| 1/2Cys | ND | ND | ND | ND | ND |
| Met | 2.1 | 2.6 | 0.9 | 1.5 | 2.7 |
| Ile | 2.4 | 4.3 | 3.6 | 1.7 | 5.2 |
| Leu | 4.2 | 5.9 | 7.0 | 2.7 | 6.9 |
| Tyr | 1.2 | 3.4 | 3.4 | 0.5 | 4.2 |
| Phe | 1.3 | 2.7 | 2.2 | 1.4 | 3.7 |
| Lys | 0.4 | 3.5 | 1.8 | 2.3 | 4.6 |
| His | 1.1 | 1.0 | 3.2 | 1.0 | 1.7 |
| Arg | 2.7 | 2.2 | 4.7 | 0.8 | 3.4 |
| Trp | ND | ND | ND | ND | ND |

Hyp: Hydroxyproline,
ND: not determined

TABLE 3.6

Peptide sequences obtained from Peaks 2A and 2B

| Peak | Peptide sequence | |
|---|---|---|
| Peak 2A | T—O—A—O—A (N-terminal) | (SEQ ID NO:75) |
| | V—S—X—O—V—Q—S—O—A—X—O | (SEQ ID NO:77) |
| | V—X—X—O—V—Q—S—O—A—S—O—O—O—T—T | (SEQ ID NO:78) |
| | I—S—O—A—S—T—O—O—T— | (SEQ ID NO:79) |
| | I—S—O—A—S—T—O—O—T—O—A—S—O—O—T | (SEQ ID NO:80) |
| | F—S—O—T—I—S—O—A | (SEQ ID NO:81) |
| | X—A—(A)—T—O—S—L—D—V—G—I—O—S—S—N—A—T | (SEQ ID NO:82) |
| | T/P—S—O—A—T—O—O—A—T | (SEQ ID NO:83) |
| | X—A—A—O—A—O—S—(O)—X—P—T—(N)—T | (SEQ ID NO:84) |
| Peak 2B | A—E—A—E—A—X—T—X—A—L—Q—V—V—A—E—A—X—E—L (N-terminal)* # | (SEQ ID NO:74) |
| | A—E—A—E—A—O—T—O—A—L—Q—V—V—A—E—A—O—E—L (N-terminal)** # | (SEQ ID NO:76) |
| | V—V—A—E—A—O—E—L—V—O—T—O—V—O—T—O—S-# | (SEQ ID NO:85) |
| | L—V—O—T—O—V—O—T—O—S—Y # | (SEQ ID NO:86) |
| | Y—T—E—R— # | (SEQ ID NO:87) |

Note:
All the residues of ambiguous assignments are shown, uncertain residues are in brackets.
"X" indicates no signal or an unknown residue. "O" represents hydroxyproline. Sequences included in the cDNA are marked #.
*Obtained from the AGP in Peak 2B before deglycosylation.
**Obtained from the deglycosylated protein backbone of the AGP in Peak 2B.

In another embodiment of the invention, AGPs were isolated from *N. alata* styles. In this example, the total native *N. alata* style AGPs were not purified by the Yariv reagent precipitation technique, but by ion exchange chromatography (IEC) followed by gel filtration chromatography (GFC). The presence of AGP in column fractions was verified by precipitation of AGP with a Yariv reagent. The AGPs were then deglycosylated by HF and fractionated by reversed phase HPLC.

Two major peaks: RT25 and RT35 (FIG. 4C) were obtained after deglycosylation and HPLC fractionation. Amino acid analysis of each fraction and the native materials are shown in Table 4.1.

Distinct differences are apparent in the amino acid composition between the three fractions. The unbound fraction contains little Hyp but is rich in Gly, Glx, Ser and Asx. The RT35 fraction is also Hyp-poor but rich in Asx, Glx and Ala. Together, these two fractions account for the bulk of the Asx and Glx detected in the native and deglycosylated AGPs. The amino acid composition of the material in fraction RT25 is dominated by Hyp (18%), Ala (20%) and Ser (15%) with very little Tyr. This RT25 protein backbone was thus selected for further analyses.

Peak RT25 gave four sequences (SEQ ID NOS:50–53) which are OAST-enriched. Three of these sequences (SEQ ID NOS:50, 51, and 52) closely matched SEQ ID NOS:27–29, respectively, for RT21 from N. plumbaginafolia.

An N-terminal sequence was not obtained for the RT25 peak. Pyroglutamate aminopeptidase was then used to remove the N-terminal blocked pyroglutamate residue and the sequence Ala-Hyp-Gly was obtained. The RT25 backbone was also fragmented by treatment with the endoproteinase thermolysin. The resulting peptides were separated and further purified by RP-HPLC. Six major peptides (FIG. 4I) were subjected to amino acid sequencing and four sequences were obtained (SEQ ID NOS:50, 51, 53, 67). All the sequences were rich in Hyp, Ser and Ala (33 of 52 amino acid residues).

Endoproteinase Asp-N was also used to cleave the RT25 protein backbone at the Asp residues. Two major peptides were produced (A1 and A2; FIG. 4J) indicating that there is only one Asp residue in the RT25 protein. The cleavage was incomplete as indicated by the presence of the starting material (RT25 protein; FIGS. 4K-1 and 4K-2). Peptide sequence was obtained for A2 (SEQ ID NO:68). The other peptide (A1) gave no sequence data, indicating a blocked N-terminal residue. Overlaps were identified between A2 (SEQ ID NO:68) (FIG. 4J) and Peak 3 (SEQ ID NO:51) (FIG. 4I) and gave a continuous amino acid sequence of 26 reisdues: LASOOAOOTADTOAFAOSGGVALPOS (SEQ ID NO:69).

Peak RT35 gave four sequences (SEQ ID NOS:54–57) which had a low OAST content. Three of these sequences (SEQ ID NOS:55–57) were characterized by the sequence T-A-I-N-T-E-F-G-P (SEQ ID NO:58).

In an alternative method of preparation, N. alata style AGPs were isolated according to Bacic et al. (1988) Phytochem. 27:679–684. The sample was deglycosylated with TFMS, separated and blotted onto a PVDF membrane as described previously for N. alata suspension-cultured cells. An approximately 30 kD band, running at the same position as the major band prepared by Yariv precipitation from N. alata suspension cultured cells, was sequenced. The sequence A-V-F-K-N-K-X-X-L-T-X-X-P-X-I-I (SEQ ID NO:59) was obtained.

In other embodiments of the invention, AGP genes from N. alata style were isolated. The cloning strategy of FIG. 4D was used to obtain the genes. Several of the peptide sequences of peak RT35 isolated from N. alata style contained the sequence T-A-I-N-T-E-F-G-P (SEQ ID NO:58). In a specific embodiment, gene-specific degenerate oligonucleotide primers were designed based on the sequence A-I-N-T-E-F-G (SEQ ID NO:60) and a PCR fragment was amplified in vitro from style RNA of N. alata. A 380-bp PCR fragment (SEQ ID NO:62; FIG. 4E) was used to screen a style cDNA library and a cDNA clone was isolated and fully sequenced. The N. alata style cDNA clone was designated Na35_1. The insert of the cDNA clone was 800 bp in length with a poly(A) tail at the 3'-end. The cDNA sequence (SEQ ID NO:63) matched the PCR sequence except that it was 3 bp shorter at the 3'-end (FIG. 4E and FIGS. 4F-1 and 4F-2).

The Na35_1 sequence (SEQ ID NO:63) had an open reading frame starting with an initiation codon (ATG) at position 21 and ending with a termination codon (TAA) at position 530 (FIGS. 4F-1 and 4F-2). The open reading frame encoded a polypeptide containing 169 amino acid residues with a calculated molecular weight of 19.5 kD and a predicted pI of 8.1. The most abundant residues in the sequence were: proline (11.2%), phenylalanine (9.5%), alanine (7.7%), leucine (7.7%), and lysine (7.7%) (Table 4.2).

TABLE 4.2

Amino acid composition of the predicted Na35_1 polypeptide and purified RT35 peptide peak

| Amino Acid | Na35_1 cDNA | RT35 peptide |
|---|---|---|
| Asn/Asp | 11.8 | 14.5 |
| Thr | 3.0 | 6.7 |
| Ser | 5.9 | 5.5 |
| Gln/Glu | 7.1 | 12.4 |
| Pro/Hyp | 11.2 | 7.8 |
| Gly | 1.8 | 4.3 |
| Ala | 7.7 | 10.8 |
| Val | 2.4 | 4.2 |
| 1/2 Cys | 4.7 | 1.1 |
| Met | 2.4 | 3.0 |
| Ile | 7.7 | 4.8 |
| Leu | 7.7 | 6.6 |
| Tyr | 3.0 | 3.1 |
| Phe | 9.5 | 4.2 |
| Trp | 1.8 | ND |
| Lys | 6.5 | 5.3 |
| His | 1.8 | 2.1 |
| Arg | 4.1 | 3.4 |

N.D.: not determined

The amino acid sequence derived from the N. alata style cDNA (SEQ ID NO:63) comprised regions that matched peptide fragments of peak 35 isolated from N. alata styles, i.e., SEQ ID NO:55, SEQ ID NO:56, and SEQ ID NO:57. Northern blot analyses of the Na35_1 gene (FIG. 4G) indicated a specificity of the gene to N. alata and to style tissue. Signals were not detected in transcripts from tomato style, N. alata cell suspension, N. plumbaginafolia cell suspension, and pear cell suspension (FIG. 4H) indicating that the Na35_1 PCR fragment was specific for an N. alata style AGP gene.

Further, the isolation of a different gene for an N. alata style AGP is described in another specific embodiment of the invention. The five peptides isolated from fragments of the AGP protein backbone (SEQ ID NOS:50,51,53,67 and 68) together gave 52 amino acid residues. Much of the sequence contained adjacent residues of Hyp, Ser and Ala for which the codons are highly redundant and GC-rich. These sequences are not useful for cloning. However, the sequence TADTOAF from the continuous 26 amino acid sequence resulting from the overlaps of the isolated peptides contains two amino acids which are not GC-rich and only have two degenerate codons. This TADTOAF sequence allowed design of an oligonucleotide suitable for PCR and the eventual cloning of the AGPNal 1 cDNA.

A gene-specific oligonucleotide (20 nucleotides) was designed from one region of the continuous 26 amino acid sequence: TADTOAF (SEQ ID NO:70). Inosine was used at the third position of the first two codons to reduce the degeneracy of the oligonucleotide to 128. The resulting oligonucleotide contained 60% GC. cDNA was synthesized from total style RNA using poly T linked with an adaptor sequence. Rapid amplification of the cDNA 3' end (3' RACE) was performed using the gene-specific primer together with a 3' primer in the adaptor sequence. A PCR fragment of 400 base pairs (bp) was produced. This PCR fragment was cloned and sequenced. The deduced amino acid sequence from this PCR clone matched isolated AGP sequences, i.e., SEQ ID NOS: 50, 51, 53, 67, 68.

The PCR clone was then used as a probe to screen a style cDNA library (300,000 plaques). Two cDNA clones were obtained which differ only in the length of the 3' and 5' ends. One of the clones, designated AGPNal 1 (SEQ. ID NO:72; FIGS. 4K-1 and 4K-2) was used for all subsequent analyses. The 3' end of the AGPNal 1 cDNA clone was identical to the PCR clone except that the PCR clone was 20 bp shorter and contained a poly A tail. The 712-bp AGPNal 1 clone encodes a putative protein of 12.5 kD (FIGS. 4K-1 and 4K-2). The derived amino acid sequence includes sequences identical to isolated AGP peptides (SEQ ID NOS:50, 51, 53, 67 and 68). Most of the proline residues in the peptide sequences obtained by amino acid sequencing are hydroxylated. A secretion signal peptide is predicted (FIGS. 4K-1, 4K-2 and 4L). The deduced N-terminus of the mature protein (10 kD; pI 6.8) is Gln-Ala-Pro-Gly which matches the N-terminal sequence data obtained. The Pro residue in the N-terminal sequence is also hydroxylated. The amino acid composition of the deduced mature protein and the isolated RT25 protein backbone are in general agreement (Table 4.1). The C-terminus of the deduced protein is very hydrophobic and predicted to be a transmembrane helix.

The cDNA clone obtained (FIGS. 4K-1 and 4K-2) predicts a 132 amino acid protein characterized by hydrophobic stretches at both the N-and C-termini (FIG. 4L). The N-terminal hydrophobic sequence corresponds to a signal peptide which would lead to secretion of the encoded protein. This is consistent with the known secretion and extracellular localization of the style AGPs [Sedgley et al. (1985) *Micron Microscop. Acta* 16:247–254]. Modification of the N-terminal residue, Gln, by intra-molecular cyclization to form pyroglutamate is not unusual. The cyclization could occur during purification, or it could occur in situ and might be involved in the stabilization of the AGP backbones. The same N-terminal sequence: Gln-Ala-Pro-Gly-Ala is also present in the AGP backbone isolated from pear (FIGS. 5A-1 and 5A-2). The C-terminal hydrophobic sequence is predicted to be a transmembrane helix (FIG. 4L) which might anchor the AGP in plasma membrane. The hydrophobic C-terminal region could also potentially enable the interaction of the AGP with other proteins, such as S-RNase which also contains a very hydrophobic sequence (in this case at the N-terminus of the mature protein; Mau et al. (1986) *Planta* 169:184–191. The central part of the protein contains most of the Hyp, Ala, Ser residues. The fact that most of the Pro residues within the peptide sequences are hydroxylated suggests extensive O-glycosylation in the central part of the protein. No potential N-glycosylation sites are present. The abundance of potential O-glycosylation sites is consistent with the high content of carbohydrate (85% w/w). Individual AGPs may differ in the types of saccharide chains and in the number and location of glycosylation sites along the protein backbone.

mRNA hybridizing to AGPNal 1 cDNA is present in most tissues of *N. alata* and in the styles of related solanaceous species (FIGS. 4M-1 and 4M-2) suggesting a general role of this transcript (or closely related transcripts) in plant development. Various tissues from *N. alata* were examined for the expression of the AGPNal 1 gene. As shown in FIG. 4M-1, mRNA transcripts of similar length of about 700–750 nucleotide were detected in all tissues examined. This suggests that the AGPNal 1 gene or its homologs are expressed in many parts of the plant. Style, ovary, petal, leaf and stem have similar levels of transcript, but the highest level of mRNA expression is found in roots.

Some expression of hybridizing transcript was detected in the styles of *N. sylvestris* and *N. tabacum* and a lower level in *N. glauca* and *Lycopersicon peruvianum* (FIG. 4M-2). Arabidopsis and rye grass (*Lolium perenne*, a monocot) leaves had no detectable hybridizing transcript.

In another embodiment of the invention, an AGP gene was isolated from *P. communis* using a guessmer oligonucleotide sequence encoding a hydroxyproline-rich pear AGP segment and linked to a double-stranded promoter sequence for RNA polymerase, allowing the synthesis of an antisense RNA probe (see FIG. 1) (strategy B). Strategy B thus enabled the isolation of an AGP gene (SEQ ID NO:66) that specifically encodes a particular hydroxyproline-rich peptide segment (see FIGS. 5A-1 and 5A-2). Hydroxyproline-rich and OAST-rich domains appear to represent characterizing features of AGPs.

AGP peptide fragments were isolated and sequenced essentially as described in Example 3(a). The sequence A-K-S-O-T-A-T-O-O-T-A-T-O-O-S-A-V (SEQ ID NO:37) of an isolated pear AGP fragment exhibited hydroxyproline-enrichment and OAST-enrichment. This sequence was selected for the isolation of a corresponding pear AGP gene. The codon usage for proline is strongly biased towards CCA which accounts for 73.3% of all proline codons; the codon for alanine is biased, to a lesser extent, to CCT (44.8%); there is no significant bias in codon usage for other amino acids.

Two hybrid oligonucleotides (AF1T3 and AR2T7), each comprising a GC-enriched sequence encoding a hydroxyproline-rich AGP segment, were constructed as primers. The sequences of primers AF1T3 and AR2T7, each comprising a GC-rich domain, are presented in Table 5.1. AF1T3 (SEQ ID NO:64) includes a T3 promoter sequence, a 42-bp GC-enriched nucleotide sequence corresponding to an isolated *N. plumbaginafolia* AGP peptide fragment (SEQ ID NO:27), that is OAST-enriched, and an 18-bp sequence corresponding to position 150–167 from the NaAGP1 (SEQ ID NO:24). The AR2T7 primer (SEQ ID NO:65) consists of a T7 promoter, a 47-bp GC-enriched nucleotide sequence corresponding to a hydroxyproline-rich (OAST-enriched) AGP sequence from pear (SEQ ID NO:37) and another 18-bp sequence corresponding to position 444–461 from the NaAGP1 cDNA (SEQ ID NO:24).

An antisense RNA probe was synthesized from the guessmer oligonucleotide template by using T7 polymerase, and was used to screen a cDNA library prepared from pear cell suspension culture essentially as described in Example 3(b). Three cDNA clones were isolated and sequenced. The sequence of the longest clone PcAGP9 (SEQ ID NO:66) is shown in FIGS. 5A-1 and 5A-2. The cDNA clone contains an insert of 893 bp and encodes an open reading frame of 145 amino acid residues. There is a putative secretion signal peptide at the N-terminus. The predicted polypeptide is highly rich in Pro, Ala, Ser, and Thr (Table 5.2) and contains two sequences which match exactly two peptide sequences obtained previously from pear AGPs by protein sequencing: AKSOTATOOTATOOSAV (SEQ ID NO:37) and VTAOTOSASOOSSTOA(S)TXA (SEQ ID NO:38). The PcAGP9 sequence (with the secretion signal included) gave an estimated pI of 10.79 and an apparent molecular weight of 13.622 kD. The PcAGP9 sequence (excluding the secretion signal) gave an estimated pI of 11.07 and an apparent molecular weight of 11.238 kD.

TABLE 5.1

Nucleotide sequences of the primers AF1T3 and AR2T7

AF1T3: (Forward primer) (SEQ ID NO: 64)

```
                  N-terminus  →→→→→→→→→→  C-terminus           Nucleotide 150-167
T3 promoter                  A T  O  O  A  O  O  T  A D  T  P  A    of the NaAGP1 cDNA
5'TGTTATTAACCCTCACTAAAGCATCACCACCAGCACCACCAACAGCAGACACACCAGCAGCTATGATCATACCTGCATCT3'
```

AR2T7 (Reverse primer) (SEQ ID NO:65)

```
                  C-terminus       ←←←←←←    N-terminus           Nucleotide 444-461
T7 promoter                  A S O  O  T  A  T  O  O O  T  A T  O T  K A  of the NaAGP1 cDNA
5'NCTAATACGACTCACTATAGGCTGATGGTGGTGTTGCTGTTGGTGGTGGTGTTGCTGTTGGTGATTTGCGGGAGTATCAGTCAAAAG3'
```

Promomter sequences are underlined once. Sequences from NaAGP1 cDNA are double underlined.

TABLE 5.2

Amino acid composition of the PcAGP9 sequence

| Amino acid | +Secretion Signal | | −Secretion Signal | |
|---|---|---|---|---|
| | No. | Mol % | No. | Mol % |
| Pro | 30 | 20.6 | 30 | 24.5 |
| Ala | 29 | 20.0 | 26 | 21.3 |
| Ser | 25 | 17.2 | 24 | 19.6 |
| Thr | 17 | 11.7 | 16 | 13.1 |
| Val | 8 | 5.5 | 6 | 4.9 |
| Gly | 8 | 5.5 | 5 | 4.1 |
| Leu | 6 | 4.0 | 2 | 1.6 |
| Ile | 5 | 3.4 | 4 | 3.2 |
| Lys | 4 | 2.7 | 3 | 2.4 |
| Phe | 4 | 2.7 | 2 | 1.6 |
| Met | 3 | 2.0 | 0 | 0.0 |
| Gln | 2 | 1.3 | 1 | 0.8 |
| Asn | 1 | 0.6 | 1 | 0.8 |
| Asp | 1 | 0.6 | 1 | 0.8 |
| Arg | 1 | 0.6 | 1 | 0.8 |
| Cys | 1 | 0.6 | 0 | 0.0 |
| Glu | 0 | 0.0 | 0 | 0.0 |
| His | 0 | 0.0 | 0 | 0.0 |
| Tyr | 0 | 0.0 | 0 | 0.0 |
| Trp | 0 | 0.0 | 0 | 0.0 |

As illustrated in the hydropathy profile of FIG. 5C, the cDNA has three domains, an N-terminal hydrophobic sequence encoding a secretion signal, a central hydrophilic domain containing most of the proline residues and a hydrophobic C-terminal domain which is predicted to be a transmembrane helix. The N-terminus of the mature protein corresponds to the sequence predicted from processing of the secretion signal. The proline residues within the central region are mainly hydroxylated and would bear the glycosyl chains. A cDNA encoding the protein backbone of an AGP from the styles of *Nicotiana alata*, has three domains with similar characteristics. Although the amino acid composition of the proteins encoded by these cDNAs is similar, the only common sequence is at the N-terminal sequence of the mature proteins, Q-A-P-G-A-A (SEQ ID NO:73). The cDNAs encode protein backbones of single AGPs from several present in the plant extracts which are quantitatively a minor part of these proteoglycans.

The central part (amino acids 24–123) of the sequence is dominated by four amino acids (Pro, 29%; Ala, 19%; Ser, 23% and Thr 15%). The dominant feature of this part of the sequence is that the four residues are interspersed with each other; there are no obvious motifs and few runs of any single amino acid. There are no predicted N-glycosylation sites.

The C-terminal region of 22 amino acid residues is very hydrophobic and is predicted to be a transmembrane helix [Eisenberg et al. (1984) *J. Mol. Biol.* 179:125–142; Klein et al (1985) *Biochem Biophys. Acta* 815:468–476; Rao et al. (1986) *Biochem Biophys. Acta* 869:197–214]. There are several potential sites for proteolytic cleavage (Endoprotease Asp-N, $Ala^{114}/Asp^{115}$; V8 protease, $Asp^{115}/Ala^{116}$; Clostripain and Trypsin, $Arg^{127}/Val^{128}$) around the border between the C-terminal transmembrane helix and the extracellular domain [Allen et al. (1989) *Sequencing of Proteins and Peptides* (2nd ed.); Drapeau (1978) *Can. J. Chem.* 56:534–544; (1980) *J. Biol. Chem.* 255:839–840]. These represent single cleavage sites, with the exception of trypsin for which there are several cleavage sites within the sequence.

The PcAGP9 cDNA was used to probe northern blots containing RNA from six plants representing both dicotyledonous (Pyrus, Nicotiana, Brassica, Arabidopsis, and Lycopersicon) and monocotyledonous (Lolium) plants (FIGS. 5B-1 and 5B-2). At high stringency (65° C.), a 0.9 kb transcript was detected in an RNA sample from suspension culture cells of *Pyrus communis*. A smaller transcript was also detected in pedicels of the same plant together with a larger transcript in *N. plumbaginafolia* suspension culture cells (FIG. 5B-2). Under reduced stringency conditions (55° C.), RNA transcripts were also detected in all other RNA samples tested indicating the expression of AGP genes homologous to PcAGP9 in both dicotyledonous and monocotyledonous plants tested (FIG. 5B-1).

The PcAGP9 cDNA has similarity to the *N. alata* sytle cDNA (AGPNa1 1 clone). In both cases the cDNA clones predict protein sequences composed mainly of Pro, Ala, Ser and Thr. Despite the similarity in amino acid composition, these cDNA clones have little sequence identity. In fact, the AGPNa1 1 cDNA and PcAGP9 cDNA did not cross hybridize at medium to high stringency on RNA blot analysis; the AGPNa1 1 detected a single 700–750 nt transcript in most tissues examined while the PcAGP9 detected a 800–900 nt mRNA. Other AGP-like peptide sequences have also been reported from *N. plumbaginifolia*, pear, *L. multiflorum* and a histidine-rich HRGP from maize suspension cell culture filtrate [Kieliszewski et al (1992) *Plant Physiol.* 99:538–547]. Again, these peptides are composed mainly of Hyp, Ala and Ser residues yet the exact sequences is different. For example, the Ala-Pro-Ala-Pro repeats present in *L. multiflorum* are not present in the deduced amino acid sequence from the AGPNa1 1 and PcAGP9 cDNA.

In another embodiment of the invention, another *P. communis* cDNA (PcAGP2; SEQ ID NO:91) was isolated and shown to be distinct from both the PcAGP9 (SEQ ID NO:66) and the PcAGP23 (SEQ ID NO:49) clones. The approach to cloning the PcAGP2 cDNA was essentially the same as for the PcAGP9 cDNA (Example 5).

The 10k protein purified in FPLC as Peak 2B (FIG. 5D-2,D4) and having the amino acid sequence of AEAE-AOTOALQVVAEAOELVOTOVOTOSY (SEQ ID NO:88) was selected for the isolation of a corresponding pear AGP gene. Two reverse and partially complementary long "guess-mers" [AcF1 (SEQ ID NO:89) and AcR2 (SEQ ID NO:90), Table 5.3] were synthesized.

TABLE 5.3

Nucleotide and corresponding peptide sequences of the "guessmers" AcF1 and AcR2

AcF1 (SEQ ID NO:89)

5' TTCCTGCAGAAGCAGAAGCACCAACACCAGCACTACAAGTAGTAGCAGAAGCACCAGAA 3'

AcR2 (SEQ ID NO:90)

5' CTGGAGCTCATATGATGGTGTTGGTACTGGTGTTGGTACTAGTTCTGGTGCTTCTGCTAC 3'

Note: Restriction enzyme cut sites incorporated into the guessmer for subcloning are underlined. Reverse-complementary regions are double-underlined.

In the "guessmers," nucleotide A was used at the third codon position for all amino acids, and CTA and TCA were assigned for Leu and Ser residues, respectively. The last 18 bp sequence at the 3' of the two "guessmers" were reverse-complementary, and they were annealed to each other in PCR to produce a double-stranded DNA fragment of 101 bp encoding the amino acid sequence A-E-A-E-A-O-T-O-A-L-Q-V-V-A-E-A-O-E-L-V-O-T-O-V-O-T-O-S-Y (SEQ ID NO:88). The PCR fragment was subcloned into the pBluescriptII (Ks) vector. A $^{32}$P-labeled anti-sense RNA probe was synthesized using T3 RNA polymerase from the 101-bp DNA fragment and used to screen a pear cDNA library. Five cDNA clones were isolated and sequenced. The consensus sequence of 1040 bp is shown in FIGS. 5E-1 and 5E-2. This cDNA is referred to as PcAGP2 (SEQ ID NO:91).

The PcAGP2 cDNA sequence encodes a polypeptide of 294 residues and can be divided into four domains (FIGS. 5E-1 and 5E-2). The first 20 amino acid sequence is hydrophobic and predicted to be a secretion signal with a potential cleavage site between Ser$^{20}$ and Phe$^{21}$. The second domain (residues 21–51) is rich in Asn and contains a stretch of five Asn residues. The third domain (residues 52–135) is rich in Pro, Ala, Thr, and Glu. Most of these four residues are located in this domain. This domain also includes all the peptide sequences obtained by protein sequencing. The fourth domain (residues 136–294) is rich in Asn and Gly and contains two direct repeated sequences of 34 residues. The amino acid composition of the deduced protein, excluding the signal sequence, differs from that obtained from the glycosylated and deglycosylated AGP in Peak 2B in that it is rich in Asn (14.2%), Glu (8.0%), Gly (10.5%) and Ser (9.1%) (Table 3.5). However, the sequence from residues 53 to 88 has an amino acid composition closely matching that obtained from the AGP in Peak 2B.

Except as noted hereafter, standard techniques for isolation and purification of proteins and protein fragments, sequencing, chromatography, cloning, DNA isolation, amplification and purification, for enzymatic reactions involving DNA ligase, DNA polymerase, restriction endonuclease and the like, the PCR technique and various protein separation and purification techniques are those known and commonly employed by those skilled in the art. A number of standard techniques are described in Deutscher (1990) *Methods in Enzymology* 182:309–539; Maniatis et al. (1982) *Molecular Cloning*, Cold Spring Harbor Laboratory, Cold Spring Harbor, N.Y.; Wu (ed.) (1979) *Meth. Enzymol.* 68; Sambrook, et al. (1989) supra; Wu et al. (1983) *Meth. Enzymol.* 100 and 101; Grossman and Moldave (eds.) (1980) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Method of Molecular Biology;* Glover (ed.) (1985) *DNA Cloning* Vols. I and II, IRL Press, Oxford, UK; Hames and Higgins (eds.) (1985) *Nucleic Acid Hybridization*, IRL Press, Oxford UK; Setlow, Hollaender (1979) *Genetic Engineering: Principles and Methods*, Vols. 1–4, Plenum Press, New York and Deutscher (ed.) (1990) *Guide to Protein Purification*, Academic Press, New York. Abbreviations and nomenclature, where employed, are deemed standard in the field and commonly used in professional journals such as those cited herein.

It will be appreciated by those of ordinary skill in the art that the objects of this invention can be achieved without the expense of undue experimentation using well known variants, modifications, or equivalents of the methods and techniques described herein. The skilled artisan will also appreciate that alternative means, other than those specifically described, are available in the art to attain protein purification and to achieve the functional features of the molecules described herein and how to employ those alternatives to achieve functional equivalents of the molecules of the present invention. It is intended that the present invention include those variants, modifications, alternatives, and equivalents which are appreciated by the skilled artisan and encompassed by the spirit and scope of the present disclosure.

The following examples are provided to better elucidate the practice of the present invention and should not be interpreted in any way to limit the scope of the present invention. Those skilled in the art will recognize that various modifications can be made to the methods and genes described herein while not departing from the spirit and scope of the present invention.

EXAMPLE 1

General Method for the Isolation and Purification of AGP Peptides from Plant Cells Comprising AGP 1. Preparation of Cell Suspension Cultures Suspension cultures of plant cells comprising AGP were initiated from cotyledons of seedlings germinated in the medium of Murashige and Skoog (1977) *Physiol. Plant*

15:473–497 supplemented with plant hormones, factors, buffers, salts, etc., as are routinely used in the art to enhance and improve the quality of cell growth.

2. Preparation of Plant Tissue Extracts

Plants were grown from commercial seed stock and were maintained under standard glass house conditions.

3. Isolation of Total AGPs

Total AGPs were prepared from suspension-cultured cells by precipitation of AGPs from the culture medium with Yariv reagent [Yariv et al. (1967), *Biochem. J.* 105:1C], followed by dissociation of the AGP-Yariv reagent complex and recovery of the AGP. Alternatively, total AGPs were prepared from plant tissue extracts by $(NH_4)_2SO_4$ precipitation, anion exchange chromatography and/or immunoaffinity chromatography with, for example, an antibody specific for Gal 1-6-B-Gal sequences, followed by gel filtration chromatography using, for example, a superose matrix.

The AGPs of the total AGP fraction were separated using either ion exchange or reverse phase HPLC. The individual AGPs were then subjected to amino acid sequencing. Alternatively, the total AGP fraction was subjected to deglycosylation using, for example, TFMS or HF, and the deglycosylated AGPs were separated either on SDS-PAGE or reverse phase HPLC and prepared for amino acid sequencing. In some cases, the peptides were digested by treatment with proteolytic enzymes before separation of the different deglycosylated peptides.

Hydroxyproline-rich AGP fragments are separated from hydroxyproline-poor fragments by chromatographic methods based on differentiating characteristics, e.g., polarity, immunogenicity, etc. For example, affinity chromatography supports to which are attached ligands specific for amino acid R-group hydroxyls or antibodies to a hydroxyproline-rich peptide fragment that is OAST-enriched are used to retain preferentially hydroxyproline-rich peptides. Other protein purification techniques useful in the separation of hydroxyproline-rich and hydroxyproline-poor fragments are found in Deutscher, *Guide to Protein Purification* (1990) Methods in Enzymology 182.

EXAMPLE 2

Cloning of Genes Encoding a Protein Backbone of an AGP from *Nicotiana alata*, and *N. plumbaginafolia*

(a) Isolation and Purification of AGP Peptides from Suspension Cultures of *Nicotiana alata*

1. Preparation of Suspension Cultures

Suspension cultures of *N. alata* cells were initiated from cotyledons of seedlings germinated in the medium of Murashige and Skoog (1977), supra, supplemented with 1 g/l myo-inositol, 2g/l Mes/KOH pH 5.7, 4% (w/v) sucrose, 0.1 mg/l gibberellic acid and 5 mg/l α-napthalene-acetic acid. The cells were subcultured weekly in this medium without gibberellic acid.

2. Purification and Deglycosylation and Sequencing of AGPs

Cells of *N. alata* were removed from the culture medium by filtration through two layers of Miracloth. The supernatant was centrifuged (10,000×g; 50 min) to remove any cell debris. To the supernatant, NaCl and β-glucosyl Yariv reagent Yariv et al. 1967) were added to a final concentration of 1% and 0.2%, respectively. The AGP-Yariv complex was pelleted by centrifugation (10,000×g; 50 min), washed twice with 1% NaCl, followed by centrifugation as above. The pellet was dissolved in $H_2O$ and undissolved material removed by centrifugation (10,000×g; 20 min). The AGP-Yariv complex was re-precipitated by adding NaCl to 1%, and the precipitate washed and redissolved in $H_2O$. The Yariv precipitation and NaCl wash steps were repeated twice. The AGP-Yariv precipitate was finally dissolved in $H_2O$ and sodium dithionite (30%) was added to disrupt the AGP-Yariv complex. The volume of the sample was reduced by Diaflo (YM30 membrane; Mr 30,000 Dalton cut off) filtration and the solution desalted by passage through a PD10 column (Pharmacia) equilibrated with 10 mM $NH_4HCO_3$.

AGPs from *N. alata* were deglycosylated by trifluoromethane sulphonic acid (TFMS) using a modification of the procedure of Edge et al. (1981). The deglycosylated AGPs were separated on 17.5% SDS-PAGE according to Laemmli (1970). The 17.5% SDS-PAGE gels were run at 200 V with thioglycollic acid (1 mM) in the upper reservoir until the tracking dye reached the bottom of the gel. The peptides were transblotted onto a PVDF membrane with blotting buffer [10 mM 3-(cyclohexylamino)-1-propanesulfonic acid (CAPS) buffer pH 11, 15% methanol, thioglycollic acid (70 µl/l)]. Blotting was for 1.5 h at 90 V with cooling. The blot was stained with 0.1% Coomassie Blue in 50% methanol, 10% acetic acid for 5 min and de-stained in 50% methanol, 10% acetic acid for 5 min. The blot was washed with distilled water overnight and bands excised and sequenced. A major band having a molecular weight of approximately 20–30 kD was obtained from the deglycosylated *N. alata* AGPs.

3. Sequencing

Purified protein was chromatographed on a reverse phase HPLC microbore column prior to automated Edman degradation on a gas phase sequencer [Mau et al. (1986), *Planta* 169:184–191]. Phenylthiohydantoin amino acids were analyzed by HPLC, as described by Grego et al. (1985), *Eur. J. Biochem.* 264:857–862. An N-terminal amino acid sequence, A-K-S-K-F-M-I-I-P-A-S-X-T-X-A (SEQ ID NO:11) was obtained.

(b) Cloning of Genes from *N. alata* and *N. plumbaginafolia* Cell Cultures

1. In Vitro Amplification of 5' End of the cDNA

Total RNA (10 µg) from *N. alata* suspension cultured cells was mixed with 1.0 pmoles gene specific radioactive primers in 10 µl of 40 mM PIPES (pH 6.0), 1 mM EDTA and 0.4M NaCl. The mixture was heated at 80° for 5 min and incubated at 37° overnight. The RNA/primer mixture was precipitated by ethanol and resuspended in 20 µl of reverse transcription buffer containing: 50 mM Tris-HCl (pH 8.3), 60 mM KCl, 10 mM $MgCl_2$, 1 mM DTT, 20 U RNase inhibitor and 50 U AMV reverse transcriptase. After 1 h incubation, the reaction was stopped by addition of EDTA. The RNA was removed by treatment with RNase and the primer extension product was purified by polyacrylamide gel electrophoresis.

The primer extension product was tailed with dGTP by terminal transferase and amplified by PCR using a $(dC)_{15}$-adaptor primer and the gene specific primers. The PCR was carried out in 100 µl solution containing: 1× PCR buffer (100 mM Tris-HCl pH 8.3, 500 mM KCl), 2 mM $MgCl_2$, 200 µM dNTPs, 100 ng poly dC primer, 100–200 ng of gene-specific primer and 2.5 U of Taq DNA polymerase. Samples were denatured by boiling for 5 min and then cooled to 80° before Taq DNA polymerase was added. The PCR cycles are: 25×: 93°, 30 sec.; 42°, 30 sec.; 72° C., 2 min; 4×: 93°, 30 sec.; 42°, 30 sec.; 72°, 5 min and 1×: 93°, 30 sec; 42°, 30 sec; 72°, 10 min. The PCR product was subcloned and sequenced.

2. In Vitro Amplification of 3'-End of the cDNA cDNA was synthesized in a volume of 20 μl solution containing 10 μg total RNA, 1× PCR buffer, 50 mM MgCl$_2$, 10 mM dNTPs, 5 μM of dT$_{(17)}$+adaptors, 30 U of RNasin and 50 U AMV reverse transcriptase at 42° for 1 h. cDNA (2 μl) was subjected to PCR reaction described as above, except that the annealing temperature was 60° in this case.

3. Screening of cDNA Libraries with the PCR Fragment

About 5×10$^4$ pfu phage/plate of cDNA libraries (in λzap) were plated out. After overnight growth at 37°, phage were blotted onto nitrocellulose membranes and hybridized with $^{32}$p-labeled DNA fragment at 68° overnight in a hybridization buffer containing 2× SSPE, 1% SDS, 0.5% BLOTTO, 1% PEG and 0.5 mg/ml carrier DNA [Sambrook et al. (1989) supra]. The membranes were washed at 68° for 30 min in 1× SSC+0.1% SDS and exposed to X-ray film. Positive λzap clones were converted into plasmid DNA by in vivo excision as described in the Stratagene's instruction manual for the sequence analysis.

4. Purification and N-terminal Sequencing of AGPs from the Cell Suspension Culture The purified AGPs were deglycosylated with TFMS and the resulting peptides separated on a 17.5% SDS-PAGE gel and blotted onto a PVDF membrane. The major band (MW: 20–30 kD) (FIG. 1C) was excised and sequenced. An N-terminal peptide sequence: A-K-S-K-F-M-I-I-P-A-S-X-T-X-A (SEQ ID NO:11), was obtained.

5. In Vitro Amplification of an AGP Gene from N. alata cDNA by PCR

The strategy to clone the gene corresponding to the peptide sequence is illustrated in FIGS. 1D-1 and 1D-2. Two groups of degenerate reverse primers of 17 bp corresponding to part of the AGP amino acid sequence were synthesized (Table 1.1). When the group 1 primers were used in a primer extension experiment (FIG. 1D-1), a single 160-bp cDNA fragment was obtained (FIG. 1E). The primers of group 1 were further divided into six subgroups each containing three 17-mers (Table 1.1). Primer extension experiments showed that group NaR1 gave the highest yield of the 160-bp fragment and these oligonucleotides were therefore used as the gene-specific primer in subsequent scale-up preparation of primer extension product and PCR experiments. The 160-bp primer extension product was purified and tailed with dGTP. The tailed, single-stranded cDNA was then amplified by PCR with the oligo NaR1 and a (dC)$_{15}$-adaptor as primers (FIG. 1D-1). The PCR fragment was subcloned and sequenced (SEQ ID NO:21; FIG. 1E). The sequence included a derived peptide which matched with the sequence obtained from the isolated AGP peptide (SEQ ID NO:11). There was one mismatch, the Ala obtained from the peptide sequencing was replaced with an Arg in the cDNA derived sequence. On the basis of this close match (8/9 amino acids), the 160-bp fragment was concluded to represent a correct sequence for part of the gene.

Two specific primers with sequences: 5'CATTATGGGT-CATTTCACTAAGC3' (SEQ ID NO:22) (NaF1); 5 5'GGT-GATCTCAACTCCATTGGTGC3' (SEQ ID NO:23) (NaF2), corresponding to positions 56–78 and 101–123 (FIG. 1E) were then designed and used in conjunction with the two 3'-end nonspecific primers (Ad1 and Ad2) to amplify the 3'-part of the AGP gene by nested PCR (FIG. 1D-2). A 1.6-kb fragment was amplified and sequenced. The alignment of the sequences obtained from the two PCR reactions gave rise to a DNA sequence of 1679 bp (FIGS. 1F-1 and 1F-2). The PCR fragment encodes a protein containing the peptide obtained by protein sequencing with two mismatches: Arg for Ala at position 1 and Pro for His at position 12 (FIGS. 1F-1 and 1F-2).

6. Isolation and Sequence Analysis of cDNA Clones from N. alata and N. plumbaginafolia cDNA Libraries The 1.6-kb PCR fragment was used to screen a cDNA library made from RNA isolated from N. alata cells in suspension culture and three positive clones were isolated and sequenced. The alignment of the PCR sequence with the cDNA sequences gave rise to a 1700-bp sequence including a poly(A) tail of 7 bp (FIGS. 1F-1 and 1F-2). This sequence is designated NaAGP1 (SEQ ID NO:24). Further primer extension experiments suggested that the 1.7 kb NaAGP1 cDNA represents the full-length sequence of the AGP transcript.

The NaAGP1 cDNA encodes an open reading frame, which starts with an initiation codon (ATG) at position 60 and ends with a termination codon (TAA) at position 1443 (FIGS. 1F-1 and 1F-2). The open reading frame encodes a polypeptide containing 461 amino acid residues with a calculated molecular weight of 51.8 kD and a predicted pI of 3.84. The protein is highly rich in asparagine (25%), and relatively rich in serine (8.9%), tyrosine (7.5%), proline (7.2%) and glutamine (7.0%) (Table 1.2), and can be divided into four domains (FIG. 1G). There is a putative transmembrane helix at the N-terminus (1–25), which is very hydrophobic. The next one-third of the protein (26–173 aa) is also hydrophobic and contains most of the proline (93.8%), alanine (76.5%) and threonine (76.2%) residues. These three amino acids account for 39.7% of all the amino acids in this domain (Pro, 20.2%; Thr, 10.8% and Ala, 8.7%) (FIG. 1G). This domain is predicted to be the site of glycosylation by Gal/Ara containing chains, linked through hydroxyproline residues. The proline residues (Nos. 25, 27, 29 and 31 in FIGS. 1H-1 and 1H-2) are known to be hydroxylated, as they appear as hydroxyproline in the peptide sequence obtained from deglycosylated AGPs of N. plumbaginafolia. Such hydroxylation and glycosylation would make the molecule considerably more hydrophilic.

The portion of the protein corresponding to amino acid positions 174–436 is hydrophilic and contains most of the asparagine (95.1%) and tyrosine (94.1%) residues which account for 44.1% and 12.1%, respectively, of all amino acids in this domain (FIGS. 1F-1, 1F-2 and 1G). The asparagine residues are distributed in clusters (2–11 amino acids) along the polypeptide chain. It contains no proline residues. The final 25 residues at C-terminus are hydrophilic (FIG. 1G).

An N. plumbaginafolia cell suspension cDNA library was also screened with the PCR-fragment, and four cDNA clones were isolated and sequenced. The four clones were identical and contained an insert of 1430 bp (FIGS. 1H-1 and 1H-2). This AGP gene is designated NpAGP1 (SEQ ID NO:25). These cDNAs are incomplete and predicted to be about 100 bp shorter at the 5'-end than the full-length sequence of the transcript. The NpAGP1 is not identical, but very similar to, the NaAGP1 at both the nucleotide and derived amino acid sequence levels (86% and 84.7% identity, respectively) (FIGS. 1I-1, 1I-2, and 1J-1 through 1J-4, and Table 1.2). The transmembrane helix is missing in the NpAGP1 cDNA due to the incomplete sequence. The difference between the two AGP genes is mainly in the middle one-third of the sequence while the N-terminal and C-terminal parts are highly conserved (FIGS. 1I-1, 1I-2 and 1J-1 through 1J-4).

7. Northern and Southern Blot Analyses of the Putative AGP Gene

The NaAGP1 was cut into a 5' half (1–540 bp) corresponding to the nontranslated part, the transmembrane helix and the proline-rich domain and a 3'-half (541–1700 bp)

including the asparagine-rich domain, C-terminus and the 3'-nontranslated part. These two parts of the cDNA were used separately to probe northern blots of RNA [Sambrook et al. (1989) supra] isolated from suspension-cultured cells of *N. alata* and *N. plumbaginafolia* and various tissues of *N. alata* plants. The two probes gave an identical hybridization pattern, confirming that these two distinct domains are parts of the same transcript (FIGS. 1K-1 and 1K-2). The NaAGP1 cDNA probes hybridized to the RNA samples from all the tissues tested, although the degree of hybridization and size of transcripts are different in different tissues. The highest signal was detected in RNA from *N. alata* suspension-cultured cells whereas the signal in petals was barely detected. Pollen and style tissues had a smaller transcript of approximately 1.0 kb compared with 1.6 kb in *N. plumbaginafolia* cultured cells and 1.7 kb in all other tissues (FIGS. 1K-1 and 1K-2). Genomic southern blot analysis indicated that the AGP gene is a single copy or low copy gene in the genome of *N. alata*.

(c) Isolation and Purification of AGP Peptides from Suspension Cultures of *Nicotiana plumbaginafolia*

1. Isolation of Total Native AGPs from *N. plumbaginafolia* Biopolymer

The total native AGPs were purified from the Biopolymer product by precipitation with the Yariv reagent after depleting the starting material of pectins by CTAB (hexadecyl trimethyl ammonium bromide) precipitation prior to Yariv precipitation. The medium from the cell suspension culture was separated from the cells by filtration and the high molecular materials precipitated with four volumes of ethanol. This is referred to as the Biopolymer product.

Biopolymer product (1 g) was dissolved in 1% NaCl solution (100 ml) and filtered through two layers of Miracloth. The filtrate was centrifuged (10,000×g, 10 min) and the supernatant collected. An equal volume of CTAB solution (2% CTAB in 20 mM $Na_2SO_4$) was added. After 1 h incubation at 37°, the solution was filtered through two layers of Miracloth and then centrifuged (10,000×g, 20 min) to remove any remaining precipitate. Four volumes of ethanol were then added to the supernatant and centrifuged at 10,000×g for 20 min. The pellet was dissolved in 100 ml of 1% NaCl solution and AGPs precipitated with Yariv reagent as described in Example 2(a) 2. The desalted AGP sample was re-dissolved in 6M guanidinium-HCl and incubated at 50° for 15 min. The sample was then chromatographed on a FPLC Superdex™75 column equilibrated with 6M urea and 20 mM Tris-HCl, pH 8.8. The void (Vo) fraction was collected, dialysed against distilled water and freeze dried. This sample is the total native AGPs. The total native AGPs were treated by one of two paths:

Path 1: Deglycosylation followed by reverse phase HPLC fractionation before direct sequencing, or sequencing after enzymatic (proteolytic) digestion.

Path 2: Reverse phase HPLC fractionation followed by deglycosylation and further separation by reverse phase HPLC fractionation.

Path 1 [Comprising Steps (2)–(5)]

(2) Deglycosylation of Total Native AGPs Using Anhydrous HF

The AGP sample was dried in a vacuum oven at 40° in the presence of $P_2O_5$ overnight; 0.2 ml anhydrous MeOH and 1 ml of anhydrous HF [Mort and Lamport (1977) *Anal. Biochem.* 82:289–309] was added and mixed well to dissolve all the sample. This mixture was incubated at room temperature, under argon, for 3 h and the HF removed by vacuum aspiration. Ice cold TFA (0.5 ml) was added and the sample desalted on a PD10 column equilibrated with 0.1% TFA, and freeze dried. This sample is referred to as the total deglycosylated AGPs.

(3) Reduction and Carboxymethylation of the Total Deglycosylated AGP Sample

The total deglycosylated AGP sample was dissolved in 6M guanidinium-HCl (in 0.2M Tris-HCl, pH 8.5 and 20 mM DTT; 600 µl); and incubated at 25° under argon for 2 h. Freshly prepared iodoacetic acid (100 µl) was added. The mixture was incubated for 3 h at 25° and stopped by addition of DTT to 100 mM and following dilution was chromatographed as above.

(4) HPLC Separation of the Total Deglycosylated AGPs

After reduction and carboxymethylation, the total deglycosylated AGPs were separated on a RP-300 HPLC column with a linear gradient (60 ml) (0–100% solvent B; flow rate 1 ml/min) (solvent A: 0.1% TFA in water, solvent B: 60% acetonitrile in solvent A). The profile is shown in FIG. 2A. Two major peaks RT21 and RT32 (retention times 21 min and 32 min, respectively) were collected for further analysis. Amino acid analysis was performed on both peaks (see Table 2.1). The RT32 peak was sequenced without further treatment. The RT21 peak was subjected to thermolysin digestion before sequencing.

(5) Thermolysin digestion of RT21

RT21 sample (12 µg) was concentrated and Tween 20 added to give a final volume of 100 µl with a final concentration of 0.01% Tween 20. $NH_4HCO_3$ (1% in 0.01% Tween 20; 500 µl), $CaCl_2$ (0.1M; 7 µl) and thermolysin (1 mg/ml; 7 µl) were added and the mixture incubated at 55° for 3 h. The products were purified on reverse phase HPLC and sequenced. The peptide sequences obtained are shown in FIG. 2A and were used to construct primers for cloning. The sequences L—A—S—O—O—A—O—O—T—A (SEQ ID NO:26), L—A—S—O—O—A—O—O—T—A—D—T—O—A (SEQ ID NO:27), F—A—O—S/N—G—G—V—A—L—P—O—S (SEQ ID NO:28), and I—G—A—A—O—A—G—S—O—T—S—S—P—N (SEQ ID NO:29) from RT21 are either similar to or identical with that obtained from fraction RT25 of *N. alata* styles (FIGS. 4A–4C) and represent conserved, tissue-nonspecific *N. alata* AGP fragments.

Peak 32 gave the sequence R—K—S—K—F—M—I—I—P—A—S—O—T—O—A—O—T—O—I—N—E—I—S—F (SEQ ID NO:30) which at the 5'-end, matched very closely the N-terminal sequence (SEQ ID NO:1) obtained from *N. alata* suspension culture.

Path 2 [Comprising Steps (6)–(8)]

(6) HPLC fractionation of total native AGPs

Figure 2B:
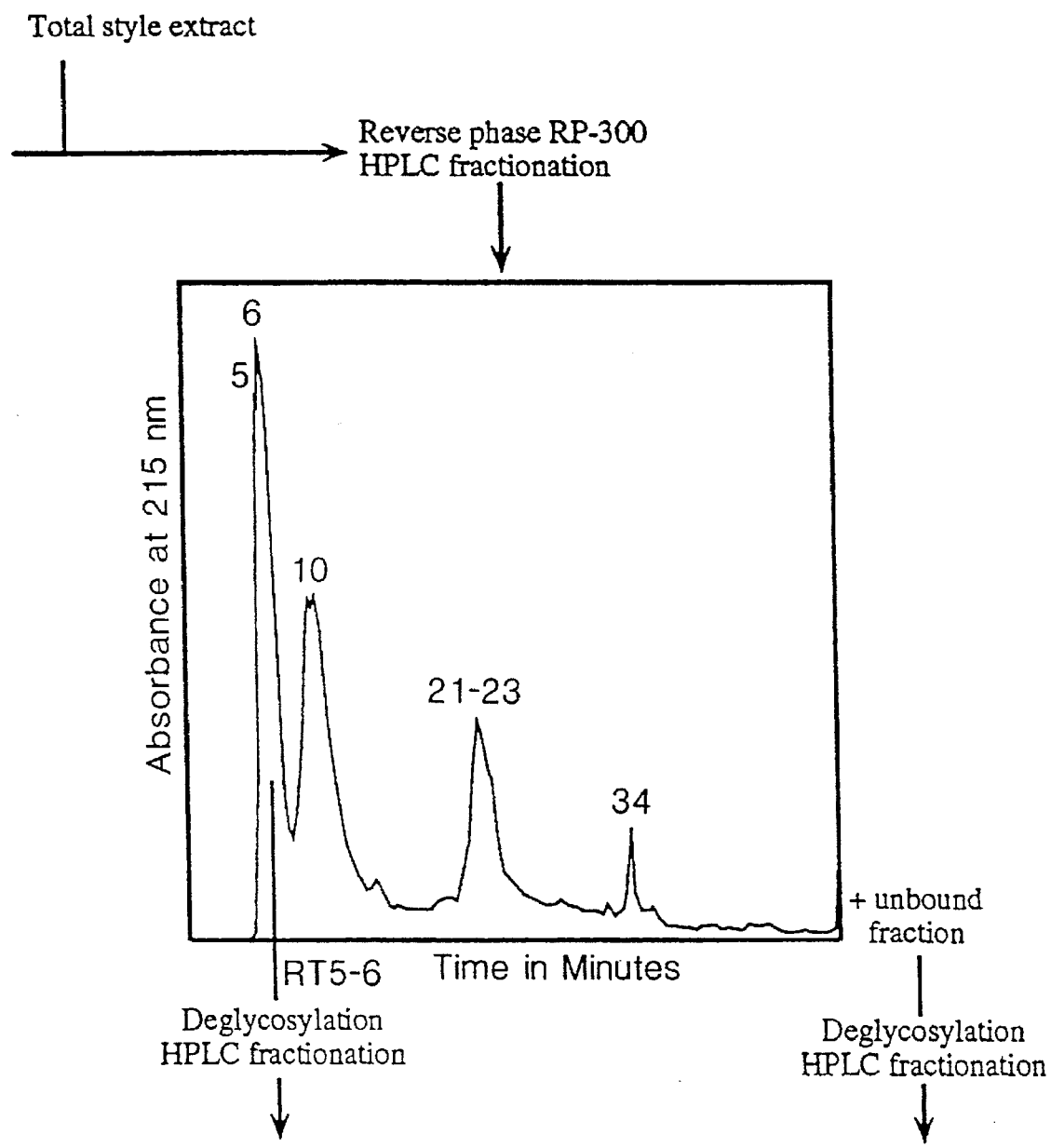

The total native AGPs sample was dissolved in 6M guanidinium-HCl and left at 50° for 15 min. The sample was then fractionated on reverse phase HPLC (RP-300; 4.6 mm×10 cm column) with a linear gradient (60 ml) (0–100% solvent B; flow rate 1 ml/min) (solvent A: 0.1% TFA in water, solvent B: 60% acetonitrile in solvent A). A number of major peaks were obtained from this separation all of which reacted with Yariv reagent in a gel diffusion test (van Holst and Clarke, 1985) (unbound, RT5, RT6, RT10, RT21–23 and RT34) (FIG. 2B). Each fraction was quantified for AGP content (Table 2.1) as described by van Holst and Clarke (1985). Amino acid analyses of each fraction of native AGPs are shown in the Table 2.1.

(7) Deglycosylation of native AGP fractions from HPLC

Individual native AGP fractions from reverse phase HPLC (FIG. 2B) were deglycosylated using anhydrous HF as described above.

(8) HPLC separation of the deglycosylated AGPs

Figure 2D:
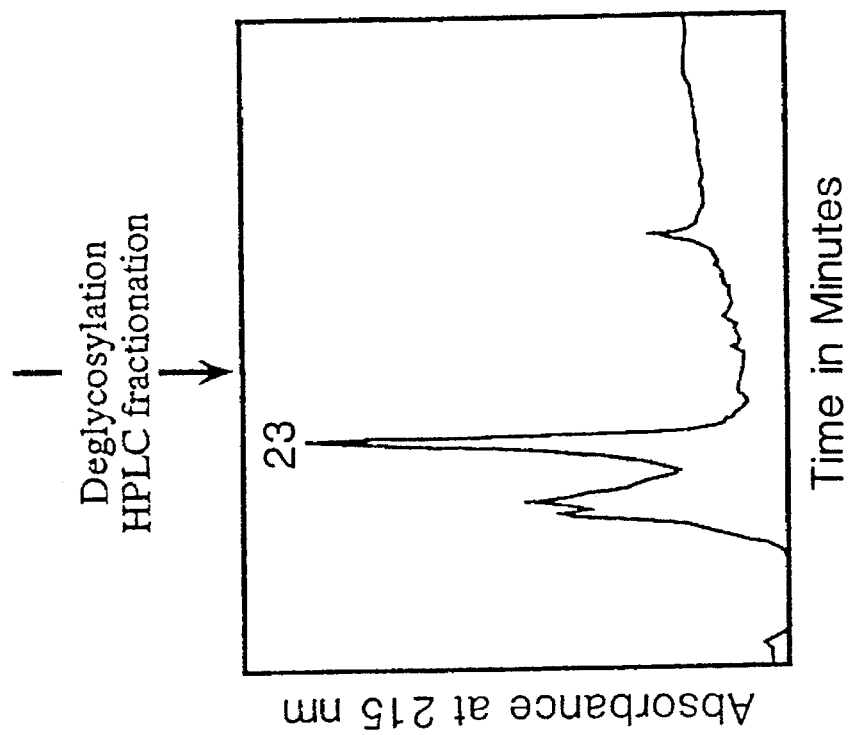
Figure 2C:
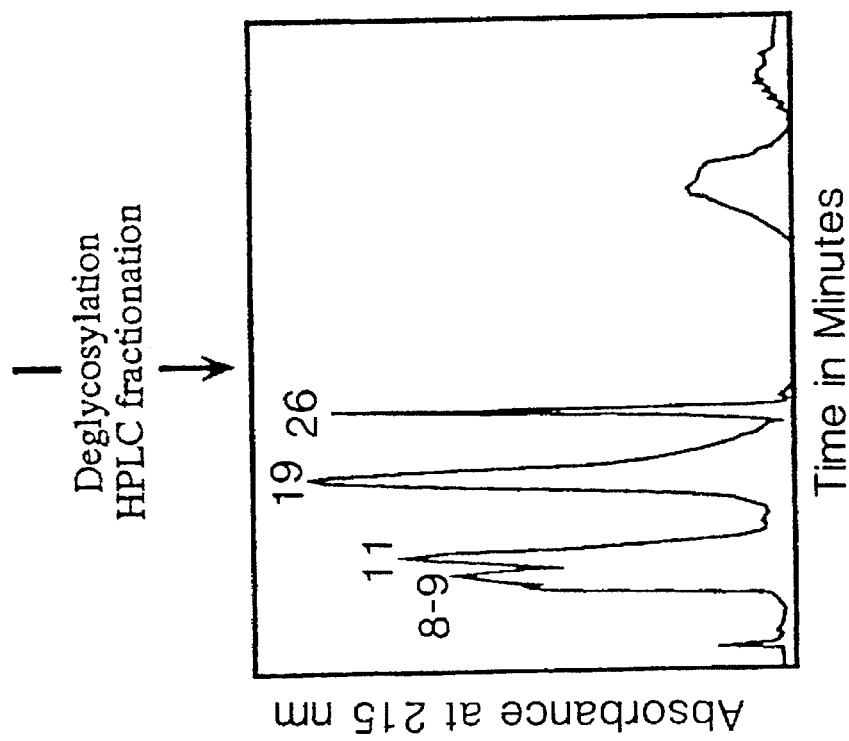

After deglycosylation, each sample was reduced and carboxymethylated before reverse phase HPLC separation (FIGS. 2C and 2D). The fractions obtained were reserved for further sequencing.

EXAMPLE 3

Cloning of a Gene Encoding a Protein Backbone of an AGP from *P. communis* Suspension Cultured Cells (a) Isolation and Purification of AGP Peptides From Cell Cultures of *Pyrus communis* (Pear)

1. Isolation of total native AGPs from *Pyrus communis* (pear) Biopolymer

The total native AGPs were purified by Yariv precipitation from pear Biopolymer as described for AGPs of *Nicotiana plumbaginafolia* in Example 2(c)1. The AGPs were deglycosylated and resulting peptides separated by reverse phase HPLC (RP-300) (Path 1). Alternatively, the total native AGPs were fractionated by reverse phase HPLC (RP-300), deglycosylated, digested with thermolysin and peptides purified for sequencing.

Path 1 [Comprising Steps (2) and (3)]

(2) HPLC separation of total deglycosylated AGPs for sequencing

The total native AGPs were deglycosylated using HF. The sample was reduced and carboxymethylated before separation on reverse phase HPLC (RP-300) as described in Example 2(c)(2). The profile is shown in FIG. 3A. The results of amino acid analysis of major peaks are summarized in Table 3.1.

(3) Separation of thermolysin digested peaks on a C18 microbore column

Deglycosylated AGP fractions (unbound, RT16.4 and RT18.2 from FIG. 3A) were subjected to thermolysin digestion. The products were separated on an RP-300 column (2.1 mm×10 cm); linear gradient (6 ml) (0–100% B; flow rate at 0.1 ml/min) (solvent A: 0.1% TFA in water, solvent B: 60% acetonitrile in solvent A). The unbound fraction after digestion remained unbound, i.e., gave no peptide which bound to the RP-300 column. The RP-300 profile for digested RT16.4 is shown in FIG. 3B and for RT18.2 is shown in FIG. 3C.

Individual peaks (peaks 1–5, FIG. 3B) from thermolysin digested RT16.4 (FIG. 3A) were separated on a C18 microbore column (2.1 mm×10 cm) and resolved on a linear gradient (50 ml, 0–50% B; flow rate 0.1 ml/min) (solvent A: 1% NaCl, solvent B: 100% acetonitrile). Peaks were further separated on the same column with TFA-acetonitrile system (solvent A: 0.1% TFA, solvent B: 60% methanol in solvent A; 0–100% B in 60 min at 0.1 ml/min). Neither solvent system gave further separation of peaks. Three of the peaks (peaks 1, 3 and 5) were subjected to amino acid sequencing. Peak 1 was a pure peptide and gave clear sequence L—S—O—K—K—S—O—T—A—O—S—O—S—(S)—T—O—O—T—(T) (SEQ ID NO:31). Peaks 3 and 5 were not single peptides and at least two stretches of sequence were obtained from each of these two peaks with less certainty. Peak 3 gave the sequence:

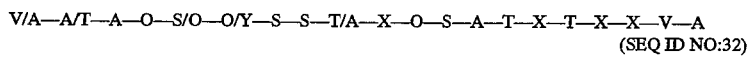
(SEQ ID NO:32)

whereas Peak 5 gave the sequence:

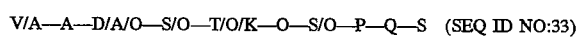 (SEQ ID NO:33)

Individual peaks (peaks 1–5, FIG. 3C) from thermolysin digested RT18.2 were separated as described above for RT16.4. A number of peptides were obtained and sequenced:

(i) L—G—I—S—O—A—O—S—O—A—G—E—V—D—(G)   (SEQ ID NO:34)

(ii) X—X—O—O—A—A—O—V—X—A—O/S   (SEQ ID NO:35)

(iii) V—T—A—O—T—O—S—A—S—O—O—S—S—T—(T)—A—A—T—(T)—A   (SEQ ID NO:36)

(iv) A—K—S—O—T—A—T—O—O—T—A—T—O—O—S—A—V   (SEQ ID NO:37)

(v) V—T—A—O—T—O—S—A—S—O—O—S—S—T—O—A—(S)—T—X—A   (SEQ ID NO:38)

(vi) L—S—O—K—K—S—O—T—A—O—S—O—S—(S)—T—O—O—T—(T)   (SEQ ID NO:31)

The last sequence is identical to the sequence obtained from Peak 1 of RT16.4.

Path 2 [Comprising Steps (4)–(7)]

(4) Fractionation of total native AGPs by reverse phase HPLC

The total native AGPs samples were separated by reverse phase HPLC essentially as described in Example 2(c)2–4. A number of major peaks were obtained from this separation all of which reacted with Yariv reagent in a gel diffusion test (van Holst and Clarke, 1985) (unbound, RT7,8, RT17.2 and RT19.1) (FIG. 3D). Amino acid analyses of unbound and RT7.8 fractions are shown in the Table 3.1.

(5) Deglycosylation of native AGP fractions from HPLC

Individual native AGP fractions from reverse phase HPLC were deglycosylated using anhydrous HF as in Example 2(c)(7).

(6) HPLC separation of the deglycosylated AGPs

After deglycosylation, each sample was reduced and carboxymethylated before separation on reverse phase HPLC (RP-300) as described previously. The profiles of each sample are shown in FIG. 3E and FIG. 3F. The major peaks RT16–19 in FIG. 3F have similar retention times with the group of peaks RT16–19.9 in FIG. 3A. These peaks may arise from the one component or a group of closely related components.

(7) Thermolysin digest of deglycosylated pear AGPs

Peak RT23 from FIG. 3E was digested with thermolysin and the resulting peptides were further purified on reverse phase HPLC (RP-300). Six peptides were selected for sequencing and gave the following amino acid sequences (also shown in FIGS. 3A–3F):

(i)   I—S—O—A—S—T/Q—O—O—T—T—S—O—A—O—O—T        (SEQ ID NO:39)

(ii)  V—S—P/S—O—V—Q—S—O—A—S—O—O—O—T—(T)        (SEQ ID NO:40)

(iii) L—V—V—V—V—M—T—P—R—K—H                    (SEQ ID NO:41)

(iv)  X—N—O—A—T—O—O—A—T/K—P                    (SEQ ID NO:42)

(v)   I—A—A—T—O—S—(L)                          (SEQ ID NO:43)

(vi)  (G)/(S)—N—A—O—A—O—X—O—K—P                (SEQ ID NO:44)

(b) Cloning of Genes From *P. communis* Cell Suspension Culture

To obtain an AGP gene from *P. communis* the methods and procedures essentially as described for the cloning of genes from *N. alata* and *N. plumbaginafolia* were followed.

A number of primers corresponding to the L—V—V—V—V—M—T—P—R—K—H (SEQ ID NO:41) sequence (FIGS. 3D and 3E) were designed and synthesized for PCR experiments (Table 3.2). The same nested PCR procedure used for the cloning of the NaAGP1 gene (FIG. 1D-2) was used to clone the gene encoding the above peptide, except that the annealing temperature was 52° C. in this case. A 350-bp fragment was amplified after two successive PCR reactions using the PcA23F1 as the first primer and the PcA23F2a as the second primer. The fragment was sequenced and found to encode the correct peptide sequence (SEQ ID NO:48; FIG. 3G).

The PCR fragment was used to screen a cDNA library made from mRNA from pear cell suspension culture, as described above for *N. alata* cell suspension. One positive clone (PcAGP23) was isolated and sequenced (SEQ ID NO:49; FIGS. 3H-1 and 3H-2). This clone contains an insert of 760 bp and matches the PCR sequence.

The PcAGP23 cDNA (SEQ ID NO:49) encodes an open reading frame, which starts with an initiation codon (ATG) at position 20 and ends with a termination codon (TAG) at position 560 (FIGS. 3H-1 and 3H-2). The open reading frame encodes a polypeptide containing 180 amino acid residues with a calculated molecular weight of 19.2 kD and a predicted pI of 8.46. The predicted amino acid sequence contains the peptide sequence, L—V—V—V—V—M—T—P—R—K—H (SEQ ID NO:41), which was used for the cloning of the PCR fragment. In addition, another peptide sequence, L—G—I—S—O—A—O—S—O—A—G—E—V—D—(G) obtained from RT18.2 (SEQ ID NO:34) is also present. However, other sequences, e.g., I—S—O—A—S—T/Q—O—O—T—T—S—O—A—S—O—O—T (SEQ ID NO:39); and V—S—P/S—O—V—Q—S—O—A—S—O—O—O—T—(T) (SEQ ID NO:40), obtained from peak RT7.8, are absent from the PcAGP23 sequence, indicating they are from different AGP backbones.

EXAMPLE 4

Cloning of Genes Encoding a Protein Backbone of an AGP From *Nicotiana alata* Style (a) Isolation and Purification of AGP Peptides From the Styles of *Nicotiana alata*

Total native AGPs of *N. alata* styles were purified by ion exchange chromatography (IEC) and gel filtration chromatography (GFC). The AGPs were then deglycosylated by HF and fractionated by reverse phase HPLC. Peptide sequence data were obtained after thermolysin digestion of these deglycosylated fractions.

1. Purification of total native AGPs

Styles (500–1000 styles including the stigma) were collected fresh or were stored at −70° C. The styles were ground with polyvinyl pyrrolidone (1% w/v) in the presence of liquid nitrogen, and extraction buffer (50–100 ml; 100 mM Tris pH8, 1 mM EDTA, 14 mM β-mercaptoethanol) was added. The mixture was centrifuged (10,000 xg, 20 min) and cell debris discarded. The extract was brought to 95% ammonium sulfate at 4°, centrifuged (10,000 xg, 20 min) and the supernatant collected and concentrated by ultrafiltration using a Diaflo system (YM-30 membrane, Mr 30 kD cut off) to about 10–20 ml. The solution was desalted on a PD-10 column (Pharmacia) equilibrated with 10 mM Tris pH8. The sample was applied to a FPLC Mono Q column (Pharmacia; buffer A: 10 mMTris pH8; buffer B: 10 mM Tris pH8, 1M NaCl; gradient: 0–30% B 15 min, 30–100% B 0.1 min). The bound AGP fractions were detected by the Yariv reagent gel diffusion test on samples of each fraction; AGP containing fractions eluted at about 5–15% buffer B (FIG. 4A). The AGP fractions were pooled, equilibrated into 10 mM NH$_4$HCO$_3$ with a PD-10 desalting column, freeze dried, and further purified on a Superose 6 β column (Pharmacia) in 6M urea, 10 mM Tris pH8 (FIG. 4B). The AGP containing fractions were exchanged as above into 10 mM NH$_4$HCO$_3$ and freeze dried.

Recovery of style AGP during the purification procedure is as follows: crude style extract (1000 styles), 100% ; 95% (NH$_4$)$_2$SO$_4$-supernatant, 68.2% ; Mono Q anion-exchange column, Unbound AGPs 5.4% , Bound AGPs 44.5% ; Superose 6 gel filtration column, 25.4% . The presence of AGPs at different stages of purification is demonstrated on SDS-PAGE gels in FIGS. 4N-1 and 4N-2. Crossed-electrophoresis of AGPs from styles of *N. alata* during fractionation is presented in FIGS. 40-1 through 40-4.

2. Deglycosylation of total native AGPs and sequencing of peptides

Deglycosylation, peptide cleavage and sequencing were performed as described in Example 2(c)2. Two major peaks, RT25 and RT35 (FIG. 4C), were obtained after deglycosylation as well as an unbound fraction. Amino acid analysis of each fraction and the native materials are shown in Table 4.1. Each fraction was digested with thermolysin. No peptide which bound to the RP-300 column (2.1×100 mm) was obtained from the unbound fraction. Three of the sequences from RT25, F—A—O—S—G—G—V—A—L—P—O—S (SEQ ID NO:50), L—A—S—O—O—A—O—O—T—A—D—T—O—A (SEQ ID NO:51), and I—G—S—A—O—A—G—S—O—T—S—S—P—N (SEQ ID NO:53) match closely that obtained for RT21 from *N. plumbagin-*

*afolia* (SEQ ID NOS:27–29, respectively; FIG. 2A). A fourth fragment gave the sequence I/V—G/S—A/S—A/O—O/S—A/Q—G/S—S/O—O/S—T/A—S/A—S/A—P—O (SEQ ID NO:52).

Since no N-terminal sequence was obtained for the RT25 protein backbone, pyroglutamate aminopeptidase was used to remove the N-terminal blocked pyroglutamate residue [20 μg pyroglutamate aminopeptidase (Boehringer Mannheim) in 100 mM potassium phosphate buffer pH 8.0, 10 mM EDTA, 5 mM DTT, 5% glycerol at 37° C. overnight; deblocked protein was separated by RP—HPLC and N-terminal amino acid sequencing was performed] and the sequence Ala—Hyp—Gly was obtained. The RT25 backbone was also fragmented by treatment with thermolysin [thermolysin (Boehringer Mannheim) at 0.2 μg/μg protein was added to RT25 protein backbone (2–10 μg) and incubated at 55° C. for 2 hours in 500 μl of 1% ammonium bicarbonate, pH 7.8, 1 mM $CaCl_2$ and 0.01% Tween 20]. The resulting peptides were separated by RP—HPLC. Six major peptides were obtained (FIG. 4I). Peak 2 gave the amino acid sequence VSAOSQSOSTAA (SEQ ID NO:67), as well as IGSAOAGSOTSSPN (SEQ ID NO:53) and IGSAOAGSO (contained in SEQ ID NO:53). Peak 3 gave the sequence LASOOAOOTADTOA (SEQ ID NO:51) and peak 5 gave the sequence FAOSGGVALPOS (SEQ ID NO:50). Both sequences were rich in Hyp, Ser and Ala (33 of 52 amino acid residues).

Endoproteinase Asp—N (Sigma; 0.1 μg/μg protein) was also used to cleave the RT25 protein backbone at the Asp residue [30° C. overnight in 500 μl of 1% ammonium bicarbonate, pH 7.8, and 0.01% Tween 20], followed by separation with RP—HPLC. Two major peptides were produced (peaks A1, A2; FIG. 4J), indicating that there is only one Asp residue in the RT25 protein. The cleavage was incomplete as indicated by the presence of the starting material. The first peptide eluted (peak A1) gave no sequence data indicating a blocked N-terminal residue. The A2 peak gave the sequence DTOAFAOSGGVAL (SEQ ID NO:68). The peptide sequence of A2 (FIG. 4J) overlaps with that of peak 3 (SEQ ID NO:51) (FIG. 4I) and yields a continuous amino acid sequence of 26 residues LASOOAOOTADTOAFAOSGGVALPOS (SEQ ID NO:69).

Four sequences were obtained from the RT35 peak of *N. alata* style:

K—N—K—X—X—L—T—X—X—P—X—I—I (SEQ ID NO:59) was obtained.

(b) Cloning of Genes From *N. alata* Styles

1. In vitro amplification of 3'-end of the cDNA cDNA was synthesized in a volume of 20 μl solution containing 5 μg total style RNA from *N. alata*, 1×PCR buffer (10 mM Tris-HCl pH 8.3, 50 mM KCl, 5 mM $MgCl_2$, 1 mM dNTPs; 5 μM of $dT_{(17)}$+adaptors, 30 U of RNasin and 50 U AMV reverse transcriptase at 42° for 1 h cDNA (2 μl) was subjected to polymerase chain reaction. The PCR was carried out in 100 μl solution containing: 1×PCR buffer, 1.5 mM $MgCl_2$, 200 μM dNTPs, 30 pmole of the gene-specific primer (FIGS. 1D-1 and 1D-2) 30 pmole of adaptor primer and 2.5 U of Taq DNA polymerase. Samples were denatured by heating at 94° for 2 min and then cooled to 80° before Taq DNA polymerase was added. The PCR cycles are: 35 X: 94°, 30 sec; 52°, 30 sec; 72°, 1 min 30 sec. The PCR product was subcloned and sequenced.

2. Screening of cDNA library with the PCR fragment

About $5 \times 10^4$ pfu phage/plate of cDNA libraries (in λzap) were plated out. After overnight growth at 37°, phage were blotted onto nitrocellulose membranes and hybridized with $^{32}$P-labeled PCR fragment at 65° overnight in a hybridization buffer containing 0.22M NaCl, 15 mM $NaH_2PO_4$, 1.5 mM EDTA, 1% SDS, 1% BLOTTO and 4 mg/ml carrier DNA [Sambrook et al. (1989) supra]. The membranes were washed at 65° for 2×15 min in 0.2×SSC and 1% SDS and exposed to X-ray films. Positive λzap clones were converted into plasmid DNA by in vivo excision as described in the Stratagene's instruction manual for the sequence analysis.

3. Design of a gene-specific primer based on the AINTEFG sequence

As described in Example 2(c)2, pp. 37–38, the purified AGPs were deglycosylated with HF and the resulting AGP backbones were separated on reverse phase HPLC. Two major peaks: RT25 and RT35 were obtained after deglycosylation as well as an unbound fraction. Amino acid sequences were obtained from both peaks after protease digestion. Three of the four peptide sequences from peak RT35 contain the sequence: TAINTEFGP (SEQ ID NO:58). A degenerate oligonucleotide was synthesized based on the sequence: AINTEFG (SEQ ID NO:60).

(i) X—X—X—Q—S—A—O—A—A—(D)—X—N (SEQ ID NO:54)

(ii) X—T—F—S/A—Y/L—D/I—I—K/E—T/A—A—I—N—T—E—F—G—P—(E) (SEQ ID NO:55)

(iii) X—T—F—S/A—Y/L/V—D/I/A—I—E—T—A—I—N—T—E—F—G—P—X—E—X—X—Q (SEQ ID NO:56)

(iv) X—T—F—S—Y—D/I—K/E—T—A—I—N—T—E—F—G/M—P—A—E (SEQ ID NO:57)

Three of these sequences were characterized by the sequence T—A—I—N—T—E—F—G—P (SEQ ID NO:58).

3. Purification of style AGPs by J539 affinity chromatography

AGPs were prepared from styles according to Bacic et al. (1988), Phytochem. 27:679–684. The sample was deglycosylated with TFMS, separated and blotted onto a PVDF membrane as described in Example 1(*b*). A 30 kD band, running at the same position as the major band prepared by Yariv precipitation from *N. alata* suspension cultured cells Example 1(*b*) was sequenced. The sequence A—V—F—

RT35-specific primers synthesized had the sequence:

```
5'GCIATTAATACTCAATTTGG3'    (SEQ ID NO:61)
    C   C   C  G C
    A       A
            G
``` where I is an inosine residue (a) In Vitro Amplification of an AGP Gene From *N. alata* cDNA by PCR The strategy to clone the gene encoding the RT35 peptide sequence is illustrated in FIG. 4D. The RT35-specific primer was used in conjunction with the adaptor primer in a polymerase chain reaction and a single 380-bp DNA fragment was obtained. The PCR fragment was subcloned and sequenced (SEQ ID NO:62; FIG. 4E). The sequence included a derived peptide ID NO:62; FIG. 4E). The sequence included a derived peptide that matched with the sequence obtained from the isolated AGP peptide.

(b) Isolation and Sequence Analysis of a cDNA Clone From *N. alata*

The 380-bp PCR fragment (SEQ ID NO:62; FIG. 4E) was used to screen a cDNA library made from RNA isolated from *N. alata* styles and one positive clone was isolated and sequenced (SEQ ID NO:63; FIGS. 4F-1 and 4F-2). The insert of the cDNA clone is 800 bp in length with a poly(A) tail at the 3'-end. The cDNA sequence matches the PCR sequence except that it is 3 bp shorter at the 3'-end. The cDNA sequence is designated Na35_1.

The Na35_1 sequence (SEQ ID NO:63) has an open reading frame which starts with an initiation codon (ATG) at position 21 and ends with a termination codon (TAA) at position 530 (FIG. 4E). The open reading frame encodes a polypeptide containing 169 amino acid residues with a calculated molecular weight of 19.5 kD and a predicted pI of 8.1. The most abundant amino acid residues in this sequence are: proline (11.2%), phenylalanine (9.5%), alanine (7.7%), leucine (7.7%) and lysine (7.7%) (Table 4.2).

(c) Northern Blot Analyses of the Na35_1 Gene

The Na35_1 PCR fragment was used to probe northern blots of RNA [Sambrook et al. (1989) supra] isolated from various parts of *N. alata* plants (FIG. 4G) *L. peruvianum* (tomato) style and suspension-cultured cells of *N. alata, N. plumbaginafolia* and pear (FIG. 4H). The Na35_1 probe hybridized to a style transcript of 800 nucleotide which corresponds to the length of the Na35_1 cDNA. Longer exposure of the northern blot did not reveal any signal in other parts of the plant (i.e., leaf, stem, root). The signal strength varies in different genotypes of *N. alata*. The strongest signal was detected in RNA from $S_6S_6$ style. The same probe did not detect any transcript from tomato style or suspension-cultured cells (FIG. 4H).

4. Design of a gene-specific primer based on the TADTOAF sequence (a) Oligonucleotide Design and Synthesis A gene-specific primer of 20 nucleotides long was designed according to the overlapping peptide sequences of SEQ ID NOS:50, 51, 53, 67 and 68. Inosine was used to reduce the degeneracy as shown:

```
      T    A    D    T    O    A    F       (SEQ ID NO:70)

5'   ACI  GCI  GAT  ACT  CCT  GCT  TT  3'   (SEQ ID NO:71)
           C    A    A    A
                C    C    C
                G    G    G
```

The oligonucleotide was synthesized on an Applied Biosystems DNA synthesizer (model 391, ABI).

(b) Rapid Amplification of 3' End of the cDNA (3' RACE)

Total RNA was isolated from *N. alata* styles as described by McClure et al. (1990) Nature 342:955–957. Complementary DNA (cDNA) was synthesized from total style RNA (5 µg) in a 20 µl solution containing 10 mM Tris-HCl, pH 8.3, 50 mM KCl, 5 mM $MgCl_2$, 1 mM dNTPs, 5 µM $dT_{(17)}$+ adaptors, 30 U RNasin, and 50 U AMV reverse transcriptase (Promega) at 42° C. for 1 hour. cDNA (2 µl) was subjected to polymerase chain reaction (PCR) in 100 µl solution containing: 10 mM Tris-HCl, pH 8.3, 50 mM KCl, 1.5 mM $MgCl_2$, 200 µM dNTPs, 30 pmole of the gene-specific primer, 30 pmole of the adaptor primer and 2.5 U of Taq DNA polymerase (Perkin Elmer-Cetus). Samples were denatured by heating at 96° C. for 2 min and then cooled to 80° C. before Taq DNA polymerase was added. The PCR cycles were: 35×: 96° C., 45 sec; 55° C., 45 sec; 72° C., 1 min. The PCR product (400 bp) was cloned and sequenced on an Applied Biosystems DNA sequencer (model 373A, ABI). The deduced amino acid sequence from this PCR clone matched isolated AGP sequences, i.e., SEQ ID NOS:50, 51, 53, 67, 68.

(c) cDNA Library Screening

A style cDNA library (λZAP II; Stratagene) was constructed using mRNA from styles (6 hours after touching) of *N. alata* ($S_6S_6$) by Dr. Joaquin Royo, Plant Cell Biology Research Center, School of Botany, The University of Melbourne, Parkville, Australia (PCBRC). cDNA library (300,000 pfu) was plated out and blotted onto Hybond-N nylon membranes (Amersham) according to the manufacturer's instruction. The PCR fragment was labeled to $10^8$ cpm/µg with $^{32}$P-dCTP. Hybridization was carried out at 55° C. overnight in 0.22M NaCl, 15mM $NaH_2PO_4$, 1.5 mM EDTA, 1% SDS, 1% BLOTTO and 4 mg/ml herring sperm DNA. The membranes were washed for 2×10 min at room temperature in 2×SSC, 1% SDS followed by 2>10 min at 55° C. in 0.2×SSC, 1% SDS. Positive λZAP clones were in vivo excised (Stratagene) and DNA sequences were analyzed. The clone encoding the RT25 protein backbone was designated AGPNa1 1 cDNA. The nucleotide and deduced protein sequences were analyzed using the PC/Gene software (IntelliGenetics).

The PCR clone, used as a probe to screen a style cDNA library (300,000 plaques), produced two cDNA clones which differed only in the length of the 3' and 5' ends. One of the clones, designated AGPNa1 1 (FIGS. 4K-1 and 4K-2) was used for all subsequent analyses. The 3' end of the AGPNa1 1 cDNA clone was identical to the PCR clone except that the PCR clone was 20 bp shorter and contains a poly A tail. The 712-bp AGPNa1 1 clone encodes a putative protein of 12.5 kD (FIGS. 4K-1 and 4K-2). The derived amino acid sequence included sequences identical to isolated peptides (SEQ ID NOS:50, 51, 53, 67, 68). Most of the proline residues in the peptide sequences obtained by amino acid sequencing are hydroxylated. A secretion signal peptide is predicted (FIGS. 4K-1, 4K-2 and 4L). The deduced N-terminus of the mature protein (10 kD; pI 6.8) is Gln—Ala—Pro—Gly which matches the N-terminal sequence data obtained. The Pro residue in the N-terminal sequence is also hydroxylated. The amino acid composition of the deduced mature protein and the RT25 protein backbone are in general agreement. The C-terminus of the deduced protein is very hydrophobic and predicted to be a transmembrane helix.

(d) RNA Blot Analysis

RNA blot analysis was performed as described by Sambrook et al. (1989) supra. Hybridization and washing conditions were the same as described above except that the AGPNa1 1 cDNA was used as probe and hybridization was carried out at 60° C.

EXAMPLE 5

Cloning of an AGP Gene from *P. communis* Using an Antisense RNA Probe

1. The PcAGP9 cDNA Clone (SEQ ID NO:66)

(a) Isolation and purification of AGP peptides from cell cultures of *Pyrus communis* (pear)

The procedure essentially as described in Example 3(a) was followed to obtain amino acid sequences of AGP peptide fragments. The sequence A—K—S—O—T—A—T—O—O—T—A—T—O—O—S—A—V (SEQ ID NO:37) was selected as a template for the isolation of a corresponding AGP gene.

(b) Cloning of a Pear AGP Gene Encoding SEQ ID NO:37

In the previous examples of the invention (Examples 2, 3, and 4) AGP genes were isolated by utilizing a hydroxyproline-poor sequence of an isolated AGP peptide fragment to synthesize an oligonucleotide primer which was not enriched in GC. In contrast, in this example (Example 5), a hydroxyproline-rich peptide sequence is utilized for the construction of an antisense RNA probe.

The sequences of two oligonucleotide (AF1T3) and (AR2T7) used for the construction of a GC-rich probe are presented in Table 5.1 AF1T3 includes a T3 promoter sequence, 42-bp GC-enriched nucleotide sequence corresponding to an isolated AGP peptide fragment from *N. plumbaginafolia*, L—A—S—O—O—A—O—O—T—A—D—T—O—A (SEQ ID NO:27), and an 18-bp sequence corresponding to position 150–167 of the NaAGP1 (SEQ ID NO:24). The other oligonucleotide (AR2T7) consists of a T7 promoter, a 47-bp nucleotide sequence corresponding to a hydroxyproline-rich AGP sequence from pear, A—K—S—O—T—A—T—O—O—T—A—T—O—O—S—A—V (SEQ ID NO:37) and an 18-bp sequence corresponding to position 444–461 from the NaAGP1 cDNA (SEQ ID NO:24). These oligonucleotide primers were used to amplify the proline-rich domain (nucleotide position 150–461) of the NaAGP1 cDNA (SEQ ID NO:24).

An antisense RNA probe was synthesized from the PCR fragment by using T7 RNA polymerase (Promega) and used to screen a cDNA library prepared from pear cell suspension culture. The hybridization was carried out at 40° C. in hybridization buffer containing 2×SSPE, 1% SDS, 0.5% BLOTTO, 50% formamide and 0.5 mg/ml denatured herring sperm DNA. After overnight hybridization, lifts were first rinsed at room temperature with 2×SSC, 0.1% SDS and then washed at 50° C. with the same buffer for 30 min. The lifts were finally washed at 50° C. with 1×SSC, 0.1% at 50° C. for another 30 min. Three cDNA clones were isolated and sequenced. The sequence of the longest cDNA clone PcAGP9 (SEQ ID NO:66) is shown in FIGS. 5A-1 and 5A-2.

2. The PcAGP2 cDNA Clone (SEQ ID NO:91)

(a) Further purification of AGP peptides from cell cultures of *Pyrus communis* (pear)

AGPs in pear cell culture filtrate were purified by precipitation with the β-glucosyl Yariv reagent and fractionated by HPLC as described in Example 3(a). A flow chart of the purification procedure is presented in FIGS. 5D-1 and 5D-2. The major peak of FIG. 5D-1, which accounted for approximately 27% of the AGPs loaded onto the column, was collected and reapplied to the same column. Upon elution with a shallow gradient, two peaks (Fractions 1 and 2) were resolved (FIG. 5D-2). The AGPs in Fraction 1 were described in Example 3 and Example 5[1].

Fraction 2 (FIG. 5D-2) was subjected to size-exclusion fractionation on superose-6 FPLC and was resolved into two components, peaks 2A and 2B (FIG. 5D-2,C3). N-terminal amino acid sequencing of material in Peak 2B gave the sequence AEAEAXTXALQVVAEAXEL (SEQ ID NO:74).

AGPs in Peaks 2A and 2B were separately deglycosylated and the resulting protein backbones were isolated by size-exclusion FPLC (FIG. 5D-2,D1–D4). Peak 2B gave one protein backbone with a molecular weight of 10 k. Peak 2A resulted in two protein peaks having molecular weights of 54 k and 10 k. N-terminal amino acid sequencing of the 54 k protein backbone gave the sequence TOAOA (SEQ ID NO:75), while the 10 k protein backbone in Peak 2B gave the sequence AEAEAOTOALQVVAEAOEL (SEQ ID NO:76).

The 10 k and 54 k protein backbones were digested separately with thermolysin and the resulting peptides were purified by RP-HPLC for sequencing. Sequences of eight peptides were obtained from the 54 k protein of Peak 2A and three from the 10 k protein in Peak 2B (Table 3.6). Two of the three sequences and the N-terminal sequence overlap to give a sequence AEAEAOTOALQVVAEAOELVOTOVO-TOSY (SEQ ID NO:88) for the 10 k protein in peak 2B.

(b) Isolation of a cDNA encoding the 10 k AGP protein backbone

The approach to cloning of cDNA encoding the 10 k protein backbone was essentially the same as that used to clone the PcAGP9 cDNA. Two reverse and partially complementary long "guessmers" [AcF1 (SEQ ID NO:89) and AcR2 (SEQ ID NO:90), Table 5.3] were synthesized. In the "guessmers," nucleotide A was used at the third codon position for all amino acids, and CTA and TCA were assigned for Leu and Ser residues, respectively. The last 18 bp sequence at the 3' of the two "guessmers" were reverse-complementary, and they were annealed to each other in PCR to produce a double-stranded DNA fragment of 101 bp encoding the amino acid sequence A—E—A—E—A—O—T—O—A—L—Q—V—V—A—E—A—O—E—L—V—O—T—O—V—O—T—O—S—Y (SEQ ID NO:88). The PCR fragment was subcloned into the pBluescriptII (Ks) vector. A $^{32}$P-labeled anti-sense RNA probe was synthesized using T3 RNA polymerase from the 101-bp DNA fragment and used to screen a pear cDNA library. Five cDNA clones were isolated and sequenced. The consensus sequence of 1040 bp is shown in FIGS. 5E-1 and 5E-2. This cDNA is referred to as PcAGP2.

EXAMPLE 6

Cloning and Expression of Genomic AGP Genes

(a) Cloning of Genomic AGP Genes and Identification of an AGP Promoter Region The procedure essentially as used for the isolation of cDNA clones is used to obtain a genomic clone of a plant AGP. Whenever possible, AGP cDNA clones will be used to screen genomic libraries. The following procedure describing the isolation of a genomic AGP clone from suspension-cultured cells of *N. alata* and *N. plumbaginafolia* represents a general procedure which can be adapted for the isolation of a genomic AGP gene from a desired plant cell.

To isolate an AGP genomic clone, genomic DNA is isolated from suspension-cultured cells of *N. alata* and *N.*

*plumbaginafolia* and partly digested with Sau3AI. After size selection by ultracentrifugation under a glycerol gradient, DNA fragments of 10–23 kb in size are ligated into vectors such as λDash (Stratagene) to form a genomic library. The libraries are then screened with the NaAGP1 and NpAGP1 cDNAs, respectively, to isolate their corresponding genomic clones. The resulting genomic clones are studied by Southern analysis and some clones are sequenced. The promoter region of the AGP gene is then identified from the DNA sequence.

(b) Recombinant Gene Construction

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3'-nontranslated region which adds polyadenylate nucleotides to the 3'-end of the RNA. Transcription of DNA into mRNA is regulated by a promoter. The promoter region contains a sequence of bases that signals RNA polymerase to associate with the DNA and to initiate the transcription of mRNA using one of the DNA strands as a template to make a corresponding strand of RNA.

A number of promoters which are active in plant cells have been described in the literature. These include the nopaline synthase (NOS) and octopine synthase (OCS) promoters (which are carried on tumor-inducing plasmids of *Agrobacterium tumefaciens*, the Cauliflower Mosaic Virum (CaMV) 19S and 35S promoters, the light-inducible promoter from the small subunit of ribulose bis-phosphate carboxylase (ssRUBISCO) and the mannopine synthase (MAS) promoter [Velten & Schell (1985) *Nucl. Acids Res.* 13:6981–6998]. All of these promoters have been used to create various types of DNA constructs which have been expressed in plants (see, e.g., PCT publication WO84/02913).

Promoters which are known or are found to cause transcription of RNA in plant cells can be used in the present invention. Such promoters may be obtained from plants or plant viruses and include, but are not limited to, the CAMV35S promoter and promoters isolated from plant genes such as ssRUBISCO genes. It is preferred that the particular promoter selected should be capable of causing sufficient expression to result in the production of an effective amount of protein.

The promoters used in the DNA constructs (i.e., chimeric plant genes) of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purpose of this description, the phrase "CaMV35S" promoter thus includes variations of CaMV35S promoter, e.g., promoters derived by means of ligation with operator regions, random or controlled mutagenesis, etc. Furthermore, the promoters may be altered to contain multiple "enhancer sequences" to assist in elevating gene expression.

The RNA produced by a DNA construct of the present invention also contains a 5'-nontranslated leader sequence. This sequence can be derived from the promoter selected to express the gene, and can be specifically modified so as to increase translation of the mRNA. The 5'-nontranslated regions can also be obtained from viral RNAs, from suitable eukaryotic genes, or from a synthetic gene sequence. The present invention is not limited to constructs as presented in the following examples. Rather, the nontranslated leader sequence can be part of the 5'-end of the nontranslated region of the coding sequence for the virus coat protein, or part of the promoter sequence, or can be derived from an unrelated promoter or coding sequence in any case. It is preferred that the sequence flanking the initiation site conform to the translational consensus sequence rules for enhanced translation initiation reported by Kozak (1984) *Nature* 308:241–246.

The DNA construct of the present invention also contains a modified or fully-synthetic structural coding sequence which has been changed to enhance the performance of the gene in plants. For example, the enhancement method can be applied to design modified and fully synthetic genes encoding a plant AGP protein. The structural genes of the present invention may optionally encode a fusion protein comprising an amino-terminal chloroplast transit peptide or secretory signal sequence, etc.

The DNA construct also contains a 3'-nontranslated region. The 3'-nontranslated region contains a polyadenylation signal which functions in plants to cause the addition of polyadenylate nucleotides to the 3'-end of the viral RNA. Examples of suitable 3'- regions are (1) the 3'-transcribed, nontranslated regions containing the polyadenylation signal of Agrobacterium tumor-inducing (Ti) plasmid genes, such as the nopaline synthase (NOS) gene, and (2) plant genes like the soybean storage protein (7S) genes and the small subunit of the RuBP carboxylase (E9) gene. An example of a preferred 3'-region is that from the 7S gene.

(c) Plant Transformation

A chimeric plant gene containing a structural coding sequence of the present invention can be inserted into the genome of a plant by any suitable method. Suitable plants for use in the practice of the present invention include, but are not limited to, soybean, cotton, alfalfa, oilseed rape, flax, tomato, sugarbeet, sunflower, potato, tobacco, maize, rice and wheat. Suitable plant transformation vectors include those derived from a Ti plasmid of *Agrobacterium tumefaciens*, as well as those disclosed., e.g., by Herrera-Estrella et al. (1983) *Nature* 303:209, Bevan et al. (1983) *Nature* 304.:184, Klee et al. (1985) *Bio/Technology* 3:637–642, and EPO publication 120,516. In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen.

A useful Ti plasmid cassette vector for transformation of dicotyledonous plants, for example, may consist of the enhanced CaMV35S promoter and the 3'-end including polyadenylation signals from a soybean gene encoding the alpha-prime subunit of beta-conglycinin. A multilinker containing multiple restriction sites for the insertion of genes may be positioned between these two elements.

(d) Over- and Under-production of AGPs by Transformed Cell Lines

It is generally acknowledged that all plant natural cell lines produce some AGPs, probably at the level of approximately 2–10% (w/w) of total structural complex carbohydrate [Showalter (1993) *Plant Cell* 5:9–23] These natural plant cells comprise all the regulatory factors (promoters, enhancers, enzymes, etc.) for transcription, translation and post-translational processing to produce a glycosylated AGP as the natural product. Glycosylation comprises the steps of (a) proline hydroxylation with a prolyl hydroxylase, (b) galactosylation using a unique β-Hyp-galactosyl transferase, (c) the addition of galactose chains by a separate galactosyl transferase for each linkage type, and (d) the addition of arabinose by arabinosyl transferase. Thus, cultured natural plant cells (e.g., monocots or dicots) can be transformed with heterologous recombinant gene fragments and used for overproduction or underproduction of nonglycosylated AGPs. In some cases, a dicot host may be transformed with a monocot gene or, alternatively a monocot host may be transformed with a dicot gene. Alternatively, a host cell which normally does not produce glycosylated AGP (e.g., *E. coli*) may be transformed and used for the over- or underproduction of a nonglycosylated AGP peptide backbone in which the proline residues have not been hydroxylated.

To transform a host cell for overproduction of AGP, an AGP cDNA (e.g., NaAGP1 or NpAGP1) is linked at the 5'-end with a heterologous promoter (e.g., CaMV 35S promoter) and at the 3'-end with a terminator (e.g., NOS-terminator). Thus, the AGP gene will be under the control of the CaMV 35S promoter, which is known to be a strong promoter. This expression cassette is then subcloned into a binary vector derived from the *A. tumefaciens* Ti plasmid to transform the cultured cells of either *N. alata* or *N. plumbaginafolia* to create cell lines that overproduce AGPs. The AGP is also tagged by histidines at the C-terminus by introducing a six-histidine coding DNA fragment into the AGP cDNAs. The six-histidine tagged AGP can then be readily isolated by using nickel-nitrolotriacetic acid Sepharose column (Hochuli et al., 1988, *Bio/Technology* 6:1321–1325). An alternative approach is to use the tag, Flag™, [Hopp, T. P. et al. (1988) *Biotechnology* 6:1204–1210], which can be incorporated into the AGP sequence to allow purification with an anti-Flag™ monoclonal antibody.

To transform a host cell for underproduction of AGP, an antisense construct is utilized. In this construct, the AGP cDNA is situated in the opposite direction of the CaMV 35S promoter so that an antisense transcript is produced. This transcript hybridizes to its corresponding sense mRNA eventually leading to the inhibition of gene expression.

We claim:

1. A cloned DNA fragment encoding a protein backbone of a plant arabinogalactan protein (AGP), characterized by a high content of hydroxyproline, alanine, serine and threonine such that the sum of the hydroxyproline, alanine, serine and threonine constitutes at least about 35% of the amino acyl residues, wherein said cloned DNA fragment hybridizes at high stringency to a nucleotide sequence selected from the group consisting of SEQ ID NO:11, SEQ ID NO:21, SEQ ID NO:24, SEQ ID NO:25, SEQ ID NO:62, SEQ ID NO:63, SEQ ID NO:69 and SEQ ID NO:72.

2. The cloned DNA fragment of claim 1 wherein said arabinogalactan protein is from an Angiosperm.

3. The cloned DNA fragment of claim 2 wherein said Angiosperm is a monocot.

4. The cloned DNA fragment of claim 2 wherein said Angiosperm is a dicot.

5. The cloned DNA fragment of claim 1 wherein said arabinogalactan protein is from Solanaceae.

6. The cloned DNA fragment of claim 5 wherein said arabinogalactan protein is from Nicotiana.

7. The cloned DNA fragment of claim 6 wherein said arabinogalactan protein is from *Nicotiana alata*.

8. The cloned DNA fragment of claim 6 wherein said arabinogalactan protein is from *Nicotiana plumbaginafolia*.

9. The cloned DNA fragment of claim 6 wherein said arabinogalactan protein is from style.

10. The cloned DNA fragment of claim 7 wherein said arabinogalactan protein is from style.

11. The cloned DNA fragment of claim 6 wherein said cloned DNA fragment hybridizes at high stringency to a nucleotide sequence encoding SEQ ID NO:11.

12. The cloned DNA fragment of claim 6 wherein said cloned DNA fragment hybridizes at high stringency to a nucleotide sequence comprising a sequence selected from a group of sequences consisting of SEQ ID NO:21, and SEQ ID NO:24.

13. The cloned DNA fragment of claim 6 wherein said cloned DNA fragment comprises the nucleotide sequence SEQ ID NO:24.

14. The cloned DNA fragment of claim 6 wherein said cloned DNA fragment is cDNA clone NaAGP1.

15. The cloned DNA fragment of claim 6 wherein said cloned DNA fragment comprises the nucleotide sequence SEQ ID NO:25.

16. The cloned DNA fragment of claim 6 wherein said cloned DNA fragment is cDNA clone NpAGP1.

17. The cloned DNA fragment of claim 6 wherein said cloned DNA fragment is a genomic AGP gene.

18. The cloned DNA fragment of claim 17 wherein said genomic AGP gene is from *Nicotiana alata*.

19. The cloned DNA fragment of claim 17 wherein said genomic AGP gene is from *Nicotiana plumbaginafolia*.

20. The cloned DNA fragment of claim 9 wherein said cloned DNA fragment comprises nucleotide sequence SEQ ID NO:63 or SEQ ID NO:72.

21. The cloned DNA fragment of claim 9 wherein said cloned DNA fragment is cDNA clone Na35_1 or AGPNal 1.

22. The cloned DNA fragment of claim 9 wherein said cloned DNA fragment is a genomic AGP gene.

23. The cloned DNA fragment of claim 10 wherein said DNA fragment is a genomic AGP gene.

24. The cloned DNA fragment of claim 9 wherein said DNA fragment is a genomic AGP gene.

25. A DNA recombinant vector comprising a cloned DNA fragment of claim 1.

26. A DNA recombinant vector comprising a cloned DNA fragment of claim 5.

27. A DNA recombinant vector comprising a cloned DNA fragment of claim 6.

28. A DNA recombinant vector comprising a cloned DNA fragment of claim 14.

29. A DNA recombinant vector comprising a cloned DNA fragment of claim 16.

30. A DNA recombinant vector comprising a cloned DNA fragment of claim 17.

31. A DNA recombinant vector comprising a cloned DNA fragment of claim 21.

32. A DNA recombinant vector comprising a cloned DNA fragment of claim 22.

33. A host cell transformed with a cloned DNA fragment of claim 1 so that a glycosylated or nonglycosylated arabinogalactan protein is expressed.

34. A host cell transformed with a cloned DNA fragment of claim 5 so that a glycosylated or nonglycosylated arabinogalactan protein is expressed.

35. A host cell transformed with a DNA fragment of claim 6 so that a glycosylated or nonglycosylated arabinogalactan protein is expressed.

36. A host cell transformed with a DNA fragment of claim 14 so that a glycosylated or nonglycosylated arabinogalactan protein is expressed.

37. A host cell transformed with a DNA fragment of claim 16 so that a glycosylated or nonglycosylated arabinogalactan protein is expressed.

38. A host cell transformed with a DNA fragment of claim 17 so that a glycosylated or nonglycosylated arabinogalactan protein is expressed.

39. A host cell transformed with a DNA fragment of claim 21 so that a glycosylated or nonglycosylated arabinogalactan protein is expressed.

40. A host cell transformed with a DNA fragment of claim 22 so that a glycosylated or nonglycosylated arabinogalactan protein is expressed.

41. The host cell of claim 33 wherein said host cell is a bacterium.

42. The host cell of claim 41 wherein said host cell is *Escherichia coli*.

43. The host cell of claim 33 wherein said host cell is a plant cell.

44. The host cell of claim 43 wherein said host cell is a monocot cell.

45. The host cell of claim 43 wherein said host cell is a dicot cell.

46. The host cell of claim 33 wherein said host cell is a mammalian cell.

47. The host cell of claim 46 wherein said host cell is a COS cell.

48. A genetically-engineered DNA molecule comprising a plant arabinogalactan portein gene, hybridizing at high stringency to a nucleotide sequence selected from the group consisting of SEQ ID NO:11, SEQ ID NO:21, SEQ ID NO:24, SEQ ID NO:25, SEQ ID NO:62, SEQ ID NO:63, SEQ ID NO:69 and SEQ ID NO:72, under control of a heterologous promoter so that a glycosylated or nonglycosylated arabinogalactan protein, characterized by a high content of hydroxyproline, alanine, serine and threonine such that the sum of the hydroxyproline, alanine, serine and threonine constitutes at least about 35% of the amino acyl residues, is expressed.

49. The genetically-engineered DNA molecule of claim 48 wherein said heterologous promoter is a constitutive promoter.

50. The genetically-engineered DNA molecule of claim 49 wherein said constitutive promoter is a CaMV promoter.

51. The genetically-engineered DNA molecule of claim 48 wherein said heterologous promoter is an inducible promoter.

52. The genetically-engineered DNA molecule of claim 51 wherein said inducible promoter is an alcohol dehydrogenase (ADB) promoter.

53. The genetically-engineered DNA molecule of claim 48 wherein said arabinogalactan protein is overexpressed.

54. The genetically-engineered DNA molecule of claim 48 wherein said arabinogalactan protein is underexpressed.

55. The genetically-engineered DNA molecule of claim 48 wherein said arabinogalactan protein gene hybridizes at high stringency to a cDNA selected from the group of cDNA clones consisting of NaAGP1, NpAGP1, Na35_1, AGPNal 1.

56. The genetically-engineered DNA molecule of claim 48 wherein said arabinogalactan protein gene comprises a cDNA sequence selected from a group consisting of NaAGP1, NpAGP1, Na35_1 and AGPNal 1 cDNA sequences.

* * * * *

UNITED STATES PATENT AND TRADEMARK OFFICE
CERTIFICATE OF CORRECTION

PATENT NO. : 5,646,029

DATED : July 8, 1997

INVENTOR(S) : Chen et al.

It is certified that error appears in the above-identified patent and that said Letters Patent is hereby corrected as shown below:

In Table 1.0 please delete "Isolectric" and replace with -- Isoelectric--.
In column 13, line 1, please delete "horizonatally" and replace with --horizontally--.
In column 23, line 37, please delete "complimentarity" and replace with --complementarity--.
In column 33, line 36, please delete "reisdues" and replace with --residues--.
In the table legend for Table 5.1, please delete "Promomter," and replace with --Promoter--.
In column 43, line 12, please delete "$^{32}$p" and replace with --$^{32}$P--.
In column 45, line 50, please delete "dialysed" and replace with --dialyzed--.
In column 50, line 33, please delete "pHS" and replace with --pH8--.
In claim 48, line 27, please delete "portein" and replace with --protein--.
In claim 52, line 52, please delete "(ADB)" and replace with --(ADH)--.

Signed and Sealed this

Twentieth Day of October, 1998

*Attest:*

BRUCE LEHMAN

*Attesting Officer*      *Commissioner of Patents and Trademarks*